US008048899B2

(12) United States Patent
Bartolozzi et al.

(10) Patent No.: US 8,048,899 B2
(45) Date of Patent: *Nov. 1, 2011

(54) COMPOUNDS WHICH SELECTIVELY MODULATE THE CB2 RECEPTOR

(75) Inventors: Alessandra Bartolozzi, Norwalk, CT (US); Angela Berry, Gaylordsville, CT (US); Eugene Richard Hickey, Danbury, CT (US); Markus Ostermeier, Biberach (DE); Doris Riether, Newtown, CT (US); Achim Sauer, Ravensburg-Torkenweiler (DE); David Smith Thomson, Ridgefield, CT (US); Lifen Wu, New Milford, CT (US); Renee M. Zindell, New Milford, CT (US); Patricia Amouzegh, Didcot (GB); Nigel James Blumire, Didcot (GB); Stephen Peter East, Wallingford (GB); Monika Ermann, Wantage (GB); Someina Khor, Didcot (GB); Innocent Mushi, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/564,132

(22) Filed: Sep. 22, 2009

(65) Prior Publication Data

US 2010/0081644 A1    Apr. 1, 2010

Related U.S. Application Data

(60) Provisional application No. 61/100,077, filed on Sep. 25, 2008.

(51) Int. Cl.
| | | |
|---|---|---|
| *A61K 31/433* | (2006.01) | |
| *A61K 31/42* | (2006.01) | |
| *A61K 31/422* | (2006.01) | |
| *A61K 31/4196* | (2006.01) | |
| *C07D 285/135* | (2006.01) | |
| *C07D 413/12* | (2006.01) | |
| *C07D 261/14* | (2006.01) | |
| *C07D 249/16* | (2006.01) | |

(52) U.S. Cl. ........ 514/363; 514/380; 514/383; 548/139; 548/245; 548/265.4

(58) Field of Classification Search .......... None
See application file for complete search history.

(56) References Cited

U.S. PATENT DOCUMENTS

| | | |
|---|---|---|
| 3,116,284 A | 12/1963 | Testa |
| 3,117,128 A | 1/1964 | Mooradian |
| 3,577,462 A | 5/1971 | Bruce et al. |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,571,921 A | 11/1996 | Bender et al. |
| 5,583,147 A | 12/1996 | Ko et al. |
| 5,656,634 A | 8/1997 | Chang et al. |
| 5,847,153 A | 12/1998 | Warpehoski et al. |
| 5,968,929 A | 10/1999 | Blythin et al. |
| 6,057,371 A | 5/2000 | Glennon |
| 6,176,442 B1 | 1/2001 | Eicher et al. |
| 6,221,866 B1 | 4/2001 | Brendel et al. |
| 6,355,653 B1 | 3/2002 | Trottmann et al. |
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 7,476,756 B2 | 1/2009 | Almario-Garcia et al. |
| 7,585,881 B2 | 9/2009 | Edwards et al. |

(Continued)

FOREIGN PATENT DOCUMENTS

| | | |
|---|---|---|
| CH | 312963 A | 3/1956 |
| DE | 1080563 B | 12/1957 |
| EP | 0628555 | 12/1994 |
| EP | 0929519 | 7/1999 |
| EP | 0970046 | 1/2000 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |

(Continued)

OTHER PUBLICATIONS

Katz, L, et al., "Hydrazine Derivatives. II. Ortho-Mercapto-Pyridinecarbohydrazides", Contribution from Schenley Laboratories, Inc., 1953, p. 711.

(Continued)

*Primary Examiner* — Rebecca Anderson
*Assistant Examiner* — Alicia L Otton
(74) *Attorney, Agent, or Firm* — Michael P. Morris; Anthony P. Bottino

(57) ABSTRACT

Compounds of formula (I)            (I)

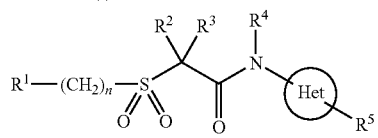

are disclosed. Compounds according to the invention bind to and are agonists, antagonists or inverse agonists of the CB2 receptor, and are useful for treating inflammation. Those compounds which are agonists are additionally useful for treating pain.

32 Claims, No Drawings

U.S. PATENT DOCUMENTS

| | | | |
|---|---|---|---|
| 7,595,397 | B2 | 9/2009 | Zindell et al. |
| 7,935,715 | B2 | 5/2011 | Berry et al. |
| 2002/0099035 | A1 | 7/2002 | Sandanayaka et al. |
| 2004/0067999 | A1 | 4/2004 | Block et al. |
| 2004/0242913 | A1 | 12/2004 | Ducray et al. |
| 2005/0059663 | A1 | 3/2005 | Martin et al. |
| 2005/0182108 | A1 | 8/2005 | Carson et al. |
| 2006/0061726 | A1 | 3/2006 | Okuyama |
| 2006/0079557 | A1 | 4/2006 | Dolle et al. |
| 2007/0021403 | A1 | 1/2007 | Abouabdellah et al. |
| 2007/0021430 | A1 | 1/2007 | Chen et al. |
| 2007/0093501 | A1 | 4/2007 | Kubo et al. |
| 2007/0179126 | A1 | 8/2007 | Casellas et al. |
| 2007/0191340 | A1 | 8/2007 | Zindell et al. |
| 2007/0213311 | A1 | 9/2007 | Li et al. |
| 2008/0039464 | A1 | 2/2008 | Berry et al. |
| 2008/0064690 | A1 | 3/2008 | Atkinson et al. |
| 2008/0081342 | A1 | 4/2008 | Fung |
| 2008/0081822 | A1 | 4/2008 | Berry et al. |
| 2009/0163545 | A1 | 6/2009 | Goldfarb |
| 2009/0275611 | A1 | 11/2009 | Riether et al. |
| 2010/0009964 | A1 | 1/2010 | Berry et al. |
| 2010/0029644 | A1 | 2/2010 | Riether et al. |
| 2010/0076029 | A1 | 3/2010 | Bartolozzi et al. |
| 2010/0081644 | A1 | 4/2010 | Bartolozzi et al. |
| 2010/0261708 | A1 | 10/2010 | Cirillo et al. |
| 2010/0331304 | A1 | 12/2010 | Berry et al. |
| 2011/0071127 | A1 | 3/2011 | Berry et al. |
| 2011/0071196 | A1 | 3/2011 | Bartolozzi et al. |
| 2011/0124696 | A1 | 5/2011 | Regan et al. |
| 2011/0130431 | A1 | 6/2011 | Berry et al. |
| 2011/0136869 | A1 | 6/2011 | Bartolozzi et al. |

FOREIGN PATENT DOCUMENTS

| | | |
|---|---|---|
| GB | 884258 A | 12/1961 |
| JP | 61027905 U | 2/1986 |
| JP | 61027955 A | 2/1986 |
| JP | 61126071 A | 6/1986 |
| JP | 2003155285 | 5/2003 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9813340 | 4/1998 |
| WO | 9838163 A1 | 9/1998 |
| WO | 0100573 | 1/2001 |
| WO | 0129007 | 4/2001 |
| WO | 0164651 | 9/2001 |
| WO | 0251806 | 7/2002 |
| WO | 0262750 | 8/2002 |
| WO | 03037274 | 5/2003 |
| WO | 03055482 | 7/2003 |
| WO | 03000807 | 12/2003 |
| WO | 2004000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004029027 | 4/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006060461 | 6/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 | 6/2007 |
| WO | 2007070760 A2 | 6/2007 |
| WO | 2007080382 A1 | 7/2007 |
| WO | 2007102059 | 9/2007 |
| WO | 2007118041 | 10/2007 |
| WO | 2008014199 | 1/2008 |
| WO | 2008023159 A1 | 2/2008 |
| WO | 2008039645 | 4/2008 |
| WO | 2008048914 A1 | 4/2008 |
| WO | 2008064054 | 5/2008 |
| WO | 2008098025 A1 | 8/2008 |
| WO | 2008104994 A2 | 9/2008 |
| WO | 2009055357 A1 | 4/2009 |
| WO | 2009061652 A1 | 5/2009 |
| WO | WO 2009/061652 * | 5/2009 |
| WO | 2009077533 A1 | 6/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |

OTHER PUBLICATIONS

Klein, T. W., et al., "The Cannabinoid system and immune modulation", J. Leukocyte Biology, 2003, vol. 74, p. 486.

Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

Leffler, M. T. et al. "N-Arylalkylmorpholines". Journal of the American Chemical Society, vol. 60, 1938, pp. 896-899.

Lutz, R. E. et al., "Antimalarials. Some piperazine derivatives". Journal of Organic Chemistry, vol. 12, 1947, pp. 771-775.

Mahmoud, A. M. et al., "Synthesis and Biological Activity of Some new 2-(N-Substituted Carboxamidomethyl Thio)-Naphth[1,2-d]Oxazoles-Part V". XP002068972, J. Indian Chem. Soc., vol. LIX, May 1982, pp. 675-677.

Malan Jr., T. P., et al., "CB2 cannabinoid receptor-mediated peripheral antinociception", Pain, 2001, vol. 93, p. 239.

Markley, L. D., et al., "Antipicornavirus activity of substituted Phenoxybenzenes and Phenoxypyridines", J. Med. Chem., 1986, vol. 29, p. 427.

Marx, I. E. et al., "Discovery of a-amidosulfones as potent and selective agonists of CB2: Synthesis, SAR, and pharmacokinetic properties". Bioorganic and Medicinal Chemistry Letters, 2008. In press, accepted manuscript.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp. 5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Sharkey, K. A. et al., "CB2 cannabinoid receptors: new vistas", The first International Conference devoted to studies of the CB2 cannabinoid receptor. Banff, Alberta, Canada, May 31-Jun. 3, 2007.

Smith, S. R., et al., "The anti-inflammatory activities of cannabinoid receptor ligands in mouse peritonitis models", Eur. J. Pharmacology, 2001, vol. 432, p. 107.

Swanson, D. M. et al., "Identification and biological evaluation of 4-*(3-trifluoremethylpyridin-2-yl)piperzine-1-carboxylic acid (5-trifluoremethylpyridin-2-yl)amide, a high affinity TRPV1 (VR1) vanilloid receptor antagonist". Journal Med. Chem, 2005, 48, pp. 1857-1872.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. and Uhde, R., "Ueber sulfonirte buttersauren", J. Prakt. Chem., 1899, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.

Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.

Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.

Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.

Arevalo-Martin, A. et al., "Therapeutic Action of Cannabinoids in a Murine model of Multiple Sclerosis", J. of Neuroscience, 2003, vol. 23, No. 7, p. 2511.

Atwell, G. J. et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.

Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.

Baker, D. et al., "Cannabinoids control spasticity and tremor in a multiple sclerosis model", Nature, 2000, vol. 404, p. 84.

Baltzly, R. et al., "The preparation of N-mono-substituted and unsymmetrically disubstituted piperzines". Journal of American Chemical Society, vol. 66, 1944, pp. 263-265.

Baltzly,R. et al., "Unsymmetrically substituted piperazines. V. Piperazine ureas". The Journal of the American Chemical Society, vol. 76, 1954, pp. 1165-1166.

Balzarini, J. et al., "Antiretroviral activity of semisynthetic derivatives of glycopeptide antibiotics". J. Med. Chem., 2003, vol. 46, No. 13, pp. 2755-2764.

Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, vol. 36, p. 809.

Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.

Buckley, N. E. et al., "Immunomodulation by cannabinoids is absent in mice deficient for the cannabinoid CB2 receptor", Eur. J. Pharmacology, 2000, vol. 396, p. 141.

Caplus—RN 112298-90-5, retrieved from CAPLUS on Jan. 2, 2009.
Caplus—RN 262371-16-4, retrieved from CAPLUS on Jan. 2, 2009.
Caplus—RN 57992-82-2, retrieved from CAPLUS on Jan. 2, 2009.

Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.

Chang, M. Y. et al, "Reaction of different a-sulfonyl acetamides with methyl acrylate". Tetrahedron 58 (2002) p. 5075-5080.

ChemAbstract: 1990:497413, Zara-Kaczian, Acta Chimica Hungarica.

Chen, D. et al., "Preparation, properties, and synthetic potentials of novel boronates in a flourous version (flourous boronates)". Organic Letters, vol. 4. No. 6, 2002, pp. 1003-1005.

Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.

Dav, Jr., R. A. et al., "Polarography of phenyl 2-thienyl and 2,2'-dithienyl ketones". 1953.

El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.

Ermann, M. et al., "Arylsulfonamide CB2 receptor agonists: SAR and optimization of CB2 selectivity", Bioorganic and Medicinal Chemistry Letters 18 (2008) 1725-1729.

Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.

Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.

Faucher, A. M. et al., "Discovery of Small-Molecule Inhibitors of the ATPase Activity of Human Papillomavirus E1 Helicase", J. Med. Chem., 2004, vol. 47, p. 18.

Field, L. et al., "Grignard Reagents of Sulfones. IV. Reactions with Nitriles, Esters and an Isocyanate". XP002465788, Mar. 30, 1956.

Field, L., et al., "Methyl p-Tolyl Sulfone", Organic Syntheses, Coll. vol. 4, p. 674, 1963; vol. 38, p. 62, (1958).

Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.

Gao, M., et al "Synthesis of new carbon-11 labeled benzoxazole derivatives for Pet imaging of 5-HT3 receptor", Science Direct, European Journal of Medicinal Chemistry, 43, 2008, pp. 1570-1574.

Gartst, M., et al., "Hydroformylation of bisolefinic amine derivatives catalyzed by cobalt and rhodium". Journal of Organic Chemistry, vol. 46, 1981, pp. 4433-4438.

Gavalda, et al N-Sulfonyl hydroxamate derivataives as inhibitors of class II fructose-1, 6-diphosphate aldolase, Bioorganic & Medicinal Chemistry Letter, 2005, vol. 15, No. 24, pp. 5375-5377.

Goldschmidt,St. et al., "Biphenyl derivatives II. Basic 4-Biphenyl Compounds". Receuil Travaux Chimiques Des Pays-Bas, vol. 69, 1950, pp. 1109-1117.

Hanus, L. et al., "HU-308: A specific agonist for CB2, a peripheral cannabinoid receptor", PNAS, 1999, vol. 96, No. 25, p. 14228.
Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.
Huang, X. et al., "A Novel Synthesis of Sulfones via the O,O-Diethylphosphorotellurite Ion-assisted Coupling of Arenesulfonyl Chlorides with Active Halides". Synthetic Communications, 20(15), 2291-2291-2295 (1990).
Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.
Igarashi, J. et al., "Improved synthesis of quinine alkaloids with the Teoc protective group". Tetrahedron letters, Elsevier, Amsterdam, vol. 46, No. 37, 2005, pp. 6381-6384.
Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).
Johansen et al., AMPA Receptor Agonists: Resolution, Configurational Assignment, and Pharmacology of (+)-(S)and (−)-(R)-2-Amino-3-(3-Hydroxy-5-(2-Pyridyl) Isoxazol-4-y1)Propionic Acid (1-Py-AMPA); Chirality, NewYork, 1997, vol. 9, No. 3, pp. 274-280.
Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.
Watson, R. J., et al., "An enantioselective synthesis of sulphonamide hydroxamic acids as matrix metalloproteinase inhibitors", Pergamon, Tetrahedron Letters 43 (2002) 683-685.
Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.
Yordanova, K. et al. "New method for the synthesis of 2,4-disubstituted morpho- lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.
Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.
Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.
Zindell, R. et al., "Discovery of a novel class of CB2 agonists". General Poster Session. The 235th ACS National Meeting, New Orleans, LA, USA. Apr. 6-10, 2008.
Abstract in English for JP 61-027905, Feb. 7, 1986, and WO199626925, Sep. 1996, Derwent Abstract.
Abstract in English for JP 61-027955, Feb. 7, 1986, Derwent.
Abstract in English for JP2003155285, May 27, 2003, Inventor: T. Makoto.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.
EP Office Action for Case 09-0388 dated Mar. 22, 2010.
Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.
International Search Report for PCT/US2009/057776 mailed Mar. 11, 2010.
Krutosikova, A. et al., "Furan derivatives. LV. Preparation of 5-aryl-2-furfuryl phenyl and 5-aryl-2-furfuryl 4-tolyl1sulfones". Chemick Zvesti—Chemical Papers, Veda Bratislava, SK. vol. 28, Jan. 1, 1974, pp. 414-417, ISSN: 0366-6352, p. 414, compounds I-IX.
Messinger, P., "Sulfones via Mannich bases" Archiv der Pharmazie, 1973, vol. 306, No. 8, pp. 603-610, ISSN: 0365-6233. p. 607, compounds 28A-29C.
Office Action from the EPO for 09-0388 dated Mar. 22, 2010.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.
Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.
Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.
Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.
Caplus—1990:497413, Zara-Kaczian, Acta Chimica Hungarica, 1989.
ChemAbstract: 246020-62-2 registry copyright ACS on STN, entered 1999. CHEMCATS.
ChemAbstracts: 693218-49-4 and 402562-90-7. 2004.
Clark, N. G. et al., "The Fungicidal Activity of Substituted Acetanilides and Related Compounds". Biochemical Journal, 1953, vol. 55, p. 839-851.
Evans, W. J. et al., "A Rearrangement of Carbamyl-sulphones and -sulphides". Journal of the Chemical Society, 1936, p. 329-331.
Grothe, V. W. et al. "Effect of Potassium Sulfhydrate etc. on Chloroacetylanilides". Archiv der Pharmazie (Weinheim), vol. 238, 1980, p. 600-614.
Iddon, B. et al., "Polyhalogenoaromatic Compounds. Part 42. C N. m.r. Spectra of Polyhalogeno-pyridines and—pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.
Lambeng, N. et al., "Discovery of a Novel Piperidinyl-Sulfonyl Benzoic Ester, Active as CB1 Agonist" POSTER. 231st ACS National Meeting, Atlanta, GA. Mar. 26-30, 2006.
Lesser, R. et al. "Homo-?-oxythionaphthene (4-Ketoisothiochromane". Charlottenburg, Industrial Chemistry Laboratory of the Institute of Technology, 1923, pp. 1642-1648.
Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.
Seidel M. C. et al., "Reaction of Substituted 2-carbethoxyacetyl-aminopyridines and similar compounds with triethyl orthoformate and zinc chloride". Rohm and Haas Company, Spring House, Pennsylvania 19477, 1989.
Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.
Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.
Troeger, J. et al., "Regarding sulfonated Butyric Acids". From the Laboratory for Pharmaceutical and Synthetic Chemistry of the Braunschweig Institute of Technology.1991, 40, 506.
U.S. Appl. No. 13/022,866, filed Feb. 8, 2011, Inventor: Angela Berry. (The cited pending U.S. application is stored in the USPTO IFW system (MPEP 609.04(a)(II)(C)).
U.S. Appl. No. 13/037,422, filed Mar. 1, 2011, Inventor: Monika Ermann. (The cited pending U.S. application is stored in the USPTO IFW system (MPEP 609.04(a)(II)(C)).
Venkov, A.P. et al., "A new synthesis of 1,2,3,40tetrahydro-2-methyl-4-phenylisoquinolines". Dept of Chemistry, University of Plovdiv, Bulgaria, pp. 253-255, Mar. 1990.

* cited by examiner

COMPOUNDS WHICH SELECTIVELY MODULATE THE CB2 RECEPTOR

APPLICATION DATA

This application claims benefit to U.S. provisional application Ser. No. 61/100,077 filed Sep. 25, 2008.

BACKGROUND OF THE INVENTION

1. Technical Field

The present invention relates to novel compounds which modulate the CB2 receptor and their use as medicaments.

2. Background Information

WO2008014199, WO2008039645 discuss the CB2 receptor, and the therapeutic uses of the CB2 receptor agonist compounds disclosed therein. It is believed that the highly selective activation of the CB2 receptor with an agonist may offer avenues of harnessing the beneficial effects while avoiding the adverse effects seen with dual CB1/CB2 cannabinoid receptor agonists (see e.g. Expert Opinion on Investigational Drugs (2005), 14(6), 695-703). It is desirable therefore to provide agonists of CB2 with minimized CB1 activity.

WO2008014199, WO2008039645 and WO 2009061652 disclose sulfone derivatives having CB2 agonist activity. The compounds of the present invention differ structurally from the above disclosed compounds, for example the present $R^5$ in the formula (I) disclosed hereinbelow. Additionally, the compounds of the present invention have lower CB1 activity than the compounds disclosed in the cited art.

BRIEF SUMMARY OF THE INVENTION

The present invention provides novel compounds which bind to and modulate the CB2 receptor and have lower CB1 receptor activity. The invention also provides methods and pharmaceutical compositions for treating inflammation by way of the administration of therapeutic amounts of the compounds of the invention. Lastly, the invention provides a method and pharmaceutical compositions for treating pain by way of the administration of therapeutic amounts of the compounds of the invention.

DETAILED DESCRIPTION OF THE INVENTION

In the broadest generic embodiment 1, the invention provides compounds of the formula

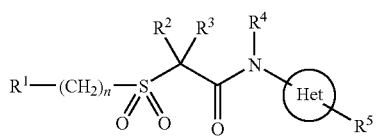

(I)

wherein:
Het is a 5-membered heteroaryl ring;
$R^1$ is $C_{1-10}$ alkyl, $C_{1-10}$ alkoxy, $C_{3-10}$ cycloalkyl, 3-10 membered saturated heterocyclic ring, 5-10 membered mono or bicyclic heteroaryl ring or phenyl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, phenyl, hydroxyl and halogen;
$R^2$ and $R^3$ are $C_1$-$C_4$ alkyl or hydrogen with the proviso that both $R^2$ and $R^3$ cannot be hydrogen; or $R^2$ and $R^3$ together with the carbon atom to which they are attached form a 3- to 6-membered cycloalkyl or heterocyclic ring;
$R^4$ is hydrogen or methyl;
$R^5$ is chosen from

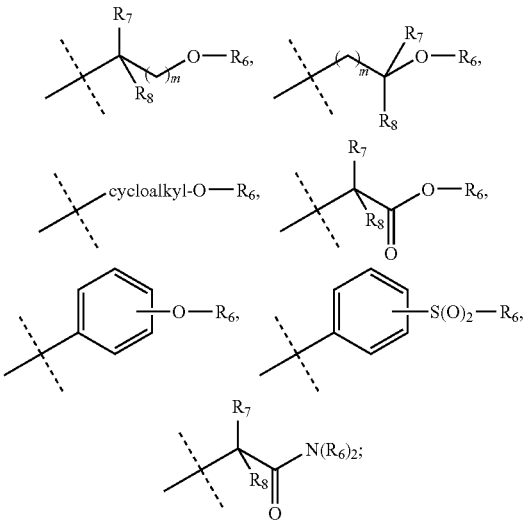

m is 0, 1, 2 or 3
$R^6$ is hydrogen or $C_{1-4}$ alkyl;
wherein $R^7$ and $R^8$ are each independently hydrogen or $C_{1-4}$ alkyl with the proviso that both $R^7$ and $R^8$ cannot be hydrogen; and wherein $R^7$ and $R^8$ optionally can cyclize to form a $C_{3-7}$ cycloalkyl ring;
n is 0, 1 or 2;
wherein any carbon atom on the formula (I) or any R substituent listed above is optionally partially or fully halogenated where possible;
or a pharmaceutically acceptable salt thereof.

In another embodiment 2, the invention provides compounds of the formula (I) according to any of the preceding embodiments described above, and wherein
Het is

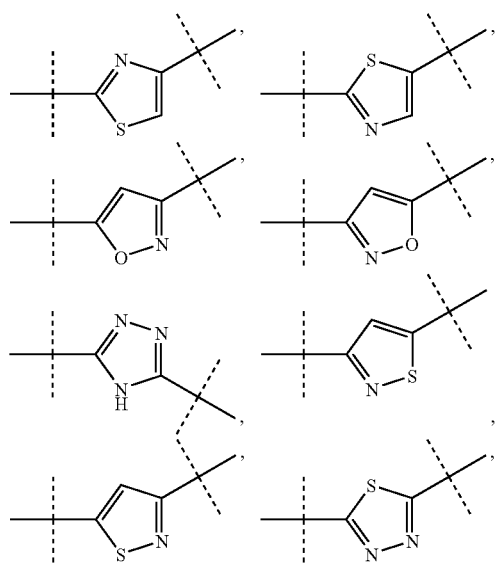

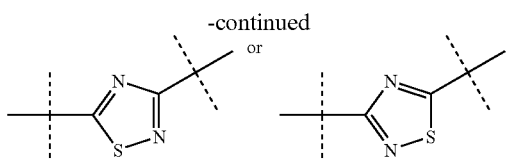

R¹ is $C_{1-4}$ alkyl, phenyl, cyclopropyl, cyclobutyl, cyclopentyl, cyclohexyl, cycloheptyl, cyclooctyl, tetrahydrofuranyl, tetrahydropyranyl, azetidinyl, piperidinyl; benzoxazolyl, benzothiazolyl, benzimidazolyl, dioxanyl, oxazolyl, isoxazolyl, thiazolyl, pyrazolyl, pyrrolyl, imidazolyl, thienyl, thiomorpholinyl, 1,1-Dioxo-1λ⁶-thiomorpholinyl, morpholinyl, pyridinyl, pyrimidinyl, pyridazinyl, pyrazinyl, triazinyl, pyrrolidinyl, piperazinyl, purinyl, quinolinyl, Dihydro-2H-quinolinyl, isoquinolinyl, quinazolinyl, indazolyl, indolyl, benzofuranyl, benzopyranyl or benzodioxolyl each optionally substituted by a substituent chosen from halogen, $C_{1-4}$ alkyl, $C_{1-4}$ alkylsulfonyl or oxo;

R² and R³ are independently methyl, ethyl, n-propyl, isopropyl, or hydrogen with the proviso that both R² and R³ cannot be hydrogen; or R² and R³ together with the carbon to which they are attached form a cyclopropyl, cyclobutyl, or cyclopentyl ring;

R⁴ is hydrogen;

R⁵ is chosen from

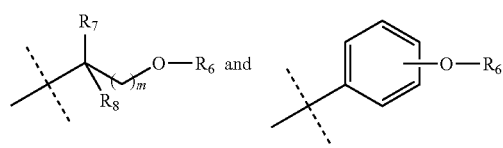

R⁶ is hydrogen or $C_{1-3}$ alkyl;

wherein R⁷ and R⁸ are each $C_{1-3}$ alkyl or $C_{3-6}$ cycloalkyl

In another embodiment 3, the invention provides compounds of the formula (I) according to any of the preceding embodiments above, and wherein R¹ is $C_{1-4}$ alkyl, cyclopropyl, cyclobutyl, cyclopentyl, cyclohexyl, cycloheptyl, cyclooctyl, tetrahydrofuranyl, tetrahydropyranyl, azetidinyl, piperidinyl, dioxanyl, thiomorpholinyl, 1,1-Dioxo-1λ⁶-thiomorpholinyl, morpholinyl, pyrrolidinyl, piperazinyl, each optionally substituted by a substituent chosen from halogen, $C_{1-4}$ alkyl, $C_{1-4}$ alkylsulfonyl or oxo.

In another embodiment 4, the invention provides compounds of the formula (I) according to the embodiment 2, and wherein Het is

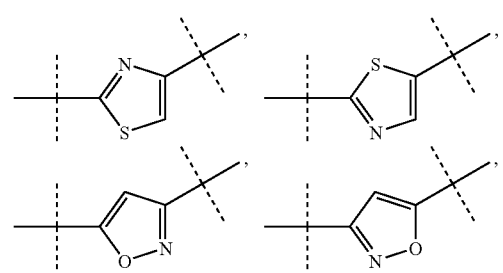

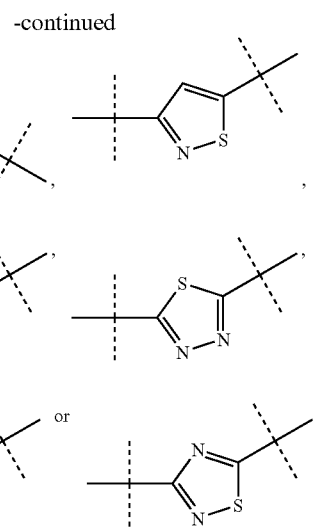

R¹ is phenyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, purinyl, quinolinyl, Dihydro-2H-quinolinyl, isoquinolinyl, quinazolinyl, indazolyl, indolyl, benzofuranyl, benzopyranyl or benzodioxolyl each optionally substituted by a substituent chosen from halogen, $C_{1-4}$ alkyl, $C_{1-4}$ alkylsulfonyl or oxo;

R² and R³ are independently methyl, ethyl, n-propyl, isopropyl, or hydrogen with the proviso that both R² and R³ cannot be hydrogen; or R² and R³ together with the carbon to which they are attached form a cyclopropyl, cyclobutyl, or cyclopentyl ring.

In another embodiment 5, the invention provides compounds of the formula (I) according to the embodiment described immediately above, and wherein Het is

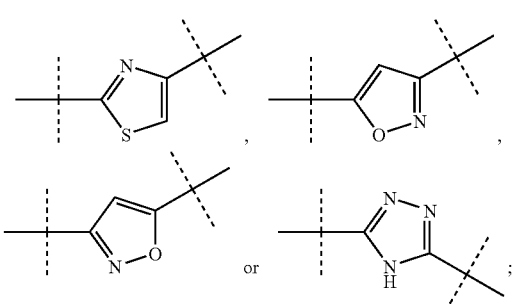

R¹ is phenyl or benzimidazoyl each optionally substituted by a substituent chosen from halogen, $C_{1-4}$ alkyl, $C_{1-4}$ alkylsulfonyl or oxo;

R² and R³ are methyl; or R² and R³ together with the carbon to which they are attached form a cyclopropyl or cyclobutyl ring R⁶ is hydrogen or $C_{1-2}$ alkyl;

wherein R⁷ and R⁸ are each $C_{1-2}$ alkyl.

In a another embodiment 6, the invention provides compounds of the formula (I) according to the embodiment 3, and wherein Het is

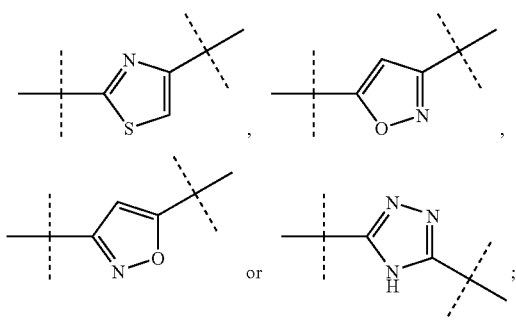

$R^1$ is $C_{1-2}$ alkyl, cyclopropyl, cyclobutyl, cyclopentyl, cyclohexyl, tetrahydropyranyl, tetrahydrofuranyl, azetidinyl, pyrrolidinyl or piperidinyl each optionally substituted by a substituent chosen from by halogen, $C_{1-4}$ alkyl, $C_{1-4}$ alkylsulfonyl or oxo;

$R^2$ and $R^3$ are methyl, or $R^2$ and $R^3$ together with the carbon to which they are attached form a cyclopropyl or cyclobutyl ring $R^6$ is hydrogen or $C_{1-2}$ alkyl;

wherein $R^7$ and $R^8$ are each $C_{1-2}$ alkyl.

In another embodiment 7, the invention provides compounds of the formula (I) according embodiment 5 above and wherein Het is

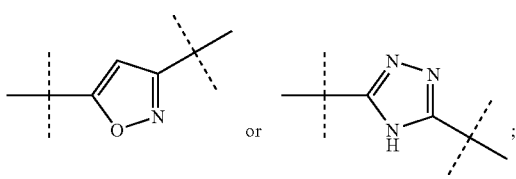

$R^1$ is phenyl optionally substituted by a substituent chosen from by halogen, $C_{1-4}$ alkyl or $C_{1-4}$ alkylsulfonyl.

In another embodiment 8, the invention provides compounds of the formula (I) according to embodiment 6, and wherein Het is

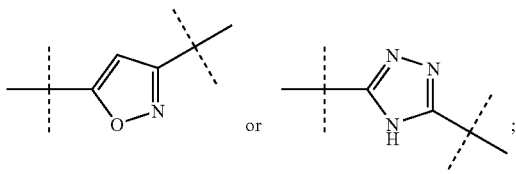

$R^1$ is cyclopropyl, cyclobutyl, tetrahydropyranyl, tetrahydrofuranyl or azetidinyl each optionally substituted by a substituent chosen from by halogen, $C_{1-4}$ alkyl, $C_{1-4}$ alkylsulfonyl or oxo.

In another embodiment 9 the invention provides compounds of the formula (I) according to any of the embodiment described herein, and wherein Het is

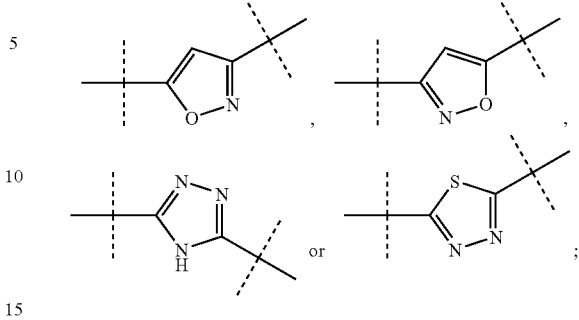

$R^2$ and $R^3$ are methyl.

In another embodiment 10, the invention provides compounds of the formula (I) according to any of the embodiments described herein, and wherein Het is

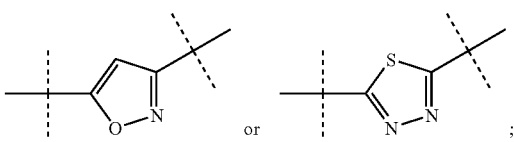

and
$R^5$ is chosen from

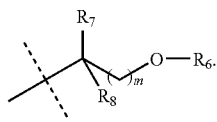

In another embodiment 11, the invention provides compounds of the formula (I) according to any of the embodiments described herein, and wherein Het is

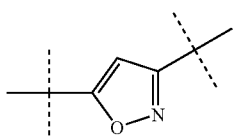

In another embodiment 12, the invention provides compounds of the formula (I) according to any of the embodiments described herein, and wherein
$R^5$ is

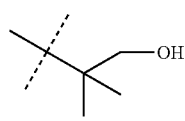

In another embodiment 13, the invention provides compounds of the formula (I) according to any of the embodiments described herein, and wherein
$R^1$ is optionally substituted by a substituent chosen from halogen, $C_{1-4}$ alkyl, $C_{1-4}$ alkoxy, $C_{1-4}$ alkylsulfonyl or oxo.

In another embodiment 14, the invention provides compounds of the formula (I) according to any of the embodiments described herein, and wherein
R$^1$ is C$_{1-4}$ alkyl, cyclopropyl, cyclobutyl, cyclopentyl, cyclohexyl, tetrahydropyranyl, tetrahydrofuranyl, azetidinyl, piperidinyl or pyrrolidinyl each optionally substituted by a substituent chosen from by halogen, C$_{1-4}$ alkyl, C$_{1-4}$ alkoxy, C$_{1-4}$ alkylsulfonyl or oxo.

In another embodiment 15, the invention provides compounds of the formula (I) according to the embodiment immediately described herein, and wherein
R$^1$ is CF$_3$—CH$_2$—CH$_2$—CH$_2$— or tetrahydropyranyl.

In another embodiment there is provided a compound of the formula (II)

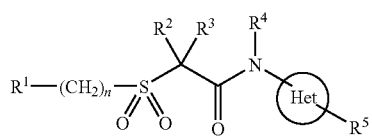

(II)

wherein

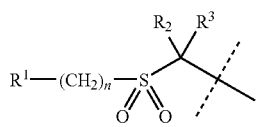

of the formula (I) is chosen from column A1-A26 in Table I, and

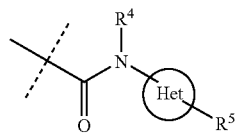

of the formula (I) is chosen from column B1-B20 in Table I,

TABLE I

| | |
|---|---|
| A1 | 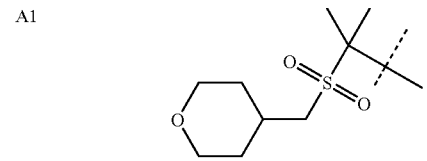 |
| A2 | 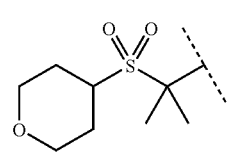 |
| A3 | 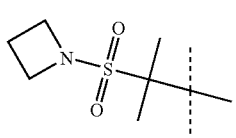 |

TABLE I-continued

| | |
|---|---|
| A4 | 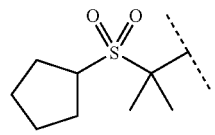 |
| A5 | 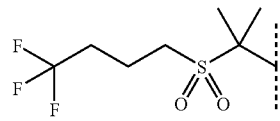 |
| A6 | 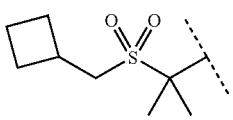 |
| A7 | 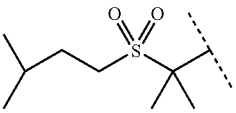 |
| A8 | 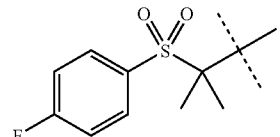 |
| A9 | 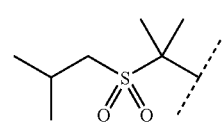 |
| A10 | 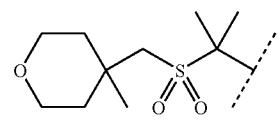 |
| A11 | 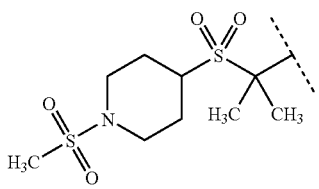 |
| A12 | 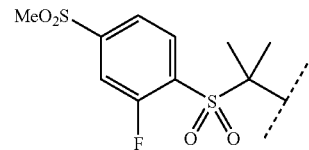 |
| A13 | 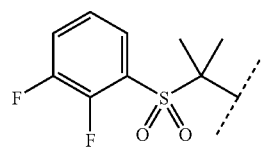 |
| A14 | 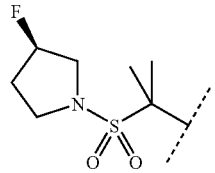 |

TABLE I-continued
| | | | | |
|---|---|---|---|---|
| A15 | 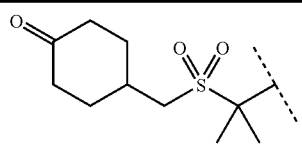 | | A25 | 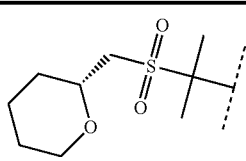 |
| A16 | 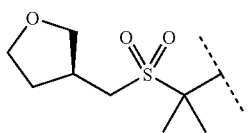 | | A26 | 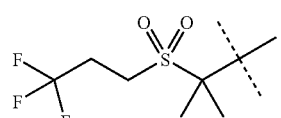 |
| A17 | 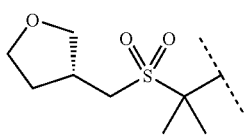 | | B1 | 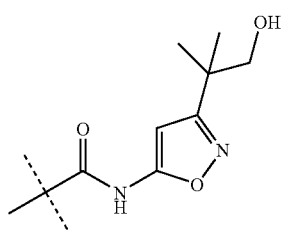 |
| A18 | 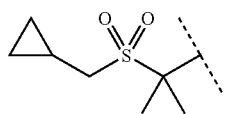 | | B2 | 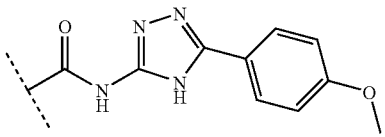 |
| A19 | 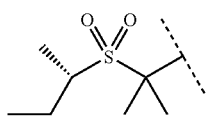 | | B3 | 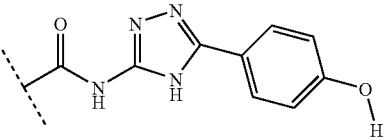 |
| A20 | 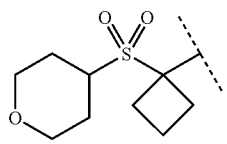 | | B4 | 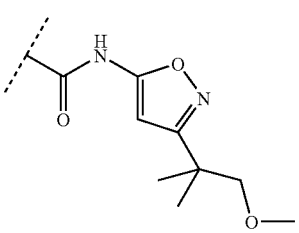 |
| A21 | 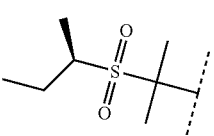 | | B5 | 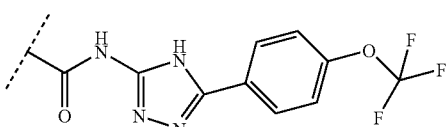 |
| A22 | 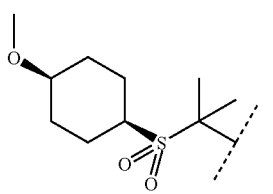 | | B6 | 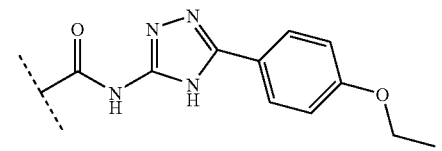 |
| A23 | 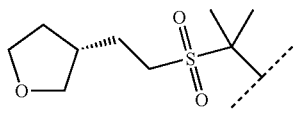 | | B7 | 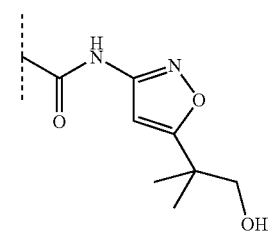 |
| A24 | 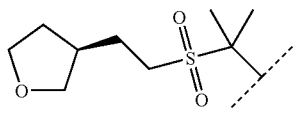 | | | |

TABLE I-continued
B8 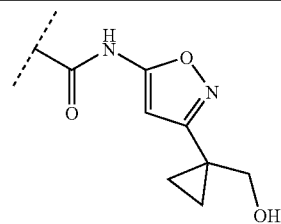
B9 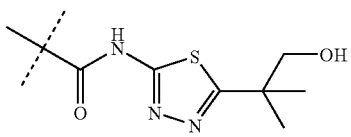
B10 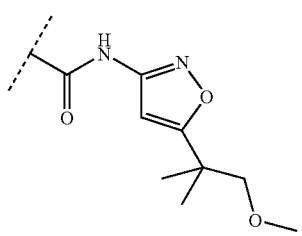
B11 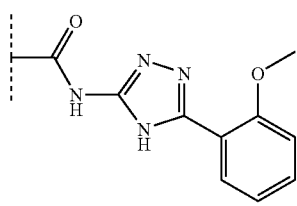
B12 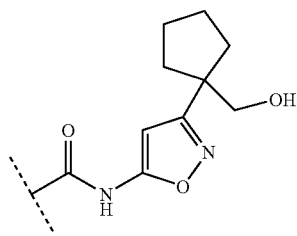
B13 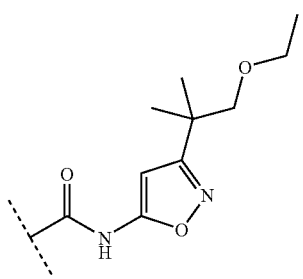
B14 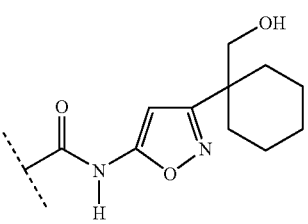
TABLE I-continued
B15 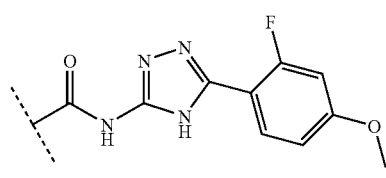
B16 
B17 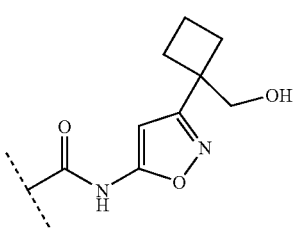
B18 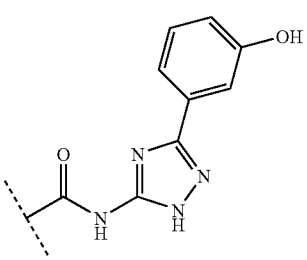
B19 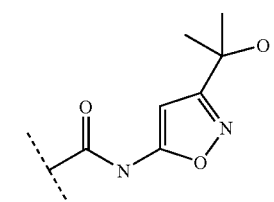
B20 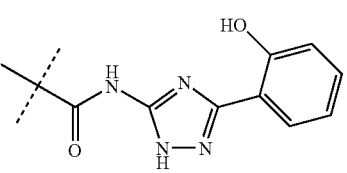
or a pharmaceutically acceptable salt thereof.
In another embodiment, the invention provides made compounds in Table II which can be made in view of the general schemes, examples and methods known in the art.

TABLE II

| Structure | Name |
|---|---|

US 8,048,899 B2

15 16

TABLE II-continued

| Structure | Name |
|---|---|

TABLE II-continued
| Structure | Name |
|---|---|
or a pharmaceutically acceptable salt thereof.
In another embodiment, the invention provides made compounds in Table III which can be made in view of the general schemes, examples and methods known in the art.
TABLE III
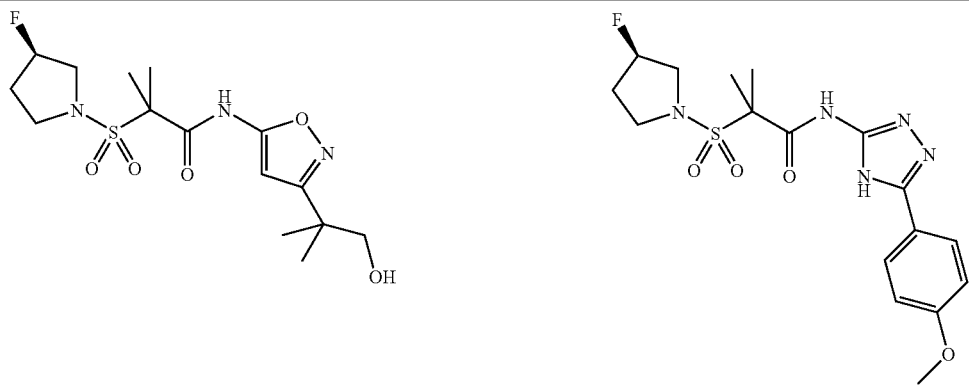

TABLE III-continued
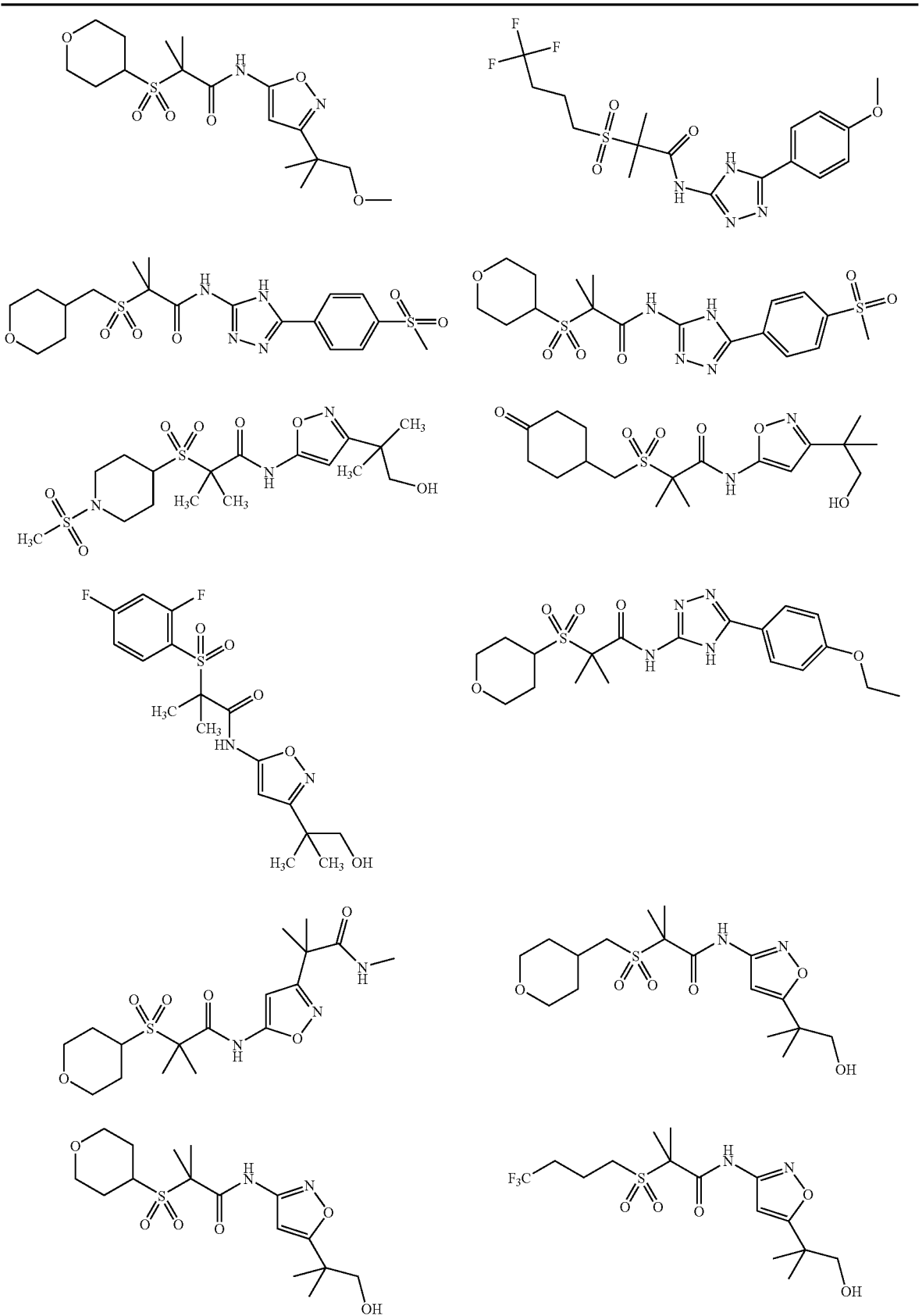

TABLE III-continued
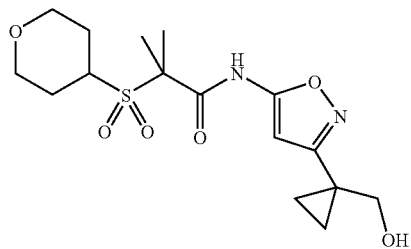
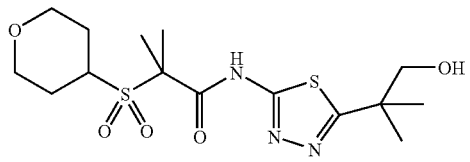
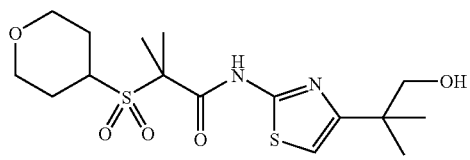
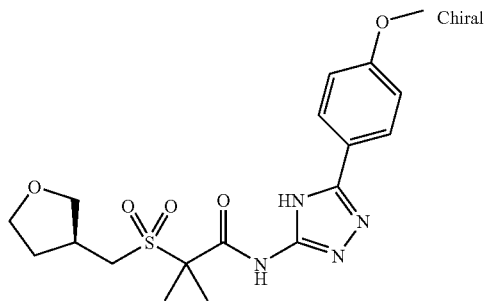
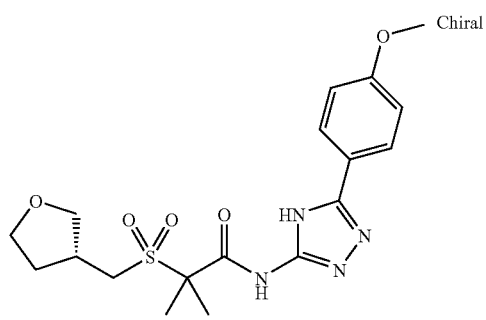
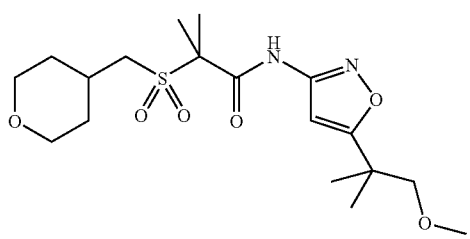
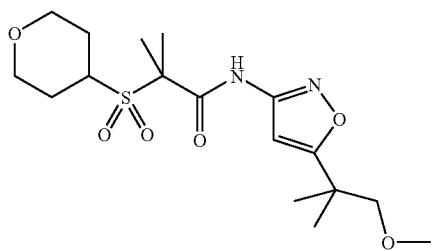
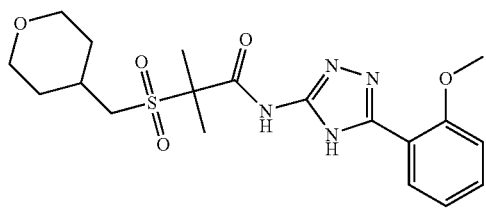
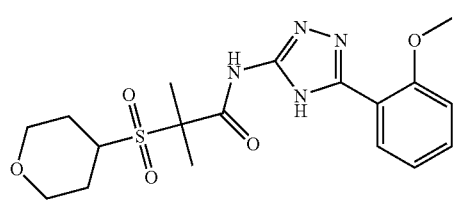
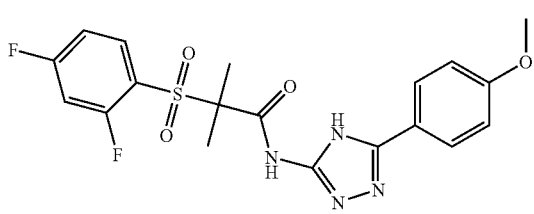
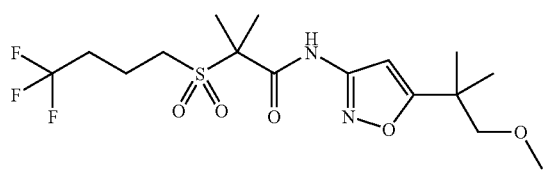
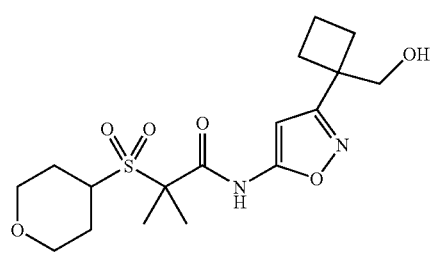

TABLE III-continued
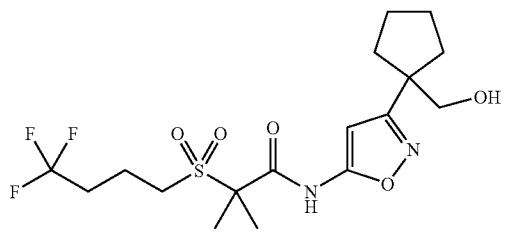
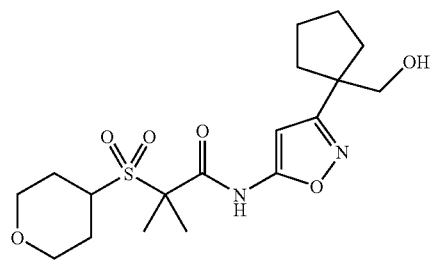
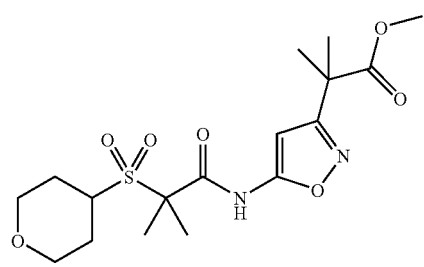
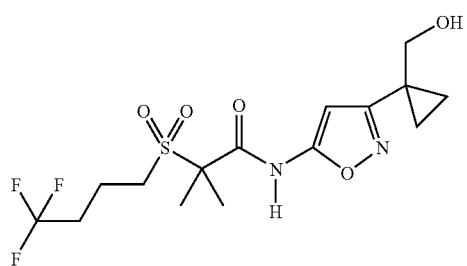
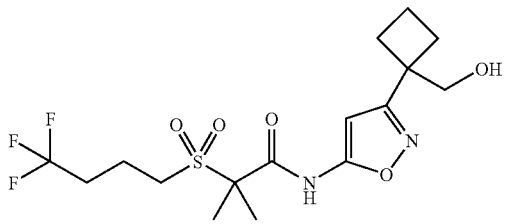
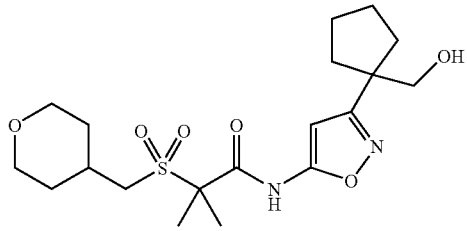
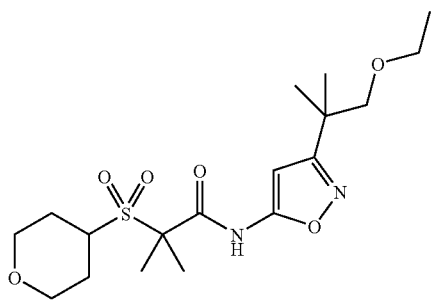
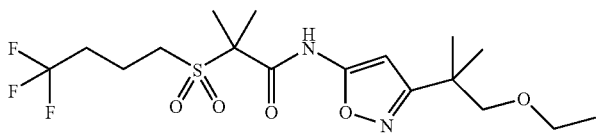
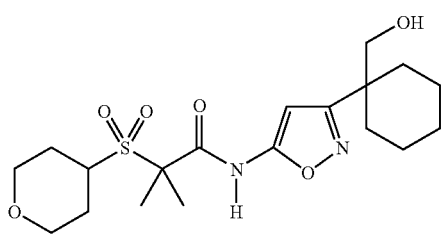
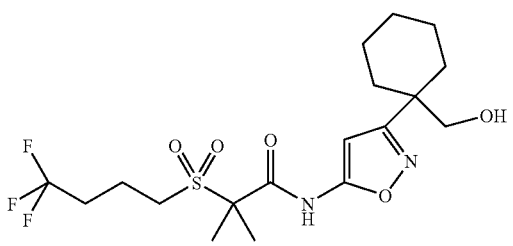
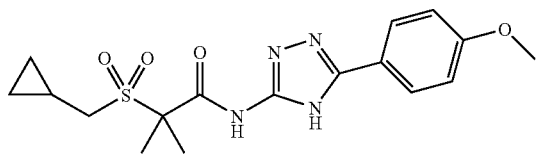
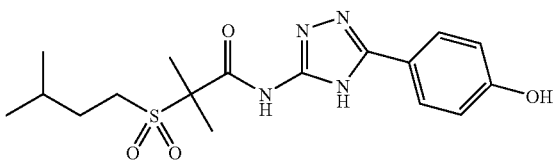

TABLE III-continued
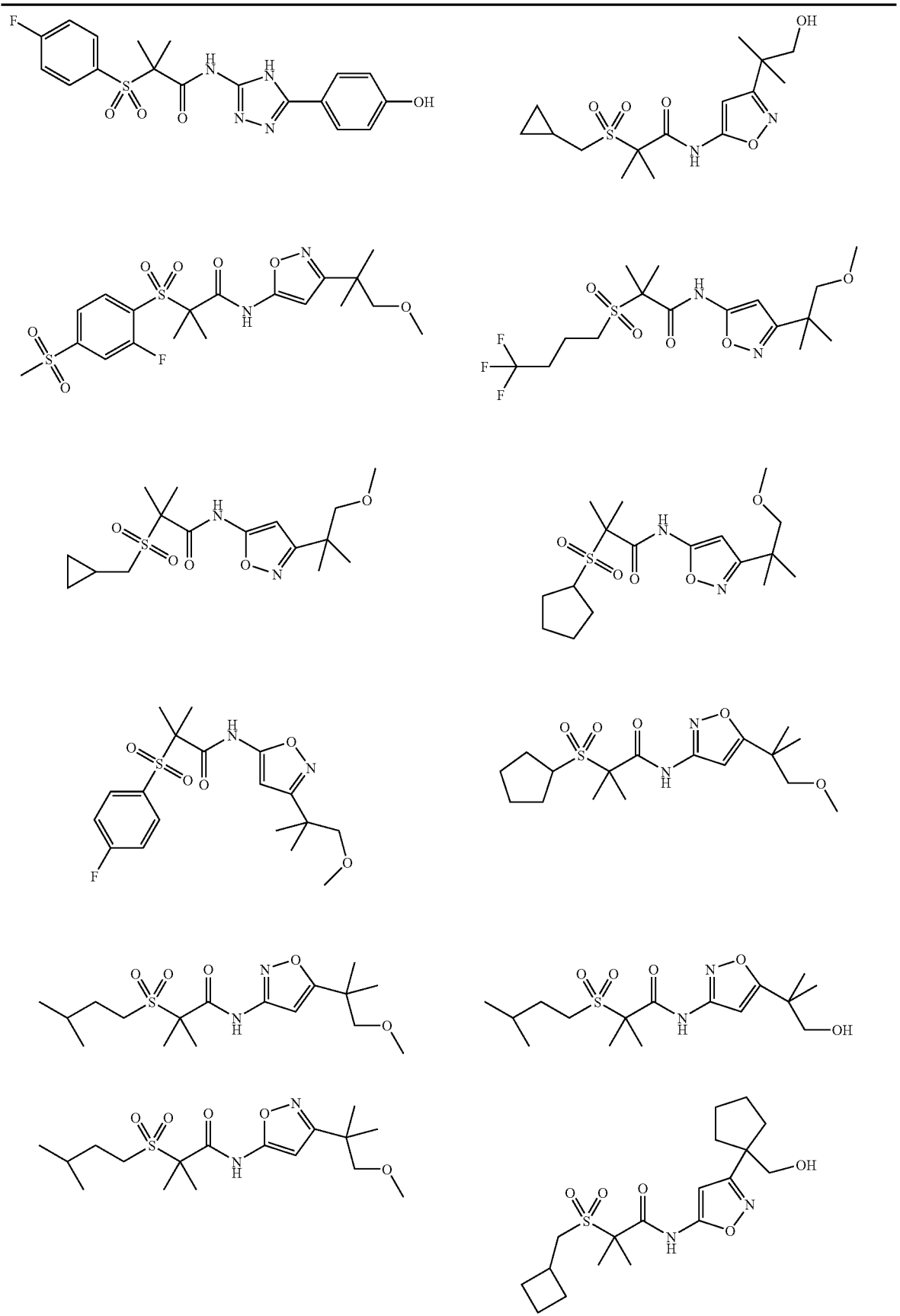

TABLE III-continued
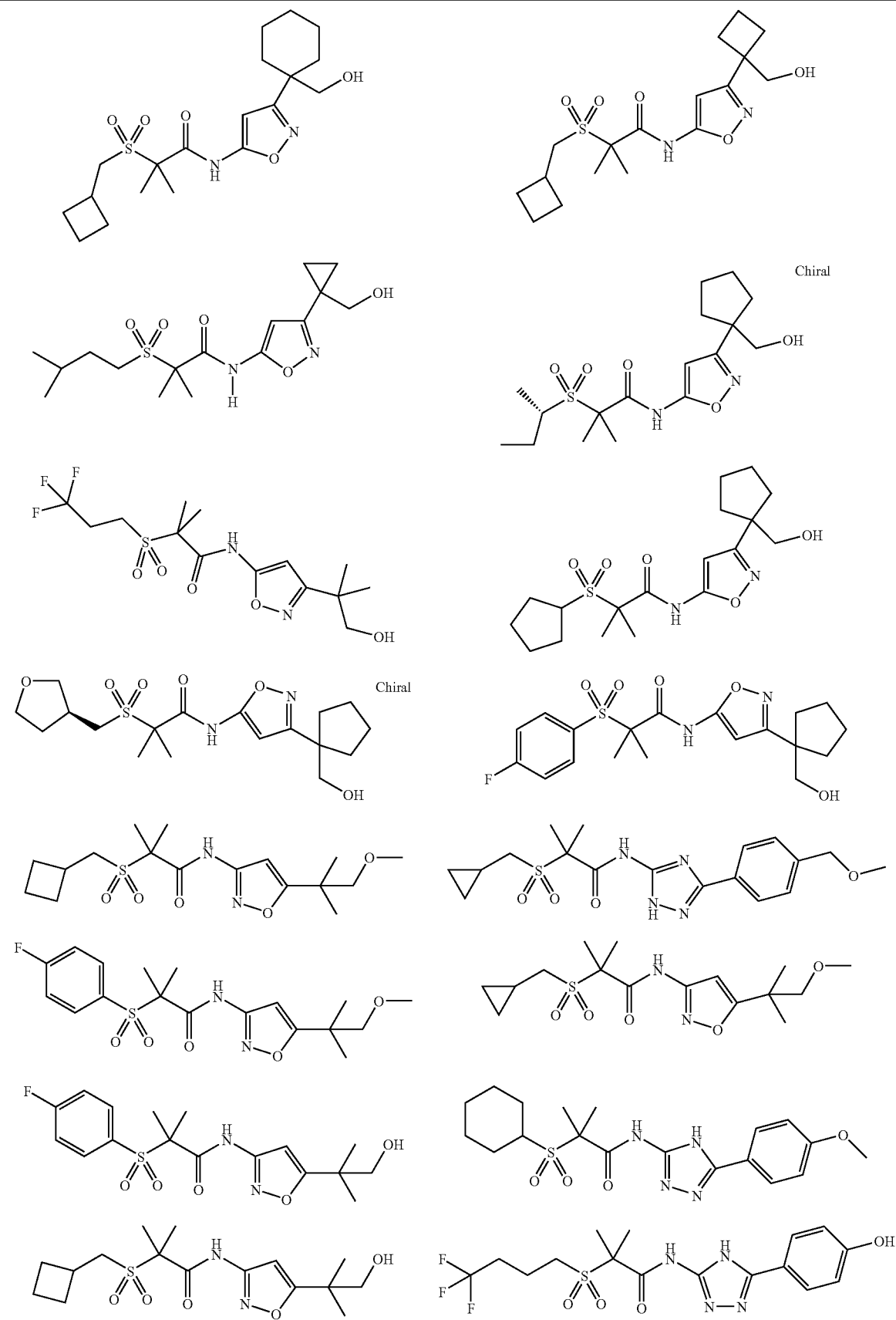

TABLE III-continued
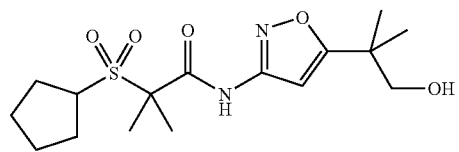 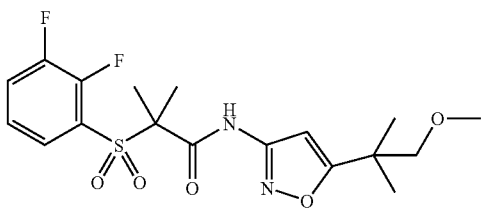
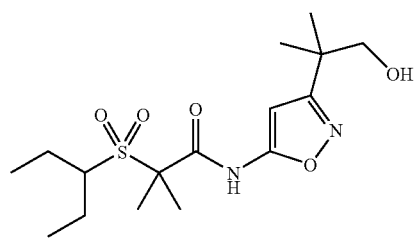 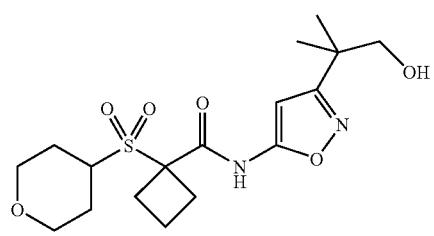
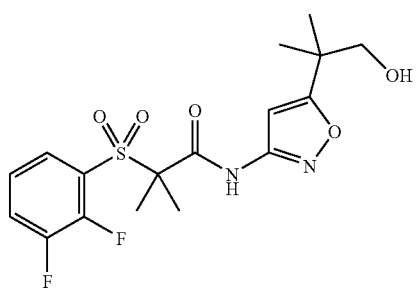 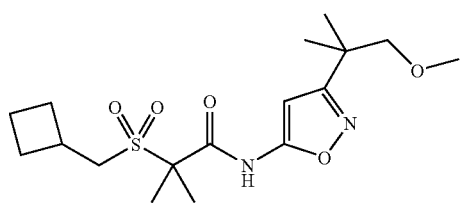
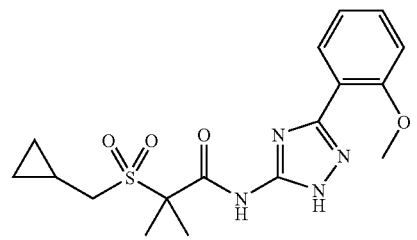 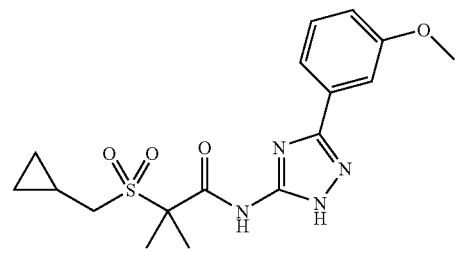
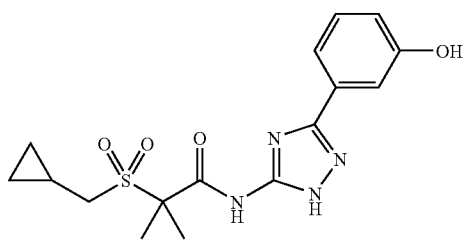 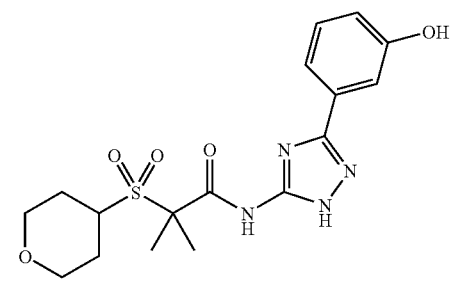
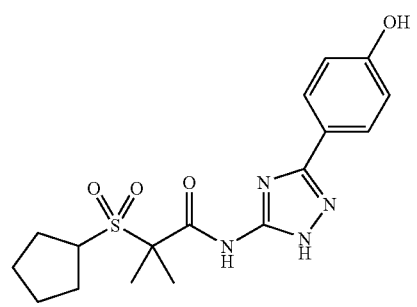 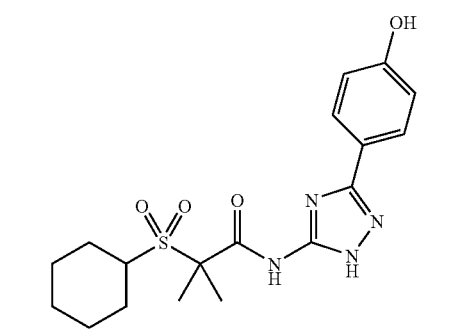

TABLE III-continued
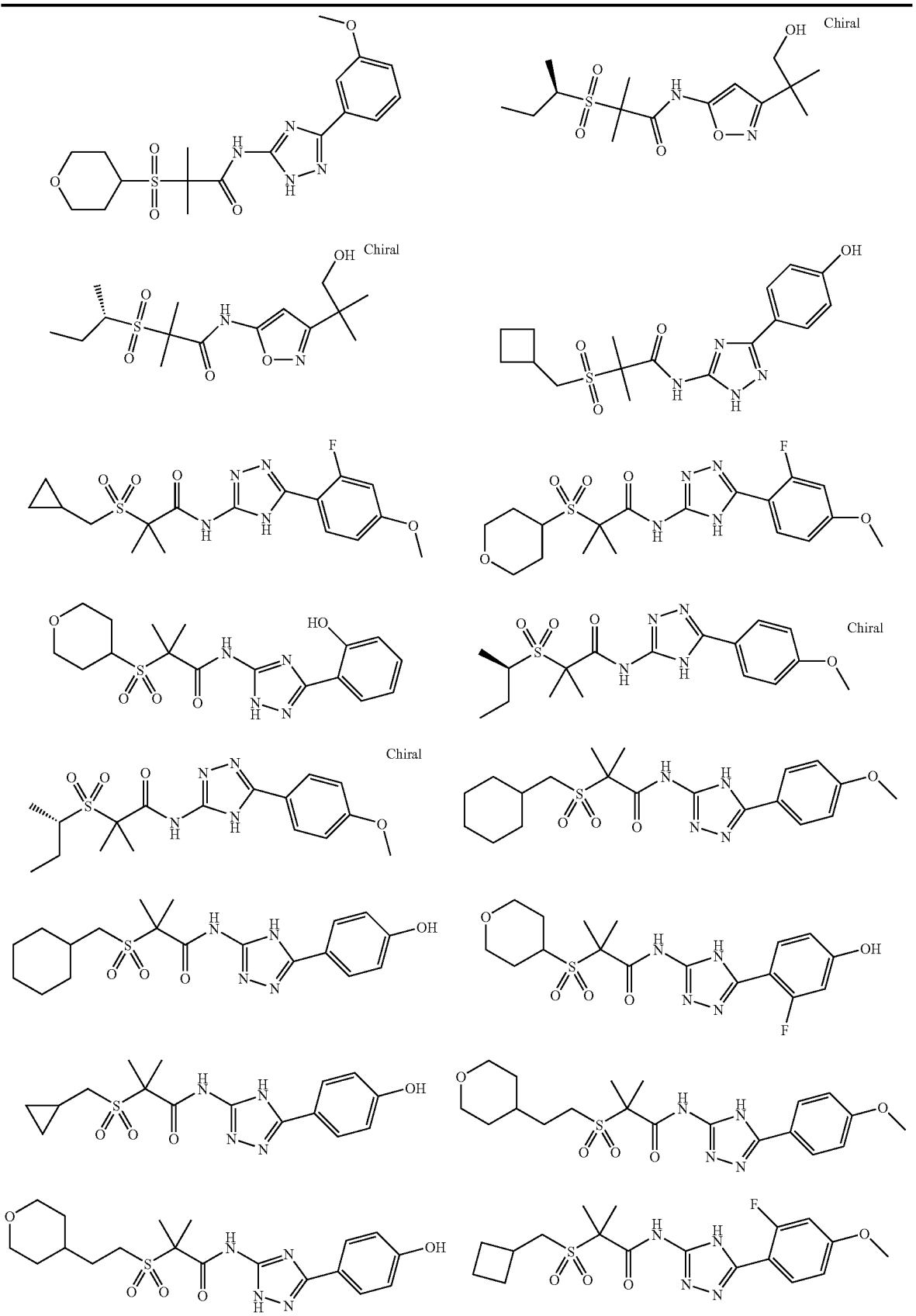

TABLE III-continued
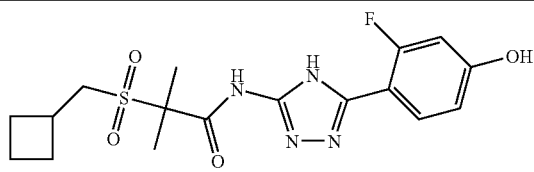
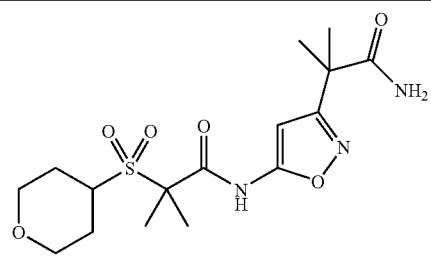
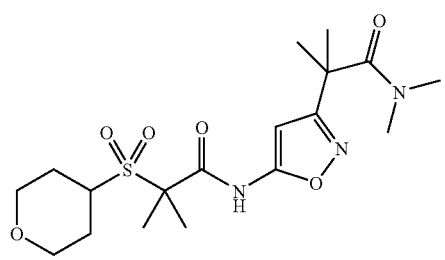
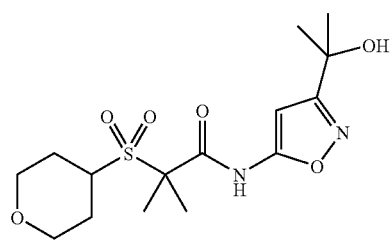
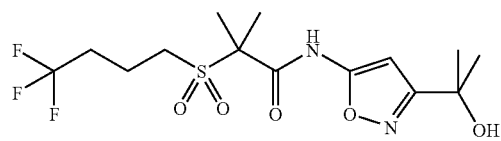
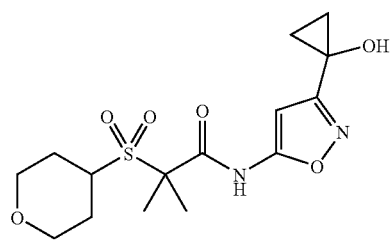
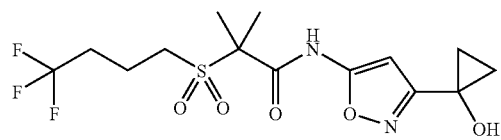
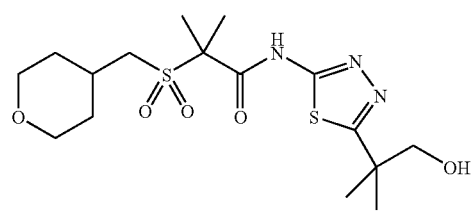
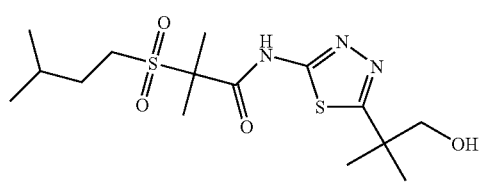
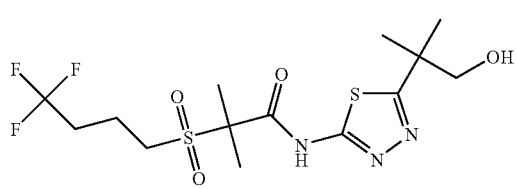
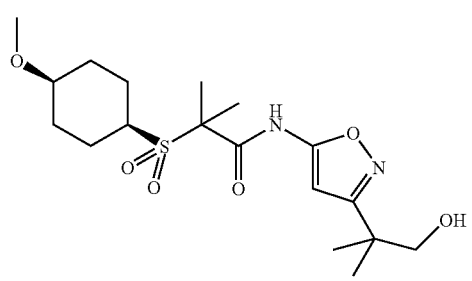

TABLE III-continued
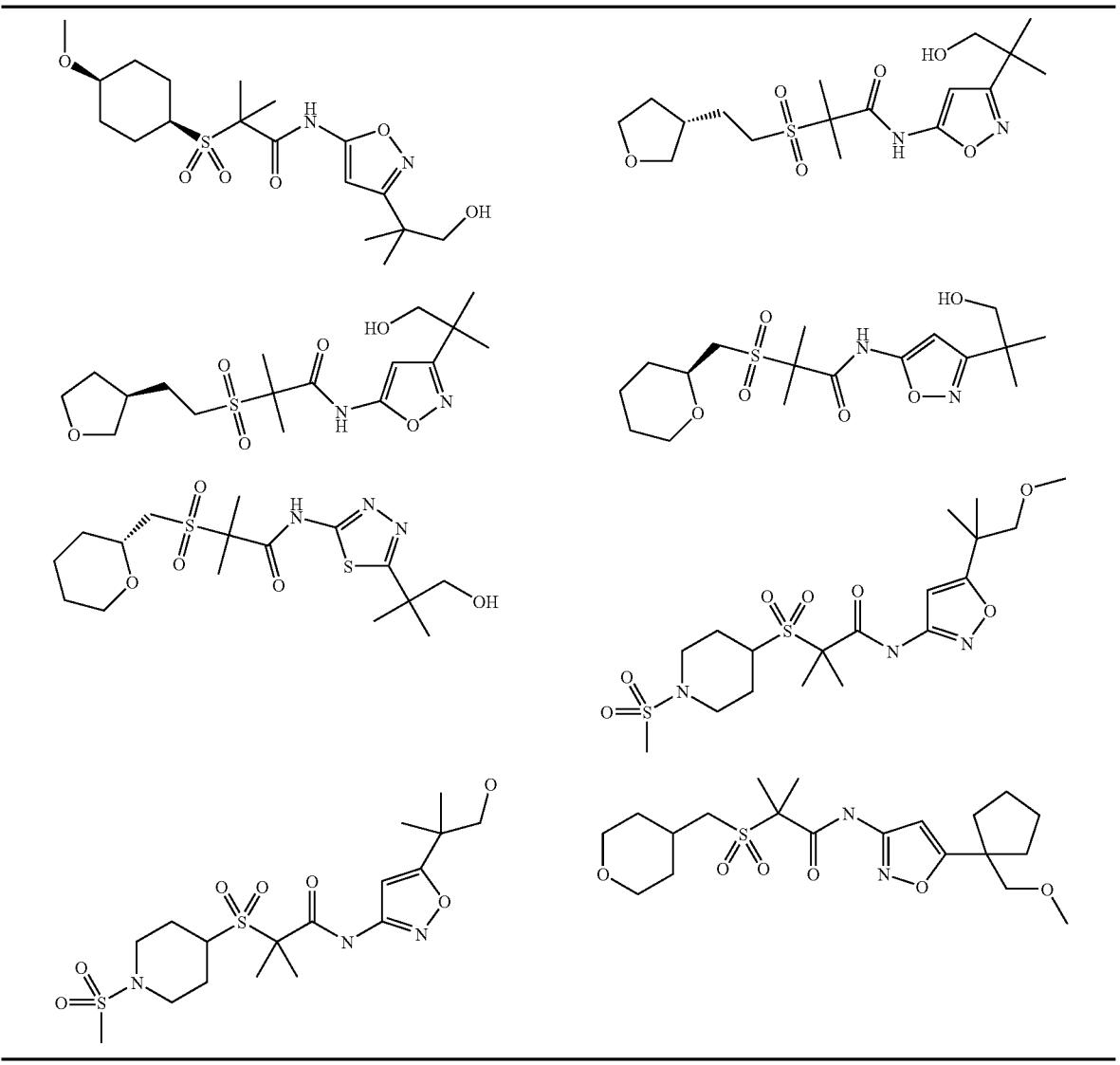
or a pharmaceutically acceptable salt thereof.
Of the above compounds, the following are preferred CB2 agonists:
TABLE IV
| Compound | CB2 EC$_{50}$ (nM) | CB1 EC$_{50}$ (nM) |
|---|---|---|
| | 39 | >50000 |
| | 11 | >50000 |

TABLE IV-continued
| Compound | CB2 EC$_{50}$ (nM) | CB1 EC$_{50}$ (nM) |
|---|---|---|
| 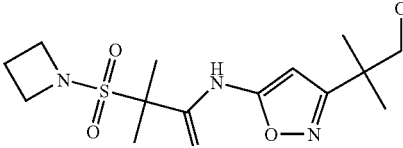 | 288 | >20000 |
| 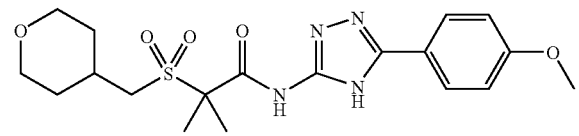 | 9.5 | >50000 |
| 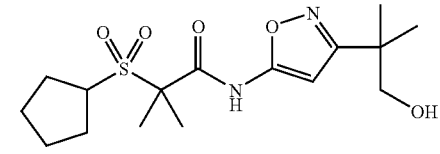 | 75 | >20000 |
| 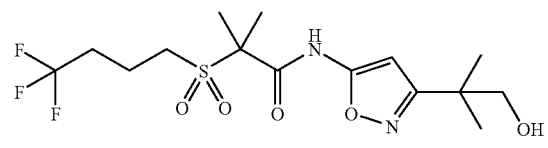 | 15 | >20000 |
| 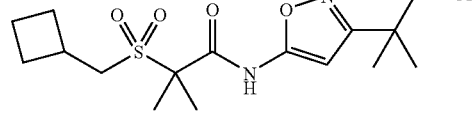 | 82 | >20000 |
| 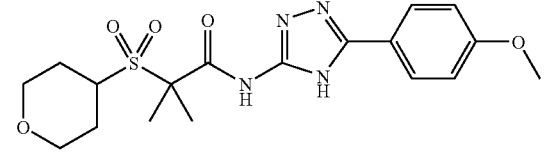 | 0.66 | >20000 |
| 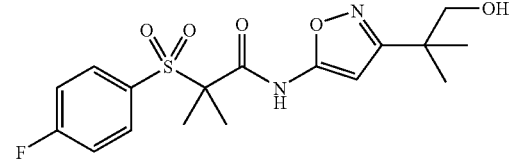 | 30 | >20000 |
| 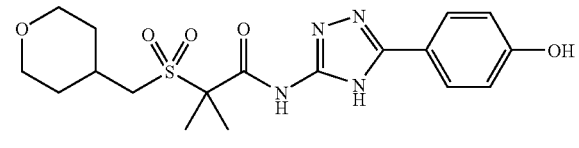 | 100 | >20000 |
| 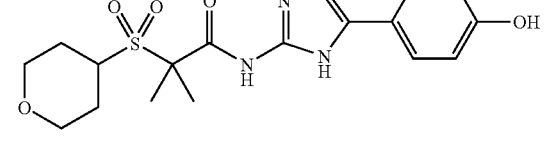 | 5.0 | >20000 |

TABLE IV-continued

| Compound | CB2 EC$_{50}$ (nM) | CB1 EC$_{50}$ (nM) |
|---|---|---|
| (tetrahydropyran-4-ylmethylsulfonyl-dimethyl-acetamide, N-[3-(2-methoxy-1,1-dimethyl-ethyl)-isoxazol-5-yl]) | 29 | >20000 |
| (cyclopentylsulfonyl-dimethyl-acetamide, N-[5-(4-methoxyphenyl)-4H-1,2,4-triazol-3-yl]) | 14 | >20000 |
| (isobutylsulfonyl-dimethyl-acetamide, N-[5-(4-methoxyphenyl)-4H-1,2,4-triazol-3-yl]) | 69 | >20000 |
| ((4-methyl-tetrahydropyran-4-ylmethyl)sulfonyl-dimethyl-acetamide, N-[5-(4-methoxyphenyl)-4H-1,2,4-triazol-3-yl]) | 186 | >20000 |
| (tetrahydropyran-4-ylmethylsulfonyl-dimethyl-acetamide, N-[5-(4-trifluoromethoxyphenyl)-4H-1,2,4-triazol-3-yl]) | 337 | >20000 |
| (tetrahydropyran-4-ylsulfonyl-dimethyl-acetamide, N-[5-(4-trifluoromethoxyphenyl)-4H-1,2,4-triazol-3-yl]) | 194 | >20000 |

TABLE IV-continued

| Compound | CB2 EC$_{50}$ (nM) | CB1 EC$_{50}$ (nM) |
|---|---|---|
| (structure) | 16 | 29444 |
| (structure) | 2.1 | >20000 |
| (structure) | 172 | >20000 |
| (structure) | 32 | >20000 |
| (structure) | 33 | >50000 |

TABLE IV-continued

| Compound | CB2 EC$_{50}$ (nM) | CB1 EC$_{50}$ (nM) |
| --- | --- | --- |
| (tetrahydropyran-4-sulfonyl-dimethyl-acetamide-isoxazole-methoxymethyl-dimethyl) | 3.1 | >20000 |
| (1-methanesulfonyl-piperidin-4-sulfonyl-dimethyl-acetamide-isoxazole-hydroxymethyl-dimethyl) | 14 | >50000 |
| (4-oxo-cyclohexylmethanesulfonyl-dimethyl-acetamide-isoxazole-hydroxymethyl-dimethyl) | 68 | >50000 |
| (tetrahydropyran-4-sulfonyl-dimethyl-acetamide-triazole-4-ethoxyphenyl) | 208 | >50000 |
| (tetrahydropyran-4-ylmethanesulfonyl-dimethyl-acetamide-isoxazole-hydroxymethyl-dimethyl) | 208 | >50000 |
| (tetrahydropyran-4-sulfonyl-dimethyl-acetamide-isoxazole-hydroxymethyl-dimethyl) | 33 | >50000 |
| (4,4,4-trifluorobutanesulfonyl-dimethyl-acetamide-isoxazole-hydroxymethyl-dimethyl) | 25 | >20000 |

TABLE IV-continued

| Compound | CB2 EC$_{50}$ (nM) | CB1 EC$_{50}$ (nM) |
| --- | --- | --- |
| (tetrahydropyran-4-yl sulfonyl dimethyl acetamide N-linked to isoxazole with cyclopropyl-CH$_2$OH substituent) | 117 | >50000 |
| (tetrahydropyran-4-yl sulfonyl dimethyl acetamide N-linked to thiadiazole with C(CH$_3$)$_2$CH$_2$OH substituent) | 48 | >50000 |
| (chiral tetrahydrofuran-3-yl-methylsulfonyl dimethyl acetamide N-linked to triazole with 4-methoxyphenyl substituent) | 90 | >50000 |
| (chiral tetrahydrofuran-3-yl-methylsulfonyl dimethyl acetamide N-linked to triazole with 4-methoxyphenyl substituent) | 240 | >50000 |
| (tetrahydropyran-4-yl-methylsulfonyl dimethyl acetamide N-linked to isoxazole with C(CH$_3$)$_2$CH$_2$OCH$_3$ substituent) | 137 | >20000 |
| (tetrahydropyran-4-yl sulfonyl dimethyl acetamide N-linked to isoxazole with C(CH$_3$)$_2$CH$_2$OCH$_3$ substituent) | 3.5 | >50000 |

TABLE IV-continued

| Compound | CB2 EC$_{50}$ (nM) | CB1 EC$_{50}$ (nM) |
|---|---|---|
| (structure) | 77 | >50000 |
| (structure) | 15 | >50000 |
| (structure) | 247 | >50000 |
| (structure) | 206 | >50000 |
| (structure) | 3.6 | >20000 |
| (structure) | 38 | >20000 |

TABLE IV-continued

| Compound | CB2 EC$_{50}$ (nM) | CB1 EC$_{50}$ (nM) |
|---|---|---|
| (structure) | 32 | >50000 |
| (structure) | 4.0 | >20000 |
| (structure) | 120 | >50000 |
| (structure) | 15 | >20000 |
| (structure) | 25 | >20000 |
| (structure) | 67 | >20000 |
| (structure) | 74 | >50000 |

TABLE IV-continued
| Compound | CB2 EC$_{50}$ (nM) | CB1 EC$_{50}$ (nM) |
|---|---|---|
| 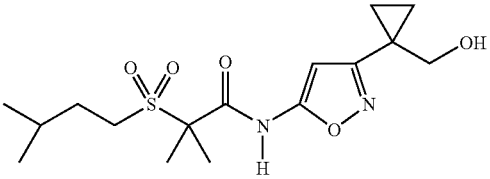 | 14 | >20000 |
| 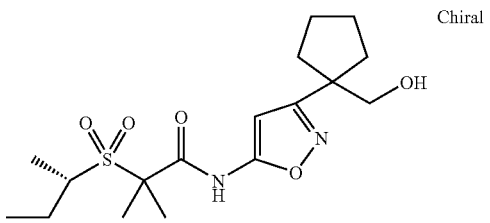 Chiral | 82 | >20000 |
| 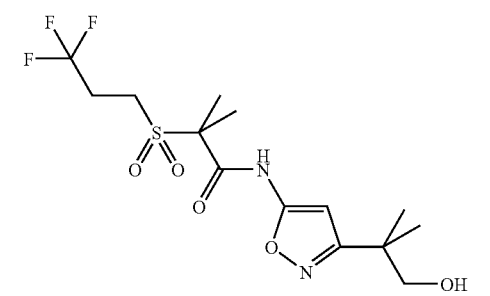 | 105 | >50000 |
| 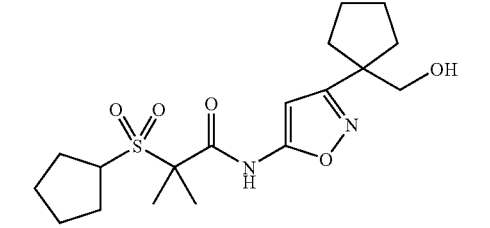 | 45 | >20000 |
| 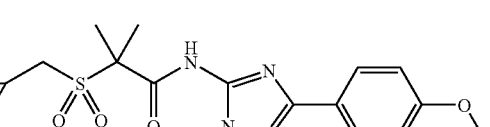 | 488 | >50000 |
| 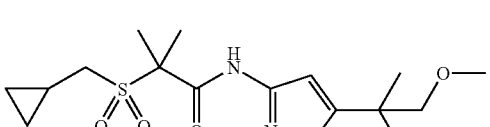 | 121 | >50000 |
| 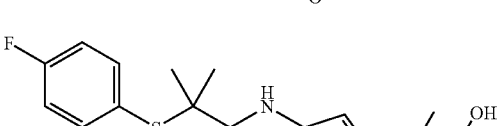 | 45 | >50000 |
|  | 96 | >50000 |

TABLE IV-continued

| Compound | CB2 EC$_{50}$ (nM) | CB1 EC$_{50}$ (nM) |
| --- | --- | --- |
| (cyclopentyl-SO$_2$-C(CH$_3$)$_2$-C(O)NH-isoxazole-C(CH$_3$)$_2$-CH$_2$OH) | 222 | 50000 |
| (tetrahydropyran-SO$_2$-cyclobutyl-C(O)NH-isoxazole-C(CH$_3$)$_2$-CH$_2$OH) | 212 | >50000 |
| (2,3-difluorophenyl-SO$_2$-C(CH$_3$)$_2$-C(O)NH-isoxazole-C(CH$_3$)$_2$-CH$_2$OH) | 69 | >50000 |
| (cyclopropylmethyl-SO$_2$-C(CH$_3$)$_2$-C(O)NH-triazole-(2-methoxyphenyl)) | 15 | >20000 |
| (cyclopropylmethyl-SO$_2$-C(CH$_3$)$_2$-C(O)NH-triazole-(3-hydroxyphenyl)) | 283 | >50000 |
| (tetrahydropyran-SO$_2$-C(CH$_3$)$_2$-C(O)NH-triazole-(3-hydroxyphenyl)) | 130 | >50000 |

TABLE IV-continued

| Compound | CB2 EC$_{50}$ (nM) | CB1 EC$_{50}$ (nM) |
|---|---|---|
| (cyclopentyl-SO$_2$-C(CH$_3$)$_2$-C(O)-NH-triazole-4-hydroxyphenyl) | 36 | >50000 |
| (sec-butyl-SO$_2$-C(CH$_3$)$_2$-C(O)-NH-isoxazole-C(CH$_3$)$_2$-CH$_2$OH), Chiral | 118 | >50000 |
| (cyclobutylmethyl-SO$_2$-C(CH$_3$)$_2$-C(O)-NH-triazole-4-hydroxyphenyl) | 22 | >50000 |
| (cyclopropylmethyl-SO$_2$-C(CH$_3$)$_2$-C(O)-NH-triazole-2-fluoro-4-methoxyphenyl) | 34 | >50000 |
| (tetrahydropyran-4-yl-SO$_2$-C(CH$_3$)$_2$-C(O)-NH-triazole-2-fluoro-4-methoxyphenyl) | 13 | >50000 |
| (tetrahydropyran-4-yl-SO$_2$-C(CH$_3$)$_2$-C(O)-NH-triazole-2-hydroxyphenyl) | 30 | >20000 |
| (sec-butyl-SO$_2$-C(CH$_3$)$_2$-C(O)-NH-triazole-4-methoxyphenyl), Chiral | 83 | >50000 |

TABLE IV-continued

| Compound | CB2 EC$_{50}$ (nM) | CB1 EC$_{50}$ (nM) |
|---|---|---|
| (Chiral structure) | 47 | >50000 |
| (structure) | 7.7 | >50000 |
| (structure) | 34 | >50000 |
| (structure) | 7.6 | >20000 |
| (structure) | 9.4 | 35000 |
| (structure) | 88 | >50000 |
| (structure) | 49 | >20000 |
| (structure) | 18 | >20000 |

TABLE IV-continued
| Compound | CB2 EC$_{50}$ (nM) | CB1 EC$_{50}$ (nM) |
|---|---|---|
| 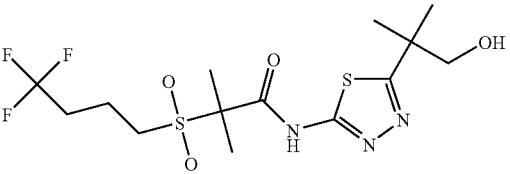 | 93 | >50000 |
| 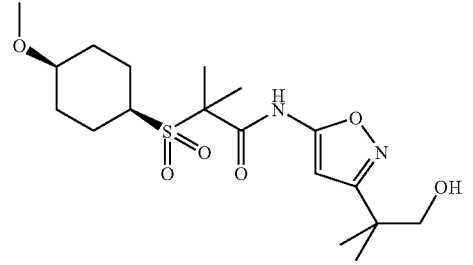 | 57 | >50000 |
| 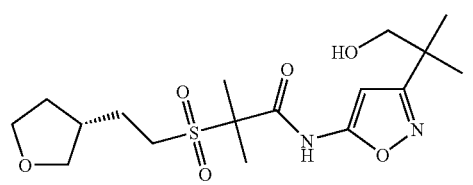 | 6.2 | >20000 |
| 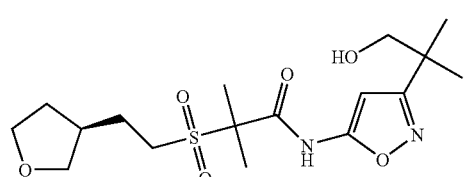 | 14 | >50000 |
| 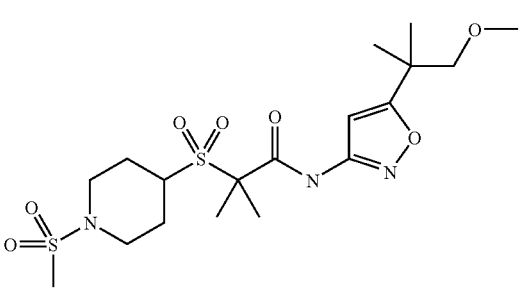 | 6.2 | >50000 |
| 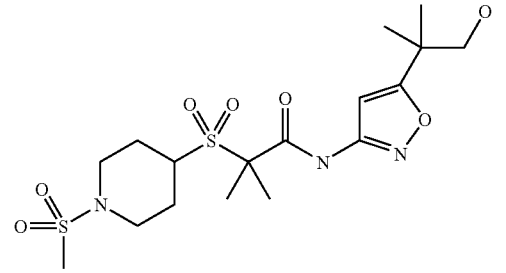 | 91 | >50000 |

TABLE IV-continued

| Compound | CB2 EC$_{50}$ (nM) | CB1 EC$_{50}$ (nM) |
|---|---|---|
| (structure) | 28 | >50000 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all methods, unless specified otherwise, $R^1$, $R^2$, $R^3$, $R^4$, $R^5$, n and Het in the formulas below shall have the meaning of $R^1$, $R^2$, $R^3$, $R^4$, $R^5$, n and Het in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art. Synthetic methods disclosed in WO2008098025, WO2008014199, WO2008039645, and WO2009061652 may also be used in preparing compounds of the invention.

Compounds of Formula (I) may be synthesized by the method illustrated in Scheme 1

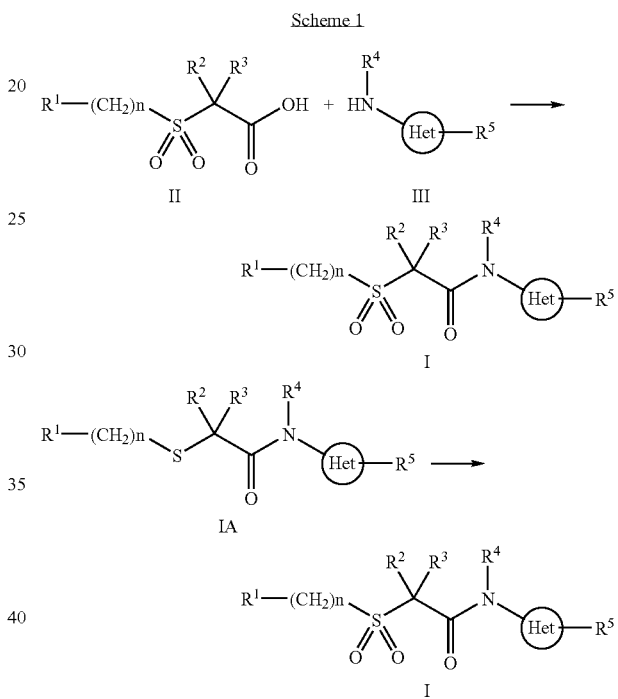

As shown in scheme 1, reacting the acid of formula II with a reagent such as thionyl chloride or oxalyl chloride, provides the acid chloride which is then reacted with an amine of formula III, in a suitable solvent, in the presence of a suitable base, to provide a compound of formula (I). Alternatively, the acid of formula II may also be coupled with an amine of formula III under standard coupling conditions, to provide a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Oxidation of the compound of formula IA, under standard reaction conditions, using standard reagents, provides a compound of formula (I).

Further modification of the initial product of formula (I) by methods known in the art and illustrated in the Examples below, may be used to prepare additional compounds of this invention.

Intermediate acid II may be made by the method outlined in Scheme 2

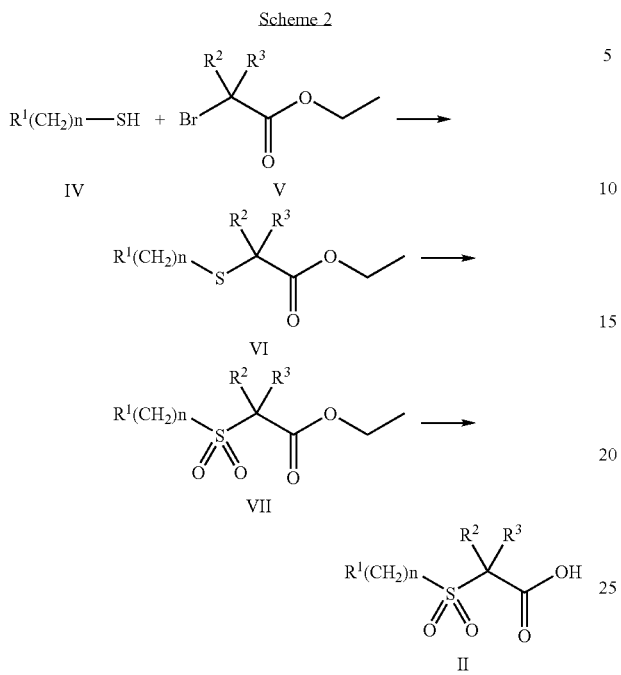

As illustrated in above, reaction of a thiol of formula IV with a bromo ethyl ester of formula V, in a suitable solvent, in the presence of a suitable base, provides a thioether of formula VI. Reacting the thioether of formula VI with a suitable oxidizing agent provides the corresponding sulfone of formula VII. Hydrolysis of the ester group of sulfone of formula VII, in a suitable solvent, in the presence of a suitable base such as lithium hydroxide, provides the corresponding acid of formula II.

Intermediate acid II may be made by the method outlined in Scheme 3

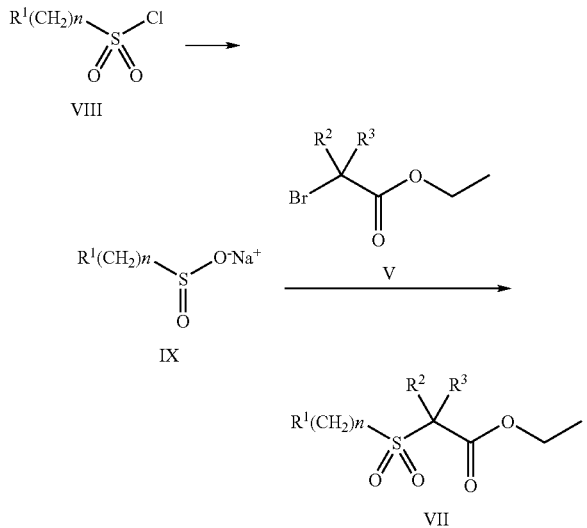

As shown in scheme 3, sulfonyl chloride of formula VIII is converted to the corresponding sulfinic acid sodium salt of formula IX, using procedures reported in the literature. Reaction of the sulfone of formula IX with a bromo ethyl ester of formula V in a suitable solvent, provides a sulfone of formula VII. The sulfone of formula VII is hydrolyzed, as in scheme 2, to provide the in intermediate acid of formula II.

Intermediate acid II may also be made by the method outlined in Scheme

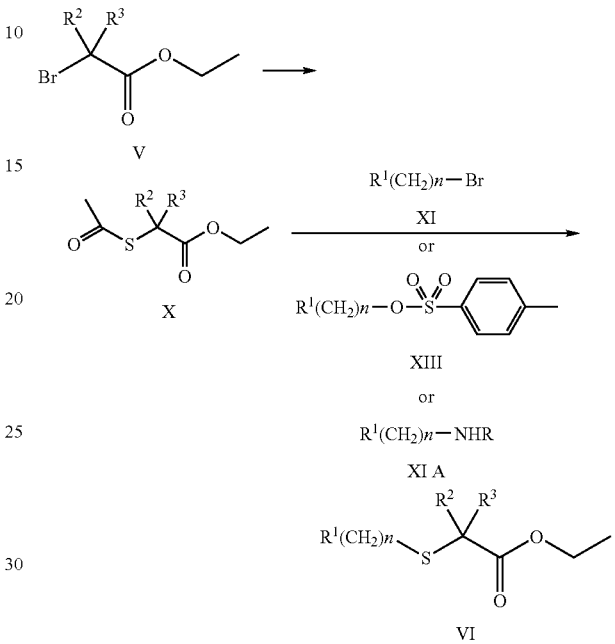

Reaction of the starting bromoester of formula V with a reagent such as potassium thioacetate, in a suitable solvent, provides a thioacetic acid ester of formula X. Reaction of the thioacetic acid ester X with a bromide of formula XI, in a suitable solvent in the presence of a suitable base, provides the corresponding sulfanyl acid ethyl ester of formula VI. Reaction of the thioacetic acid ester of formula X with a tosylate of formula XIII, in a suitable solvent, in the presence of a suitable base, provides the sulfanyl acid ethyl ester of formula VI. Alternatively, reaction of the thioacetic acid ester of formula X with an amine of formula XI A, wherein R=hydrogen, alkyl or R and $R^1$ together form a ring, under suitable conditions, provides a sulfanyl acid ethyl ester of formula VI. The sulfanyl acid ethyl ester of formula VI may be converted to intermediate acid of formula II by the sequence of steps shown in scheme 2.

Intermediate acid II may be made by the method outlined in Scheme 5

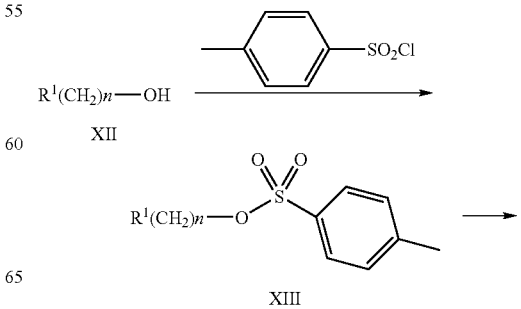

-continued

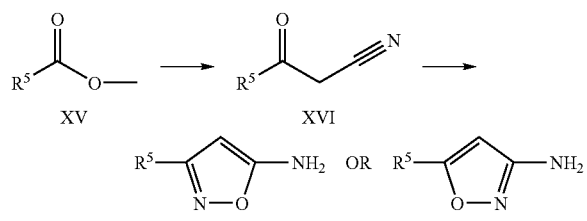

As illustrated in scheme 5, reaction of an alcohol of formula XII with p-toluenesulfonyl chloride, in a suitable solvent, in the presence of a suitable base, provides the sulfonic acid ester of formula XIII. Reaction of the compound of formula XIII with potassium thioacetate, in a suitable solvent, provides a compound of formula XIV. Reaction of the intermediate of formula XIV with the bromoester of formula V, in a suitable solvent, in the presence of a suitable base, provides the intermediate of formula VI which may be converted to the desired intermediate acid of formula II by the reaction sequence shown in scheme 2.

Intermediate amine III may be made by the method outlined in Scheme 6

Scheme 6

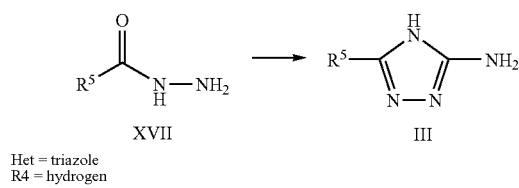

Het = isoxazole
R4 = hydrogen

As outlined in scheme 6, reaction of an ester of formula XV with acetonitrile, in the presence of a suitable base, provides the nitrile of formula XVI. Reaction of the nitrile of formula XVI with hydroxylamine, in a suitable solvent, in the presence of a suitable base, provides the amine of formula III, wherein Het=isoxazolyl and $R^4$=H.

Alternatively, adjusting the pH in step 2, provides the other isoxazole isomer.

Intermediate amine III may be made by the method outlined in Scheme 7

Scheme 7

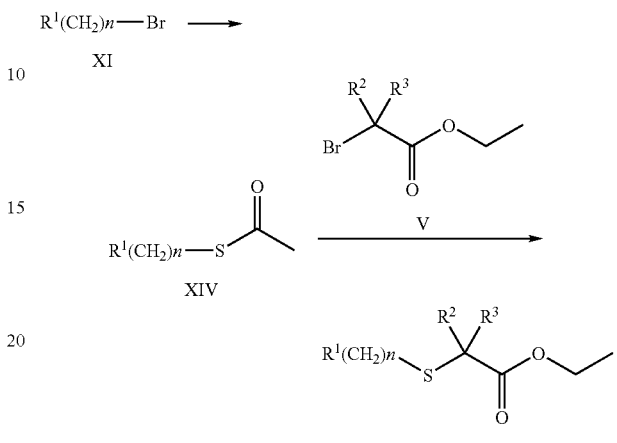

Het = triazole
R4 = hydrogen

As shown above in scheme 7, reaction of a hydrazide of formula XVII with a reagent such as methyl thiopseudourea, in a suitable solvent, in the presence of a suitable base, provides an amine of formula III, wherein Het=triazolyl and $R^4$=H.

Intermediate acid II may be prepared by the method outlined in Scheme 8

Scheme 8

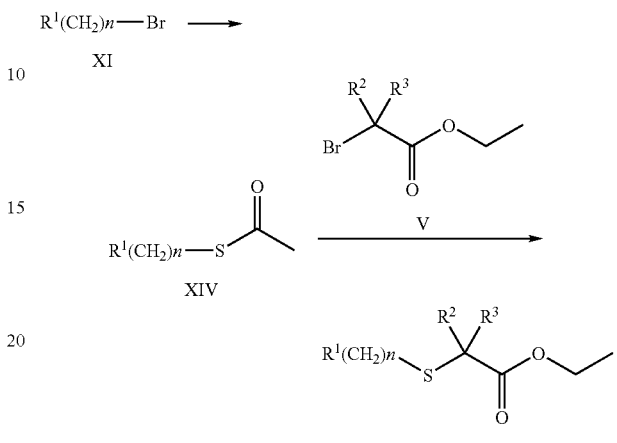

As illustrated in scheme 8, reaction of a bromo compound of formula XI with a reagent such as potassium thioacetate, in a suitable solvent, provides an acetylsulfanyl compound of formula XIV. Reaction of the compound of formula XIV with a bromo ethyl ester of formula V, in a suitable solvent, in the presence of a suitable base, provides a thioether of formula VI. The thioether of formula VI may be converted to the corresponding acid of formula II by the reaction sequence shown in scheme II.

Intermediate amine III may also be made by the reaction in Scheme 9.

Scheme 9

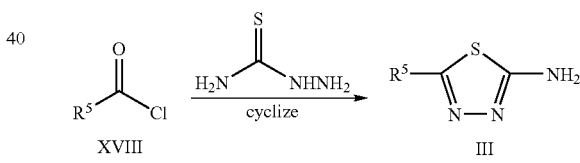

Het = thiadiazole
R4 = hydrogen

As shown in scheme 9 above, reaction of an acid chloride of formula XVIII with thiosemicarbazide, in a suitable solvent, provides an amine of formula III, wherein Het=thiadiazolyl and $R^4$=H.

Intermediate amine III may be also synthesized as shown in Scheme 10.

Scheme 10

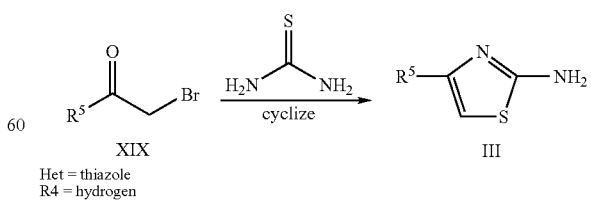

Het = thiazole
R4 = hydrogen

As shown in scheme 10, reaction of a bromo compound of formula XIX with thiourea, in a suitable solvents provides an amine of formula III, wherein Het=thiazolyl and $R^4$=H.

Compounds of Formula I may be synthesized by the method outlined in Scheme 11.

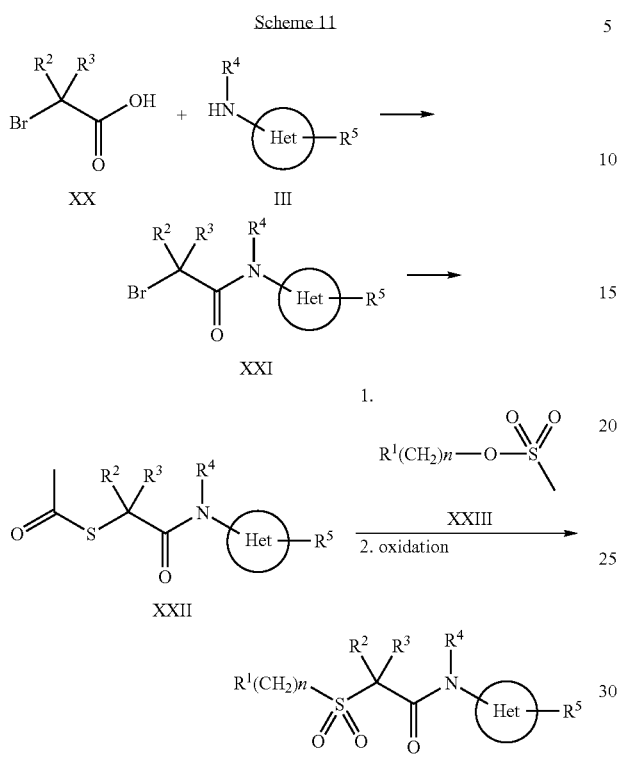

As outlined in scheme 11, coupling of an acid of formula XX with an amine of formula III, under standard coupling conditions and as described in scheme 1 and the examples, provides an amide of formula XXI. Reaction of the amide of formula XXI with potassium thioacetate, in a suitable solvent, provides a compound of formula XXII. Reaction of the compound of formula XXII with a methanesulfonic acid ester of formula XXIII followed by oxidation to sulfone, under standard conditions, provides a compound of formula I.

Intermediate acid II may also be prepared by the method in Scheme 12.

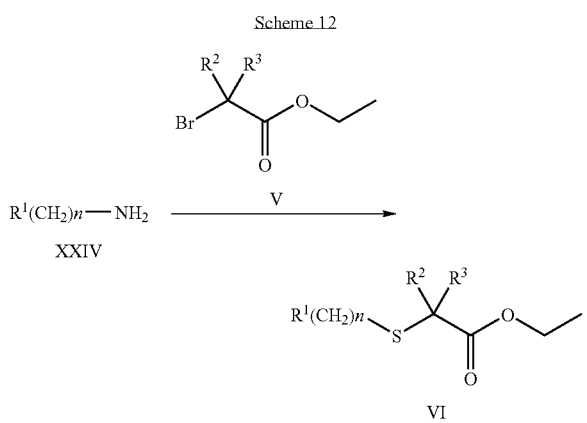

As outlined in scheme 12 and described in the example section, reaction of an amine of formula XXIV, with sulfuric acid, sodium nitrite and CuI, followed by reaction with potassium ethyl xanthate in a suitable solvent, at a suitable temperature, provides an intermediate which is reacted with the bromoester of formula V to provide the sulfanyl acid ethyl ester of formula VI. The sulfanyl acid ethyl ester of formula VI may be converted to the corresponding acid of formula II by the reaction sequence shown in scheme II.

SYNTHETIC EXAMPLES

The manner in which the compounds of the invention can be made will be further understood by way of the following Examples.

Acid Method A

Synthesis of 2-Cyclopentanesulfonyl-2-methyl-propionic acid

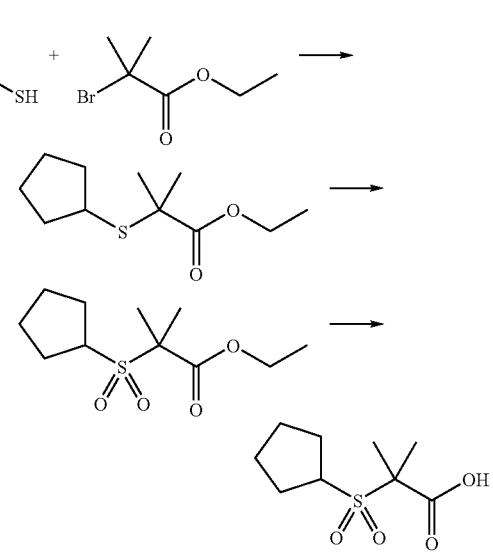

Step 1: Synthesis of 2-Cyclopentylsulfanyl-2-methyl-propionic acid ethyl ester

Prepared as described by adaptation of the following reference: Brown et al. *J. Med. Chem.* 1999, 42, 3785-3788.

To a solution of 5 g (48.7 mmol) of cyclopentyl thiol in ethanol (50 mL) are added 2.7 g (48.75 mmol) of KOH pellets, followed by 9.5 g (48.7 mmol) of ethyl α-bromoisobutyrate. The reaction is heated to reflux for 2 h and then cooled to room temperature. The solid (KBr) is separated by filtration and rinsed with ethanol (20 mL). The filtrate is concentrated under reduced pressure and the residue dissolved in DCM (50 mL). The organic layer is washed with saturated aqueous NaHCO$_3$ solution (50 mL). The aqueous washes are back-extracted with DCM (10 mL). The combined organics are washed with brine, dried over Na$_2$SO$_4$. Filtration and concentration under reduced pressure affords 8.1 g of 2-cyclopentylsulfanyl-2-methyl-propionic acid ethyl ester. Yield: 77%, ES-MS: m/z 217 [M+H]

According to this procedure the following thioethers are synthesized:

TABLE V

| Structure | ¹H-NMR | Yield [%] | m/z [M + H] |
|---|---|---|---|
| ethyl 2-(cyclopentylsulfanyl)-2-methylpropanoate | (250 MHz, CHLOROFORM-d) δ ppm 1.29 (3 H, t, J = 7.14 Hz), 1.36-1.77 (12 H, m), 1.95-2.13 (2 H, m), 3.08-3.26 (1 H, m), 4.18 (2 H, q, J = 7.14 Hz) | 77 | 217 |
| ethyl 2-((4-fluorophenyl)sulfanyl)-2-methylpropanoate | (400 MHz, CHLOROFORM-d) δ ppm 1.22 (3 H, t, J = 7.09 Hz), 1.47 (6 H, s), 4.11 (2 H, q, J = 7.25 Hz), 7.01 (2 H, t, J = 8.68 Hz), 7.39-7.50 (2 H, m) | 66 | 243 |
| ethyl 2-((4-chlorophenyl)sulfanyl)-2-methylpropanoate | (400 MHz, CHLOROFORM-d) δ ppm 1.23 (3 H, t, J = 7.21 Hz), 1.48 (6 H, s), 4.12 (2 H, q, J = 7.09 Hz), 7.28-7.33 (2 H, m), 7.37-7.43 (2 H, m) | 79 | 259 |
| ethyl 2-methyl-2-(p-tolylsulfanyl)propanoate | (250 MHz, CHLOROFORM-d) δ ppm 1.22 (3 H, t, J = 7.14 Hz), 1.47 (6 H, s), 2.34 (3 H, s), 4.11 (2 H, q, J = 7.14 Hz), 7.12 (2 H, d, J = 7.78 Hz), 7.35 (2 H, d, J = 8.23 Hz) | 85 | 239 |
| ethyl 2-(cyclohexylsulfanyl)-2-methylpropanoate | (250 MHz, CHLOROFORM-d) δ ppm 1.16-1.42 (9 H, m), 1.49 (6 H, s), 1.58-1.78 (2 H, m), 1.81-1.91 (2 H, m), 2.67-2.91 (1 H, m), 4.15 (2 H, q, J = 7.14 Hz) | 84 | 231 |
| ethyl 2-((2,4-difluorophenyl)sulfanyl)-2-methylpropanoate | (400 MHz, CHLOROFORM-d) δ ppm 1.24 (3 H, t, J = 18 Hz), 1.48 (6 H, s), 4.12 (2 H, q, J = 18 Hz), 6.84-6.89 (2 H, m), 7.43-7.49 (1 H, m) | 90 | N/A |

Step 2: Synthesis of 2-Cyclopentanesulfonyl-2-methyl-propionic acid ethyl ester Prepared as described by adaptation of the following reference:
Aranapakam, V. et al. *J. Med. Chem.*, 2004, 47, 6255-6269.

To a solution of 6 g (27.7 mmol) of 2-cyclopentylsulfanyl-2-methyl-propionic acid ethyl ester in 1,4-dioxane/water (4/1, 100 mL) are added in several portions 51.2 g (83 mmol) of potassium monopersulfate triple salt (OXONE®). The white suspension is stirred at room temperature for 3 h. The white solid is separated by filtration and washed with 1,4-dioxane (10 mL). The filtrate is concentrated under reduced pressure to remove the organic solvent. The resulting aqueous solution is extracted with DCM (3×40 mL). The combined organic extracts are washed with saturated aqueous $NaHCO_3$ solution, brine, dried over $Na_2SO_4$ and filtered. The filtrate is concentrated under reduced pressure to afford 5.4 g of 2-cyclopentanesulfonyl-2-methyl-propionic acid ethyl ester. Yield: 78%, ES-MS: m/z 249 [M+H]

According to this procedure the following sulfones are synthesized:

TABLE VI

| Structure | ¹H-NMR | Yield [%] | m/z [M + H] |
|---|---|---|---|
| ethyl 2-(cyclopentylsulfonyl)-2-methylpropanoate | (400 MHz, CHLOROFORM-d) δ ppm 1.32 (3 H, t, J = 7.21 Hz), 1.55-1.70 (8 H, m), 1.71-1.86 (2 H, m), 1.96-2.20 (4 H, m), 3.83-3.96 (1 H, m), 4.25 (2 H, q, J = 7.09 Hz) | 78 | 249 |

TABLE VI-continued

| Structure | ¹H-NMR | Yield [%] | m/z [M + H] |
|---|---|---|---|
| 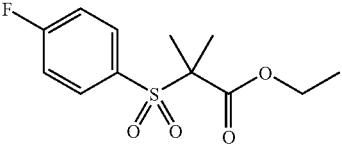 | (400 MHz, CHLOROFORM-d) δ ppm 1.15 (3 H, t, J = 7.09 Hz), 1.55 (6 H, s), 4.08 (2 H, q, J = 7.17 Hz), 7.13-7.22 (2 H, m), 7.78-7.86 (2 H, m) | 98 | 275 |
| 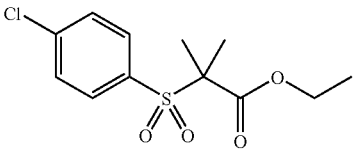 | (250 MHz, CHLOROFORM-d) δ ppm 1.22 (3 H, q, J = 7.17 Hz), 1.60 (6 H, s), 4.13 (2 H, q, J = 7.14 Hz), 7.51 (2 H, d, J = 8.51 Hz), 7.71-7.82 (2 H, m) | 86 | 291 |
| 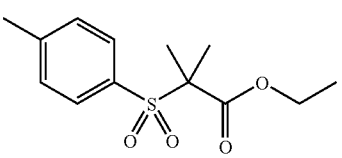 | (250 MHz, CHLOROFORM-d) δ ppm 1.22 (3 H, t, J = 7.14 Hz), 1.57 (6 H, s), 2.41 (3 H, s), 4.10 (2 H, q, J = 7.14 Hz), 7.31 (2 H, d, J = 7.96 Hz), 7.69 (2 H, d, J = 8.32 Hz) | 69 | 271 |
| 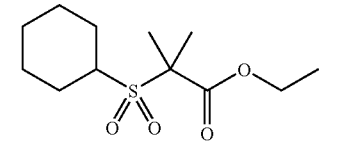 | (400 MHz, CHLOROFORM-d) δ ppm 1.08-1.38 (6 H, m), 1.48-1.72 (9 H, m), 1.83-1.95 (2 H, m), 2.11 (2 H, d, J = 13.94 Hz), 3.45-3.58 (1 H, m), 4.24 (2 H, q, J = 7.17 Hz) | 50 | 263 |
| 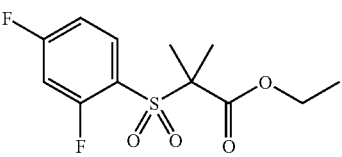 | (400 MHz, CHLOROFORM-d) δ ppm 1.24 (3 H, t, J = 18 Hz), 1.65 (6 H, d, J = 1 Hz), 4.18 (2 H, q, J = 18 Hz), 6.94-7.00 (1 H, m), 7.03-7.08 (1 H, m), 7.85-7.90 (1 H, m) | 99 | N/A |

Step 3: Synthesis of 2-Cyclopentanesulfonyl-2-methyl-propionic acid

Prepared as described by adaptation of the following reference:
Troeger, Uhde., *J. Prakt. Chem.* 1899, 59, 320-349.

To a solution of 5.4 g (21.7 mmol) of 2-cyclopentanesulfonyl-2-methyl-propionic acid ethyl ester in THF/water (4/1, 60 mL) are added 2.3 g (56.6 mmol) of lithium hydroxide monohydrate. The reaction is stirred at room temperature for 18 h. The reaction is further diluted with water (20 mL) and then washed with DCM (2×15 mL). The basic aqueous layer is cooled in an ice bath and then acidified with 2M aqueous HCl solution to pH 2. The acidic aqueous layer is extracted with 2-propanol/chloroform (1/4, 100 mL). The combined organic extracts are washed with brine, dried over Na₂SO₄ and filtered. Concentration of the filtrate under reduced pressure affords 4.34 g of 2-cyclopentanesulfonyl-2-methyl-propionic acid. Yield: 92%, ES-MS: m/z 221 [M+H]

According to this procedure the following acids are synthesized:

TABLE VII

| Structure | ¹H-NMR | Yield [%] | m/z [M + H] |
|---|---|---|---|
| 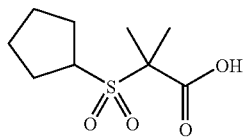 | (400 MHz, CHLOROFORM-d) δ ppm 1.54-1.72 (8 H, m), 1.72-1.88 (2 H, m), 1.98-2.22 (4 H, m), 3.87-4.00 (1 H, m), 9.26 (1 H, br. s.) | 92 | 221 |
| 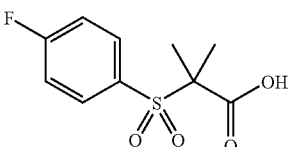 | (500 MHz, MeOD) δ ppm 1.57 (6 H, s), 7.35 (2 H, t, J = 8.85 Hz), 7.94 (2 H, dd, J = 9.00, 5.04 Hz) | 70 | 247, 264 [M + H₂O] |

TABLE VII-continued

| Structure | ¹H-NMR | Yield [%] | m/z [M + H] |
|---|---|---|---|
| (4-chlorophenylsulfonyl-dimethyl-acetic acid) | (250 MHz, CHLOROFORM-d) δ ppm 1.64 (6 H, s), 7.56 (2 H, d, J = 8.87 Hz), 7.84 (2 H, d, J = 8.87 Hz) | 60 | 263 |
| (4-methylphenylsulfonyl-dimethyl-acetic acid) | (250 MHz, CHLOROFORM-d) δ ppm 1.62 (6 H, s), 2.47 (3 H, s), 7.36 (2 H, d, J = 7.96 Hz), 7.77 (2 H, d, J = 8.51 Hz) | 98 | 243 |
| (cyclohexylsulfonyl-dimethyl-acetic acid) | (250 MHz, CHLOROFORM-d) δ ppm 1.11-1.49 (3 H, m), 1.53-1.79 (9 H, m), 1.85-2.00 (2 H, m), 2.06-2.22 (2 H, m), 3.37-3.56 (1 H, m) | 64 | 257 [M + Na] |
| (2,4-difluorophenylsulfonyl-dimethyl-acetic acid) | (400 MHz, DMSO-d6) δ ppm 1.50 (6 H, s), 7.36-7.41 (1 H, m), 7.58-7.64 (1 H, m), 7.84-7.90 (1 H, m), 13.62 (1 H, s) | 98 | 263 [M − H] |

Acid Method B

Synthesis of 2-Methyl-2-(tetrahydro-pyran-4-yl-methanesulfonyl)-propionic acid

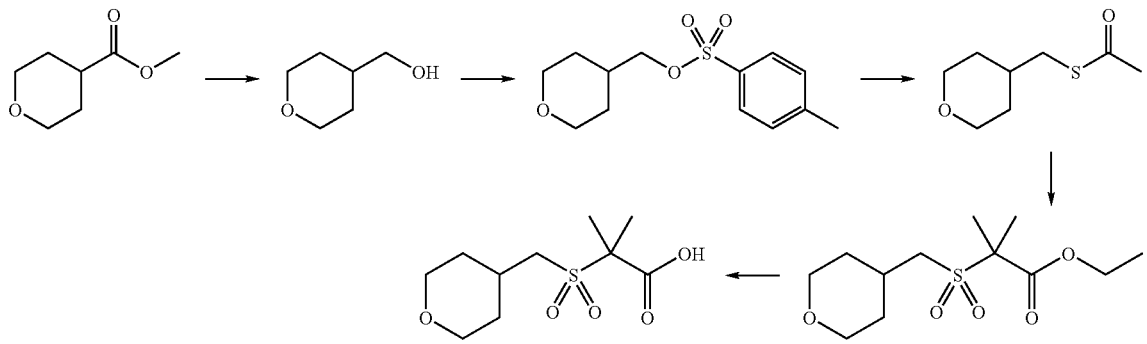

Step 1: Synthesis of (Tetrahydro-pyran-4-yl)-methanol

To a solution of 250 mL of LiAlH₄ (2.3M solution in THF, 0.575 mol) in THF (200 mL) is added dropwise a solution of 130 mL (0.974 mol) of tetrahydro-pyran-4-carboxylic acid methyl ester in THF (900 mL) under nitrogen atmosphere (CAUTION: highly exothermic reaction!). The temperature is kept at 40-45° C. with an ice-bath. Upon complete addition, the reaction is stirred at room temperature for 1.5 h. The reaction is cooled in an ice-bath and quenched with addition of water (22 mL), 15% aqueous NaOH solution (21 mL) and water (66 mL). The resulting precipitate is removed by filtration through Celite® and is rinsed with THF (300 mL). The filtrate is concentrated under reduced pressure to afford 102.5 g of (tetrahydro-pyran-4-yl)-methanol as a colorless oil. Yield: 91%; ¹H NMR (400 MHz, CHLOROFORM-d) δ ppm 1.20-1.39 (2H, m), 1.56-1.83 (3H, m), 2.03 (1H, br. s.), 3.29-3.52 (4H, m), 3.89-4.05 (2H, m)

Step 2: Synthesis of toluene-4-sulfonic acid tetrahydro-pyran-4-ylmethyl ester

Prepared as described by adaptation of the following literature reference:
Radziszewski, J. G. et al. *J. Am. Chem. Soc.* 1993, 115, 8401.

To a solution of 97 g (810 mmol) of (tetrahydro-pyran-4-yl)-methanol in 2-methyltetrahydrofuran (190 mL) are added 165 mL of 50% aqueous NaOH solution. To this stirred suspension is added dropwise with cooling a solution of p-toluene-sulfonylchloride (283 g, 1.46 mol) in 2-methyltetrahydrofuran (280 mL). The reaction is stirred at 30-35° C. for 18 h. The suspension is poured into a mixture of ice-water (280 mL) and aqueous HCl solution (37%, 203 mL). After addition of methylcyclohexane (1.4 L) and further ice-water (0.2 L), the reaction mixture is stirred for 2 h in an ice-bath. The resulting crystalline precipitate is isolated by filtration and washed with methylcyclohexane (0.5 L) and water (0.5 L). Drying under reduced pressure at 40° C. gave 216 g of toluene-4-sulfonic acid tetrahydro-pyran-4-ylmethyl ester as white crystalline solid. Yield: 99%, ES-MS: m/z 271 [M+H]; $^1$H NMR (400 MHz, CHLOROFORM-d) δ ppm 1.19-1.35 (2H, m), 1.54-1.63 (2H, m), 1.85-2.02 (1H, m), 2.45 (3H, s), 3.28-3.39 (2H, m), 3.86 (2H, d, J=6.60 Hz), 3.93 (2H, dd, J=11.37, 4.52 Hz), 7.35 (2H, d, J=9.29 Hz), 7.78 (2H, d, J=8.31 Hz)

Step 3: Synthesis of Thioacetic acid S-(tetrahydro-pyran-4-ylmethyl)ester

Prepared as described by adaptation of the following literature reference:
Watson, R. J. et al. *Tetrahedron Lett.* 2002, 43, 683-685.

To a solution of 224 g (0.83 mol) of toluene-4-sulfonic acid tetrahydro-pyran-4-ylmethyl ester in methyl isobutylketone (1.6 L) are added 189 g (1.66 mol) of potassium thioacetate. The beige suspension is stirred at 70° C. for 4.5 h. The reaction mixture is cooled to room temperature and water (1.8 L) is added. The organic layer is washed with 10% aqueous $K_2CO_3$ solution (1.8 L) and water (1 L). The organic layer is filtered through Celite® (20 g), activated charcoal (20 g) and $Na_2SO_4$ (20 g) and the filtrate is concentrated under reduced pressure. The residual oil is azeotroped with methylcyclohexane (200 mL) and n-heptanes (250 mL) to afford 138 g of thioacetic acid S-(tetrahydro-pyran-4-ylmethyl) ester as a yellow-orange oil (CAUTION: Stench!). Yield: 96%; ES-MS: m/z 175 [M+H]; $^1$H NMR (400 MHz, CHLOROFORM-d) δ ppm 1.23-1.40 (2H, m), 1.59-1.78 (3H, m), 2.33 (3H, d, J=4.16 Hz), 2.82 (2H, dd, J=6.24, 3.79 Hz), 3.27-3.39 (2H, m), 3.88-4.02 (2H, m)

Step 4: Synthesis of 2-Methyl-2-(tetrahydro-pyran-4-ylmethanesulfonyl)-propionic acid ethyl ester A solution of 90 g (516 mmol) of thioacetic acid S-(tetrahydro-pyran-4-ylmethyl) ester in toluene (500 mL) under nitrogen atmosphere is cooled in an ice-bath. A solution of sodium ethoxide in ethanol (21%, 231 mL) is added and the reaction stirred for 50 min. Then 76 mL (516 mmol) of ethyl α-bromoisobutyrate are added and the reaction stirred for 1 h. To the reaction mixture are added glacial acetic acid (8.9 mL) and water (500 mL). The organic layer is separated and washed with water (500 mL). A 3-neck round bottom flask is charged with water (500 mL), Oxone® (477 g, 775 mmol) and tetrabutylammonium-hydrogensulfate (5 g, 15 mmol) and the organic layer is added. The biphasic reaction mixture is stirred for 2 d at room temperature. The solids are removed by filtration and the layers of the filtrate are separated. The organic layer is washed with water (2×500 mL). The solvent is removed under reduced pressure and further azeotroped with toluene to give 125 g of 2-methyl-2-(tetrahydro-pyran-4-ylmethanesulfonyl)-propionic acid ethyl ester. Yield: 87%; ES-MS: m/z 279 [M+H]; $^1$H NMR (250 MHz, CHLOROFORM-d) δ ppm 1.32 (3H, t, J=7.16 Hz), 1.39-1.59 (2H, m), 1.64 (6H, s), 1.81-1.97 (2H, m), 2.29-2.53 (1H, m), 3.15 (2H, d, J=6.55 Hz), 3.45 (2H, dd, J=1.83, 0.30 Hz), 3.88-4.03 (2H, m), 4.26 (2H, d, J=7.16 Hz)

Step 5: Synthesis of 2-Methyl-2-(tetrahydro-pyran-4-ylmethanesulfonyl)-propionic acid Prepared as described by adaptation of Method A, step 3.
To a solution of 123 g (0.44 mol) of 2-methyl-2-(tetrahydro-pyran-4-ylmethanesulfonyl)-propionic acid ethyl ester in THF (450 mL) are added 663 mL of 2M aqueous sodium hydroxide solution (1.33 mol). The reaction is stirred at room temperature for 1 h. To the reaction mixture is added TBME (1.25 L) and the layers are separated. The aqueous layer is cooled in an ice bath and then acidified with 37% aqueous HCl solution (123 mL). The resulting precipitate is isolated by filtration, washed with water (200 mL) and dried under reduced pressure at 50° C. to afford 101 g of 2-methyl-2-(tetrahydro-pyran-4-ylmethanesulfonyl)-propionic acid as white crystalline solids. Yield: 91%; ES-MS: m/z 251 [M+H]; $^1$H NMR (400 MHz, DMSO-d6) δ ppm 1.31-1.45 (2H, m), 1.49 (6H, s), 1.70-1.79 (2H, m), 2.13-2.28 (1H, m), 3.24 (2H, d, J=6.60 Hz), 3.28-3.38 (2H, m), 3.76-3.85 (2H, m), 13.65 (1H, br. s.)

Acid Method C

Synthesis of 2-Methyl-2-(3-methyl-butane-1-sulfonyl)-propionic acid

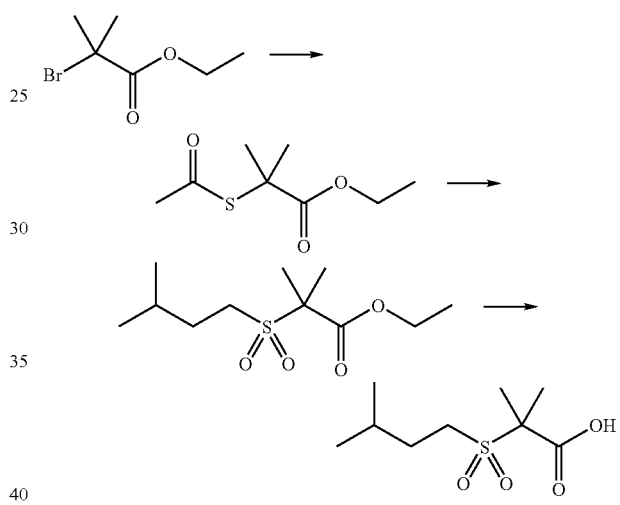

Step 1: Synthesis of 2-Acetylsulfanyl-2-methyl-propionic acid ethyl ester

To a solution of ethyl α-bromoisobutyrate (62 g, 0.32 mol) in DMF (500 mL) at room temperature is added potassium thioacetate (72 g, 0.63 mol). The reaction is stirred for 16 h and then concentrated under reduced pressure. The residue is diluted with a 2M aqueous hydrochloric acid solution (500 mL) and extracted with ethyl acetate (3×500 mL). The organic fractions are combined, washed with brine (300 mL), dried over $MgSO_4$, filtered and concentrated under reduced pressure. Purification by chromatography on silica eluting with heptanes/dichloromethane provides 44 g of 2-acetylsulfanyl-2-methyl-propionic acid ethyl ester. Yield: 73%; m/z 191 [M+H]; $^1$H NMR (250 MHz, CHLOROFORM-d) δ ppm 1.18-1.30 (3H, m), 1.57 (6H, s), 2.27 (3H, s), 4.19 (2H, q, J=7.16 Hz)

Step 2: Synthesis of 2-Methyl-2-(3-methyl-butane-1-sulfonyl)-propionic acid ethyl ester To a solution of 5 g (26.5 mmol) of 2-acetylsulfanyl-2-methyl-propionic acid ethyl ester in ethanol (30 mL) are added 5.7 g (105 mmol) of sodium methoxide, followed by 4 g (26.5 mmol) of 1-bromo-3-methylbutane. The reaction is heated to 120° C. for 0.5 h in the microwave (power: 85 W, ramp time: 20 min, hold time: 30 min). The solvent is removed under reduced pressure. The residue is dissolved in DCM (50 mL) and washed with saturated aqueous NaHCO₃ solution (2×20 mL). The aqueous layer is back-extracted with DCM (2×50 mL). The combined organic extracts are dried over Na₂SO₄, filtered and the filtrate is concentrated under reduced pressure.

The residue is dissolved in a mixture of 1,4-dioxane/water (4/1, 60 mL) and 29 g (47.2 mmol) of Oxone® are added. The reaction mixture is stirred at room temperature for 18 h. The solid is removed by filtration and the filtrate concentrated under reduced pressure. The crude is dissolved in DCM (50 mL) and is washed with saturated aqueous NaHCO₃ solution (20 mL), the aqueous layer is back-extracted with DCM (3×50 mL). The combined organic layer is dried over Na₂SO₄, filtered and concentrated under reduced pressure to afford 3.78 g of 2-methyl-2-(3-methyl-butane-1-sulfonyl)-propionic acid ethyl ester as pale yellow oil. Yield 57%; ES-MS: m/z 251 [M+H];

According to this procedure the following esters are synthesized:

TABLE VIII

| Structure | ¹H-NMR | Yield [%] | m/z [M + H] |
|---|---|---|---|
| 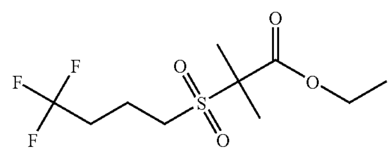 | (500 MHz, CHLOROFORM-d) δ ppm 1.32 (3 H, t, J = 7.17 Hz), 1.66 (6 H, s), 2.20 (2 H, quin, J = 7.59 Hz), 2.28-2.41 (2 H, m), 3.34 (2 H, t, J = 7.48 Hz), 4.27 (2 H, q, J = 7.17 Hz) | 81 | 291 |
| 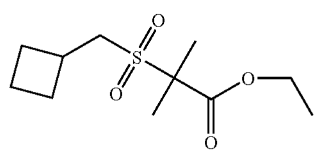 | (500 MHz, CHLOROFORM-d) δ ppm 1.32 (3 H, t, J = 7.17 Hz), 1.63 (6 H, s), 1.82-2.07 (4 H, m), 2.18-2.33 (2 H, m), 2.92-3.07 (1 H, m), 3.32 (2 H, d, J = 7.32 Hz), 4.26 (2 H, q, J = 7.07 Hz) | 43 | 249 |
| 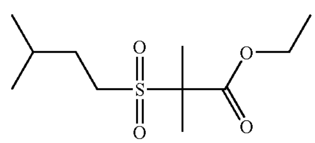 | (500 MHz, CHLOROFORM-d) δ ppm 0.96 (6 H, d, J = 6.41 Hz), 1.32 (3 H, t, J = 7.17 Hz), 1.66 (6 H, s), 1.69-1.84 (3 H, m), 3.17-3.26 (2 H, m), 4.27 (2 H, q, J = 7.07 Hz) | 57 | 251 |
| 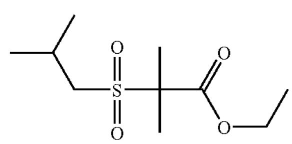 | (250 MHz, CHLOROFORM-d) δ ppm 1.14 (6 H, d, J = 5.03 Hz), 1.25-1.44 (3 H, m), 1.64 (6 H, s), 2.35-2.57 (1 H, m), 3.11 (2 H, d, J = 5.18 Hz), 4.26 (2 H, d, J = 5.94 Hz) | 33 | 237 |
| 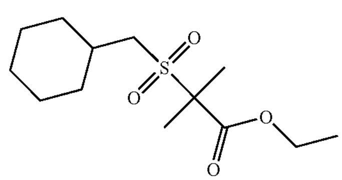 | (250 MHz, CHLOROFORM-d) δ ppm 1.03-1.37 (8 H, m), 1.61 (6 H, s), 1.65-1.74 (2 H, m), 1.90-1.96 (3 H, m), 2.03-2.26 (1 H, m), 3.08 (2 H, d, J = 6.24 Hz), 4.18-4.30 (2 H, m) | 61 | 277 |
| 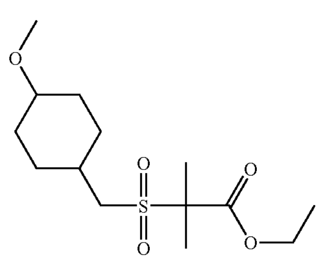 | (500 MHz, CHLOROFORM-d) δ ppm 1.30 (3 H, t, J = 7.10 Hz), 1.43-1.56 (4 H, m), 1.62 (6 H, s), 1.68-1.77 (2 H, m), 1.82-1.91 (2 H, m), 2.15-2.29 (1 H, m), 3.12 92 H, d, J = 6.41 Hz), 3.29 (3 H, s), 3.38-3.45 (1 H, m), 4.25 (2 H, q, J = 7.07 Hz) | 54 | 307, 329 [M + Na] |
| 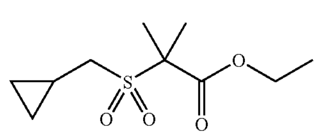 | (500 MHz, CHLOROFORM-d) δ ppm 0.42 (2 H, d, J = 4.57 Hz), 0.73 (2 H, d, J = 7.09 Hz), 1.13-1.36 (4 H, m), 1.62 (6 H, d, J = 2.21 Hz), 3.17 (2 H, d, J = 7.25 Hz), 4.19-4.29 (2 H, m) | 62 | 235, 257 [M + Na] |

TABLE VIII-continued

| Structure | ¹H-NMR | Yield [%] | m/z [M + H] |
|---|---|---|---|
| (ethyl 2-methyl-2-(pentan-3-ylsulfonyl)propanoate) | (500 MHz, CHLOROFORM-d) δ ppm 1.04 (6 H, t, J = 7.48 Hz), 1.27-1.39 (3 H, m), 1.55-1.99 (11 H, m), 4.24 (2 H, q, J = 7.17 Hz) | 42 | 251, 273 [M + Na] |

Step 3: Synthesis of 2-Methyl-2-(3-methyl-butane-1-sulfonyl)-propionic acid

Prepared as described by adaptation of Method A, step 3.

To a solution of 3.78 g (15.09 mol) of 2-methyl-2-(3-methyl-butane-1-sulfonyl)-propionic acid ethyl ester in THF/water (4/1, 50 mL) are added 1.58 g (37.74 mmol) of lithium hydroxide monohydrate. The reaction is stirred at room temperature for 18 h. The reaction mixture is concentrated under reduced pressure and the residue dissolved in DCM (20 mL) and extracted with water (50 mL). The aqueous layer is cooled in an ice bath and then acidified with 6M aqueous HCl solution to pH 1. The resulting precipitate is isolated by filtration, and dried under reduced pressure at 50° C. to afford 3.35 g of 2-methyl-2-(3-methyl-butane-1-sulfonyl)-propionic acid as white crystalline solids. Yield: 100%; ES-MS: m/z 221 [M–H].

According to this procedure the following acids are synthesized:

TABLE IX

| Structure | ¹H NMR | Yield [%] | m/z [M − H] |
|---|---|---|---|
| (4,4,4-trifluorobutylsulfonyl propanoic acid) | (500 MHz, CHLOROFORM-d) δ ppm 1.71 (6 H, s), 2.18-2.28 (2 H, m), 2.30-2.42 (2 H, m), 3.38 (2 H, t, J = 7.48 Hz), 6.96 (1 H, br. s.) | 76 | 261 |
| (cyclobutylmethylsulfonyl propanoic acid) | (500 MHz, CHLOROFORM-d) δ ppm 1.69 (6 H, s), 1.83-2.11 (4 H, m), 2.18-2.38 (2 H, m), 2.94-3.12 (1 H, m), 3.35 (2 H, d, J = 7.32 Hz) | 90 | 219 |
| (3-methylbutylsulfonyl propanoic acid) | (500 MHz, DMSO-d₆) δ ppm 0.90 (6 H, d, J = 6.56 Hz), 1.47-1.54 (6 H, m), 1.55-1.77 (3 H, m), 3.24-3.30 (3 H, m) | 89 | 221 |
| (isobutylsulfonyl propanoic acid) | (500 MHz, MeOD) δ ppm 1.13 (6 H, d, J = 6.87 Hz), 1.60 (6 H, s), 2.29-2.44 (1 H, m), 3.23 (2 H, d, J = 6.41 Hz) | 100 | 207 |
| (cyclohexylmethylsulfonyl propanoic acid) | (500 MHz, CHLOROFORM-d) δ ppm 1.05-1.25 (3 H, m), 1.27-1.43 (2 H, m), 1.63-1.79 (9 H, m), 1.89-2.04 (2 H, m), 2.15-2.26 (1 H, m), 3.12 (2 H, d, J = 6.31 Hz) | 82 | 247 |
| (4-methoxycyclohexylmethylsulfonyl propanoic acid) | (500 MHz, CHLOROFORM-d) δ ppm 1.49-1.58 (4 H, m), 1.67 (6 H, s), 1.72-1.78 (2 H, m), 1.84-1.94 (2 H, m), 2.21-2.32 (1 H, m), 3.16 (2 H, d, J = 6.41 Hz), 3.33 (3 H, s), 3.47 (1 H, d, J = 2.14 Hz), 3.78 (2 H, t, J = 6.56 Hz) | 87 | 277 |

TABLE IX-continued

| Structure | $^1$H NMR | Yield [%] | m/z [M − H] |
|---|---|---|---|
| (cyclopropylmethylsulfonyl isobutyric acid structure) | (500 MHz, CHLOROFORM-d) δ ppm 0.42-0.52 (2 H, m), 0.75-0.82 (2 H, m), 1.19-1.31 (1 H, m), 1.70 (6 H, s), 3.21 (2 H, d, J = 7.17 Hz) | 87 | 205 |
| (pentan-3-ylsulfonyl isobutyric acid structure) | (500 MHz, CHLOROFORM-d) δ ppm 1.05 (6 H, t, J = 7.48 Hz), 1.68 (6 H, s), 1.82-1.99 (5 H, m), 9.48 (1 H, br. s.) | 83 | 221 |

Synthesis of 2-Methyl-2-(4,4,4-trifluoro-butane-1-sulfonyl)-propionic acid

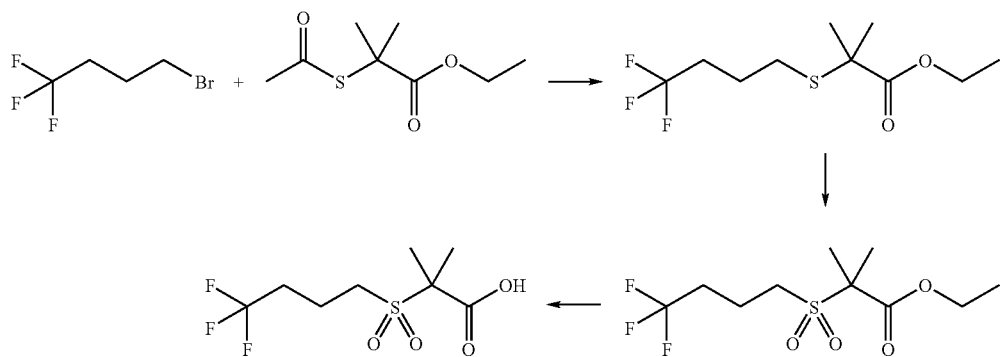

Step 1: Synthesis of 2-Methyl-2-(4,4,4-trifluoro-butylsulfanyl)-propionic acid ethyl ester To a solution of 149 g (785.4 mmol) of 2-acetylsulfanyl-2-methyl-propionic acid ethyl ester (prepared as described in Method C, step 1) in ethanol (1.2 L, degassed under nitrogen for 1 h) are added 169.7 g (105 mmol) of sodium methoxide, followed by a solution of 150 g (785.4 mmol) of 4-bromo-1,1,1-trifluoro-butane. The reaction is heated to 85° C. for 3 d. The solvent is removed under reduced pressure. The residue is dissolved in DCM (1 L) and washed with saturated aqueous NaHCO$_3$ solution (2×1 L). The organic layer is dried over Na$_2$SO$_4$, filtered and the filtrate is concentrated under reduced pressure to afford 171 g of 2-methyl-2-(4,4,4-trifluoro-butylsulfanyl)-propionic acid ethyl ester as a brown oil. Yield: 84%; ES-MS: m/z 259 [M+H]; $^1$H NMR (500 MHz, CHLOROFORM-d) δ ppm 1.29 (3H, t, J=7.17 Hz), 1.51 (6H, s), 1.76-1.86 (2H, m), 2.12-2.27 (2H, m), 2.69 (2H, t, J=7.17 Hz), 4.18 (2H, q, J=7.17 Hz)

Step 2: Synthesis of 2-Methyl-2-(4,4,4-trifluoro-butane-1-sulfonyl)-propionic acid ethyl ester To a solution of 220 g (851.7 mmol) of 2-methyl-2-(4,4,4-trifluoro-butylsulfanyl)-propionic acid ethyl ester in 1,4-dioxane/water (1/1, 4 L) are added 1047 g (1703.4 mmol) of Oxone® in portions over 0.5 h at room temperature. The reaction mixture is stirred at room temperature for 18 h. The solid is removed by filtration and rinsed with 1,4-dioxane (0.5 L). The filtrate is concentrated under reduced pressure to remove the organic solvent. The aqueous residue is extracted with DCM (2×1 L). The combined organic extracts are washed with saturated aqueous NaHCO$_3$ solution (2 L), dried over Na$_2$SO$_4$ and filtered. The filtrate is concentrated under reduced pressure to afford 226 g of 2-methyl-2-(4,4,4-trifluoro-butane-1-sulfonyl)-propionic acid ethyl ester as dark yellow oil. Yield 92%; ES-MS: m/z 291 [M+H]; $^1$H NMR (500 MHz, CHLOROFORM-d) δ ppm 1.32 (3H, t, J=7.17 Hz), 1.66 (6H, s), 2.20 (2H, quin, J=7.59 Hz), 2.28-2.41 (2H, m), 3.34 (2H, t, J=7.48 Hz), 4.27 (2H, q, J=7.17 Hz)

Step 3: Synthesis of 2-Methyl-2-(3-methyl-butane-1-sulfonyl)-propionic acid

To a solution of 170 g (585.6 mmol) of 2-methyl-2-(4,4,4-trifluoro-butane-1-sulfonyl)-propionic acid ethyl ester in THF (3.4 L) are added 225.4 g (1756.8 mmol) of potassium trimethylsilanolate in portions over 0.5 h. The reaction is stirred at room temperature for 18 h. The reaction mixture is acidified with 2M aqueous HCl solution (2 L) to pH 2 and extracted with DCM (2×2 L). The combined organic extracts are dried (Na$_2$SO$_4$) and filtered. The filtrate is concentrated under reduced pressure to afford 143 g of 2-methyl-2-(3-methyl-butane-1-sulfonyl)-propionic acid as yellow solids. Yield: 93%; ES-MS: m/z 261 [M−H]. $^1$H NMR (500 MHz, CHLOROFORM-d) δ ppm 1.71 (6H, s), 2.18-2.28 (2H, m), 2.30-2.42 (2H, m), 3.38 (2H, t, J=7.48 Hz), 6.96 (1H, br. s.)

Acid Method D

Synthesis 2-(Benzothiazole-6-sulfonyl)-2-methyl-propionic acid

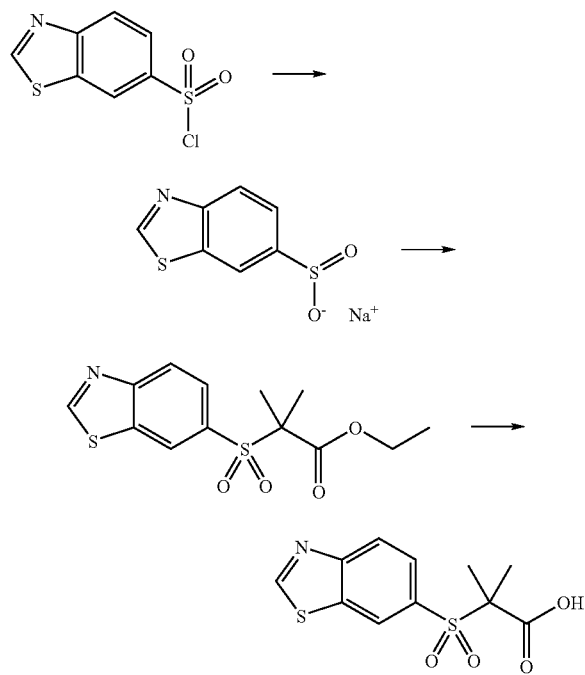

Step 1: Synthesis of 1,3-benzothiazol-6-sulfinic acid sodium salt

Prepared as described by adaptation of the following references: Faucher, A.-M. et al. *J. Med. Chem.* 2004, 47, 19-21; Binsiti, C. *Eur. J. Med. Chem. Chim. Ther.* 2001, 36, 809-828; Field, L.; Clark, R. D. *Org. Synth.* 1958, 38, 62-64.

To a solution of 0.72 g (8.56 mmol) of NaHCO$_3$ and 1.08 g (8.56 mmol) of Na$_2$SO$_3$ (4.6 mmol) in water (4.5 mL) are added 1 g (4.28 mmol) of 1,3-benzothiazol-6-sulfonyl chloride. The reaction is heated at 80° C. for 2 h. The solvent is removed under reduced pressure. The filtrate is concentrated under reduced pressure to give 1,3-benzothiazol-6-sulfinic acid sodium salt.

Step 2: Synthesis of 2-(Benzothiazole-6-sulfonyl)-2-methyl-propionic acid ethyl ester Prepared as described by adaptation of the following references: Faucher, A.-M. et al. *J. Med. Chem.* 2004, 47, 19-21; Binsiti, C. *Eur. J. Med. Chem. Chim. Ther.* 2001, 36, 809-828; Field, L.; Clark, R. D. *Org. Synth.* 1958, 38, 62-64; Troeger; Uhde, *J. Prakt. Chem.* 1899, 59, 320-349.

The crude 1,3-benzothiazol-6-sulfinic acid sodium salt (1.1 g, 4.97 mmol) is suspended in DMF (15 mL). Pyridine (0.33 mL) and ethyl α-bromoisobutyrate (0.61 mL) are added. The reaction is stirred at 50° C. under nitrogen for 2 h. The reaction mixture is cooled to room temperature and the solvent is removed under reduced pressure. The residue is dissolved in ethyl acetate (20 mL) and washed with 2M aqueous HCl solution (20 mL). The acidic aqueous layer is back-extracted with ethyl acetate (2×20 mL). The combined organic extracts are washed with brine (20 mL) and dried over Na$_2$SO$_4$. Filtration, concentration under reduced pressure, followed by column chromatography of the residue (silica, eluent DCM, 30-40% ethyl acetate) afforded 0.85 g of 2-(benzothiazole-6-sulfonyl)-2-methyl-propionic acid ethyl ester. Yield: 66%, ES-MS: m/z 314 [M+H]; $^1$H NMR (250 MHz, CHLOROFORM-d) δ ppm 1.19 (3H, t, J=7.16 Hz), 1.67 (6H, s), 4.15 (2H, q, J=7.13 Hz), 7.99 (1H, dd, J=8.68, 1.79 Hz), 8.28 (1H, d, J=8.68 Hz), 8.54 (1H, d, J=1.48 Hz), 9.26 (1H, s);

Step 3: Synthesis of 2-(Benzothiazole-6-sulfonyl)-2-methyl-propionic acid 2-(Benzothiazole-6-sulfonyl)-2-methyl-propionic acid is generally prepared as described in step 3, method A:

To a solution of 778 mg (2.48 mmol) of 2-(benzothiazole-6-sulfonyl)-2-methyl-propionic acid ethyl ester in THF/water (1/1, 24 mL) are added 208 mg (4.97 mmol) of lithium hydroxide monohydrate. The reaction is stirred at room temperature for 5 h. The organic solvent is removed under reduced pressure. The basic aqueous layer is washed with diethyl ether (10 mL), then cooled in an ice bath and acidified with 6M aqueous HCl solution to pH 2. The acidic aqueous layer is extracted with ethyl acetate (3×15 mL). The combined organic extracts are dried over Na$_2$SO$_4$ and filtered. Concentration of the filtrate under reduced pressure afforded 686 mg of 2-(benzothiazole-6-sulfonyl)-2-methyl-propionic acid as a pale yellow solid. Yield: 66%; ES-MS: m/z 569 [2M−H]; $^1$H NMR (250 MHz, DMSO-d$_6$) δ ppm 1.51 (6H, s), 7.91 (1H, dd, J=8.68, 1.98 Hz), 8.30 (1H, d, J=8.68 Hz), 8.79 (1H, d, J=1.83 Hz), 9.70 (1H, s);

Acid Method E

Synthesis of 2-Methyl-2-[2-(tetrahydro-pyran-4-yl)-ethanesulfonyl]-propionic acid

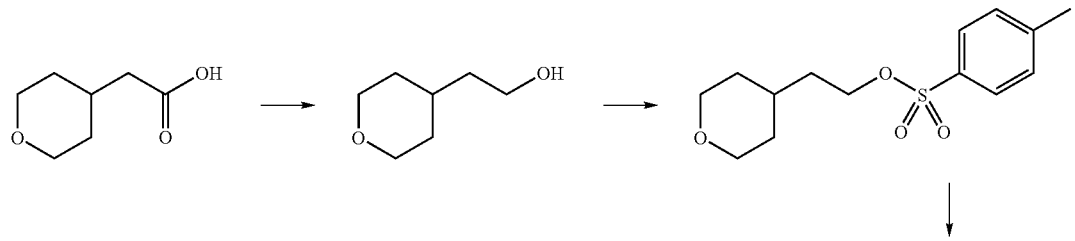

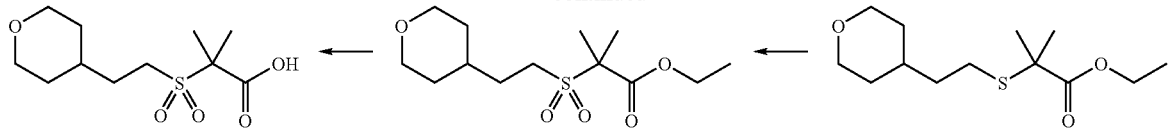

Step 1: Synthesis of 2-(Tetrahydro-pyran-4-yl)-ethanol

To a suspension of 0.55 g of LiAlH$_4$ (13.9 mmol) in THF (10 mL) is added dropwise a solution of 2 g (13.9 mmol) of (tetrahydro-pyran-4-yl)-acetic acid in THF (10 mL) under nitrogen atmosphere (CAUTION: highly exothermic reaction!). Upon complete addition, the reaction is stirred at room temperature for 18 h. The reaction is cooled in an ice-bath and quenched with addition of 1M aqueous NH$_4$Cl solution (2 mL). The resulting precipitate is removed by filtration through Celite® and is rinsed with ethyl acetate (3×100 mL). The filtrate is dried over Na$_2$SO$_4$, filtered and concentrated under reduced pressure to afford 1.63 g of 2-(tetrahydro-pyran-4-yl)-ethanol as a colorless oil. Yield: 90%; ES-MS m/z 131 [M+H].

According to this procedure the following alcohols are synthesized:

TABLE X

| Structure | $^1$H-NMR | Yield [%] | m/z [M + H] |
|---|---|---|---|
| (tetrahydropyran-4-yl)ethanol | (500 MHz, CHLOROFORM-d) δ ppm 1.29 (2 H, qd, J = 12.08, 4.04 Hz), 1.50 (2 H, qd, J = 6.71, 1.37 Hz), 1.55-1.73 (3 H, m), 1.95-2.07 (1 H, m), 3.37 (2 H, t, J = 11.83 Hz), 3.66 (2 H, t, J = 6.03 Hz), 3.92 (2 H, dd, J = 11.44, 4.12 Hz) | 90 | 131 |
| (4-methyltetrahydropyran-4-yl)methanol | (360 MHz, CHLOROFORM-d) δ ppm 1.04 (3 H, s), 1.24-1.33 (2 H, m), 1.52-1.63 (2 H, m), 3.41 (2 H, d, J = 5.68 Hz), 3.58-3.68 (2 H, m), 3.70-3.80 (2 H, m)§ | 86 | N/A |

§This intermediate is used in Method F, step 2.

Step 2: Synthesis of Toluene-4-sulfonic acid 2-(tetrahydro-pyran-4-yl)-ethyl ester Toluene-4-sulfonic acid 2-(tetrahydro-pyran-4-yl)-ethyl ester is generally prepared by adaptation of Method B, step 2.

To a solution of 1.63 g (12.5 mmol) of 2-(tetrahydro-pyran-4-yl)-ethanol in pyridine (15 mL) are added 3.58 g (18.8 mmol) of p-toluenesulfonylchloride. The reaction is stirred at room temperature for 5 h. The reaction mixture is concentrated under reduced pressure. The residue is dissolved 2M aqueous HCl solution (20 mL) and extracted with ethyl acetate (3×50 mL). The combined organic extracts are dried over Na$_2$SO$_4$, filtered and the solvent is removed to give 1.9 g of toluene-4-sulfonic acid 2-(tetrahydro-pyran-4-yl)-ethyl ester as off-white crystalline solid. Yield: 53%; ES-MS: m/z 285 [M+H]

According to this procedure the following toluene-4-sulfonic acid esters are synthesized with the following modifications to be noted: for toluene-4-sulfonic acid 3,3,3-trifluoro-propyl ester: 3,3,3-trifluoro-propan-ol (10 mmol) is reacted with p-toluenesulfonylchloride (1.2 equ.) in DCM (10 mL) in the presence of N,N-dimethylaminopyridine (0.1 equ) and triethyl amine (2 equ). The reaction is stirred for 3 d, then poured into water and extracted with DCM. The combined organics are washed with 1N aqueous HCl solution, aqueous saturated NaHCO$_3$ solution and brine, then dried over Na$_2$SO$_4$, filtered and the filtrate is concentrated under reduced pressure.

TABLE XI

| Structure | ¹H-NMR | Yield [%] | m/z [M + H] |
|---|---|---|---|
| (tetrahydropyran-4-yl)ethyl tosylate | (500 MHz, CHLOROFORM-d) δ ppm 1.17-1.29 (2 H, m), 1.45-1.52 (2 H, m), 1.57-1.67 (3 H, m), 2.46 (3 H, s), 3.32 (2 H, td, J = 11.78, 1.93 Hz), 3.91 (2 H, dd, J = 11.28, 4.13 Hz), 4.08 (2 H, t, J = 6.14 Hz), 7.36 (2 H, d, J = 8.07 Hz), 7.80 (2 H, d, J = 8.44 Hz) | 53 | 285 |
| 3,3,3-trifluoropropyl tosylate | (400 MHz, CHLOROFORM-d) δ ppm 2.47 (3 H, s), 2.47-2.6 (2 H, m), 4.22 (2 H, t, J = 6.4 Hz), 7.36 (2 H, d, J = 8.08 Hz), 7.8 (2 H, d, J = 7.8 Hz) | 87 | N/A |

Step 3: Synthesis of 2-Methyl-2-[2-(tetrahydro-pyran-4-yl)-ethylsulfanyl]-propionic acid ethyl ester To a solution of 1.9 g (6.7 mmol) of toluene-4-sulfonic acid 2-(tetrahydro-pyran-4-yl)-ethyl ester in ethanol (20 mL) are added 1.4 g (26.8 mmol) of sodium methoxide, followed by 1.27 g (6.7 mmol) of 2-acetylsulfanyl-2-methyl-propionic acid ethyl ester. The reaction mixture is heated in a microwave at 130° C. for 0.5 h. The solvent is removed under reduced pressure. The residue is partitioned between saturated aqueous $NaHCO_3$ solution (25 mL) and DCM (25 mL). The layers are separated and the aqueous phase extracted with DCM (2×25 mL). The combined organic extracts are dried over $Na_2SO_4$, filtered and the solvent is removed under reduced pressure to afford 1.9 g of 2-methyl-2-[2-(tetrahydro-pyran-4-yl)-ethylsulfanyl]-propionic acid ethyl ester. Yield: 100%; ES-MS: m/z 261 [M+H]; ¹H NMR (250 MHz, CHLOROFORM-d) δ ppm 1.15-1.38 (5H, m), 1.42-1.70 (12H, m), 2.59-2.71 (1H, m), 3.37 (2H, td, J=11.73, 1.98 Hz), 3.95 (2H, ddd, J=11.04, 3.88, 0.91 Hz), 4.18 (2H, q, J=7.16 Hz)

TABLE XII

| Structure | ¹H NMR | Yield [%] | m/z [M + H] |
|---|---|---|---|
| 2-methyl-2-[2-(tetrahydro-pyran-4-yl)-ethylsulfanyl]-propionic acid ethyl ester | (250 MHz, CHLOROFORM-d) δ ppm 1.15-1.38 (5 H, m), 1.42-1.70 (12 H, m), 2.59-2.71 (1 H, m), 3.37 (2 H, td, J = 11.73, 1.98 Hz), 3.95 (2 H, ddd, J = 11.04, 3.88, 0.91 Hz), 4.18 (2 H, q, J = 7.16 Hz) | 100 | 261 |
| 2-methyl-2-(3,3,3-trifluoropropylsulfanyl)-propionic acid ethyl ester | (400 MHz, CHLOROFORM-d) δ ppm 1.28 (3 H, t, J = 7 Hz), 1.51 (3 H, s), 2.26-2.42 (2 H, m), 2.76-2.85 (2 H, m), 4.18 (2 H, q, J = 6.96 Hz) | 83 | N/A |
| 2-[(4-methoxycyclohexyl)sulfanyl]-2-methyl-propionic acid ethyl ester | (400 MHz, CHLOROFORM-d) δ ppm 1.20 (t, 3 H), 1.43 (s, 6 H), 1.52-1.64 (m, 8 H), 2.91-2.93 (m, 1 H), 3.18 (s, 3 H), 3.20-3.23 (m, 1 H), 4.08 (q, 2 H) | 33[a] | N/A |
| 2-[(4-methoxycyclohexyl)sulfanyl]-2-methyl-propionic acid ethyl ester | (400 MHz, CHLOROFORM-d) δ ppm 1.19-1.30 (m, 7 H), 1.43 (s, 6 H), 1.87-1.93 (m, 4 H), 2.76-2.81 (m, 1 H), 3.06-3.09 (m, 1 H), 3.20 (s, 3 H), 4.09 (q, 2 H) | 21[a] | 261 |

[a] Reaction performed in a sealed tube at 120° C. in an oil bath.

Step 4: Synthesis of 2-Methyl-2-[2-(tetrahydro-pyran-4-yl)-ethanesulfonyl]-propionic acid ethyl ester A 3-neck roundbottom flask is charged with 1.9 g (7.3 mmol) of 2-methyl-2-[2-(tetrahydro-pyran-4-yl)-ethylsulfanyl]-propionic acid ethyl ester and dissolved in 1,4-dioxane/water (4/1, 40 mL). Oxone® (9 g, 14.6 mmol) is added in one portion. The biphasic reaction mixture is stirred at room temperature for 2 h. The solids are removed by filtration and the filtrate is concentrated under reduced pressure. The residue is washed with saturated aqueous $NaHCO_3$ solution (50 mL) and extracted with DCM (3×50 mL). The combined organic layers are dried over $Na_2SO_4$, filtered and the solvent is removed under reduced pressure to give 1.34 g of 2-methyl-2-[2-(tetrahydro-pyran-4-yl)-ethanesulfonyl]-propionic acid ethyl ester. Yield: 63%; ES-MS: m/z 293 [M+H], 315 [M+Na]; $^1$H NMR (250 MHz, CHLOROFORM-d) δ ppm 1.28-1.45 (5H, m), 1.59-1.71 (9H, m), 1.79-1.95 (2H, m), 3.20-3.31 (2H, m), 3.38 (2H, td, J=11.76, 1.90 Hz), 3.93-4.04 (2H, m), 4.27 (2H, q, J=7.06 Hz)

Step 5: Synthesis of 2-Methyl-2-[2-(tetrahydro-pyran-4-yl)-ethanesulfonyl]-propionic acid To a solution of 1.34 g (4.6 mmol) of 2-methyl-2-[2-(tetrahydro-pyran-4-yl)-ethanesulfonyl]-propionic acid ethyl ester in THF (40 mL) are added 1.17 g (9.2 mmol) of potassium trimethylsilanolate. The reaction is stirred at room temperature for 2 h. The solvent is removed under reduced pressure. The residue is partitioned between DCM (50 mL) and 1M aqueous HCl solution (10 mL). The aqueous layer is extracted with DCM (2×50 mL). The combined organic extracts are dried over $Na_2SO_4$, filtered and the filtrate is concentrated under reduced pressure to afford 1.02 g of 2-methyl-2-[2-(tetrahydro-pyran-4-yl)-ethanesulfonyl]-propionic acid. Yield: 84%, ES-MS: m/z 263 [M–H]

According to this procedure the following propionic acids are synthesized with the following modifications to be noted: 2-Methyl-2-(3,3,3-trifluoro-propane-1-sulfonyl)-propionic acid is synthesized using lithium hydroxide monohydrate (as described in Method C, step 3) instead of potassium trimethylsilanolate.

TABLE XIII

| Structure | $^1$H NMR | Yield [%] | m/z [M – H] |
|---|---|---|---|
| 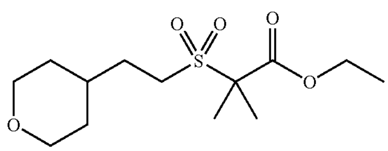 | (250 MHz, CHLOROFORM-d) δ ppm 1.28-1.45 (5H, m), 1.59-1.71 (9H, m), 1.79-1.95 (2H, m), 3.20-3.31 (2H, m), 3.38 (2H, td, J = 11.76, 1.90 Hz), 3.93-4.04 (2H, m), 4.27 (2H, q, J = 7.06 Hz) | 63 | 293 |
| 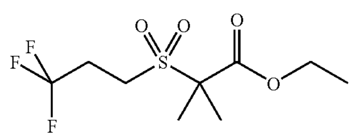 | (400 MHz, CHLOROFORM-d) δ ppm 1.301 (3H, t, J = 7.2 Hz), 1.66 (3H, s), 2.58-2.77 (2H, m), 3.42-3.52 (2H, m), 4.26 (2H, q, J = 6.8 Hz) | 64 | N/A |
| 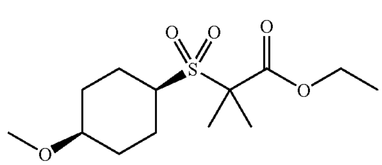 | (400 MHz, CHLOROFORM-d) δ ppm 1.32 (3H, t, 7.2 Hz), 1.42-1.49 (2H, m), 1.65 (6H, s), 1.86-2.10 (6H, m), 3.28 (3H, s), 3.43 (1H, m), 3.52-3.56 (1H, m), 4.18 (2H, q, 7.2 Hz) | 93 | 293 |
| 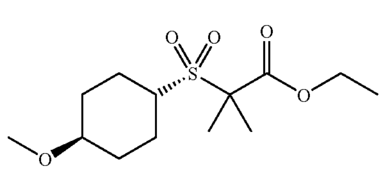 | (400 MHz, CHLOROFORM-d) δ ppm 1.23-1.26 (2H, m), 1.30 (3H, t, 7.2 Hz), 1.65 (6H, s), 1.68-1.71 (2H, m), 2.19-2.22 (4H, m), 3.10-3.17 (1H, m), 3.34 (3H, s), 3.48-3.55 (1H, m), 4.23 (2H, q, 7.2 Hz) | 92 | 293 |

TABLE XIV

| Structure | $^1$H NMR | Yield [%] | m/z [M – H] |
|---|---|---|---|
| (tetrahydropyran-CH2CH2-SO2-C(CH3)2-COOH) | (500 MHz, MeOD) δ ppm 1.29 (2H, dt, J = 12.17, 2.08 Hz), 1.56-1.85 (11H, m), 3.35-3.45 (4H, m), 3.88-3.97 (2H, m) | 84 | 263 |
| (CF3-CH2CH2-SO2-C(CH3)2-COOH) | (400 MHz, CHLOROFORM-d) δ ppm 1.72 (3H, s), 2.64-2.81 (2H, m), 3.46-3.6 (2H, m) | 84 | N/A |
| (trans-4-methoxycyclohexyl-SO2-C(CH3)2-COOH) | (500 MHz, CHLOROFORM-d) δ ppm 1.40-1.50 (2H, m), 1.71 (6H, s), 1.86-1.94 (2H, m), 1.98-2.08 (2H, m), 2.09-2.16 (2H, m), 3.31 (3H, s), 3.37-3.45 (1H, m), 3.47 (1H, quin, J = 2.94 Hz) | 90 | 263 |
| (cis-4-methoxycyclohexyl-SO2-C(CH3)2-COOH) | (500 MHz, CHLOROFORM-d) δ ppm 1.21-1.37 (2H, m), 1.64-1.81 (8H, m), 2.19-2.32 (4H, m), 3.18-3.28 (1H, m), 3.40 (3H, s), 3.45 (1H, tt, J = 11.96, 3.53 Hz) | 79 | 263 |

Acid Method F

Synthesis of 2-Methyl-2-(tetrahydro-pyran-4-sulfonyl)-propionic acid

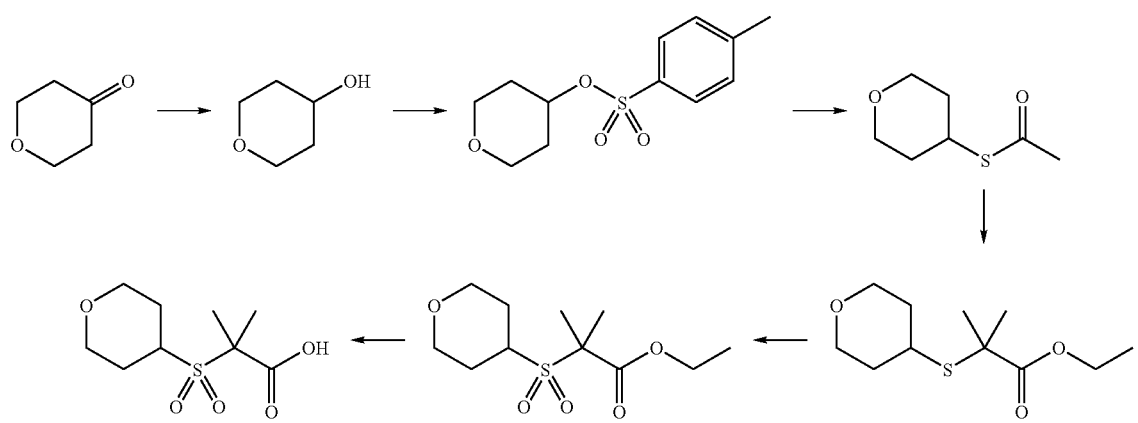

Step 1: Synthesis of Tetrahydropyran-4-ol

To a solution of 75 g (0.75 mol) of tetrahydropyran-4-one in THF (150 mL) is added a suspension of 28.4 g (0.75 mol) LiAlH$_4$ in THF (600 mL) under nitrogen atmosphere maintaining the temperature below 30° C. with the aid of an ice-bath. Then the reaction is allowed to warm to room temperature and stirred for 5 h. The reaction is quenched by addition of saturated aqueous NH$_4$Cl solution until effervescence ceased. The resulting precipitate is removed by filtration through Celite® and washed with THF (150 mL). The filtrate is concentrated under reduced pressure to afford 71.1 g of tetrahydropyran-4-ol as a pale yellow oil. Yield: 92%, $^1$H NMR (500 MHz, CHLOROFORM-d) δ ppm 1.54 (2H, m), 1.81-1.92 (2 H, m), 2.11 (1H, br. s.), 3.38-3.47 (2H, m), 3.83 (1H, tt, J=9.10, 4.38 Hz), 3.94 (2H, dt, J=11.88, 4.15 Hz)

Step 2: Synthesis of Toluene-4-sulfonic Acid tetrahydropyran-4-yl ester

To a solution of 133 g (1.31 mol) of tetrahydropyran-4-ol in pyridine (1.5 L) are added 373 g (1.95 mol) of p-toluenesulfonylchloride portionwise at 10° C. After complete addition the reaction is allowed to warm to room temperature and stirred for 18 h. The reaction is poured onto a stirred mixture of aqueous HCl/ice. The resulting precipitate is isolated by filtration and dissolved in DCM (1 L). The organic layer is washed with 1M aqueous HCl solution (1 L), followed by saturated aqueous $NaHCO_3$ solution (1 L) and is then dried over $Na_2SO_4$. Filtration and concentration of the filtrate under reduced pressure gives 300 g of toluene-4-sulfonic acid tetrahydropyran-4-yl ester as an orange oil. Yield: 90%, ES-MS: m/z: 257 [M+H], 279 [M+Na]

According to this procedure the following esters are synthesized:

Step 3: Synthesis of Thioacetic acid S-(tetrahydro-pyran-4-yl)ester

To a solution of 300 g (1.175 mol) of toluene-4-sulfonic acid tetrahydropyran-4-yl ester in DMF (3 L) are added 268 g (2.35 mol) potassium thioacetate, followed by a catalytic amount of NaI (0.12 g, 10 mol %) at room temperature. After complete addition, the reaction is heated to 50° C. for 20 h. The reaction mixture is partitioned between TBME (3 L) and water (3 L), the aqueous layer is extracted with TBME (2 L), then saturated with NaCl and extracted again with TBME (2×2 L). The combined organic extracts are dried over $Na_2SO_4$, filtered and the solvent is removed under reduced pressure to afford 153 g of thioacetic acid S-(tetrahydro-pyran-4-yl)ester. Yield: 81%; ES-MS: m/z 161 [M+H].

According to this procedure the following esters are synthesized:

TABLE XV

| Structure | $^1$H NMR | Yield [%] | m/z [M + H] |
|---|---|---|---|
| 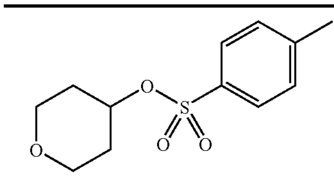 | (250 MHz, CHLOROFORM-d) δ ppm 1.66-1.96 (4H, m), 2.45 (3H, s), 3.47 (2H, ddd, J = 11.76, 8.19, 3.50 Hz), 3.79-3.95 (2H, m), 4.69 (1H, tt, J = 8.13, 4.13 Hz), 7.35 (2H, d, J = 8.07 Hz), 7.76-7.87 (2H, m) | 90 | 257 |
|  | (250 MHz, CHLOROFORM-d) δ ppm 1.02 (3H, s), 1.20-1.34 (2H, m), 1.40-1.56 (2H, m), 2.45 (3H, s), 3.48-3.69 (4H, m), 3.75 (2H, s), 7.35 (2H, d, J = 8.03 Hz), 7.78 (2H, d, J = 8.34 Hz)[§] | 90 | 307 [M + Na] |
|  | (500 MHz, CHLOROFORM-d) δ ppm 1.51-1.61 (1H, m), 1.96-2.07 (1H, m), 2.46 (3H, s), 2.55-2.66 (1H, m), 3.50 (1H, dd, J = 9.00, 5.04 Hz), 3.70 (1H, q, J = 7.78 Hz), 3.74-3.83 (2H, m), 3.89-3.95 (1H, m), 3.97-4.02 (1H, m), 7.36 (2H, d, J = 8.09 Hz), 7.80 (2H, d, J = 8.24 Hz)[#] | 89 | 257 |
|  | (500 MHz, CHLOROFORM-d) δ ppm 1.51-1.60 (1H, m), 1.96-2.06 (1H, m), 2.46 (3H, s), 2.60 (1H, dt, J = 13.58, 6.79 Hz), 3.50 (1H, dd, J = 9.16, 5.04 Hz), 3.69 (1H, q, J = 7.68 Hz), 3.73-3.83 (2H, m), 3.89-3.95 (1H, m), 3.97-4.02 (1H, m), 7.36 (2H, d, J = 8.09 Hz), 7.79 (2H, d, J = 8.24 Hz)[#] | 95 | 257 |
| 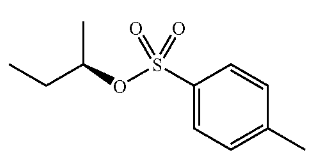 | (500 MHz, CHLOROFORM-d) δ ppm 0.83 (3H, t, J = 7.48 Hz), 1.26 (3H, d, J = 6.26 Hz), 1.47-1.70 (2H, m), 2.45 (3H, s), 4.57 (1H, sxt, J = 6.23 Hz), 7.34 (2H, d, J = 8.39 Hz), 7.81 (2H, d, J = 8.24 Hz); | 62 | $[α]^{25}_{578}$* |
| 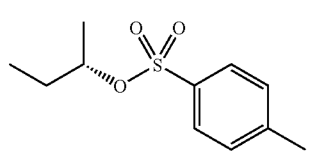 | (500 MHz, CHLOROFORM-d) δ ppm 0.82 (3H, t, J = 7.48 Hz), 1.25 (3H, d, J = 6.26 Hz), 1.48-1.71 (2H, m), 2.45 (3H, s), 4.56 (1H, sxt, J = 6.26 Hz), 7.33 (2H, d, J = 8.24 Hz), 7.80 (2H, d, J = 8.24 Hz) | 57 | $[α]^{25}_{578}$ 12.59 (3, $CCl_4$) |

*$[α]^{25}_{578}$-12.36 (3, $CCl_4$) (lit. $[α]^{25}_{578}$-10.9 (2-4, $CCl_4$), Allen et al. J. Org. Chem, 2003, 48, 4527-4530)

[§]The corresponding starting material, (4-methyl-tetrahydro-pyran-4-yl)-methanol, is synthesized as described in method E, step 1.

[#]3-tetrahydrofuran carboxylic acid is resolved according to WO2007/068739 (Glaxo Group Ltd.) to afford (3S)-tetrahydro-3-furanylmethanol and (3R)-tetrahydro-3-furanylmethanol, which are used as the corresponding starting materials.

TABLE XVI

| Structure | ¹H-NMR | Yield [%] | m/z [M + H] |
|---|---|---|---|
| 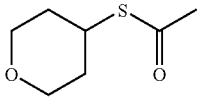 | (250 MHz, CHLOROFORM-d) δ ppm 1.47-1.98 (4H, m), 2.30 (3H, s), 3.41-3.74 (3H, m), 3.88 (2H, dt, J = 11.76, 3.86 Hz) | 86 | 161 |
| 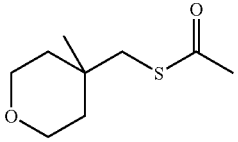 | (250 MHz, CHLOROFORM-d) δ ppm 0.99 (3H, s), 1.25-1.60 (4H, m), 2.33 (3H, s), 2.93 (2H, s), 3.49-3.79 (4H, m) | 100 | 189 |
| 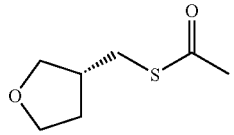 | (500 MHz, CHLOROFORM-d) δ ppm 1.58-1.68 (1H, m), 2.06-2.13 (1H, m), 2.37 (3H, s), 2.46 (1H, dt, J = 14.08, 6.92 Hz), 2.90-3.01 (2H, m), 3.47 (1H, dd, J = 8.62, 6.18 Hz), 3.76 (1H, q, J = 7.73 Hz), 3.83-3.91 (2H, m) | 100 | 161 |
| 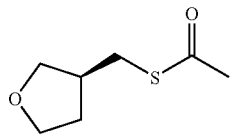 | (500 MHz, CHLOROFORM-d) δ ppm 1.57-1.69 (1H, m), 2.07-2.15 (1H, m), 2.36 (3H, s), 2.47 (1H, dt, J = 14.OO, 6.96 Hz), 2.92-3.04 (2H, m), 3.48 (1H, dd, J = 8.70, 6.10 Hz), 3.77 (1H, q, J = 7.73 Hz), 3.84-3.93 (2H, m) | 81 | 161 |
| 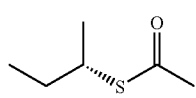 | (500 MHz, CHLOROFORM-d) + residual Et₂O) δ ppm 0.96 (3H, t, J = 7.40 Hz), 1.29 (3H, d, J = 7.02 Hz), 1.60 (2H, quin, J = 7.25 Hz), 2.31 (3H, s), 3.46-3.55 (1H, m under Et₂O peak) | 76 | N/A |
| 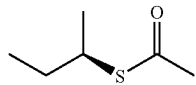 | (500 MHz, CHLOROFORM-d + residual Et₂O) δ ppm 0.96 (3H, t, J = 7.40 Hz), 1.29 (3H, d, J = 6.87 Hz), 1.59 (2H, quin, J = 7.25 Hz), 2.31 (3H, s), 3.43-3.54 (1H, m under Et₂O peak) | 97 | N/A |

Step 4: Synthesis of 2-Methyl-2-(tetrahydro-pyran-4-ylsulfanyl)-propionic acid ethyl ester A solution of 153 g (0.96 mol) of thioacetic acid S-(tetrahydro-pyran-4-yl)ester in ethanol (3.5 L) is degassed with nitrogen over 0.5 h and 125 g (2.23 mol) of KOH are added. Then a solution of 250 mL (1.68 mol) of ethyl α-bromoisobutyrate in EtOH (1 L) are added over 0.5 h, during which the temperature is increased to 40° C. The reaction is stirred for 18 h at room temperature under a nitrogen atmosphere. The reaction mixture is filtered, the solid is washed with ethanol (0.5 L) and the filtrate is concentrated under reduced pressure. The crude material is dryloaded onto silica and purified by dry-flash column chromatography (silica, eluent: n-heptanes, 2-10% ethyl acetate) to afford 158 g of 2-methyl-2-(tetrahydro-pyran-4-ylsulfanyl)-propionic acid ethyl ester as an orange-brown oil. Yield: 71%; ES-MS: m/z 233 [M+H]

According to this procedure the following esters are synthesized with the following modifications to be noted: for 1-(tetrahydro-pyran-4-ylsulfanyl)-cyclobutanecarboxylic acid ethyl ester: ethyl-1-bromocyclobutane carboxylate is used instead of ethyl α-bromoisobutyrate and the product is taken to the next step without further purification.

TABLE XVII

| Structure | ¹H NMR | Yield [%] | m/z [M + H] |
|---|---|---|---|
| 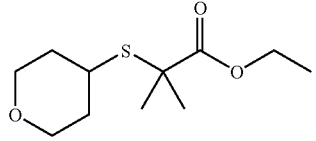 | (500 MHz, CHLOROFORM-d) δ ppm 1.28 (3H, t, J = 7.17 Hz), 1.52 (6H, s), 1.56-1.67 (2H, m), 1.85 (2H, dt, J = 13.35, 1.64 Hz), 3.04 (1H, tt, J = 10.60, 4.20 Hz), 3.40-3.49 (2H, m), 3.88 (2H, dt, J = 11.75, 3.81 Hz), 4.14-4.20 (2H, m) | 76 | 233 |
| 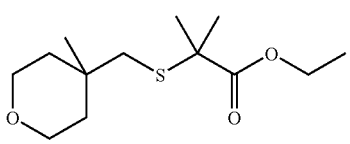 | (360 MHz, CHLOROFORM-d) δ ppm 1.03 (3H, s), 1.27 (3H, t, J ==7.10 Hz), 1.31-1.42 (2H, m), 1.45-1.60 (8H, m), 2.60 (2H, s), 3.52-3.71 (4H, m), 4.15 (2H, q, J = 7.15 Hz) | 49 | 261 |

TABLE XVII-continued

| Structure | ¹H NMR | Yield [%] | m/z [M + H] |
|---|---|---|---|
| (tetrahydropyran-4-yl-S-cyclobutane-carboxylic acid ethyl ester) | (360 MHz, CHLOROFORM-d) δ ppm 1.23-1.37 (3H, m), 1.56-1.76 (4H, m), 1.81-2.01 (3H, m), 2.14-2.26 (1H, m), 2.58-2.75 (1H, m), 2.83-2.98 (1H, m), 3.35-3.52 (2H, m), 3.82-4.05 (3H, m), 4.12-4.29 (2H, m) | 83 | 245 |
| (tetrahydrofuran-3-yl-CH₂-S-C(CH₃)₂-COOEt) | (500 MHz, CHLOROFORM-d) δ ppm 1.22-1.35 (3H, m), 1.47-1.55 (6H, m), 1.63 (1H, dd, J = 12.66, 6.71 Hz), 2.05-2.13 (1H, m), 2.32-2.43 (1H, m), 2.60-2.73 (2H, m), 3.43-3.51 (1H, m), 3.75 (1H, q, J = 7.48 Hz), 3.82-3.92 (2H, m), 4.09-4.28 (2H, m) | 77 | 233 |
| (tetrahydrofuran-3-yl-CH₂-S-C(CH₃)₂-COOEt, other enantiomer) | (500 MHz, CHLOROFORM-d) δ ppm 1.25-1.35 (3H, m), 1.51 (6H, s), 1.59-1.68 (1H, m), 2.03-2.13 (1H, m), 2.37 (1H, dt, J = 14.27, 7.06 Hz), 2.60-2.73 (2H, m), 3.47 (1H, dd, J = 8.70, 6.26 Hz), 3.70-3.79 (1H, m), 3.82-3.91 (2H, m), 4.18 (2H, q, J = 7.12 Hz) | 47 | 233 |
| (sec-butyl-S-C(CH₃)₂-COOEt) | (500 MHz, CHLOROFORM-d) δ ppm 0.95 (3H, t, J = 7.40 Hz), 1.22-1.35 (7H, m), 1.47-1.59 (7H, m), 2.86 (1H, sxt, J = 6.77 Hz), 4.17 (2H, q, J = 7.12 Hz) | 100 | 205 |
| (sec-butyl-S-C(CH₃)₂-COOEt, other enantiomer) | (500 MHz, CHLOROFORM-d) δ ppm 0.95 (3H, t, J = 7.32 Hz), 1.23-1.35 (7H, m), 1.47-1.56 (7H, m), 2.86 (1H, sxt, J = 6.77 Hz), 4.17 (2H, q, J = 7.07 Hz) | 87 | 205 |

Step 5: Synthesis of 2-Methyl-2-(tetrahydro-pyran-4-sulfonyl)-propionic acid ethyl ester To a solution of 158 g (0.68 mol) of 2-methyl-2-(tetrahydro-pyran-4-ylsulfanyl)-propionic acid ethyl ester in 1,4-dioxane/water (4/1, 1.6 L) are added 835 g (1.35 mol) of Oxone® in portions over 50 min. The reaction mixture is stirred at room temperature for 18 h. The solid is removed by filtration and washed with 1,4-dioxane (1 L). The combined filtrates are concentrated under reduced pressure. The residue is dissolved in ethyl acetate (1.5 L) and washed with water (1 L). The organic layer is dried over Na₂SO₄, filtered and the solvent is removed under reduced pressure to afford 166 g of 2-methyl-2-(tetrahydro-pyran-4-sulfonyl)-propionic acid ethyl ester as a yellow oil. Yield: 92%, ES-MS: m/z 265 [M+H], 287 [M+Na].

According to this procedure the following esters are synthesized:

TABLE XVIII

| Structure | ¹H-NMR | Yield [%] | m/z [M + H] |
|---|---|---|---|
| (tetrahydropyran-4-yl-SO₂-C(CH₃)₂-COOEt) | (250 MHz, CHLOROFORM-d) δ ppm 1.30 (3H, J = 7.08 Hz), 1.65 (6H, s), 1.89-2.10 (4H, m), 3.34-3.51 (2H, m), 3.72-3.90 (1H, m), 4.06 (2H, dt, J = 11.69, 3.60 Hz), 4.24 (2H, q, J = 7.16 Hz) | 90 | 265, 287 [M + Na] |
| (4-methyl-tetrahydropyran-4-yl-CH₂-SO₂-C(CH₃)₂-COOEt) | (250 MHz, CHLOROFORM-d) δ ppm 1.31 (3H, t, J = 7.14 Hz), 1.38 (3H, s), 1.53-1.69 (8H, m), 1.71-1.89 (2H, m), 3.27 (2H, s), 3.68 (4H, t, J = 5.27 Hz), 4.25 (2H, q, J = 7.13 Hz) | 91 | 293 |
| (tetrahydropyran-4-yl-SO₂-cyclobutane-carboxylic acid ethyl ester) | (250 MHz, CHLOROFORM-d) δ ppm 1.37 (3H, t, J = 7.16 Hz), 1.83-2.22 (6H, m), 2.54-2.71 (2H, m), 2.87-3.07 (2H, m), 3.29-3.61 (3H, m), 3.98-4.15 (2H, m), 4.35 (2H, q, J = 7.16 Hz) | 28 | 277, 299 [M + Na] |

TABLE XVIII-continued

| Structure | ¹H-NMR | Yield [%] | m/z [M + H] |
|---|---|---|---|
| (tetrahydrofuran-CH₂-SO₂-C(CH₃)₂-C(O)-O-Et) | (500 MHz, CHLOROFORM-d) δ ppm 1.33 (3H, td, J = 7.10, 1.37 Hz), 1.66 (6H, s), 1.73-1.84 (1H, m), 2.24-2.34 (1H, m), 2.91 (1H, dt, J = 14.15, 7.19 Hz), 3.34 (2H, d, J = 7.02 Hz), 3.55-3.63 (1H, m), 3.74-3.82 (1H, m), 3.86-3.94 (1H, m), 4.00-4.07 (1H, m), 4.27 (2H, qd, J = 7.12, 1.37 Hz) | 100 | 265, 287 [M + Na] |
| (tetrahydrofuran-CH₂-SO₂-C(CH₃)₂-C(O)-O-Et) | (500 MHz, CHLOROFORM-d) δ ppm 1.34 (3H, t, J = 7.10 Hz), 1.67 (6H, s), 1.74-1.83 (1H, m), 2.30 (1H, m, J = 12.57, 7.68, 7.68, 4.88 Hz), 2.91 (1H, dt, J = 14.23, 7.15 Hz), 3.35 (2H, d, J = 7.17 Hz), 3.60 (1H, dd, J = 8.85, 6.71 Hz), 3.79 (1H, q, J = 8.14 Hz), 3.91 (1H, td, J = 8.32, 4.88 Hz), 4.05 (1H, dd, J = 8.70, 7.32 Hz), 4.28 (2H, q, J = 7.17 Hz) | 83 | 265, 287 [M + Na] |
| (sec-butyl-SO₂-C(CH₃)₂-C(O)-O-Et) | (500 MHz, CHLOROFORM-d) δ ppm 1.05 (3H, t, J = 7.48 Hz), 1.34 (3H, t, J = 7.10 Hz), 1.40 (3H, d, J = 6.87 Hz), 1.62-1.70 (7H, m), 2.06 (1H, ddd, J = 13.96, 7.55, 3.81 Hz), 3.54-3.63 (1H, m), 4.27 (2H, q, J = 7.17 Hz) | 80 | 237, 259 [M + Na] |
| (sec-butyl-SO₂-C(CH₃)₂-C(O)-O-Et) | ¹H NMR (500 MHz, CHLOROFORM-d) δ ppm 1.03 (3H, t, J = 7.48 Hz), 1.32 (3H, t, J = 7.17 Hz), 1.38 (3H, d, J = 7.02 Hz), 1.59-1.69 (7H, m), 1.98-2.10 (1H, m), 3.52-3.62 (1H, m), 4.25 (2H, q, J = 7.07 Hz) | 73 | 237, 259 [M + Na] |

Step 6: Synthesis of 2-Methyl-2-(tetrahydro-pyran-4-sulfonyl)-propionic acid To a solution of 166 g (0.63 mol) of 2-methyl-2-(tetrahydro-pyran-4-sulfonyl)-propionic acid ethyl ester in THF/water (4/1, 1.66 L) are added 50.5 g (1.26 mol) of NaOH pellets in portions over 20 min. The reaction is stirred at room temperature for 2.5 d. The organic solvent is removed under reduced pressure and the aqueous residue is diluted with water (2 L) and washed with DCM (2 L). The aqueous layer is acidified to pH 1-2 with concentrated HCl and then extracted with DCM (3×2 L). The acidic aqueous is further saturated with NaCl and extracted again with DCM (6×2 L). The combined organic extracts are concentrated under reduced pressure to give 123 g of 2-methyl-2-(tetrahydro-pyran-4-sulfonyl)-propionic acid as a white solid. Yield: 83%, ES-MS: m/z 235 [M–H]

According to this procedure the following acids are synthesized with the following modification to be noted: for 1-(tetrahydro-pyran-4-sulfonyl)-cyclobutanecarboxylic acid and 2-[(2R)-butane-2-sulfonyl]-2-methylpropanoic acid, lithium hydroxide monohydrate is used instead of NaOH pellets.

TABLE XIX

| Structure | ¹H NMR | Yield [%] | m/z [M – H] |
|---|---|---|---|
| (tetrahydropyran-SO₂-C(CH₃)₂-COOH) | (500 MHz, CHLOROFORM-d) δ ppm 1.71 (6H, s), 1.94-2.12 (4H, m), 3.47 (2H, td, J = 11.41, 2.98 Hz), 3.73-3.86 (1H, m), 4.07-4.15 (2H, m), 6.82 (1H, br. s.) | 69 | 235 |
| (4-methyl-tetrahydropyran-CH₂-SO₂-C(CH₃)₂-COOH) | (250 MHz, CHLOROFORM-d) δ ppm 1.39 (3H, s), 1.53-1.72 (8H, m), 1.72-1.90 (2H, m), 3.31 (2H, s), 3.62-3.76 (4H, m) | 94 | 263 |
| (tetrahydropyran-SO₂-cyclobutane-COOH) | (250 MHz, CHLOROFORM-d) δ ppm 1.86-2.35 (6H, m), 2.59-2.79 (2H, m), 2.92-3.15 (2H, m), 3.29-3.68 (3H, m), 3.95-4.20 (2H, m), 5.64 (1H, br. s.) | 86 | 249 [M + H] |

TABLE XIX-continued

| Structure | ¹H NMR | Yield [%] | m/z [M − H] |
|---|---|---|---|
| 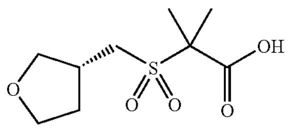 | (500 MHz, CHLOROFORM-d) δ ppm 1.69 (6H, s), 1.79-1.88 (1H, m), 2.32 (1H, m, J = 12.66, 7.78, 7.78, 4.88 Hz), 2.97 (1H, dt, J = 13.89, 7.10 Hz), 3.32-3.38 (1H, m), 3.38-3.45 (1H, m), 3.72 (1H, dd, J = 9.00, 5.95 Hz), 3.80 (1H, q, J = 7.73 Hz), 3.97 (1H, td, J = 8.39, 4.88 Hz), 4.03 (1H, dd, J = 8.93, 7.10 Hz) | 98 | 237 [M + H], 259 [M + Na] |
| 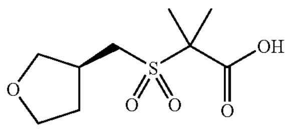 | (500 MHz, CHLOROFORM-d) δ ppm 1.66-1.71 (6H, m), 1.79-1.89 (1H, m), 2.32 (1H, m, J = 12.61, 7.73, 7.73, 4.88 Hz), 2.92-3.02 (1H, m), 3.32-3.38 (1H, m), 3.38-3.45 (1H, m, 3.72 (1H, m), 3.38-3.45 (1H, q, J = 8.09 Hz), 3.97 (1H, td, J = 8.32, 4.88 Hz), 4.03 (1H, dd, J = 8.93, 7.10 Hz) | 100 | 237 [M + H], 259 [M + Na] |
| 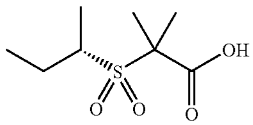 | (500 MHz, CHLOROFORM-d) δ ppm 1.06 (3H, t, J = 7.48 Hz), 1.42 (3H, d, J = 7.02 Hz), 1.59-1.75 (7H, m), 1.98-2.15 (1H, m), 3.43-3.58 (1H, m), 6.09 (1H, br. s.) | 40 | 207 |
| 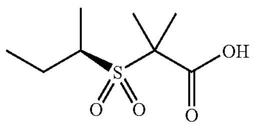 | (500 MHz, CHLOROFORM-d) δ ppm 1.06 (3H, t, J = 7.48 Hz), 1.42 (3H, d, J = 6.87 Hz), 1.60-1.77 (7H, m), 2.07 (1H, ddd, J = 13.96, 7.48, 3.74 Hz), 3.45-3.58 (1H, m), 5.30 (1H, br. s.) | 98 | 207 |

Alternative Acid Method F

Synthesis of 2-Methyl-2-(tetrahydro-pyran-4-sulfonyl)-propionic acid

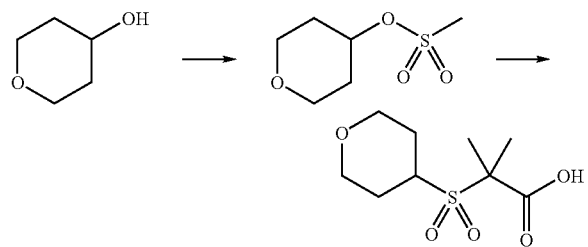

Step 1: Synthesis of Methansulfonic Acid Tetrahydropyran-4-yl ester 10 kg tetrahydropyran-4-ol are dissolved in a mixture of 50 L toluene and 10.4 kg triethylamine. 11.55 kg methanesulfonyl chloride in 100 ml toluene are added while maintaining the internal temperature below 20° C. by cooling, and the addition funnel is rinsed with 50 ml toluene. The stirring is continued for one hour. The precipitate is filtered and the filter cake is washed twice with 20 L toluene each. The filtrate is concentrated by vacuum evaporation (60 L were distilled of), seeding crystals and 50 L methylcyclohexane are added. The suspension is cooled to 2° C. After 1 h the product is isolated by filtration, washed with 30 L methylcyclohexane and dried at 30° C. 16.6 kg of the product are obtained as a white solid. Yield: 94%; ¹H NMR (400 MHz, DMSO-d6) δ ppm 1.62-1.73 (2H, m), 1.92-2.00 (2H, m), 3.19 (3H, s), 3.42-3.49 (2H, m), 3.77-3.83 (2H, m), 4.80-4.88 (1H, m).

Step 2: Synthesis of 2-Methyl-2-(tetrahydro-pyran-4-sulfonyl)-propionic Acid 30 g tetrahydro-2H-pyran-4-yl methansulfonate are dissolved in 270 ml degassed ethanol. 19.96 g potassium thioacetate are added and the reaction mixture is stirred at 77° C. for 12-18 h. Upon cooling to 20° C., the precipitate is filtered and rinsed twice with 90 ml degassed ethanol. 6.66 g sodium hydroxide solution (50%) are added to the filtrate, and the addition funnel is rinsed with 15 ml water. The reaction mixture is stirred at 25° C. for 1 h. 32.47 g 2-bromo-2-methyl-propionic acid ethyl ester ethyl are added to the mixture, and the addition funnel is rinsed with 30 ml ethanol. The stirring is continued for 1 h at 25° C. Afterwards, 450 ml solvent are removed by vacuum evaporation. 240 ml toluene are added and 120 ml solvent are distilled of 90 ml water are added and the phases are separated. To the organic layer subsequently 90 ml water, 2.75 g sodium tungstate dihydrate and 2.83 g tetrabutylammonium hydrogen sulfate are added. The reaction mixture is heated to 85° C. and 80.88 g hydrogen peroxide solution (35%) are added over a period of 1 h. The addition funnel is rinsed with 30 ml water. The stirring is continued for 1 h at 85° C. The reaction mixture is filtered and the phases are separated. The organic phase is subsequently washed with 12.66 g sodium metabisulfite dissolved in 114 ml water and again with 126 ml water. 19.98 g sodium hydroxide solution (50%) are added to the organic layer and the addition funnel is rinsed with 45 ml water. The reaction mixture is warmed to 50° C. for 1 h. The phases are separated. The water phase is cooled to 5° C. and acidified with 27.07 g HCl (37%). The stirring at 5° C. is continued for 1 h. The precipitate is filtered, rinsed with 37.5 ml water and dried at 50° C. 14.03 g of the product are obtained as a white solid. Yield: 35%. ES-MS: m/z 237 [M+H]; ¹H NMR (400 MHz, DMSO-d6) δ ppm 1.53 (6H, s), 1.62-1.75 (2H, m), 1.85-1.92 (2H, m), 3.39 (2H, dt, $^3J_{H,H}$=2.1 Hz, $^3J_{H,H}$=11.7 Hz), 3.88-3.98 (3H, m), 13.63 (1H, s).

Acid Method G

Synthesis of 2-(Azetidine-1-sulfonyl)-2-methyl-propionic acid

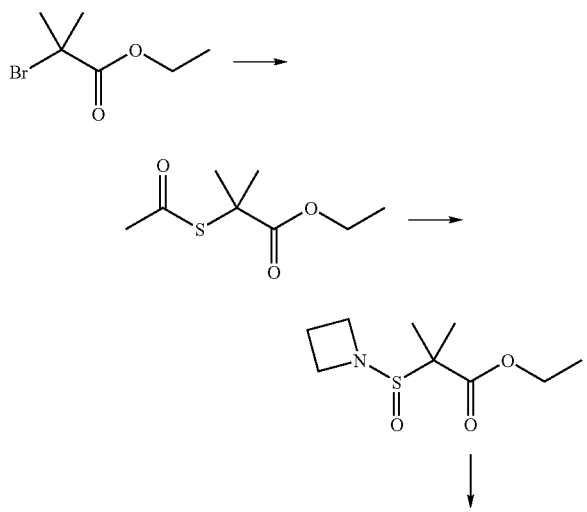

Step 1: Synthesis of 2-acetylsulfanyl-2-methyl-propionic acid ethyl ester

To a solution of 62 g (0.32 mol) of ethyl α-bromoisobutyrate in DMF (500 mL) at room temperature are added 72 g (0.63 mol) of potassium thioacetate. The reaction is stirred for 16 h and then concentrated under reduced pressure. The residue is diluted with a 2M aqueous hydrochloric acid solution (500 mL) and extracted with ethyl acetate (3×500 mL). The organic fractions are combined, washed with brine (300 mL), dried over MgSO₄, filtered and concentrated under reduced pressure. Purification of the residue by column chromatography (silica, eluent heptanes, DCM) provides 44 g of 2-acetylsulfanyl-2-methyl-propionic acid ethyl ester. Yield: 73%; ES-MS: m/z 191 [M+H]; $^1$H NMR (400 MHz, CHLOROFORM-d) δ ppm 1.27 (3H, t, J=7.09 Hz), 1.58 (6H, s), 2.28 (3H, s), 4.20 (2H, q, J=7.09 Hz)

Step 2: Synthesis of 2-(azetidine-1-sulfinyl)-2-methyl-propionic acid ethyl ester Chlorine gas is bubbled through a biphasic mixture of 5 g (26 mmol) of 2-acetylsulfanyl-2-methyl-propionic acid ethyl ester in DCM (50 mL) and water (50 mL) at 10° C. for 10 min. After this time, the organic phase is separated, dried over Na₂SO₄, filtered and concentrated under reduced pressure. The crude sulfinyl chloride is re-dissolved in DCM (50 mL) and N,N-diisopropylethylamine (4.58 mL, 26 mmol) and azetidine (1.5 g, 26 mmol) are introduced. The reaction is stirred at room temperature for 1 h and then concentrated under reduced pressure. The residue is purified by column chromatography (silica, eluent heptanes, ethyl acetate) provides 4.62 g of 2-(azetidine-1-sulfinyl)-2-methyl-propionic acid ethyl ester. Yield: 80%, ES-MS: m/z 220 [M+H].

According to this procedure the following esters are synthesized:

TABLE XX

| Structure | $^1$H NMR | Yield [%] | m/z [M + H] |
|---|---|---|---|
| (structure with fluoropyrrolidine) | (500 MHz, CHLOROFORM-d) δ ppm 1.21-1.33 (3H, m), 1.37-1.45 (3H, m), 1.45-1.54 (3H, m), 1.73-1.94 (1H, m), 2.02-2.24 (1H, m), 3.16-3.30 (1H, m), 3.32-3.47 (1H, m), 3.51-3.82 (2H, m), 4.11-4.29 (2H, m), 5.11-5.29 (1H, m) | 86 | 252 |
| (structure with azetidine) | (400 MHz, CHLOROFORM-d) δ ppm 1.23 (3H, t), 1.26 (3H, s), 1.37 (3H, s), 2.23 (2H, quin, J = 7.79 Hz), 3.63 (2H, q, J = 7.66 Hz), 3.94 (2H, q, J = 7.76 Hz), 4.08-4.23 (2H, m) | 80 | 220 |

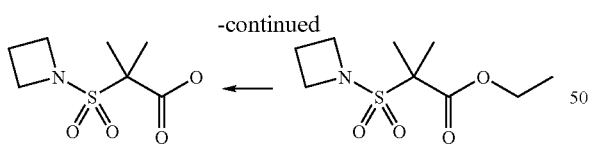

Step 3: Synthesis of 2-(azetidine-1-sulfonyl)-2-methyl-propionic acid ethyl ester To a solution of 4.62 g (21 mmol) of 2-(azetidine-1-sulfinyl)-2-methyl-propionic acid ethyl ester in DCM (100 mL) at room temperature are added 5.46 g (32 mmol) of meta-chloroperbenzoic acid. The reaction is stirred for 1 h before Ambersep 900-OH resin (2.9 g) is introduced. The suspension is shaken for 2 h and then filtered. The filtrate is concentrated under reduced pressure. The residue is dissolved in DCM (50 mL) and washed with a saturated aqueous NaHCO₃ solution (50 mL). The organic layer is dried (Na₂SO₄) and filtered. The solvent is removed under reduced pressure to provide 5 g of 2-(azetidine-1-sulfonyl)-2-methyl-propionic acid ethyl ester as an orange oil, which is used in the next step without further purification. Yield 100%, ES-MS: m/z 236 [M+H].

According to this procedure the following sulfonamides are synthesized:

TABLE XXI

| Structure | ¹H NMR | Yield [%] | m/z [M + H] |
|---|---|---|---|
| (azetidine sulfonyl isobutyrate ethyl ester structure) | 400 MHz, CHLOROFORM-d δ ppm 1.35 (3H, t), 1.64 (6H, s), 2.30 (2H, quin), 4.09 (4H, t), 4.27 (2H, q) | 100 | 236 |
| (3-fluoropyrrolidine sulfonyl isobutyrate ethyl ester structure) | (500 MHz, CHLOROFORM-d) δ ppm 1.24 (3H, t), 1.58 (6H, s), 1.88-2.08 (1H, m), 2.12-2.24 (1H, m), 3.52 (1H, td, J = 10.40, 6.26 Hz), 3.60-3.75 (3H, m), 4.18 (2H, q), 5.10-5.29 (1H, m) | 74 | 268 |

Step 4: Synthesis of 2-(azetidine-1-sulfonyl)-2-methyl-propionic acid

To a solution of 5 g (21 mmol) of 2-(azetidine-1-sulfonyl)-2-methyl-propionic acid ethyl ester in THF (200 mL) at room temperature are added 8.2 g (64 mmol) of potassium trimethylsilanolate. The reaction is stirred for 1 h. The mixture is diluted with 1M aqueous HCl solution (50 mL) and extracted with DCM (250 mL). The organic phase is dried over $Na_2SO_4$, filtered and the filtrate is concentrated under reduced pressure to provide 4.1 g of 2-(azetidine-1-sulfonyl)-2-methyl-propionic acid as a white solid. Yield: 94%, ES-MS: m/z 208 [M+H].

According to this procedure the following acids are synthesized:

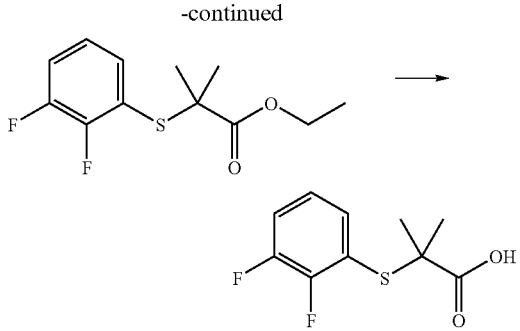

TABLE XXII

| Structure | ¹H NMR | Yield [%] | m/z [M + H] |
|---|---|---|---|
| (azetidine sulfonyl isobutyric acid structure) | (400 MHz, CHLOROFORM-d) δ ppm 1.58 (6H, s), 1.81 (2H, quin), 3.70-3.75 (2H, m), 4.02 (2H, t) | 94 | 208 |
| (3-fluoropyrrolidine sulfonyl isobutyric acid structure) | (500 MHz, CHLOROFORM-d) δ ppm 1.70 (6H, s), 1.97-2.15 (1H, m), 2.27 (1H, dt), 3.63 (1H, td, J = 10.43, 6.28 Hz), 3.68-3.74 (1H, m), 3.74-3.83 (2H, m), 5.29 (1H, d), 9.34 (1H, br. s.) | 80 | 238 [M − H] |

Acid Method H

Synthesis of 2-(2,3-Difluoro-phenylsulfanyl)-2-methyl-propionic acid

 

Step 1: Synthesis of 2-(2,3-Difluoro-phenylsulfanyl)-2-methyl-propionic acid ethyl ester Prepared as described by adaptation of the following references:

Katz et al. *J. Org. Chem.* 1954, 19, 711-715; Zhang et al. *J. Am. Chem. Soc.* 1997, 119, 1676-1681.

To a solution of 5 g (38.7 mmol) of 2,3-difluoroaniline in acetic acid (37 mL) at 0° C. are added 9 ml of sulfuric acid and the mixture is cooled to 0° C. A solution of 3.47 g (50.35 mmol) of sodium nitrite in water (23 mL) is added dropwise over 15 min whilst maintaining the temperature below 10° C. The resulting solution is stirred at 0° C. for 1 h, then 0.75 g (11.6 mmol) of urea are added and the mixture is stirred for 5 min at 0° C. Then 7.36 g (38.7 mmol) of CuI are added portionwise and the reaction mixture is stirred for a further 20 min. This mixture is then added to a solution of 22.31 g (139.4 mmol) of potassium ethyl xanthate in water (40 mL) at 0° C. and the resulting mixture is heated to 80° C. for 2 h. After cooling to 0° C., the resulting solid is removed by filtration, washed with DCM. The filtrate and the DCM washes are combined and extracted with DCM (3×100 mL). The combined organic extracts are washed with saturated aqueous NaHCO$_3$ solution (2×100 mL), dried over Na$_2$SO$_4$, filtered and concentrated under reduced pressure.

The resulting brown oil is dissolved in ethanol (140 mL), degassed under nitrogen atmosphere for 20 min, and 6.51 g (116.2 mmol) of potassium hydroxide are added. The reaction is heated to 80° C. for 1 h before 17 mL (116.2 mmol) of ethyl α-bromoisobutyrate are added. The mixture is stirred at 80° C. for 3 h, then allowed to cool to room temperature and stirred for 18 h. The reaction mixture is filtered and the filtrate is concentrated under reduced pressure. Purification by column chromatography (silica, eluent heptanes, 20-100% DCM) afforded 1.64 g of 2-(2,3-difluoro-phenylsulfanyl)-2-methyl-propionic acid ethyl ester. Yield: 16%, ES-MS: m/z 261 [M+H]

According to this procedure the following thioethers are synthesized

TABLE XXIII

| Structure | $^1$H NMR | Yield [%] | m/z [M + H] |
|---|---|---|---|
| 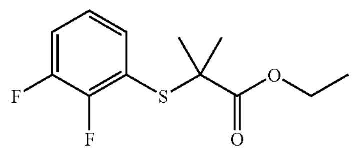 | (500 MHz, CHLOROFORM-d) δ ppm 1.25 (3H, t, J = 7.15 Hz), 1.53 (6H, s), 4.15 (2H, q, J = 7.12 Hz), 7.03-7.12 (1H, m), 7.20-7.31 (2H, m) | 16 | 261 |
| 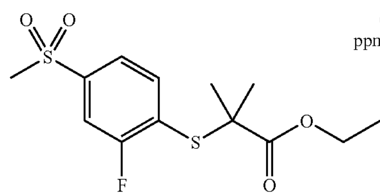 | (250 MHz, CHLOROFORM-d) δ ppm 1.17 (3H, t, J = 7.08 Hz), 1.47 (6H, s), 3.02 (3H, s), 4.08 (2H, q, J = 7.16 Hz), 7.55-7.68 (3H, m) | 22 | 321 |

Step 2: Synthesis of 2-(2,3-difluoro-phenylsulfanyl)-2-methyl-propionic acid

To a solution of 1.64 g (6.31 mmol) of 2-(2,3-difluoro-phenylsulfanyl)-2-methyl-propionic acid ethyl ester in THF (165 mL) at room temperature are added 1.62 g (12.6 mmol) of potassium trimethylsilanolate. The reaction is stirred at room temperature for 18 h. The solvent is removed under reduced pressure and the residue is partitioned between water and diethyl ether. The basic aqueous layer is separated, acidified using 1M aqueous HCl solution to pH 1 and extracted with DCM (3×100 mL). The organic phase is dried over MgSO$_4$, filtered and the filtrate is concentrated under reduced pressure to give 1.32 g of 2-(2,3-difluoro-phenylsulfanyl)-2-methyl-propionic acid as a pale yellow solid. Yield: 90%, ES-MS: m/z 231 [M−H].

According to this procedure the following acids are synthesized:

TABLE XXIV

| Structure | $^1$H NMR | Yield [%] | m/z [M − H] |
|---|---|---|---|
| 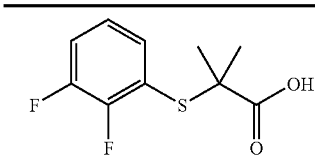 | (500 MHz, CHLOROFORM-d) δ ppm 1.37 (6H, s), 6.88-6.96 (1H, m), 7.04-7.18 (2H, m) | 90 | 231 |
| 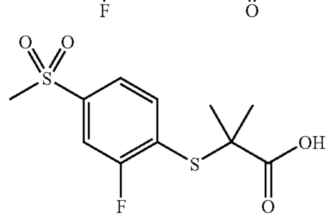 | (250 MHz, CHLOROFORM-d) δ ppm 1.59 (6H, s), 3.14 (3H, s), 7.68-7.84 (3H, m) | 98 | 291 |

Acid Method I

Synthesis of 2-(1-Methanesulfonyl-piperidine-4-sulfonyl)-2-methyl-propionic acid

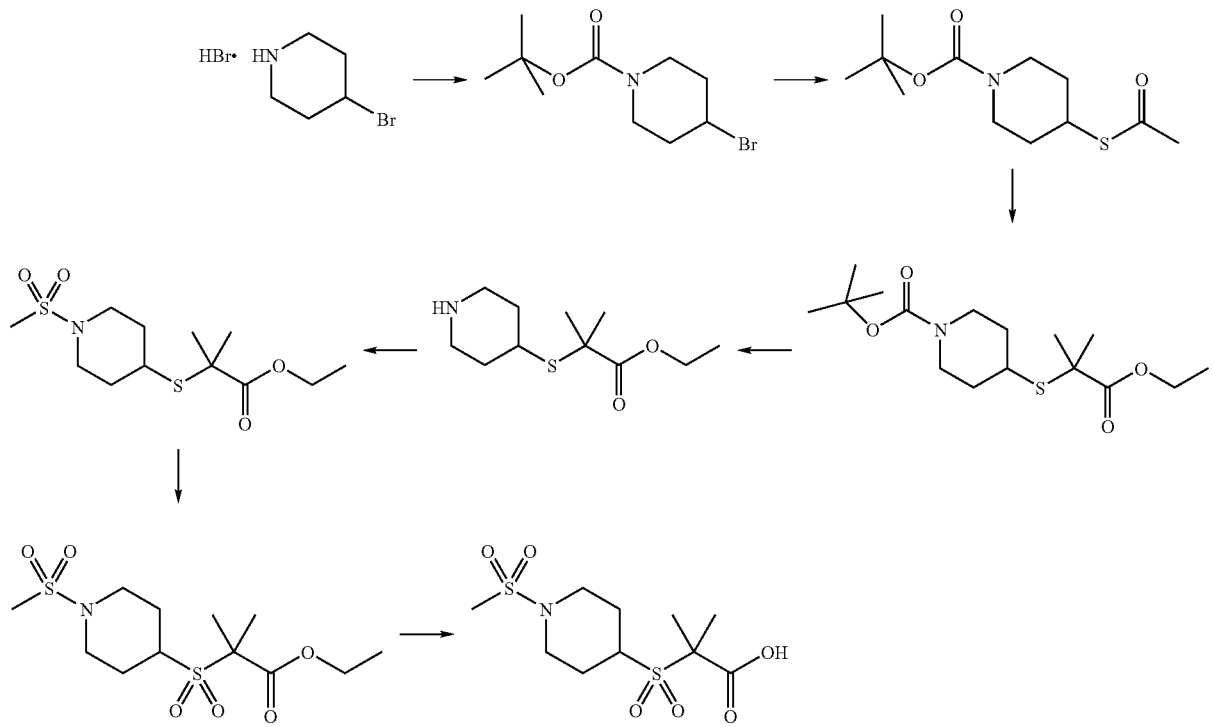

Step 1: Synthesis of 4-Bromo-piperidine-1-carboxylic acid tert-butyl ester

To a suspension of 5 g (0.02 mol) of 4-bromopiperidine hydrobromide salt in DCM (35 mL) are added 7.09 ml, (0.04 mol) of N,N-diisopropylethyl amine dropwise at 0° C. The reaction mixture is stirred for 30 min, then a solution of 6.67 g (0.31 mol) of di-tert-butyl dicarbonate in DCM (35 mL) is added dropwise to the reaction mixture. The reaction mixture is stirred for 18 h at room temperature, then washed with 1M aqueous HCl solution (2×30 mL) and brine (30 mL). The organic layer is dried over $Na_2SO_4$, filtered and the filtrate is concentrated under reduced pressure to afford 6.9 g of 4-bromo-piperidine-1-carboxylic acid tert-butyl ester as a yellow oil. Yield quantitative; $^1$H NMR (250 MHz, CHLOROFORM-d) δ ppm 1.46 (9H, s), 1.79-2.00 (2H, m), 2.00-2.16 (2H, m), 3.31 (2H, ddd, J=13.67, 7.73, 3.73 Hz), 3.68 (2H, ddd, J=13.55, 6.85, 3.65 Hz), 4.34 (1H, tt, J=7.69, 3.81 Hz)

Step 2: Synthesis of 4-Acetylsulfanyl-piperidine-1-carboxylic acid tert-butyl ester To a solution of 6.9 g (0.02 mol) of 4-bromo-piperidine-1-carboxylic acid tert-butyl ester in DMF (18 mL) are added 5.25 g (0.012 mmol) potassium thioacetate, followed by a catalytic amount of NaI (0.35 g, 10 mol %) at room temperature. After complete addition, the reaction is heated to 50° C. for 20 h. The reaction mixture is partitioned between ethyl acetate (100 mL) and water (100 mL). The organic layer is dried over $Na_2SO_4$, filtered and the solvent is removed under reduced pressure to afford 5.41 g of 4-acetylsulfanyl-piperidine-1-carboxylic acid tert-butyl ester as a brown oil. Yield: 81%; ES-MS: m/z 245 [M+H—$CH_3$], 160 [M+H—$C_5H_9O_2$]; $^1$H NMR (250 MHz, CHLOROFORM-d) δ ppm 1.37-1.64 (11H, m), 1.78-1.99 (2H, m), 2.25-2.35 (3H, m), 3.06 (2H, ddd, J=13.63, 10.43, 3.05 Hz), 3.61 (1H, tt, J=10.28, 4.04 Hz), 3.76-3.96 (2H, m)

Step 3: Synthesis of 4-(1-Ethoxycarbonyl-1-methyl-ethylsulfanyl)-piperidine-1-carboxylic acid tert-butyl ester A solution of 5.41 g (0.02 mmol) of 4-acetylsulfanyl-piperidine-1-carboxylic acid tert-butyl ester in ethanol (50 mL) is degassed with nitrogen over 0.5 h and 2.34 g (0.04 mol) of KOH are added, followed by 8.14 g (0.04 mol) of ethyl α-bromoisobutyrate. The reaction is stirred for 18 h at room temperature under a nitrogen atmosphere. The reaction mixture is concentrated under reduced pressure. The residue is partitioned between DCM (100 mL) and water (100 mL). The organic layer is washed with water (50 mL), brine (250 mL), dried over $Na_2SO_4$ and filtered. The filtrate is concentrated under reduced pressure and purified by column chromatography (silica, eluent heptanes, 50% ethyl acetate) to afford 6.05 g of 4-(1-ethoxycarbonyl-1-methyl-ethylsulfanyl)-piperidine-1-carboxylic acid tert-butyl ester as a brown oil. Yield: 87%; ES-MS: m/z 354 [M+Na], 232 [[M+H—$C_5H_9O_2$]; $^1$H NMR (500 MHz, CHLOROFORM-d) δ ppm 1.25-1.35 (3H, m), 1.46 (9H, s), 1.48-1.53 (2H, m), 1.55 (6H, s), 1.88 (2H, dd, J=13.31, 3.47 Hz), 2.94-3.04 (3H, m), 3.81-3.92 (2H, m), 4.19 (2H, q, J=7.10 Hz)

Step 4: Synthesis of 2-Methyl-2-(piperidin-4-ylsulfanyl)-propionic acid ethyl ester Deprotection of 6.05 g (18.3 mmol) of 4-(1-ethoxycarbonyl-1-methyl-ethylsulfanyl)-piperidine-1-carboxylic acid tert-butyl ester is achieved by treatment with 4M aqueous HCl solution (9.13 mL) in 1,4-dioxane (40 mL) at room temperature for 18 h. The reaction mixture is concentrated to afford 4.47 g of 2-methyl-2-(piperidin-4-ylsulfanyl)-propionic acid ethyl ester as its hydrochloride salt as a brown oil. Yield: 92%; ES-MS: m/z 232 [M+H]

$^1$H NMR (500 MHz, CHLOROFORM-d) δ ppm 1.21 (3H, t, J=7.13 Hz), 1.45 (6H, s), 1.80-1.90 (2H, m), 2.17 (2H, ddd, J=10.78, 7.31, 3.66 Hz), 2.96-3.05 (2H, m), 3.07-3.15 (1H, m), 3.18-3.30 (2H, m), 4.09 (2H, q, J=7.12 Hz), 9.44 (1H, br. s.), 9.54 (1H, br. s.)

Step 5: Synthesis of 2-(1-Methanesulfonyl-piperidin-4-ylsulfanyl)-2-methyl-propionic acid ethyl ester To a solution of 4.47 g (16.74 mmol) of 2-methyl-2-(piperidin-4-ylsulfanyl)-propionic acid ethyl ester hydrochloride salt in anhydrous THF (30 mL) are added 13.45 mL (77.36 mmol) of N,N-diisoproylethylamine, followed by 2.98 mL (38.58 mmol) of methanesulfonyl chloride. The reaction mixture is heated for 2 d to 60° C. The mixture is concentrated under reduced pressure and the residue is partitioned between saturated aqueous NaHCO$_3$ solution (75 mL) and ethyl acetate (75 mL). The basic aqueous layer is extracted with ethyl acetate (2×50 mL). The combined organic layer is separated and washed with brine (50 mL), dried over MgSO$_4$ and filtered. The filtrate is concentrated under reduced pressure and the residue is purified by column chromatography (silica, eluent: heptanes, 30% ethyl acetate) to give 2.17 g of 2-(1-methanesulfonyl-piperidin-4-ylsulfanyl)-2-methyl-propionic acid ethyl ester as a brown solid. Yield: 42%, ES-MS: m/z 310 [M+H]; $^1$H NMR (500 MHz, CHLOROFORM-d) δ ppm 1.22 (3H, t, J=7.11 Hz), 1.47 (6H, s), 1.59-1.69 (2H, m), 1.92-2.00 (2H, m), 2.70 (3H, s), 2.90-2.99 (3H, m), 3.39-3.47 (2H, m), 4.10 (2H, q, J=7.12 Hz)

Step 6: Synthesis of 2-(1-Methanesulfonyl-piperidine-4-sulfonyl)-2-methyl-propionic acid ethyl ester To a stirred solution of 2.17 g (7.02 mmol) of 2-(1-methanesulfonyl-piperidin-4-ylsulfanyl)-2-methyl-propionic acid ethyl ester in acetic acid (20 mL) are added 2.39 mL (35.1 mmol) of 50% aqueous hydrogen peroxide solution. The reaction is stirred at 80° C. for 1.5 h. After cooling the reaction mixture is concentrated under reduced pressure to afford 2.91 g of 2-(1-methanesulfonyl-piperidine-4-sulfonyl)-2-methyl-propionic acid ethyl ester as a white solid, which is used in the next step without further purification. Yield: quantitative; ES-MS: m/z 342 [M+H]; $^1$H NMR (250 MHz, CHLOROFORM-d) δ ppm 1.36 (3H, t, J=7.14 Hz), 1.70 (6H, s), 2.06-2.27 (4H, m), 2.83 (3H, s), 2.93-3.06 (2H, m), 3.75-3.89 (3H, m), 4.29 (2H, q, J=7.13 Hz)

Step 7: Synthesis of 2-(1-Methanesulfonyl-piperidine-4-sulfonyl)-2-methyl-propionic acid To a suspension of 2.91 g (8.53 mmol) of 2-(1-methanesulfonyl-piperidine-4-sulfonyl)-2-methyl-propionic acid ethyl ester in THF/water (1/1, 60 mL) are added 2.56 g (34.13 mmol) of lithium hydroxide monohydrate. The reaction is stirred at room temperature for 3 d and then concentrated under reduced pressure. The residue is partitioned between brine (20 mL) and DCM (20 mL). The aqueous layer is further acidified with 2M aqueous HCl solution to pH 1 and extracted with DCM. The combined organic extracts are concentrated under reduced pressure to afford 1.68 g of 2-(1-methanesulfonyl-piperidine-4-sulfonyl)-2-methyl-propionic acid. Yield 63%, ES-MS: 314 [M+H]; $^1$H NMR (500 MHz, MeOD) δ ppm 1.66 (6H, s), 1.86-1.97 (2H, m), 2.24 (2H, dd, J=13.64, 2.54 Hz), 2.87 (3H, s), 2.92 (2H, td, J=12.00, 2.59 Hz), 3.81 (2H, dt, J=12.45, 3.13 Hz), 3.94 (1H, tt, J=11.41, 3.79 Hz)

Acid Method J

Synthesis of 2-Methyl-2-{[(2S)-oxan-2-ylmethyl]sulfanyl}propanoic acid

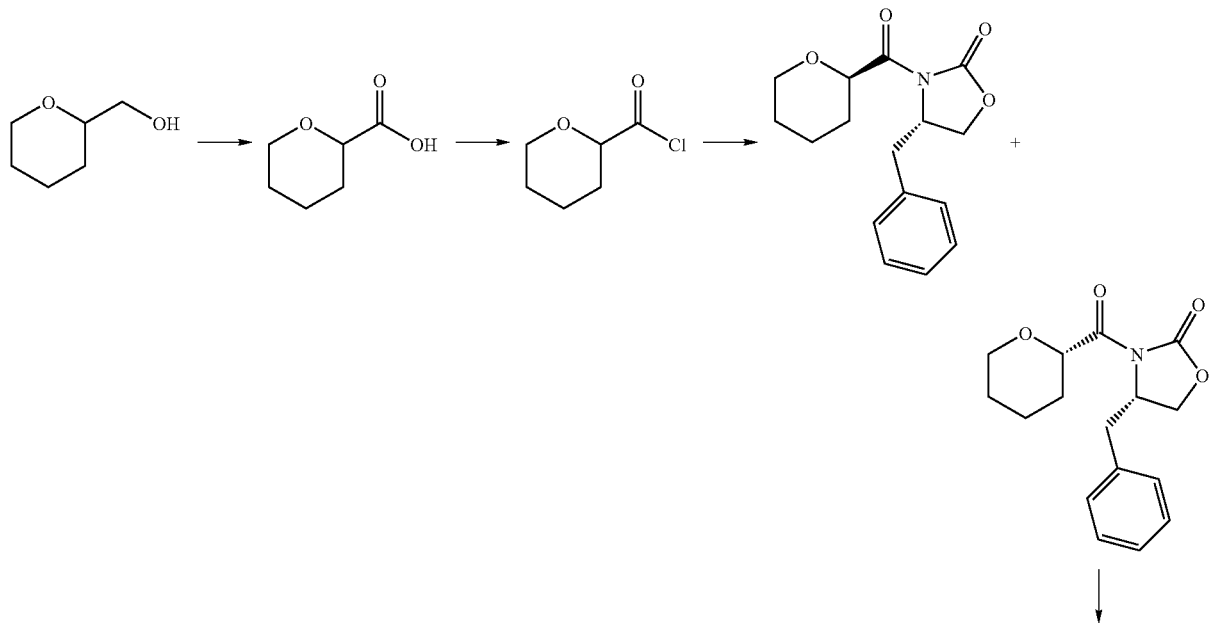

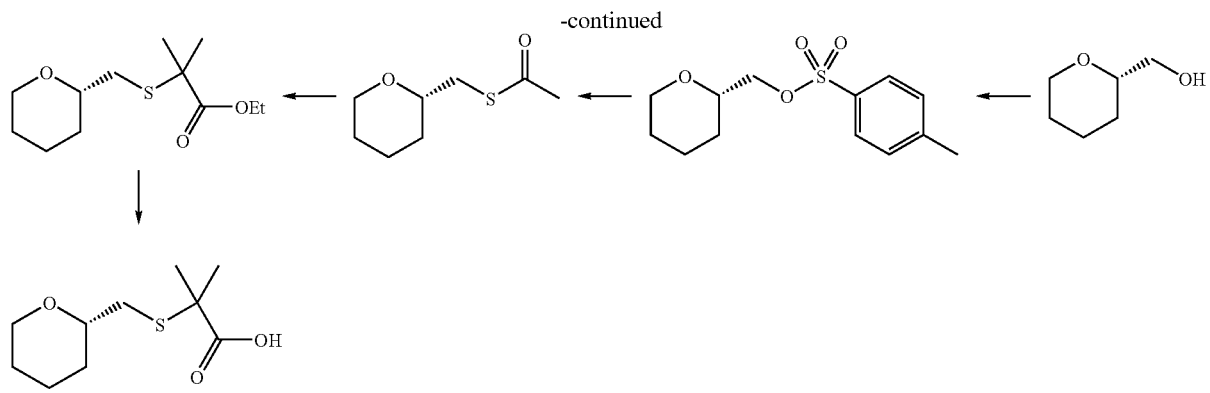

Step 1: Synthesis of Tetrahydro-pyran-2-carboxylic acid

The synthesis of tetrahydro-pyran-2-carboxylic acid is described in Buckmelter, A. et al. *J. Am. Chem. Soc.* 2000, 122, 9386-9390.

A solution of tetrahydropyran-2-methanol (15.63 g, 135 mmol) in DCM (280 mL) are cooled to 0° C. TEMPO (0.25 g, 1.59 mmol) is added, followed by Aliquat 336 (2.8 g, 6.93 mmol) and 0.5 M aqueous KBr solution (27 mL, 13.5 mmol). Under vigorous stirring a solution of NaOCl/water (pH 8.6, 960 mL) and NaHCO$_3$ (57.6 g) is added dropwise. The reaction is allowed to warm to room temperature and stirred for 18 h. Sodium hydroxide (15 g) is added and the reaction mixture is washed with DCM (2×100 mL). The basic aqueous layer is carefully acidified with concentrated aqueous HCl solution (150 mL) and then extracted with ethyl acetate (8×250 mL). The combined organic extracts are dried (MgSO$_4$), filtered and the filtrate is concentrated under reduced pressure to give a pale yellow oil, which is purified by distillation under reduced pressure (bp 144-146° C., 25 Torr) to give 6.74 g of tetrahydro-pyran-2-carboxylic acid. Yield: 35%; $^1$H NMR (250 MHz, CHLOROFORM-d) δ ppm 1.45-1.77 (4H, m), 1.79-2.19 (2H, m), 3.44-3.67 (1H, m), 3.93-4.18 (2H, m), 9.62 (1H, br. s.)

Step 2: Synthesis of Tetrahydro-pyran-2-carbonyl chloride

To a solution of tetrahydro-pyran-2-carboxylic acid (6.94 g, 47.96 mmol) in DCM (200 mL) are added oxalyl chloride (4.81 mL, 56.83 mmol) as a solution in DCM (50 mL) and DMF (3 drops). The reaction is stirred at room temperature for 18 h, then concentrated under reduced pressure to afford 7.1 g of tetrahydro-pyran-2-carbonyl chloride, which is used in the next step. Yield: 99%; by 58° C., 1 mm Hg; $^1$H NMR (250 MHz, CHLOROFORM-d) δ ppm 1.49-1.98 (5H, m), 2.02-2.19 (1H, m), 3.46-3.66 (1H, m), 3.96-4.12 (1H, m), 4.24 (1H, dd, J=9.14, 3.20 Hz)

Step 3: Synthesis of (4S)-4-benzyl-3-{[(2S)-oxan-2-yl]carbonyl}-1,3-oxazolidin-2-one To a stirred solution of (4S)-4-benzyl-1,3-oxazolidin-2-one (9.31 g, 52.56 mmol) in anhydrous THF (150 mL) is added n-butyllithium (2.5 M in hexanes, 21.05 mL, 52.56 mmol) over 25 min at −78° C. Then a solution of tetrahydro-pyran-2-carbonyl chloride (7.1 g, 47.78 mmol) in anhydrous THF (12 mL) is added dropwise. The reaction is stirred at −70° C. for 0.5 h, then allowed to warm to room temperature and stirred for 2 h. Saturated aqueous NH$_4$Cl solution (20 mL) is added and the reaction mixture is concentrated under reduced pressure. The residue is partitioned between ethyl acetate (200 mL) and water (50 mL). The organic layer is separated, washed with saturated aqueous NaHCO$_3$ solution (2×50 mL), brine (50 mL), dried (MgSO$_4$) and filtered. The filtrate is concentrated under reduced pressure and the mixture of diastereoisomers is separated by multiple column chromatography (silica, eluent: toluene, 0-20% TBME) to afford 3.81 g of (4S)-4-benzyl-3-{[(2S)-oxan-2-yl]carbonyl}-1,3-oxazolidin-2-one (78%, yield: 22%; ES-MS: m/z 290 [M+H]; $^1$H NMR (500 MHz, CHLOROFORM-d) δ ppm 1.46-1.72 (4H, m), 1.81-1.90 (2H, m), 2.71 (1H, dd, J=13.43, 9.77 Hz), 3.30 (1H, dd, J=13.43, 3.05 Hz), 3.54 (1H, td, J=11.52, 2.14 Hz), 4.06-4.19 (3H, m), 4.60 (1H, m, J=9.88, 6.75, 3.28, 3.28 Hz), 4.97 (1H, dd, J=10.60, 1.91 Hz), 7.12-7.30 (5H, m)) and 1.65 g of (4S)-4-benzyl-3-{[(2R)-oxan-2-yl]carbonyl}-1,3-oxazolidin-2-one (93%, yield: 11%; ES-MS: m/z 290 [M+H]; $^1$H NMR (500 MHz, CHLOROFORM-d) δ ppm 1.54-1.80 (4H, m), 1.90-2.06 (2H, m), 2.83 (1H, dd, J=13.58, 9.16 Hz), 3.24 (1H, dd, J=13.50, 3.28 Hz), 3.53-3.61 (1H, m), 4.11-4.17 (1H, m), 4.19-4.24 (1H, m), 4.25-4.31 (1H, m), 4.71-4.78 (1H, m), 4.96 (1H, dd, J=10.60, 2.06 Hz), 7.16-7.37 (5H, m))

Step 4: Synthesis of (2S)-oxan-2-ylmethanol

To a stirred solution of (4S)-4-benzyl-3-{[(2S)-oxan-2-yl]carbonyl}-1,3-oxazolidin-2-one (85%, 6.26 g, 18.39 mmol) and water (0.36 mL, 20.23 mmol) in diethyl ether (600 mL) is added dropwise lithium borohydride solution (2M in THF, 10.11 mL, 20.23 mmol) at 0° C. The reaction mixture is stirred at 0° C. for 0.5 h, then warmed to room temperature and stirred for 18 h. The reaction is quenched by dropwise addition of 2M aqueous NaOH solution (10.1 mL, 20.23 mmol) and stirred vigorously for 20 min. The organic layer is separated, dried (MgSO$_4$) and filtered. The filtrate is concentrated under reduced pressure and the residue is purified by column chromatography (silica, eluent: heptanes, 0-50% ethyl acetate) to afford 2.18 g of (2S)-oxan-2-ylmethanol. Yield: 97%, $^1$H NMR (500 MHz, CHLOROFORM-d) δ ppm 1.30-1.39 (1H, m), 1.45-1.74 (4H, m), 1.82-1.92 (1H, m), 2.08-2.20 (1H, m), 3.38-3.62 (4H, m), 4.02 (1H, dd, J=11.44, 1.98 Hz) *[α]$^{25}_{578}$+19.2 (1, water).

According to the above procedure, (2R)-oxan-2-ylmethanol is synthesised from (4S)-4-benzyl-3-{[(2R)-oxan-2-yl]carbonyl}-1,3-oxazolidin-2-one. Yield: 92%, $^1$H NMR (500 MHz, CHLOROFORM-d) δ ppm 1.14-1.33 (1H, m), 1.36-1.59 (4H, m), 1.71-1.85 (1H, m), 1.96 (1H, br. s.), 3.29-3.54 (4H, m), 3.88-3.99 (1H, m)

Step 5: Synthesis of (2S)-oxan-2-ylmethyl 4-methylbenzene-1-sulfonate

To a solution of 2.18 g (18.75 mmol) of (2S)-oxan-2-ylmethanol in pyridine (25 mL) are added 7.15 g (37.5 mmol) of p-toluenesulfonylchloride portionwise at 10° C. After complete addition the reaction is allowed to warm to room temperature and stirred for 18 h. The reaction is poured onto a stirred mixture of 6M aqueous HCl/ice. The mixture is extracted with DCM (3×25 mL). The organic layer is dried (MgSO$_4$), filtered and the filtrate is concentrated under reduced pressure to give 3.91 g of (2S)-oxan-2-ylmethyl 4-methylbenzene-1-sulfonate. Yield: 76%, ES-MS: m/z: 293 [M+Na]; $^1$H NMR (500 MHz, CHLOROFORM-d) δ ppm 1.21-1.32 (1H, m), 1.41-1.60 (4H, m), 1.80-1.90 (1H, m), 2.45 (3H, s), 3.37 (1H, td, J=11.41, 2.82 Hz), 3.48-3.58 (1H, m), 3.89-3.98 (3H, m), 7.34 (2H, d, J=8.09 Hz), 7.80 (2H, d, J=8.24 Hz).

According to the above procedure, (2R)-oxan-2-ylmethyl 4-methylbenzene-1-sulfonate is synthesised from (2R)-oxan-2-ylmethanol. Yield: 57%; m/z 293 [M+Na], $^1$H NMR (500 MHz, CHLOROFORM-d) δ ppm 1.19-1.34 (1H, m), 1.40-1.63 (4H, m), 1.79-1.91 (1H, m), 2.47 (3H, s), 3.39 (1H, td, J=11.41, 2.82 Hz), 3.50-3.62 (1H, m), 3.89-4.02 (3H, m), 7.36 (2H, d, J=8.39 Hz), 7.82 (2H, d, J=8.24 Hz)

Step 6: Synthesis of 1-{[(2S)-oxan-2-ylmethyl]sulfanyl}ethan-1-one

To a solution of 3.90 g (14.41 mmol) of (2S)-oxan-2-ylmethyl 4-methylbenzene-1-sulfonate in DMF (40 mL) are added 3.29 g (28.83 mmol) potassium thioacetate at room temperature.

After complete addition, the reaction is stirred at room temperature for 18 h, then heated to 50° C. for further 20 h. The reaction mixture is diluted with ethyl acetate (250 mL) and washed with saturated aqueous NaHCO$_3$ solution (2×100 mL) and water (2×100 mL). The organic layer is dried (MgSO$_4$), filtered and the filtrate is concentrated under reduced pressure to afford 2.79 g of 1-{[(2S)-oxan-2-ylmethyl]sulfanyl}ethan-1-one. Yield: 93%; ES-MS: m/z 175 [M+H]; $^1$H NMR (500 MHz, CHLOROFORM-d) δ ppm 1.17-1.36 (2H, m), 1.42-1.59 (2H, m), 1.63-1.72 (1H, m), 1.79-1.88 (1H, m), 2.34 (3H, s), 2.84-2.93 (1H, m), 3.10 (1H, dd, J=13.73, 4.27 Hz), 3.30-3.47 (2H, m), 3.98 (1H, dt, J=11.41, 2.08 Hz). According to the above procedure, 1-{[(2R)-oxan-2-ylmethyl]sulfanyl}ethan-1-one is synthesised from (2R)-oxan-2-ylmethyl 4-methylbenzene-1-sulfonate. Yield: 91%; m/z 175 [M+H]; $^1$H NMR (500 MHz, CHLOROFORM-d) δ ppm 1.14-1.41 (2H, m), 1.42-1.66 (3H, m), 1.66-1.77 (1H, m), 1.79-1.95 (1H, m), 2.31-2.42 (3H, m), 2.82-2.95 (1H, m), 3.12 (1H, dd, J=13.73, 4.27 Hz), 3.36-3.51 (1H, m), 4.00 (1H, dt, J=11.44, 2.14 Hz)

Step 7: Synthesis of ethyl 2-methyl-2-{[(2S)-oxan-2-ylmethyl]sulfanyl}propanoate A solution of 2.79 g (13.45 mmol) of 1-{[(2S)-oxan-2-ylmethyl]sulfanyl}ethan-1-one in ethanol (60 mL) is degassed with nitrogen over 0.5 h and 1.51 g (26.91 mmol) of KOH are added. Then 3.99 mL (26.91 mmol) of ethyl α-bromoisobutyrate are added slowly. The reaction is stirred for 18 h at room temperature under a nitrogen atmosphere. The reaction mixture is filtered, the solid is rinsed with ethanol and the filtrate is concentrated under reduced pressure. The crude material is purified by column chromatography (silica, eluent: n-heptanes, 0-20% ethyl acetate) to afford 2.68 g of ethyl 2-methyl-2-{[(2S)-oxan-2-ylmethyl]sulfanyl}propanoate (purity 90%). Yield: 72%; ES-MS: m/z 247 [M+H]; $^1$H NMR (500 MHz, CHLOROFORM-d) δ ppm 1.23-1.36 (5H, m), 1.45-1.59 (8H, m), 1.68 (1H, d, J=13.12 Hz), 1.83 (1H, d, J=10.99 Hz), 2.62-2.71 (1H, m), 2.72-2.80 (1H, m), 3.25-3.47 (2H, m), 3.95-4.03 (1H, m), 4.17 (2H, q, J=7.12 Hz).

According to the above procedure, ethyl 2-methyl-2-{[(2R)-oxan-2-ylmethyl]sulfanyl}propanoate is synthesised from 1-{[(2R)-oxan-2-ylmethyl]sulfanyl}ethan-1-one. Yield: 49%; m/z 247 [M+H]; $^1$H NMR (500 MHz, CHLOROFORM-d) δppm 1.26-1.37 (4H, m), 1.43-1.63 (9H, m), 1.70 (1H, d, J=13.12 Hz), 1.81-1.90 (1H, m), 2.64-2.71 (1H, m), 2.74-2.81 (1H, m), 3.36-3.47 (2H, m), 4.00 (1H, dt, J=11.29, 2.06 Hz), 4.19 (2H, q, J=7.07 Hz)

Step 8: Synthesis of 2-methyl-2-{[(2S)-oxan-2-ylmethyl]sulfanyl}propanoic acid To a solution of 2.17 g (6.18 mmol) of ethyl 2-methyl-2-{[(2S)-oxan-2-ylmethyl]sulfanyl}propanoate (70%) in THF/water (1/1, 40 mL) are added 1.39 g (18.52 mmol) of lithium hydroxide monohydrate. The reaction is stirred at room temperature for 2 d, then concentrated under reduced pressure to remove the organic solvent. The aqueous residue is washed with diethyl ether (200 mL), then acidified with 6N aqueous HCl solution and extracted with ethyl acetate (3×20 mL). The combined organic extracts are dried (MgSO$_4$), filtered and the filtrate is concentrated under reduced pressure to give 2.07 g of 2-methyl-2-{[(2S)-oxan-2-ylmethyl]sulfanyl}propanoic acid (58 wt % by NMR, residual solvent). Yield: 89%, ES-MS: m/z 219 [M+H]; $^1$H NMR (500 MHz, CHLOROFORM-d) δ ppm 1.29-1.42 (1H, m), 1.45-1.61 (9H, m), 1.65-1.73 (1H, m), 1.80-1.90 (1H, m), 2.71-2.75 (1H, m), 2.78-2.84 (1H, m), 3.37-3.49 (2H, m), 4.00 (1H, dt, J=11.41, 2.16 Hz).

According to the above procedure, 2-methyl-2-{[(2R)-oxan-2-ylmethyl]sulfanyl}propanoic acid is synthesised from ethyl 2-methyl-2-{[(2R)-oxan-2-ylmethyl]sulfanyl}propanoate. Yield: 54%, m/z 219 [M+H]; $^1$H NMR (500 MHz, CHLOROFORM-d) δppm 1.22-1.33 (1H, m), 1.34-1.55 (9H, m), 1.56-1.68 (1H, m), 1.73-1.85 (1H, m), 2.57-2.78 (2H, m), 3.31-3.43 (2H, m), 3.93 (1H, dt, J=11.29, 2.21 Hz), 9.59 (1H, br. s.).

Amine Method A

Synthesis of 2-(5-Amino-isoxazol-3-yl)-2-methyl-propan-1-ol

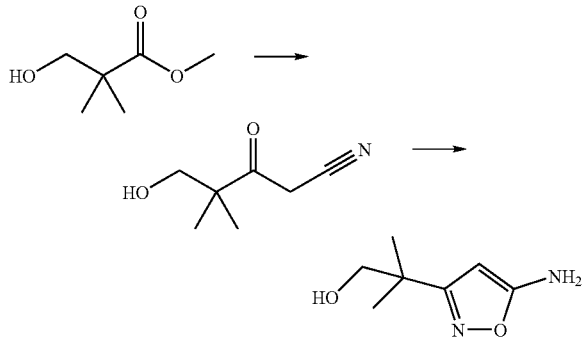

Step 1: Synthesis of 5-Hydroxy-4,4-dimethyl-3-oxo-pentanenitrile

To a solution of 4.07 mL (32 mmol) of methyl 2,2-dimethyl-3-hydroxypropionate in anhydrous DMF (60 mL) are added 3.26 g (47.90 mmol) of imidazole and 5.78 g (38.32 mmol) of tert-butyl-dimethylsilyl chloride under nitrogen atmosphere. The mixture is stirred at room temperature for 20 h.

The reaction mixture is quenched with water (200 mL) and extracted with diethyl ether (3×300 mL). The combined organic layers are washed with water and brine, dried over $Na_2SO_4$, filtered and concentrated under reduced pressure to afford 9.22 g of 3-(tert-Butyl-dimethyl-silanyloxy)-2,2-dimethyl-propionic acid methyl ester as a yellow oil. $^1$H NMR (400 MHz, CHLOROFORM-d) δ ppm −0.04-0.02 (6H, m), 0.80-0.88 (9H, m), 1.13 (6H, s), 3.55 (2H, s), 3.63 (3H, s)+residual DMF)

A solution of 9.22 g of 3-(tert-Butyl-dimethyl-silanyloxy)-2,2-dimethyl-propionic acid methyl ester and acetonitrile (2.34 mL, 44.88 mmol) in toluene (25 mL) is added dropwise over 1 h at reflux to a suspension of 1.80 g (44.88 mmol) NaH (60% dispersion in mineral oil) in anhydrous toluene (50 mL). The reaction mixture is heated to 110° C. for 18 h. The reaction mixture is diluted with 1M aqueous HCl solution to pH 7 and extracted with ethyl acetate (3×200 mL). The organic layers are combined, washed with water and brine, dried over $Na_2SO_4$ and filtered. The filtrate is concentrated under reduced pressure to afford 4.79 g of 5-hydroxy-4,4-dimethyl-3-oxo-pentanenitrile as a dark biphasic oil which is used crude in the next step. $^1$H NMR (400 MHz, CHLOROFORM-d) δ ppm 1.17 (s, 6H), 3.55 (s, 2H), 3.61 (s, 2H). Spectrum recorded on crude material, signals of TBMDS are present.

Step 2: Synthesis of 2-(5-Amino-isoxazol-3-yl)-2-methyl-propan-1-ol

To a stirred solution of 4.79 g (18.7 mmol) of 5-hydroxy-4,4-dimethyl-3-oxo-pentanenitrile and 3.08 g (76.7 mmol) of sodium hydroxide in water (300 mL) are added 3.23 g (19.7 mmol) of hydroxylamine sulfate. The reaction mixture is stirred at reflux temperature until completion.

After cooling to room temperature, the reaction mixture is neutralised to pH 7 by addition of 6M aqueous HCl solution. The aqueous layer is extracted with chloroform (2×50 mL) and then evaporated under reduced vacuum. The solid residue is washed with acetone (3×50 mL). The acetone filtrates are combined and concentrated under reduced pressure. The orange oil is purified by column chromatography (silica, eluent DCM, 50% ethyl acetate) to afford 287 mg of 2-(5-amino-isoxazol-3-yl)-2-methyl-propan-1-ol as a yellow/orange solid Yield: 10%; ES-MS: m/z 157 [M+H]; $^1$H NMR (400 MHz, CHLOROFORM-d) δ ppm 1.25 (6H, s), 3.62 (2H, s), 4.52 (2H, br. s.), 5.04 (1H, s).

Amine Method B

Synthesis of 3-[1,1-Dimethyl-2-(tetrahydro-pyran-2-yloxy)-ethyl]-isoxazol-5-ylamine

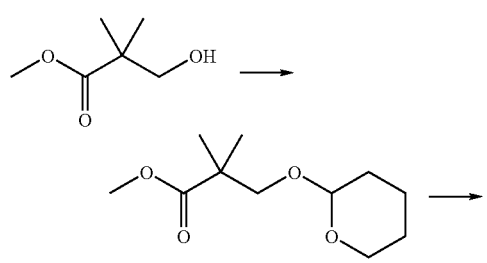

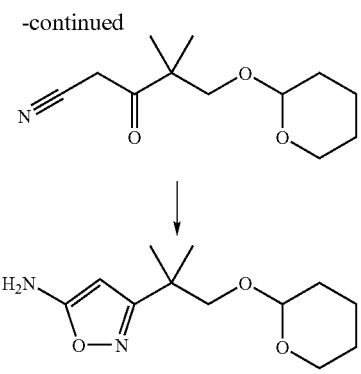

Step 1: Synthesis of 2,2-Dimethyl-3-(tetrahydro-pyran-2-yloxy)-propionic acid methyl ester To a solution of 66.3 mL (0.51 mol) of hydroxypivalic acid methyl ester in DCM (325 mL) are added 95.8 mL (1.04 mol) of 3,4-dihydro-2H-pyran. The reaction mixture is cooled to 0° C. and sulfuric acid on silica gel (2.04 g, 0.2 mL sulfuric acid/10 g silica gel) is added and the reaction mixture is stirred at room temperature for 25 minutes. After this time, the reaction mixture is filtered and concentrated under reduced pressure to yield 129 g of 2,2-dimethyl-3-(tetrahydro-pyran-2-yloxy)-propionic acid methyl ester as a yellow oil, which is used in the next step without further purification. Yield: quantitative; $^1$H NMR (400 MHz, DMSO-d6) δ ppm 1.12 (6H, s), 1.13 (6H, s), 1.4-1.7 (6H, m), 3.3 (1H, m), 3.4 (1H, m), 3.6 (3H, s), 3.65 (1H, d), 3.7 (1H, m), 4.55 (1H, t).

Step 2: Synthesis of 4,4-Dimethyl-3-oxo-5-(tetrahydro-pyran-2-yloxy)-pentanenitrile A solution of 129 g (0.60 mol) of 2,2-dimethyl-3-(tetrahydro-pyran-2-yloxy)-propionic acid methyl ester and 44 mL (0.84 mol) of acetonitrile in toluene (250 mL) is added dropwise to the refluxing suspension of 33 g (0.84 mol) of sodium hydride (60% in mineral oil) in toluene (600 mL) over a period of 2 h. After the addition, the reaction mixture is stirred at reflux for 3 h. Additional 16.7 g (0.42 mol) of sodium hydride (60% dispersion in mineral oil) and 22 mL (0.42 mol) of acetonitrile are added to the reaction mixture and the refluxing is continued for another 1.5 h. After this time, the reaction mixture is cooled to room temperature and ice water (~0.8 L) is added. The layers are separated and the aqueous layer is neutralized to pH ~6-7 by adding 1M aqueous HCl solution. The aqueous layer is extracted with ethyl acetate (3×0.8 L). The organic layers are combined, washed with brine (1.5 L), dried over $Na_2SO_4$ and filtered. The filtrate is concentrated under reduced pressure to yield 137 g of 4,4-dimethyl-3-oxo-5-(tetrahydro-pyran-2-yloxy)-pentanenitrile as a brown oil, which is used in the next step without further purification. $^1$H NMR (400 MHz, DMSO-d6) δ ppm 1.09 (6H, s), 1.10 (6H, s), 1.4-1.7 (6H, m), 3.3 (1H, m), 3.35 (1H, d), 3.4 (1H, m), 3.6 (1H, d), 3.7 (1H, m), 4.2 (1H, s); 4.55 (1H, t).

Step 3: Synthesis of 3-[1,1-Dimethyl-2-(tetrahydro-pyran-2-yloxy)-ethyl]-isoxazol-5-ylamine To a stirred solution of 134 g (0.60 mol) of 4,4-dimethyl-3-oxo-5-(tetrahydro-pyran-2-yloxy)-pentanenitrile and 51.3 g (1.28 mol) of sodium hydroxide in water (1.3 L) are added 48.9 g (0.30 mol) of hydroxylamine sulfate. The reaction mixture is stirred at reflux for 18 h. After this time, the reaction mixture is cooled to room temperature and extracted with ethyl acetate (3×0.8 L). The organic layers are combined and washed with brine (1 L), dried over $Na_2SO_4$ and filtered. The filtrate is concentrated under reduced pressure. The residual brown oil is triturated with hexanes (0.8 L) while stirring and the resulting precipitate is isolated by filtration and dried in a vacuum oven for 2 d to yield 85 g of 3-[1,1-dimethyl-2-(tetrahydro-pyran-2-yloxy)-ethyl]-isoxazol-5-ylamine as a yellow solid. Yield 60%; m/z 241 [M+H], 157 [M+H—$C_5H_8O$]; $^1$H NMR (400 MHz, DMSO-d6) δ ppm 1.18 (3H, s), 1.19 (3H, s), 1.45-1.75 (6H, m), 3.26 (1H, d, J=9.3 Hz), 3.4 (1H, m), 3.59 (1H, d, J=9.3 Hz), 3.68 (1H, m), 4.5 (1H, m), 4.88 (1H, s), 6.43 (2H, s).

Alternate Amine Method B:

To a mixture of 11.5 kg 3-hydroxy-2,2-dimethyl-propionic acid methyl ester and 80.5 g conc. HCl in 34.5 L toluene are added 7.48 kg 3,4-dihydro-2H-pyran in 5.75 L toluene during 5 min at 70° C. The dropping funnel is rinsed with 5.75 L toluene. After 1 h 6.79 kg acetonitrile and 11.5 L toluene are added. 83.49 kg potassium tert-amylate (25% in toluene) are added during 30 min. The dropping funnel is rinsed with 11.5 L toluene. After 2 h the mixture is cooled to room temperature and 80.5 L water are added. The layers are separated and the organic layer is extracted with 23 L water. The combined aqueous layers are diluted with 17.25 L water and 7.71 kg hydroxylamine hydrochloride are added. The mixture is stirred for at 80° C. for 2.5 h. 80.5 L solvent are distilled of by vacuum distillation and after cooling to 60° C. 34.5 L methanol are added. Seeding crystals are added and after 1 h the mixture is cooled to 22° C. within 1 h. After stirring for 13 h the suspension is cooled to 1° C. After 2 h the suspension is centrifuged and the filter cake is washed twice with 23 L methanol/water (1:1). After drying of the filter cake at 50° C. 15.88 kg are obtained. Yield: 76%. ES-MS: m/z 241 [M+H]; $^1$H NMR (400 MHz, DMSO-d6) δ ppm 1.18 (3H, s), 1.19 (3H, s), 1.36-1.53 (4H, m), 1.53-1.64 (1H, m), 1.64-1.76 (1H, m), 3.27 (1H, d, $^3J_{H,H}$=9.4 Hz), 3.37-3.44 (1H, m), 3.59 (1H, d, $^3J_{H,H}$=9.2 Hz), 3.64-3.73 (1H, m), 4.50-4.54 (1H, m), 4.88 (1H, s), 6.40 (2H, s).

According to these procedures the following amines are synthesized:

TABLE XXV

| Structure | $^1$H-NMR | Yield [%] | m/z [M + H] |
|---|---|---|---|
| 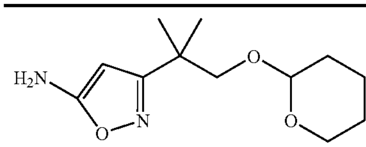 | (400 MHz, DMSO-d6) δ ppm 1.18 (3H, s), 1.19 (3H, s), 1.45-1.75 (6H, m), 3.26 (1H, d, J = 9.3 Hz), 3.4 (1H, m), 3.59 (1H, d, J = 9.3 Hz), 3.68 (1H, m), 4.5 (1H, m), 4.88 (1H, s), 6.43 (2H, s) | 60 | 241 |
| 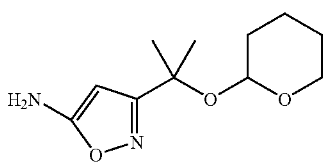 | (400 MHz, DMSO-d6) δ ppm 1.4 (3H, s), 1.45 (3H, s), 1.28-1.56 (4H, m), 1.65-1.78 (2H, m), 3.33-3.40 (1H, m), 3.77-3.85 (1H, m), 4.50-4.60 (1H, m), 4.9 (1H, s), 6.55 (2H, s). | 76[b,#] | 227 |
| 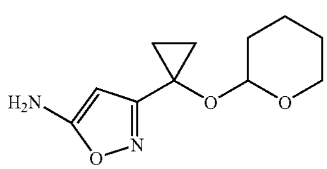 | (400 MHz, CHLOROFORM-d) δ ppm 0.93-1.02 (1H, m), 1.13-1.25 (2H, m), 1.4-1.63 (4H, m), 1.65-1.90 (3H, m), 3.4-3.5 (1H, m), 3.8-3.9 (1H, m), 4.83-4.87 (1H, m), 5.15 (1H, s). | 46[b,#] | 225 |
| 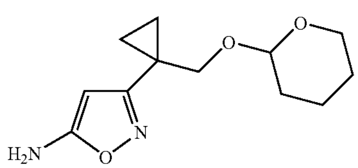 | (400 MHz, CHLOROFORM-d) δ ppm 0.91-0.97 (2H, m), 1.05-1.23 (2H, m), 1.48-1.63 (4H, m), 1.67-1.75 (1H, m), 1.78-1.86 (1H, m), 3.47-3.53 (1H, m), 3.63 (1H, d), 3.79-3.88 (2H, m), 4.29 (2H, bs), 4.67 (1H, dd), 5.14 (1H, s) | 36[a,#] | 261 [M + Na] |
| 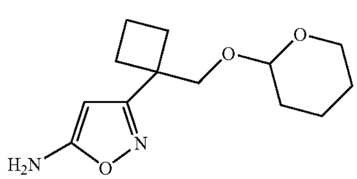 | (400 MHz, CHLOROFORM-d) δ ppm 1.45-1.62 (4H, m), 1.62-1.72 (1H, m), 1.72-1.90 (1H, m), 1.90-2.10 (2H, m), 2.10-2.35 (2H, m), 2.35-2.45 (2H, m), 3.44-3.60 (1H, m), 3.50 (1H, d), 3.75-3.90 (1H, m), 3.95 (1H, d), 4.50 (1H, t), 5.10 (1H, s) | 20[b] | 253 |
| 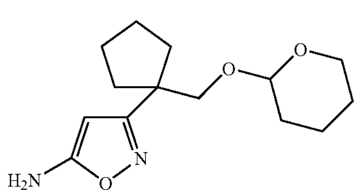 | (400 MHz, CHLOROFORM-d) δ ppm 1.40-1.90 (12H, m), 1.95-2.10 (2H, m), 3.40 (1H, d), 3.40-3.50 (1H, m), 3.70-3.80 (1H, m), 3.80 (1H, d), 4.55 (1H, t), 5.10 (1H, s) | 32[b] | 265 [M − H] |

TABLE XXV-continued

| Structure | ¹H-NMR | Yield [%] | m/z [M + H] |
|---|---|---|---|
| | (400 MHz, CHLOROFORM-d) δ ppm 1.20-1.80 (14H, m), 1.90-2.10 (2H, m), 3.25 (1H, d), 3.40-3.50 (1H, m), 3.65-3.75 (1H, m), 3.70 (1H, d), 4.50 (1H, t), 5.10 (1H, s) | 16[b] | 281 | a) 2.0 eq of NaH is used in one portion; 2.0 eq of acetonitrile is used.
b) 1.4 eq of NaH is used in one portion; 2.0 eq of acetonitrile is used.
column chromatoqraphy is performed after the third step

Amine Method C

Synthesis of 3-(1,1-Dimethyl-2-triisopropylsilanyloxy-ethyl)-isoxazol-5-ylamine

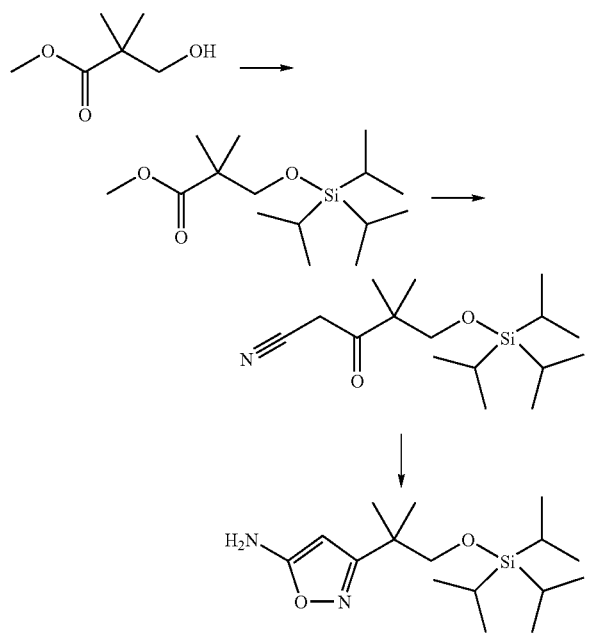

Step 1: Synthesis of 2,2-Dimethyl-3-triisopropylsilanyloxy-propionic acid methyl ester To a solution of 6.76 mL (53 mmol) of methyl 2,2-dimethyl-3-hydroxypropionate in anhydrous THF/DMF (110 mL, 10/1) are added 4.33 g (63.6 mmol) of imidazole and 11.3 mL (53 mmol) of chlorotriisopropylsilane under nitrogen atmosphere. After stirring at room temperature for 20 h, the reaction mixture is concentrated under reduced pressure and the residue is dissolved in TBME (175 mL). The organic layer is washed with water (30 mL), brine (30 mL), dried over $Na_2SO_4$ and filtered. The filtrate is concentrated under reduced pressure to afford 13.25 g of 2,2-dimethyl-3-triisopropylsilanyloxy-propionic acid methyl ester as a yellow oil, which is used in the next step without further purification. Yield: 79%; ¹H NMR (500 MHz, CHLOROFORM-d) δ ppm 1.01-1.07 (21H, m), 1.18 (6H, s), 3.66 (3H, s), 3.69 (2H, s)

Step 2: Synthesis of 4,4-dimethyl-3-oxo-5-triisopropylsilanyloxy-pentanenitrile A solution of 13.25 g (46 mmol) of, 2-dimethyl-3-triisopropylsilanyloxy-propionic acid methyl ester and 3.87 mL (74 mmol) of acetonitrile in toluene (50 mL) is added dropwise to the refluxing suspension of 2.97 g (74 mmol) of sodium hydride (60% in mineral oil) in toluene (50 mL). After the addition, the reaction mixture is stirred at reflux for 18 h. After this time, the reaction mixture is cooled to room temperature and concentrated under reduced pressure. The residue is dissolved in ethyl acetate (150 mL) and washed with 1M aqueous HCl solution (30 mL). The aqueous layer is extracted with ethyl acetate (3×150 mL). The organic layers are combined, washed with brine (30 mL), dried over $Na_2SO_4$ and filtered. The filtrate is concentrated under reduced pressure to yield 15.32 g of 4,4-dimethyl-3-oxo-5-triisopropylsilanyloxy-pentanenitrile as a brown oil, which is used in the next step without further purification. ¹H NMR (500 MHz, CHLOROFORM-d) δ ppm 0.97-1.23 (27H, m), 3.68 (2H, s), 3.74 (2H, s)

Step 3: Synthesis of 3-(1,1-Dimethyl-2-triisopropylsilanyloxy-ethyl)-isoxazol-5-ylamine To a stirred solution of 15.32 g (51 mmol) of 4,4-dimethyl-3-oxo-5-triisopropylsilanyloxy-pentanenitrile and 8.44 g (211 mmol) of sodium hydroxide in water (150 mL) are added 8.87 g (54 mmol) of hydroxylamine sulfate. The reaction mixture is stirred at reflux for 28 h. After this time, the reaction mixture is cooled to room temperature and extracted with chloroform (3×150 mL). The organic layers are combined and washed with water (30 mL), dried over $Na_2SO_4$ and filtered. The filtrate is concentrated under reduced pressure. The residual brown oil is purified by column chromatography (silica, eluent DCM, 0-1% methanol) to afford 2.82 g of 3-(1,1-dimethyl-2-triisopropylsilanyloxy-ethyl)-isoxazol-5-ylamine as a yellow solid. Yield 18%; m/z 313 [M+H]; ¹H NMR (500 MHz, CHLOROFORM-d) δ ppm 0.98-1.15 (21H, m), 1.29 (6H, s), 3.68 (2H, s), 4.30 (2H, br. s.), 5.10 (1H, s)

Amine Method D

Synthesis of 5-(2-Methoxy-1,1-dimethyl-ethyl)-isoxazol-3-ylamine

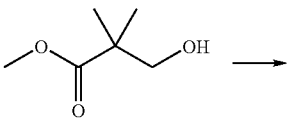

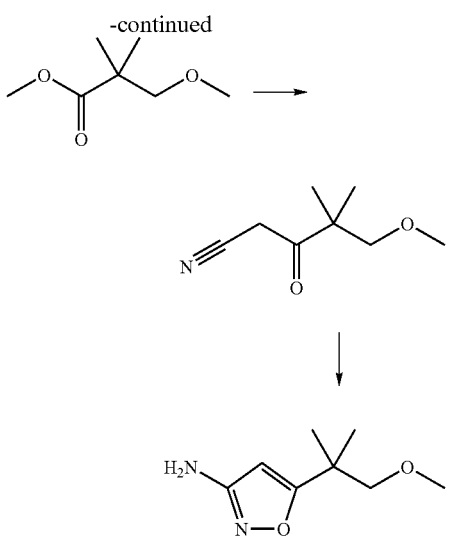

Step 1: Synthesis of 3-Methoxy-2,2-dimethyl-propionic acid methyl ester

3-Methoxy-2,2-dimethyl-propionic acid methyl ester is prepared according to the following reference:
Johnstone, R. A. W.; Rose, M. E.; *Tetrahedron,* 1979, 35, 2169-2173.

To a solution of 3.52 g (63 mmol) of powdered potassium hydroxide in DMSO (150 mL) are added 2 mL (16 mmol) of hydroxypivalic acid methyl ester, followed by 3.9 mL (63 mmol) of methyl iodide. The reaction mixture is stirred for 0.5 h, then quenched with water (300 mL). The reaction mixture is extracted with DCM (3×300 mL). The combined organic extracts are washed with water (2×150 mL), brine (50 mL), dried over $Na_2SO_4$ and filtered. The filtrate is concentrated under reduced pressure to yield 1.76 g of 3-methoxy-2,2-dimethyl-propionic acid methyl ester as a pale yellow oil, which is used in the next step without further purification. Yield: 77%; $^1$H NMR (400 MHz, DMSO-d6) δ ppm 1.1 (6H, s), 3.2 (3H, s), 3.3 (2H, s), 3.6 (3H, s).

Step 2: Synthesis of 5-Methoxy-4,4-dimethyl-3-oxo-pentanenitrile

A solution of 1.74 g (12 mmol) of 3-methoxy-2,2-dimethyl-propionic acid methyl ester and 0.9 mL (17 mmol) of acetonitrile in toluene (5 mL) is added dropwise to the refluxing suspension of 0.67 g (17 mmol) of sodium hydride (60% in mineral oil) in toluene (5 mL). After the addition, the reaction mixture is stirred at reflux for 3 h. After this time, the reaction mixture is cooled to room temperature and neutralized to pH ~6-7 by adding 1M aqueous HCl solution. The aqueous layer is extracted with ethyl acetate (3×20 mL). The organic layers are combined, washed with brine (1.5 L), dried over $Na_2SO_4$ and filtered. The filtrate is concentrated under reduced pressure to yield 1.69 g of 5-methoxy-4,4-dimethyl-3-oxo-pentanenitrile as a brown oil, which is used in the next step without further purification. Yield: 91%; $^1$H NMR (400 MHz, DMSO-d6) δ ppm 1.1 (6H, s), 3.2 (3H, s), 3.3 (2H, s), 4.2 (2H, s).

Step 3: Synthesis of 5-(2-Methoxy-1,1-dimethyl-ethyl)-isoxazol-3-ylamine

To a stirred solution of 1.68 g (10.8 mmol) of 5-methoxy-4,4-dimethyl-3-oxo-pentanenitrile and 0.49 g (11.9 mmol) of sodium hydroxide in water (13 mL) is added a solution of 0.98 g (5.9 mmol) of hydroxyamine sulfate in water (4 mL). The reaction mixture is heated to 100° C. for 1.5 h. After this time, the reaction mixture is cooled to room temperature and 0.8 mL (9.7 mmol) of 37% aqueous HCl solution is added. The reaction is heated to 100° C. for 0.5 h. After cooling, the pH of the reaction mixture is adjusted to pH~12 by addition of 1M aqueous NaOH solution and extracted with DCM (3×20 mL). The organic layers are combined and washed with brine (20 mL), dried over $Na_2SO_4$ and filtered. The filtrate is concentrated under reduced pressure. The residual brown oil is purified by column chromatography (Biotage, eluent DCM, MeOH) to yield 0.94 g of 5-(2-methoxy-1,1-dimethyl-ethyl)-isoxazol-3-ylamine as a yellow oil. Yield 51%; m/z 171 [M+H]; $^1$H NMR (400 MHz, DMSO-d6) δ ppm 1.17 (6H, s), 3.22 (3H, s), 3.26 (2H, s), 5.40 (2H, m) 5.53 (1H, s).

TABLE XXVI

| Structure | $^1$H-NMR | Yield [%] | m/z [M + H] |
|---|---|---|---|
| H₂N-isoxazole-C(CH₃)₂-CH₂-O-CH₃ | (400 MHz, DMSO-d6) δ ppm 1.17 (6H, s), 3.22 (3H, s), 3.26 (2H, s), 5.40 (2H, m) 5.53 (1H, s) | 36 | 171 |
| H₂N-isoxazole-cyclopentyl-CH₂-O-CH₃ | (400 MHz, CD₃OD) ∂ ppm 1.65-1.73 (4H, m), 1.73-1.83 (2H, m), 1.90-2.00 (2H, m), 3.31 (3H, s), 3.44 (2H, s), 3.57 (2H, brs), 5.67 (1H, s). | 23 | 197 |

Amine Method E

Synthesis of 5-[2-(4-Methoxy-benzyloxy)-1,1-dimethyl-ethyl]-isoxazol-3-ylamine

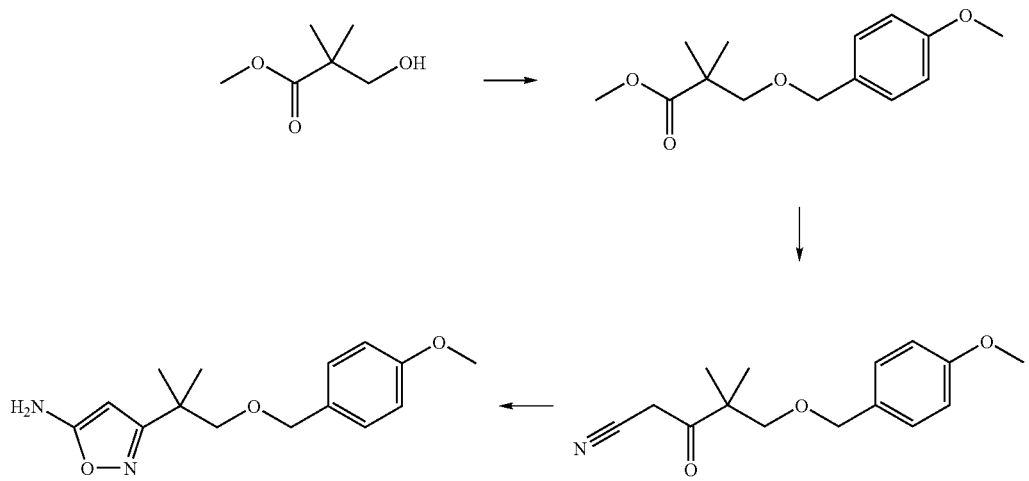

Step 1: Synthesis of 2,2-Dimethyl-3-(4-methoxybenzyl-oxy)-propionic acid methyl ester To a solution of 2.66 mL (20.8 mmol) of methyl 3-hydroxy-2,2-dimethyl-propionate and 3 mL (20.8 mmol) of 4-methoxybenzyl bromide in anhydrous THF (50 mL) at 0° C. are added 1.11 g (27.8 mmol) of sodium hydride (60% dispersion in mineral oil) in one portion. The reaction mixture is warmed to room temperature and stirred for 18 h.

The reaction mixture is then quenched with saturated aqueous $NH_4Cl$ solution and the product is extracted with ether (3×30 mL). The combined organic extracts are washed with water and brine, dried over $Na_2SO_4$ and filtered. The filtrate is concentrated under reduced pressure. The residual oil is purified by flash column chromatography using Biotage SP1 (silica, eluent hexanes, 0-25% ethyl acetate) to afford 3.66 g of 2,2-dimethyl-3-(4-methoxybenzyl-oxy)-propionic acid methyl ester. Yield: 70%; $^1$H NMR (400 MHz, CHLOROFORM-D) δ ppm 1.20 (6H, s), 3.43 (2H, s), 3.68 (3H, s), 3.82 (3H, s), 4.46 (2H, br s), 6.87-6.89 (2H, m), 7.22-7.25 (2H, m).

Step 2: Synthesis of 5-(4-Methoxy-benzyloxy)-4,4-dimethyl-3-oxo-pentanenitrile A solution of 3.66 g (14.5 mmol) of 2,2-dimethyl-3-(4-methoxybenzyl-oxy)-propionic acid methyl ester and 1.07 mL (20.5 mmol) of acetonitrile in anhydrous toluene (10 mL) is added dropwise to a refluxing suspension of 0.83 g (20.5 mmol) of sodium hydride (60% dispersion in mineral oil) in toluene (20 mL). After the addition is complete, the mixture is stirred at reflux for 3 h, then allowed to cool to room temperature. The reaction mixture is then diluted with 1M aqueous HCl solution to neutral pH, and extracted with ethyl acetate (3×40 mL). The combined organic extracts are washed with water and brine, then dried over $Na_2SO_4$ and filtered. The filtrate is concentrated under reduced pressure to afford 3.95 g of 5-(4-methoxy-benzyloxy)-4,4-dimethyl-3-oxo-pentanenitrile, which is used in the next step without further purification. Yield: assumed quantitative, no spectroscopic analysis performed.

Step 3: Synthesis of 3-[1,1-Dimethyl-2-(4-methoxy-benzyl-oxy)-ethyl]-isoxazol-5-ylamine 3-[1,1-Dimethyl-2-(4-methoxybenzyl-oxy)-ethyl]-isoxazol-5-ylamine is prepared according to Takase et al, *Heterocycles*, 1991, 32, 1153-1158, To a stirred solution of 2.0 g (7.65 mmol) of 5-(4-methoxy-benzyloxy)-4,4-dimethyl-3-oxo-pentanenitrile and 0.62 g (15.40 mmol) of sodium hydroxide in water (40 mL) are added 0.64 g (3.90 mmol) of hydroxylamine sulfate. The reaction is stirred at 100° C. for 18 h. After cooling to room temperature, the reaction is diluted with water and extracted with ethyl acetate (3×20 mL). The combined organic extracts are washed with brine, dried over $Na_2SO_4$ and filtered. The filtrate is concentrated under reduced pressure. The residual oil is purified by flash column chromatography using Biotage SP1 (silica, eluent hexanes, 5-50% ethyl acetate) to yield 0.873 g of 3-[1,1-dimethyl-2-(4-methoxybenzyl-oxy)-ethyl]-isoxazol-5-ylamine as a pale yellow solid. Yield 41%, m/z 277 [M+H]; $^1$H NMR (400 MHz, CHLOROFORM-d) δ ppm 1.29 (6H, s), 3.44 (2H, s), 3.81 (3H, s), 4.35 (2H, br. s), 4.46 (2H, br. s), 5.06 (1H, s), 7.22-7.27 (2H, m), 6.86-6.89 (2H, m).

According to this procedure the following amines are synthesized:

TABLE XXVII

| Structure | ¹H-NMR | Yield [%] | m/z [M + H] |
|---|---|---|---|
| (isoxazole with PMB ether sidechain) | (400 MHz, CHLOROFORM-d) δ ppm 1.29 (6H, s), 3.44 (2H, s), 3.81 (3H, s), 4.35 (2H, br. s), 4.46 (2H, br. s), 5.06 (1H, s), 7.22-7.27 (2H, m), 6.86-6.89 (2H, m). | 29 | 277 |
| (isoxazole with ethoxy sidechain) | (400 MHz, CHLOROFORM-d) δ ppm 1.20 (3H, t), 1.30 (6H, s), 3.42 (2H, s), 3.50 (2H, q), 3.80-4.80 (2H, s), 5.15 (1H, s) | 58 | 185 |
| (isoxazole with methoxy sidechain) | (400 MHz, CHLOROFORM-d) δ ppm 1.25 (6H, s), 3.31 (3H, s), 3.45 (2H, s), 4.30 (2H, s), 5.05 (1H, s) | 39[#] | 171 |

[#]4.1 equivalents of NaOH and 1.1 equivalent of hydroxylamine sulfate are used, the reaction is run for 2.5 h at reflux.

Amine Method F

Synthesis of 5-(2-Fluoro-4-methoxy-phenyl)-4H-[1,2,4]triazol-3-ylamine

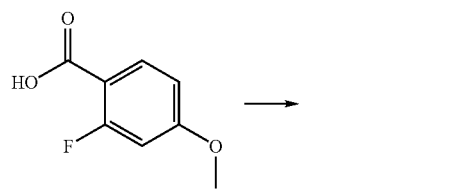

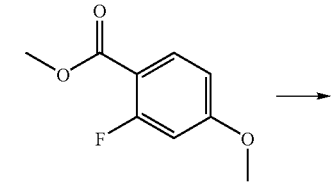

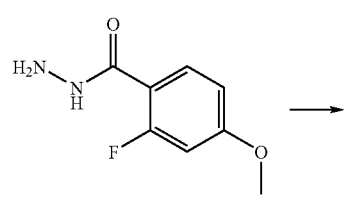

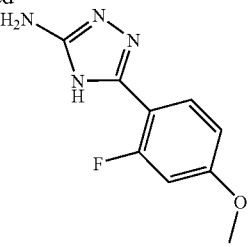

5-(2-Fluoro-4-methoxy-phenyl)-4H-[1,2,4]triazol-3-ylamine is prepared by adaptation of Akahoshi et al. U.S. Pat. No. 5,750,545 (1998)

Step 1: Synthesis of 2-Fluoro-4-methoxybenzoic acid methyl ester

To a solution of 5.0 g (29.4 mmol) of 2-fluoro-4-methoxy-benzoic acid in methanol (50 mL) at room temperature are added 2.13 mL (29.4 mmol) of thionyl chloride. The reaction is stirred at room temperature for 16 h and the solvent is removed under reduced pressure. The residue is dissolved in DCM and washed with brine. The organic layer is dried (MgSO$_4$), filtered and the filtrate is concentrated under reduced pressure to give 5.04 g (27.1 mmol) of 2-fluoro-4-methoxybenzoic acid methyl ester. Yield: 92%, ES-MS: m/z 185 [M+H].

According to this procedure the following ester are synthesized:

TABLE XXVIII

| Structure | ¹H-NMR | Yield [%] | m/z [M + H] |
|---|---|---|---|
| (methyl 4-(methylsulfonyl)benzoate) | (500 MHz, CHLOROFORM-d) δ ppm 3.09 (3 H, s), 3.97 (3 H, s), 8.04 (2 H, d, J = 8.35 Hz), 8.24 (2 H, d, J = 8.35 Hz) | 88 | 256 [M + H + MeCN] |
| (methyl 2-fluoro-4-methoxybenzoate) | (250 MHz, CHLOROFORM-d) δ ppm 3.84 (3 H, s), 3.90 (3 H, s), 6.63 (1 H, dd, J = 12.79, 2.44 Hz), 6.72 (1 H, dd, J = 8.91, 2.51 Hz), 7.90 (1 H, t, J = 8.68 Hz) | 92 | 185 |

Step 2: Synthesis of 2-Fluoro-4-methoxybenzoic acid methyl hydrazide

To a solution of 5.04 g (27.2 mmol) of 2-fluoro-4-methoxybenzoic acid methyl ester in ethanol (50 mL) are added 36.9 mL (408.6 mmol) of hydrazine hydrate. The reaction is stirred at room temperature for 15 h. The mixture is concentrated under reduced pressure and the solid is washed with DCM/heptane (2:1) to give 4.26 g (23.0 mmol) of 2 fluoro-4-methoxybenzoic acid hydrazide. Yield: 85%, ES-MS: m/z [M+H] 185.

According to this procedure the following hydrazides are synthesized:

TABLE XXIX

| Structure | ¹H-NMR | Yield [%] | m/z [M + H] |
|---|---|---|---|
| (4-(methylsulfonyl)benzohydrazide) | (500 MHz, DMSO-d₆) δ ppm 3.26 (3 H, s), 4.59 (2 H, br. s.), 8.00-8.05 (4 H, m), 10.04 (1 H, br. s.) | 98 | 215 |
| (3-methoxybenzohydrazide) | Ref: Hutton, K. J. Org. Chem. 1955, 20, 855-858 | 86 | 167 |
| (2-fluoro-4-methoxybenzohydrazide) | (250 MHz, CHLOROFORM-d) δ ppm 3.86 (3 H, s), 4.14 (2 H, br. s.), 6.63 (1 H, dd, J = 13.86, 2.44 Hz), 6.81 (1 H, dd, J = 8.83, 2.44 Hz), 7.69-7.95 (1 H, m), 8.05 (1 H, t, J = 8.98 Hz) | 85 | 185 |

Step 3: Synthesis of 5-(2-Fluoro-4-methoxyphenyl)-4H-[1,2,4]triazol-3-ylamine To a solution of 4.26 g (23.15 mmol) of 2-fluoro-4-methoxybenzoic acid hydrazide in water (100 mL) are added 12.9 g (46.3 mmol) of S-methylpseudothiourea and 1.9 g (46.3 mmol) of sodium hydroxide pellets. The reaction is stirred at room temperature for 7 d. The reaction mixture is filtered and washed with water (50 mL). The solid is dried under reduced pressure at 40° C., then melted at 220° C. to give 2.22 g (9.82 mmol) of 2-fluoro-4-methoxybenzoic acid diaminomethylene hydrazide. Yield: 42%, ES-MS: m/z. The solid is melted at 220° C. to give 1.735 g (8.34 mmol) of 5-(2-fluoro-methoxyphenyl)-4H-[1,2,4]triazol-3-ylamine. Yield 36%, ES-MS: m/z 209 [M+H].

According to this procedure the following amines are synthesized:

TABLE XXX

| Structure | $^1$H NMR | Yield [%] | m/z [M + H] |
|---|---|---|---|
| 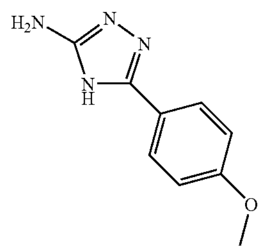 | (500 MHz, MeOD) δ ppm 3.83 (3 H, s), 6.97 (2 H, d, J = 8.25 Hz), 7.82 (2 H, d, J = 8.62 Hz) | 54 | 191 |
| 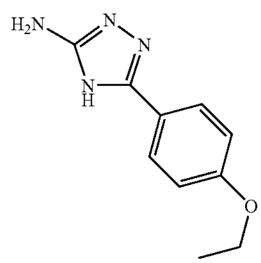 | (500 MHz, DMSO-d$_6$) δ ppm 1.32 (3 H, t, J = 6.94 Hz), 4.04 (2 H, q, J = 7.02 Hz), 6.98 (2 H, d, J = 8.85 Hz), 7.77 (2 H, d, J = 8.85 Hz) | 38 | 205 |
| 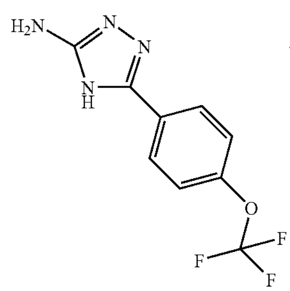 | (500 MHz, MeOD) δ ppm 7.33 (2 H, d, J = 8.39 Hz), 7.99 (2 H, d, J = 8.70 Hz) | 40 | 245 |
| 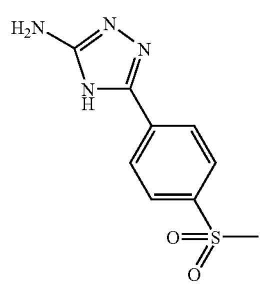 | (250 MHz DMSO-d$_6$) δ ppm 3.22 (3 H, s), 6.17 (2 H, br. s.), 7.82-8.03 (2 H, m), 8.10 (2 H, d, J = 8.38 Hz), 12.32 (1 H, br. s.) | 86 | 239 |
| 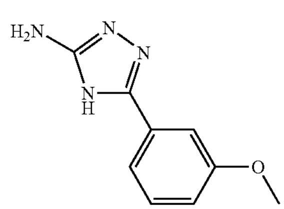 | (500 MHz, MeOD) δ ppm 3.85 (3 H, s), 6.96 (1 H, d, J = 7.02 Hz), 7.33 (1 H, t, J = 7.78 Hz), 7.44-7.53 (2 H, m) | 66 | 191 |

| Structure | ¹H NMR | Yield [%] | m/z [M + H] |
|---|---|---|---|
| (structure shown) | (500 MHz, CHLOROFORM-d) δ ppm 3.80 (3 H, s), 4.53 (2 H, br. s.), 6.45-6.91 (2 H, m), 7.75-8.18 (1 H, m) | 36 | 209 |

Amine Method G

Synthesis of 5-[2-(tert-Butyl-diphenyl-silanyloxy)-1,1-dimethyl-ethyl]-1,3,4-thiadiazol-2-ylamine

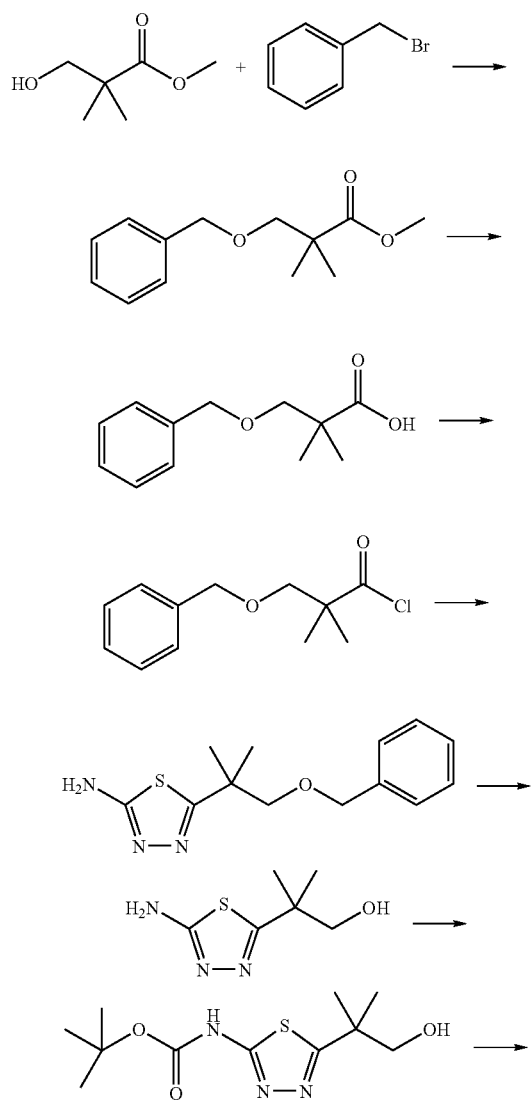

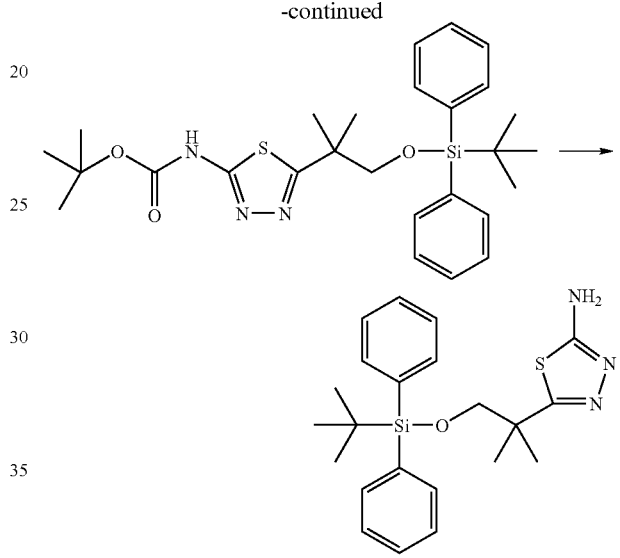

Step 1: Synthesis of 3-Benzyloxy-2,2-dimethyl-propionic Acid Methyl Ester

60% Sodium hydride in mineral oil (2.3 g, 56.8 mmol) is added to a solution of 3-hydroxy-2,2-dimethyl-propionic acid methyl ester (5.0 g, 37.8 mmol) in THF (80 mL) at 0° C., followed by the addition of benzylbromide (7.3 g, 42.6 mmol). The reaction mixture is slowly brought to room temperature, stirred for 8 h and then quenched with ice water and extracted with ethyl acetate. The organic phase is washed with water and brine, dried over $Na_2SO_4$ filtered and concentrated. The crude product is purified by column chromatography to afford 5.0 g of 3-benzyloxy-2,2-dimethyl-propionic acid methyl ester as a brown liquid; m/z 223 [M+H].

Step 2: Synthesis of 3-Benzyloxy-2,2-dimethyl-propionic acid

A solution of potassium hydroxide (1.8 g, 338 mmol) and 3-benzyloxy-2,2-dimethyl-propionic acid methyl ester in ethanol (50.0 mL) is refluxed for 24 h. The solvent is removed under reduced pressure, the crude is diluted with water and extracted with ethyl acetate. The water phase is acidified with 1N aq. HCl (pH ~2-3) and extracted with ethyl acetate. The combined organic layers are washed with water and brine; the organic phase is dried over Na₂SO₄, filtered and concentrated under reduced pressure to afford 2.5 g of 3-benzyloxy-2,2-dimethyl-propionic acid as a brown solid that is used in the next step without any further purification. Yield: 32%, over two steps; m/z 209 [M+H].

Step 3: Synthesis of 3-Benzyloxy-2,2-dimethyl-propionyl chloride

A catalytic amount of DMF is added to a solution of 3-benzyloxy-2,2-dimethyl-propionic acid (30 g, 144.2 mmol) thionyl chloride (150 mL) and the reaction mixture is heated under reflux for 2 h. The solvent is removed under reduced pressure to afford 35 g of 3-benzyloxy-2,2-dimethyl-propionyl chloride as a brown oil that is used in the next step without further purification.

Step 4: Synthesis of Synthesis of 5-(2-Benzyloxy-1,1-dimethyl-ethyl)-1,3,4-thiadiazol-2-ylamine A catalytic amount of DMF is added to a solution of 3-benzyloxy-2,2-dimethyl-propionyl chloride (35 g, 154.9 mmol) and thiosemicarbazide (15.5 g, 170.3 mmol) in THF (400 mL) and the reaction mixture is heated under reflux for 3 h. The solvent is removed under reduced pressure and the residue is diluted with ethyl acetate and washed with water. The organic layer is dried over Na₂SO₄, filtered and concentrated under reduced pressure to afford 45 g of a pale yellow liquid that is used in the next step without further purification (m/z 282 [M+H]).

A solution of the above material in phosphorus oxychloride (90.0 mL) is stirred under reflux for 2 h. The reaction mixture is concentrated under reduced pressure, water is added and the pH is adjusted to ~12 with saturated NaHCO₃ solution. The aqueous layer is extracted with ethyl acetate, the organic phase is dried over Na₂SO₄, filtered and concentrated under reduced pressure. The residue is purified by column chromatography to afford 20 g of 5-(2-benzyloxy-1,1-dimethyl-ethyl)-1,3,4-thiadiazol-2-ylamine as a yellow solid. Yield: 53% (over two steps); m/z 264 [M+H].

Step 5: Synthesis of 2-(5-Amino-1,3,4-thiadiazol-2-yl)-2-methyl-propan-1-ol

To a solution of 5-(2-benzyloxy-1,1-dimethyl-ethyl)-1,3,4-thiadiazol-2-ylamine (15.0 g, 57.0 mmol) in DCM (100 mL), boron tribromide (1N in DCM, 15.0 mL, 162.0 mmol) is added slowly at 0° C. The reaction mixture is warmed up to room temperature and stirred for 3 h. After cooling the reaction mixture to 0° C., ice water is added. The two phases are separated and the pH of the water phase is adjusted to ~13 with NaOH and extracted with n-BuOH. The organic layer is washed with brine, dried over Na₂SO₄, filtered and concentrated under reduced pressure to afford 10.0 g of 2-(5-amino-1,3,4-thiadiazol-2-yl)-2-methyl-propan-1-ol as a brown solid; m/z 174 [M+H].

Step 6: Synthesis of [5-(2-Hydroxy-1,1-dimethyl-ethyl)-1,3,4-thiadiazol-2-yl]-carbamic acid tert-butyl ester To a solution of 2-(5-amino-1,3,4-thiadiazol-2-yl)-2-methyl-propan-1-ol (10.0 g, 57.8 mmol) in DCM (100.0 mL) is added at 0° C. triethylamine (21.0 mL, 173.4 mmol) followed by di-tert-butyl dicarbonate (14.0 g, 63.6 mmol). The reaction mixture is stirred at room temperature for 24 h. Then the solvent is removed under reduced pressure and the crude is purified by column chromatography to afford 12.0 g of [5-(2-hydroxy-1,1-dimethyl-ethyl)-1,3,4-thiadiazol-2-yl]-carbamic acid tert-butyl ester as a white solid; m/z 274 [M+H].

Step 7: Synthesis of {5-[2-(tert-Butyl-diphenyl-silanyloxy)-1,1-dimethyl-ethyl]-1,3,4-thiadiazol-2-yl}-carbamic acid tert-butyl ester To a solution of [5-(2-hydroxy-1,1-dimethyl-ethyl)-1,3,4-thiadiazol-2-yl]-carbamic acid tert-butyl ester (12.0 g, 43.9 mmol) in DCM (500 mL) tert-butyldiphenylsilyl chloride (14.5 g, 52.8 mmol), a catalytic amount of DMAP and triethylamine (11.0 g, 109.9 mmol) are added. The solution is slowly brought to reflux and is heated for 14 h. The solvent is removed under reduced pressure, water is added and extracted with ethyl acetate. The organic layers are dried over Na₂SO₄, filtered and concentrated under reduced pressure to afford the crude product. Column chromatography affords 12.0 g of {5-[2-(tert-Butyl-diphenyl-silanyloxy)-1,1-dimethyl-ethyl]-1,3,4-thiadiazol-2-yl}-carbamic acid tert-butyl ester as a white solid. Yield: 41%, over three steps; ¹H NMR (400 MHz, DMSO-d6) δ ppm 0.98 (9H, s), 1.38 (6H, s), 1.48 (9H, s), 3.65 (s, 2H), 7.38-7.58 (10H, m), 11.7 (NH, br)

Step 8: Synthesis of 5-[2-(tert-Butyl-diphenyl-silanyloxy)-1,1-dimethyl-ethyl]-1,3,4-thiadiazol-2-ylamine A 10% solution of TFA in DCM (720 mL) is added at 0° C. to a solution of {5-[2-(tert-Butyl-diphenyl-silanyloxy)-1,1-dimethyl-ethyl]-1,3,4-thiadiazol-2-yl}-carbamic acid tert-butyl ester (12.0 g, 23.4 mmol) in DCM (800 mL). The reaction mixture is stirred at room temperature for 14 h. The solvent is removed under reduced pressure and the crude purified by column chromatography to afford 8.8 g of 5-[2-(tert-butyl-diphenyl-silanyloxy)-1,1-dimethyl-ethyl]-1,3,4-thiadiazol-2-ylamine as a viscous liquid. Yield: 91%; ¹H NMR (400 MHz, CHLOROFORM-d) δ ppm 1.05 (9H, s), 1.30 (6H, s), 3.60 (2H, s), 7.30-7.50 (6H, m), 7.50-7.70 (4H, m), 9.00 (2H, s); m/z 412 [M+H].

Amine Method H

Synthesis of 4-[2-(tert-Butyl-diphenyl-silanyloxy)-1,1-dimethyl-ethyl]thiazol-2-ylamine

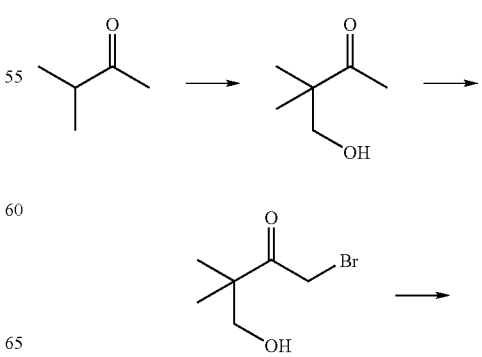

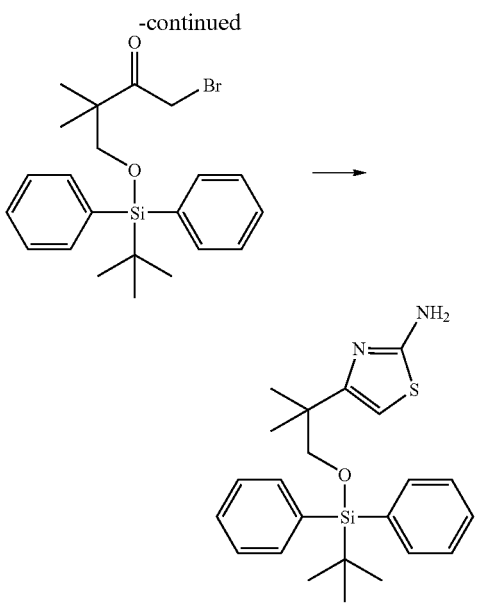

Step 1: Synthesis of 4-Hydroxy-3,3-dimethyl-butan-2-one

Trifluoroacetic acid (178.0 mL, 2.3 mol) is added to 3-methyl-butan-2-one (100.0 g, 1.1 mol) and paraformaldehyde (34.9 g, 1.2 mol) at room temperature; the reaction mixture is slowly brought to refluxing condition and it is heated for 7 h. The reaction mixture is cooled to room temperature, poured into 15% NaHCO₃ solution and stirred for 24 h. DCM is added to the reaction mixture, the two phases are separated and the aqueous layer is extracted with DCM. The combined organic layers are dried over anhydrous Na₂SO₄ and after filtration the solvent is removed under reduced pressure to afford 120.0 g of 4-hydroxy-3,3-dimethyl-butan-2-one as a pale green oil that is used in the next step without further purification; m/z 117 [M+H].

Step 2: Synthesis of 1-Bromo-4-hydroxy-3,3-dimethyl-butan-2-one

Bromine (182.0 g, 1.1 mol) is slowly added at −10° C. to a solution of 4-hydroxy-3,3-dimethyl-butan-2-one (120.0 g, 1.0 mol) in 700.0 mL of MeOH. The solution is slowly warmed up to room temperature and the reaction mixture is stirred for 2 h. Ethyl acetate and water are added to the reaction mixture, the two phases are separated, and the organic layer is washed with 10% K₂CO₃ solution. The organic layer is dried over anhydrous Na₂SO₄ and after filtration the solvent is removed under reduced pressure to afford the crude product that is purified by silica gel chromatography to afford 100.0 g of 1-bromo-4-hydroxy-3,3-dimethyl-butan-2-one as a brown liquid. Yield: 44%, over two steps; m/z 197 [M+H].

Step 3: Synthesis of 1-Bromo-4-(tert-butyl-diphenyl-silanyloxy)-3,3-dimethyl-butan-2-one tert-Butyldiphenylsilyl chloride (50.8 g, 184.6 mmol) is added at 0° C. to a solution of 1-bromo-4-hydroxy-3,3-dimethyl-butan-2-one (30.0 g, 153.8 mmol) and imidazole (26.0 g, 384.5 mmol). The reaction mixture is warmed to room temperature and stirred for 14 h. After adding ice water, the mixture is extracted with diethyl ether and the organic layer is dried over anhydrous Na₂SO₄. After filtration, removal of the solvent under reduced pressure affords the crude product that is purified by silica gel chromatography to afford 40.0 g of 1-bromo-4-(tert-butyl-diphenyl-silanyloxy)-3,3-dimethyl-butan-2-one as a light yellow liquid. ¹H NMR (400 MHz, DMSO-d6) δ ppm 0.94 (9H, s), 1.16 (6H, s), 3.61 (2H, s), 4.80 (s, 2H), 7.38-7.58 (10H, m).

Step 4: Synthesis of 4-[2-(tert-Butyl-diphenyl-silanyloxy)-1,1-dimethyl-ethyl]-thiazol-2-ylamine A solution of 1-bromo-4-(tert-butyl-diphenyl-silanyloxy)-3,3-dimethyl-butan-2-one (40 g, 92.3 mmol) and thiourea (8.4 g, 110.5 mmol) in 400.0 mL of acetonitrile is heated under reflux for 4 h. After cooling the reaction mixture to room temperature, water is added and the aqueous layer is extracted with ethyl acetate; the organic layer is dried over anhydrous Na₂SO₄, filtered and the solvent is removed under reduced pressure to afford the crude product that is purified by silica gel chromatography to afford 2.3 g of 4-[2-(tert-Butyl-diphenyl-silanyloxy)-1,1-dimethyl-ethyl]-thiazol-2-ylamine as a light brown solid. Yield: 4%, over two steps; ¹H NMR (400 MHz, CHLOROFORM-d) δ ppm 1.00 (9H, s), 1.25 (6H, s), 3.62 (2H, s), 5.60 (2H, s), 6.15 (1H, s), 7.25-7.40 (6H, m), 7.50-7.60 (4H, m); m/z 411 [M+H].

Intermediate Synthesis

Synthesis of 3-Ethoxy-2,2-dimethyl-propionic acid methyl ester

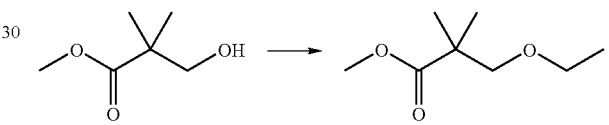

60% Sodium hydride in mineral oil (1.6 g, 39.2 mmol) is added to a solution of 3-hydroxy-2,2-dimethyl-propionic acid methyl ester (2.0 mL, 15.7 mmol) in 30.0 mL of DMF, followed by the addition of iodoethane (3.1 mL, 39.2 mmol) and the reaction mixture is stirred at room temperature for 1 hour. After this time, the reaction mixture is quenched with saturated NH₄Cl aqueous solution and then extracted with dichloromethane twice. The organics are combined and washed with water twice then brine, dried over Na₂SO₄, filtered and concentrated under reduced pressure to yield 2.512 g of the title compound. Yield: quantitative; ¹H NMR (400 MHz, CHLOROFORM-d) δ ppm 1.16 (3H, t, J=8.0 Hz), 1.20 (6H, s), 3.41 (2H, s), 3.48 (2H, q, J=8.0 Hz), 3.70 (3H, s).

Synthesis of 1-Methoxymethyl-cyclopentanecarboxylic acid ethyl ester

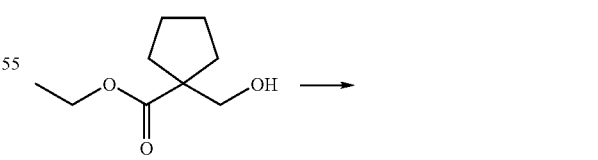

60% Sodium hydride in mineral oil (6.2 g, 130.8 mmol) is added to a solution of 1-hydroxymethyl-cyclopentanecarboxylic acid ethyl ester (15.0 g, 87.2 mmol) in 100.0 mL of THF at 0° C., followed by the addition of iodomethane (13.6 g, 95.9 mmol) and the reaction mixture is stirred at room temperature for 14 hours. After this time, the reaction mixture is quenched with ice water and then extracted with ethyl acetate twice. The organics are combined and washed with water twice then brine, dried over Na₂SO₄, filtered and concentrated under reduced pressure to afford the crude product that is purified by silica gel chromatography to afford 12.0 g of the title compound. Yield: 74%; m/z 209 [M+Na].

Synthesis of
1-hydroxymethyl-cyclopropanecarboxylic acid ethyl ester

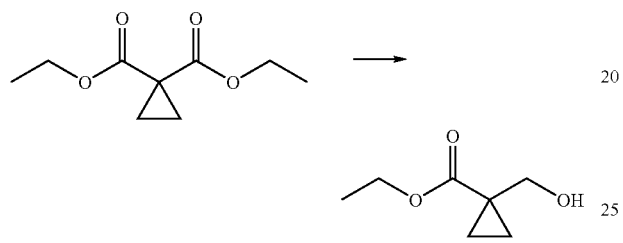

A solution of lithium aluminum-tri-tert-butoxyhydride 1.0M in THF (28.5 mL, 28.5 mmol) is added to a solution of diethyl 1,1-cyclopropanedicarboxylate (2.0 mL, 11.4 mmol) in anhydrous THF (85.0 mL). After stirring the reaction mixture for 4 h, 10 mL of lithium aluminum-tri-tert-butoxyhydride 1.0M solution in THF is added and the solution is stirred overnight. The reaction mixture is diluted with DCM, washed with 1N HCl, saturated NaHCO₃ solution and brine. After drying the organic phase over anhydrous Na₂SO₄, removal of the solvent under reduced pressure affords 1.60 g of 1-hydroxymethyl-cyclopropanecarboxylic acid ethyl ester that is used in the next step without further purification. Yield: 85%.
¹H NMR (400 MHz, CHLOROFORM-d) δ ppm 0.88 (2H, q, J=4.1 Hz), 1.21-1.33 (5H, m), 2.59 (1H, t, J=6.9 Hz), 3.63 (2H, d, J=7.2 Hz), 4.17 (2H, q, J=7.1 Hz).

Intermediate Method A

Synthesis of
1-hydroxymethyl-cyclobutanecarboxylic acid ethyl ester

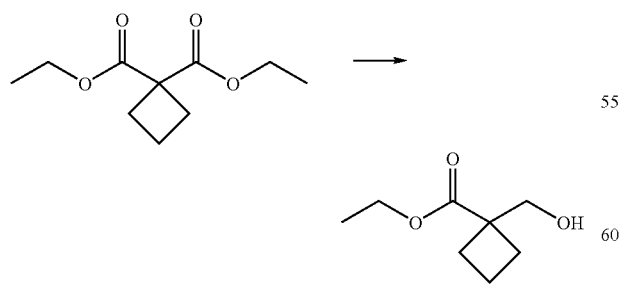

A solution of lithium aluminum-tri-tert-butoxyhydride 1.0M in THF (100.0 mL, 100.0 mmol) is added at −78° C. to a solution of diethyl 1,1-cyclobutanedicarboxylate (10.0 g, 50.0 mmol) in anhydrous THF (50.0 mL). After stirring the reaction mixture at room temperature for 14 h, 10% aq. KHSO₄ solution is added and the reaction mixture diluted with ethyl acetate. After separating the two phases, the organic phase is washed with water and brine and dried over anhydrous Na₂SO₄. Filtration and removal of the solvent under reduced pressure affords 5.0 g of 1-hydroxymethyl-cyclobutanecarboxylic acid ethyl ester that is used in the next step without further purification. Yield: 63%; m/z 159 [M+H].

The following intermediates are synthesized according to Intermediate Method A:

TABLE XXXI

| Structure | Yield [%] | m/z [M + H] |
|---|---|---|
| 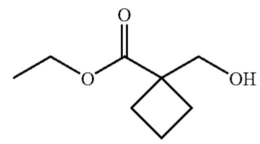 | 63 | 159 |
|  | 50 | 173 |
|  | 50 | 187 |

Amide Method A

Synthesis of 2-Cyclopentanesulfonyl-N-[3-(2-hydroxy-1,1-dimethyl-ethyl)-isoxazol-5-yl]-2-methyl-propionamide (Example 6)

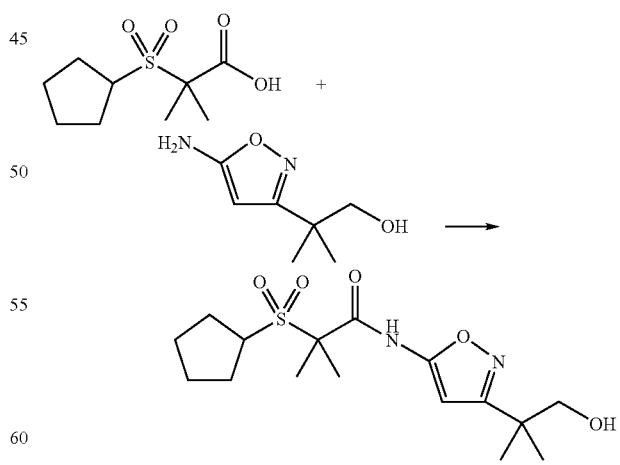

Activation of 150 mg (0.68 mmol) of 2-cyclopentanesulfonyl-2-methyl-propionic acid as the corresponding acid chloride is achieved by treatment with thionyl chloride (2 mL) at 50° C. for 2 h. The reaction is cooled to room temperature and excess thionyl chloride is removed under reduced pressure.

The crude acid chloride is dissolved in DCM (0.5 mL) and added to a solution of 106 mg (0.68 mmol) of 2-(3-amino-isoxazol-5-yl)-2-methyl-propan-1-ol and N,N-diisopropylethylamine (0.24 mL, 1.36 mmol) in DCM (2 mL). The reaction is stirred at 50° C. for 4.5 h. The reaction mixture is diluted with DCM (2 mL) and washed with saturated aqueous NH₄Cl solution (3 mL). The organic layer is dried over Na₂SO₄, filtered and concentrated under reduced pressure. The crude product is purified by column chromatography (silica, eluent: DCM, 0-50% ethyl acetate) to yield an off-white solid, which is further triturated with diethyl ether to afford 89 mg of 2-cyclopentanesulfonyl-N-[3-(2-hydroxy-1,1-dimethyl-ethyl)-isoxazol-5-yl]-2-methyl-propionamide. Yield: 37%; ES-MS: m/z 359 [M+H]

Compounds in Table XXXVIII, amide method A are made according to this procedure.

Amide Method B

Synthesis of N-[3-(2-Hydroxy-1,1-dimethyl-ethyl)-isoxazol-5-yl]-2-methyl-2-(tetrahydro-pyran-4-sulfonyl)propionamide (Example 2) and N-[3-(2-Hydroxy-1,1-dimethyl-ethyl)-isoxazol-5-yl]-2-methyl-2-(3,3,3-trifluoro-propane-1-sulfonyl)-propionamide (Example 7)

Synthesis of N-{3-[1,1-Dimethyl-2-(tetrahydro-pyran-2-yloxy)-ethyl]-isoxazol-5-yl}-2-methyl-2-(tetrahydro-pyran-4-sulfonyl)-propionamide

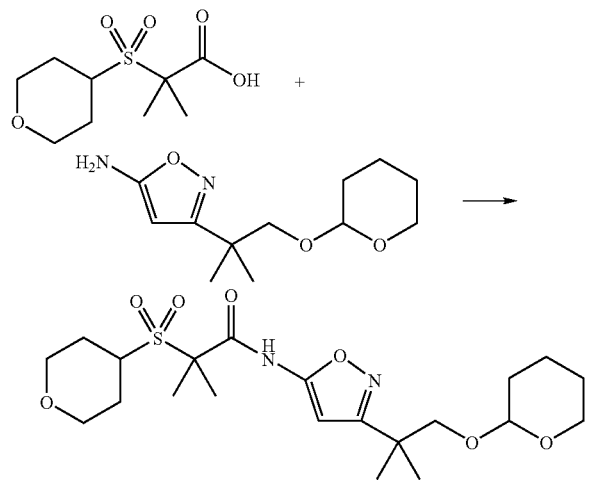

Activation of 103 g (0.44 mol) of 2-methyl-2-(tetrahydro-pyran-4-sulfonyl)-propionic acid as the corresponding acid chloride is achieved by treatment with thionyl chloride (63 mL, 0.88 mol) and DMF (cat., 10 mol %) in toluene (0.72 L) at 100° C. for 2 h. The reaction is cooled to room temperature and toluene (0.3 L) is removed by distillation, whilst adding fresh toluene (0.3 L). This process is repeated once.

This acid chloride solution is added dropwise over 0.5 h to a stirred suspension of 70 g (0.29 mol) of 3-[1,1-dimethyl-2-(tetrahydro-pyran-2-yloxy)-ethyl]-isoxazol-5-ylamine and 101 mL (0.58 mol) of N,N-diisopropylethylamine in toluene (0.28 L) at 35° C. After complete addition the reaction is heated to 60° C. for 17 h. The reaction is cooled to room temperature and the solvent is removed under reduced pressure. The residue is dissolved in ethyl acetate (2.8 L) and washed with water (2×2.8 L) and brine (2.8 L). The organic layer is concentrated under reduced pressure and the residue purified twice by dry-flash column chromatography (silica, eluent heptanes, 10-40% ethyl acetate) to yield 103 g of N-{3-[1,1-dimethyl-2-(tetrahydro-pyran-2-yloxy)-ethyl]-isoxazol-5-yl}-2-methyl-2-(tetrahydro-pyran-4-sulfonyl)-propionamide. Yield: 80%; ES-MS: m/z 481 [M+Na], 375 [M+H—C₅H₈O]

Alternate synthesis of N-{3-[1,1-Dimethyl-2-(tetrahydro-pyran-2-yloxy)-ethyl]-isoxazol-5-yl}-2-methyl-2-(tetrahydro-pyran-4-sulfonyl)-propionamide 3791 g 2-Methyl-2-(tetrahydro-pyran-4-sulfonyl)-propionic acid are suspended in 28.5 L toluene. 5 L of solvent are distilled of to remove traces of water. After addition of 5 L toluene and 20 mL dimethylformamide, 1398 mL thionyl chloride are added at 55° C. The mixture is heated to reflux for 3.5 h. Then 35 L of solvent are distilled of while adding 35 L toluene at the same time. After cooling the solution to 45° C., 3854 g 3-[1,1-Dimethyl-2-(tetrahydro-pyran-2-yloxy)-ethyl]-isoxazol-5-ylamine dissolved in 16 L toluene and 3295 mL N,N-diisopropylethylamine at 70° C., are added during 30 min. The dropping funnel are rinsed twice with 2 L toluene. The suspension is stirred for 16 h at 30° C. The mixture is added to 20 L water (rewashed with 1 L toluene). After phase separation, the organic layer is washed again with 20 L water. The organic layer is transferred back into the reaction vessel (rewashed twice with 1 L toluene) and 31.5 L solvent are distilled of. To the residue is added 40 L methylcyclohexane keeping the solution at 54° C. The mixture is cooled to 23° C. and seeding crystals are added. The suspension is stirred for 2.5 h while cooling to 1° C. The suspension is filtered and the filter cake is washed with 5 L of a 4:1 mixture of methylcyclohexane and toluene. After drying of the filter cake 6866 g product were obtained. ES-MS: m/z 459 [M+H]; ¹H NMR (400 MHz, DMSO-d6) δ ppm 1.26 (3H, s), 1.27 (3H, s), 1.68 (6H, s), 1.35-1.72 (8H, m), 1.78-1.85 (2H, m), 3.32-3.42 (4H, m), 3.60-3-69 (3H, m), 3.84-3.91 (2H, m), 4.52-4.55 (1H, m), 6.35 (1H, s), 11.29 (1H, s).

Synthesis of N-{3-[1,1-Dimethyl-2-(tetrahydro-pyran-2-yloxy)-ethyl]-isoxazol-5-yl}-2-methyl-2-(4,4,4-trifluoro-butane-1-sulfonyl)-propionamide

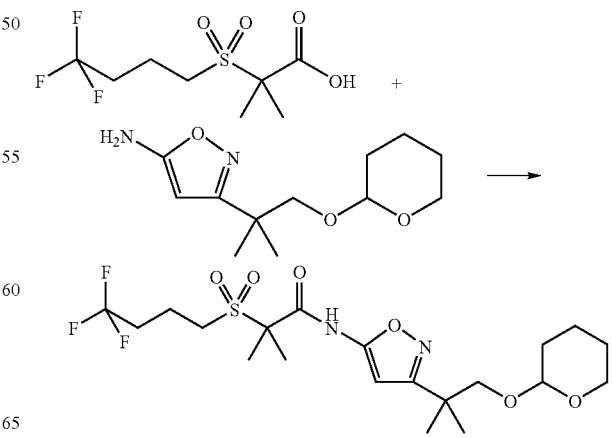

Activation of 72 g (0.27 mol) of 2-Methyl-2-(4,4,4-trifluoro-butane-1-sulfonyl)-propionic acid as the corresponding acid chloride is achieved by treatment with thionyl chloride (50 mL, 0.55 mol) and DMF (cat., 10 mol %) in toluene (0.7 L) at 100° C. for 6 h. The reaction is cooled to room temperature and toluene (0.2 L) is removed by distillation, whilst adding fresh toluene (0.2 L). This process is repeated twice.

This acid chloride solution is added dropwise over 0.5 h to a stirred suspension of 56 g (0.23 mol) of 3-[1,1-dimethyl-2-(tetrahydro-pyran-2-yloxy)-ethyl]-isoxazol-5-ylamine and 92 mL (0.55 mol) of N,N-diisopropylethylamine in toluene (0.3 L) at 35° C. After complete addition the reaction is heated to 60° C. for 17 h. The reaction is cooled to room temperature and the solvent is removed under reduced pressure. The residue is dissolved in ethyl acetate (1 L) and washed with saturated aqueous NaHCO$_3$ solution (0.7 L), brine (0.7 L) dried (Na$_2$SO$_4$) and filtered. The filtrate is concentrated under reduced pressure and the residue purified twice by dry-flash column chromatography (silica, eluent heptanes, 30% ethyl acetate) to yield 85 g of N-{3-[1,1-dimethyl-2-(tetrahydro-pyran-2-yloxy)-ethyl]-isoxazol-5-yl}-2-methyl-2-(4,4,4-trifluoro-butane-1-sulfonyl)-propionamide. Yield: 64%; ES-MS: m/z 483 [M−H]; $^1$H NMR (500 MHz, CHLOROFORM-d) δ ppm 1.36 (3H, s), 1.38 (3H, s) 1.45-1.73 (5H, m), 1.74-1.87 (7H, m), 2.15-2.25 (2H, m), 2.27-2.40 (2H, m), 3.11 (2H, t, J=7.55 Hz), 3.38 (1H, d, J=9.31 Hz), 3.46-3.53 (1H, m), 3.75-3.84 (2H, m), 4.59 (1H, t, J=3.43 Hz), 6.37 (1H, s), 9.24 (1H, s).

According to these methods the amides in table XXIX are made with the following modifications to be noted: for N-{3-[1,1-Dimethyl-2-(tetrahydro-pyran-2-yloxy)-ethyl]-isoxazol-5-yl}-2-((R)-3-fluoro-pyrrolidine-1-sulfonyl)-2-methyl-propionamide, 2 Cyclopropylmethanesulfonyl-N-{3-[1,1-dimethyl-2-(tetrahydro-pyran-2-yloxy)-ethyl]-isoxazol-5-yl}-2-methyl-propionamide, N-{3-[1,1-Dimethyl-2-(tetrahydro-pyran-2-yloxy)-ethyl]-isoxazol-5-yl}-2-methyl-2-(pentane-3-sulfonyl)-propionamide and 1-(Tetrahydro-pyran-4-sulfonyl)-cyclobutanecarboxylic acid {3-[1,1-dimethyl-2-(tetrahydro-pyran-2-yloxy)-ethyl]-isoxazol-5-yl}-amide: the acid is activated as its acid chloride by treatment with oxalyl chloride, DMF (1 drop) in DCM at room temperature. For Example 146 the reaction is run in THF. Further compounds in Table XXXVIII, amide method B are made according to this procedure.

TABLE XXXII

| Structure | $^1$H NMR | Yield [%] | m/z [M + H] |
|---|---|---|---|
| 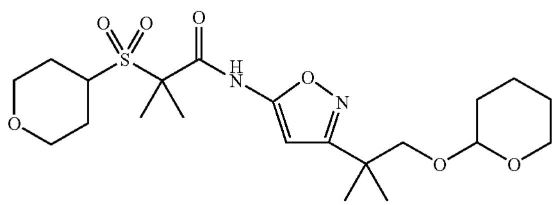 | (500 MHz, CHLOROFORM-d) δ ppm 1.35 (3 H, s), 1.37 (3 H, s), 1.45-1.63 (4 H, m), 1.64-1.72 (1 H, m), 1.75 (6 H, s), 1.77-1.90 (3 H, m), 1.92-2.03 (2 H, m), 3.34-3.53 (5 H, m), 3.74-3.82 (2 H, m), 4.06 (2 H, dd, J = 11.60, 3.51 Hz), 4.58 (1 H, t, J = 3.36 Hz), 6.33 (1 H, s), 9.58 (1 H, s) | 86 | 481 [M + Na], 375 [M + H − C$_5$H$_8$O] |
| 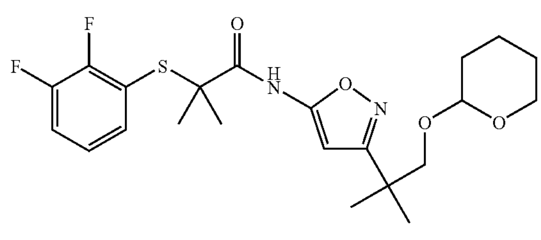 | (250 MHz, CHLOROFORM-d) δ ppm 1.36 (3 H, s), 1.38 (3 H, s), 1.47-1.65 (3 H, m), 1.73 (6 H, s), 1.76-186 (2 H, m), 3.38 (1 H, d, J = 9.44 Hz), 3.43-3.55 (2 H, m), 3.71-3.88 (3 H, m), 4.55-4.63 (1 H, m), 6.32 (1 H, s), 7.28-7.40 (1 H, m), 7.48-7.68 (1 H, m), 9.34 (1 H, s) | 100 | 477 [M + Na] |
| 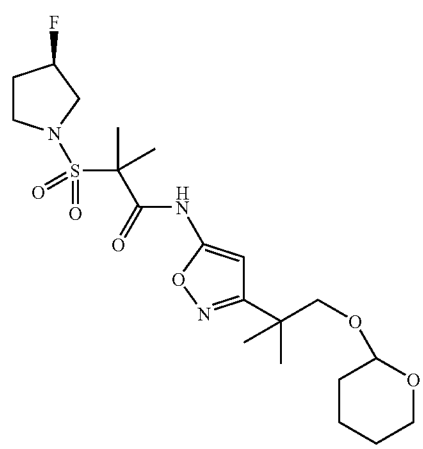 | (500 MHz, CHLOROFORM-d) δ ppm 1.36 (3 H, s), 1.38 (3 H, s), 1.48-1.54 (2 H, m), 1.58-1.63 (1 H, m), 1.65-1.71 (1 H, m), 1.74 (6 H, s), 1.76-1.84 (1 H, m), 1.96-2.10 (1 H, m), 2.21-2.34 (1 H, m), 3.38 (1 H, d, J = 9.46 Hz), 3.46-3.53 (1 H, m), 3.53-3.58 (1 H, m), 3.62-3.68 (1 H, m), 3.68-3.74 (2 H, m), 3.75-3.87 (2 H, m), 4.57-4.61 (1 H, m), 5.18-5.22 (1 H, m), 5.28-5.33 (1 H, m), 6.37 (1 H, s), 9.48 (1 H, br. s.) | 79 | 484 [M + Na] |

TABLE XXXII-continued

| Structure | ¹H NMR | Yield [%] | m/z [M + H] |
|---|---|---|---|
| 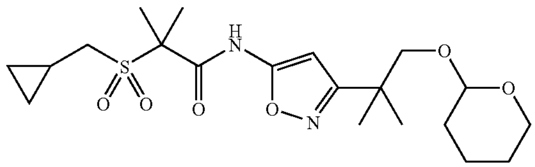 | (500 MHz, CHLOROFORM-d) δ ppm 0.22-0.51 (2 H, m), 0.61-0.76 (2 H, m), 0.96-1.17 (1 H, m), 1.36 (3 H, s), 1.37 (3 H, s), 1.46-1.63 (4 H, m), 1.63-1.71 (1 H, m), 1.74 (6 H, s), 1.76-1.87 (1 H, m), 3.02 (2 H, d, J = 7.32 Hz), 3.37 (1 H, d, J = 9.16 Hz), 3.45-3.53 (1 H, m), 3.69-3.85 (2 H, m), 4.49-4.75 (1 H, m), 6.35 (1 H, s), 9.60 (1 H, br. s.) | 62 | 451 [M + Na] |
| | intermediate not isolated, used without further purification in next step | 52 | 467 [M + Na] |
| | intermediate not isolated, used without further purification in next step | 66 | 493 [M + Na] |
| 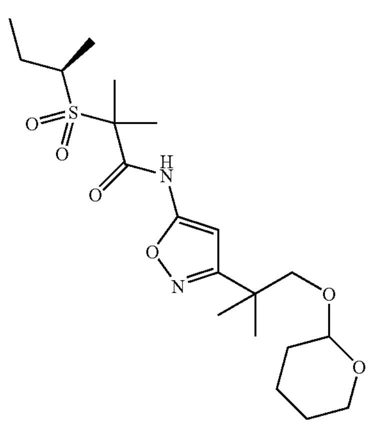 | (500 MHz, CHLOROFORM-d) δ ppm 1.00-1.08 (3 H, m), 1.30-1.40 (9 H, m), 1.57 (3 H, s), 1.58-1.69 (3 H, m), 1.73 (3 H, s), 1.74 (3 H, s), 1.77-1.86 (1 H, m), 1.95-2.10 (1 H, m), 3.13-3.26 (1 H, m), 3.38 (1 H, d, J = 9.16 Hz), 3.45-3.55 (1 H, m), 3.72-3.84 (2 H, m), 4.55-4.61 (1 H, m), 6.34 (1 H, s), 9.73 (1 H, br. s.) | 64 | 453 [M + Na] |

TABLE XXXII-continued

| Structure | ¹H NMR | Yield [%] | m/z [M + H] |
|---|---|---|---|
| 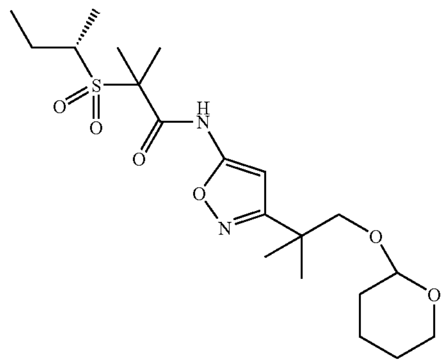 | (500 MHz, CHLOROFORM-d) δ ppm 0.89 (2 H, t, J = 6.87 Hz), 1.03 (3 H, t, J = 7.48 Hz), 1.30-1.41 (9 H, m), 1.56 (3 H, s), 1.64-1.69 (1 H, m), 1.73 (3 H, s), 1.74 (3 H, s), 1.77-1.86 (1 H, m), 1.95-2.07 (1 H, m), 3.16-3.26 (1 H, m), 3.38 (1 H, d, J = 9.16 Hz), 3.44-3.54 (1 H, m), 3.72-3.82 (2 H, m), 4.54-4.66 (1 H, m), 6.34 (1 H, s), 9.73 (1 H, s) | 75 | 453 [M + Na] |
| 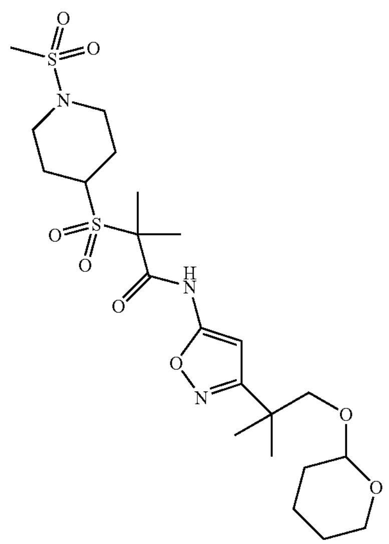 | (250 MHz, CHLOROFORM-d) δ ppm 0.77-0.94 (3 H, m), 1.37 (3 H, s), 1.38 (3 H, s), 1.47-1.67 (2 H, m), 1.76 (6 H, s), 1.92-2.15 (4 H, m), 2.74-2.92 (2 H, m), 2.81 (3 H, s), 3.24-3.43 (2 H, m), 3.43-3.56 (1 H, m), 3.70-4.03 (4 H, m), 4.52-4.66 (1 H, m), 6.34 (1 H, s), 9.44 (1 H, br. s.) | 41 | 558 [M + Na] |
| 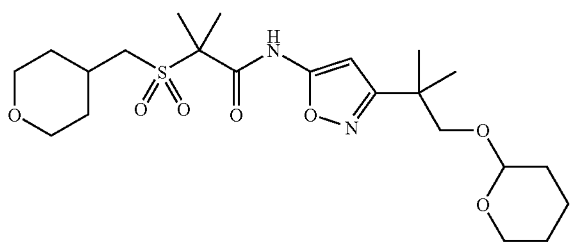 | (500 MHz, CHLOROFORM-d) δ ppm 1.37 1.36 (3 H, s), 1.38 (3 H, s), 1.43-1.96 (16 H, m), 2.35-2.47 (1 H, m), 2.92 (2 H, d, J = 6.56 Hz), 3.35-3.55 (4 H, m), 3.74-3.85 (2 H, m), 3.96 (2 H, dd, J = 11.29, 3.97 Hz), 4.59 (1 H, t, J = 3.36 Hz), 6.37 (1 H, s), 9.34 (1 H, s) | 66 | 473 [M + H] |
| | ᵃ(400 MHz, CHLOROFORM-d) δ ppm 1.45-1.52 (4 H, m), 1.55 (6 H, s), 1.60-1.64 (1 H, m), 1.74 (3 H, s), 1.75 (3 H, s), 1.80-1.90 (3 H, m), 1.90-2.05 (2 H, m), 3.35-3.45 (3 H, m), 3.90-3.98 (2 H, m), 4.00-4.10 (2 H, m), 4.60-4.65 (1 H, m), 6.35 (1 H, s), 9.60 (1 H, s) | Quantitative (not purified) | 445 [M + H] |
| 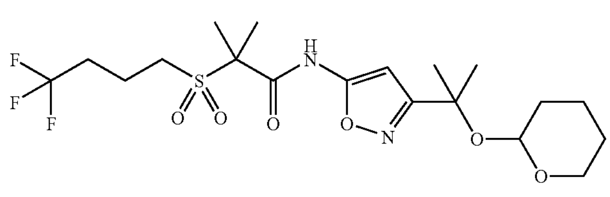 | 400 MHz, CHLOROFORM-d) δ ppm 1.40-1.53 (4 H, m), 1.54 (3 H, s), 1.55 (3 H, s), 1.57-1.63 (1 H, m), 1.73 (3 H, s), 1.74 (3 H, s) 1.77-1.85 (1 H, m), 2.10-2.23 (2 H, m), 2.23-2.38 (2 H, m), 3.08 (2 H, t), 3.35-3.45 (1 H, m), 3.85-3.95 (1 H, m), 4.60 (1 H, t), 6.35 (1 H, s), 9.25 (1 H, s) | 84 | 471 [M + H] |

TABLE XXXII-continued

| Structure | ¹H NMR | Yield [%] | m/z [M + H] |
|---|---|---|---|
| | ¹H NMR (400 MHz, DMSO-d6) δ ppm 0.98-1.13 (2 H, m), 1.20-1.30 (1 H, m), 1.35-1.55 (6 H, m), 1.57-1.68 (3 H, m), 1.68 (3 H, s), 1.69 (3 H, s), 1.75-1.84 (2 H, m), 3.30-3.42 (3 H, m), 3.69-3.76 (1 H, m), 3.83-3.95 (3 H, m), 4.78-4.83 (1 H, m), 6.30 (1 H, s), 11.42 (1 H, s) | 69 | 443 [M + H] |
| | ¹H NMR (400 MHz, MeOD) δ ppm 1.10-1.35 (4 H, m), 1.40-1.60 (4 H, m), 1.60-1.70 (2 H, m), 1.75 (6 H, s), 2.13-2.23 (2 H, m), 2.23-2.40 (2 H, m), 3.08 (2 H, t), 3.40-3.50 (1 H, m), 3.80-3.90 (1 H, m), 4.83-4.90 (1 H, m), 6.35 (1 H, s), 9.25 (1 H, s) | 75 | 469 [M + H] |
| | ¹H NMR (500 MHz, CHLOROFORM-d) δ ppm 1.36 (3 H, s), 1.38 (3 H, s), 1.45-1.73 (5 H, m), 1.74-1.87 (7 H, m), 2.15-2.25 (2 H, m), 2.27-2.40 (2 H, m), 3.11 (2 H, t, J = 7.55 Hz), 3.38 (1 H, d, J = 9.31 Hz), 3.46-3.53 (1 H, m), 3.75-3.84 (2 H, m), 4.59 (1 H, t, J = 3.43 Hz), 6.37 (1 H, s), 9.24 (1 H, s) | 64 | 483 [M − H]; |
| 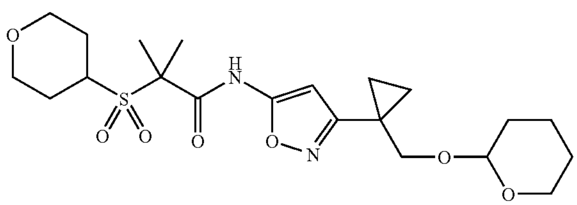 | $^b$LC-MS Retention Time: 1.54 minutes | Quantitative (not purified) | 455 [M − H] |
| 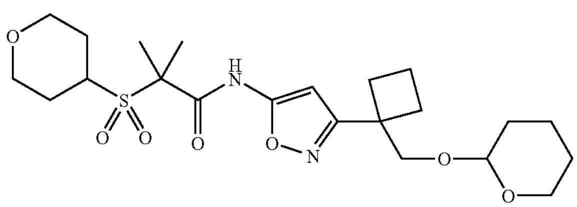 | (400 MHz, CHLOROFORM-d) δ ppm 1.43-1.56 (m, 4 H), 1.56-1.81 (m, 10 H), 1.85-2.00 (m, 4 H), 2.13-2.23 (m, 2 H), 2.32-2.40 (m, 2 H), 3.31 (td, 2 H), 3.36-3.46 (m, 2 H), 3.50 (d, 1 H), 3.71-3.77 (m, 1 H), 3.94 (d, 1 H), 3.97-4.00 (m, 2 H), 4.56 (t, 1 H), 6.22 (s, 1 H), 9.52 (s, 1 H) | 51 | 469 [M − H] |
| 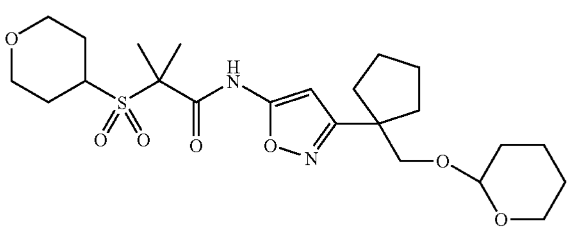 | (400 MHz, CHLOROFORM-d) δ ppm 1.48-1.58 (m, 2 H), 1.62-2.10 (m, 22 H), 3.34-3.55 (m, 5 H), 3.73-3.78 (m, 1 H), 3.84 (d, 1 H), 4.03-4.07 (m, 2 H), 4.57 (bt, 1 H), 6.30 (bt, 1 H), 9.50 (bt, 1 H) | 54 | 483 [M − H] |
| 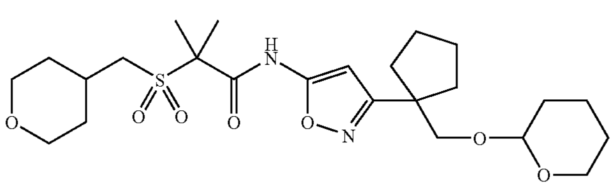 | (400 MHz, CHLOROFORM-d) δ ppm 1.41-1.93 (m, 22 H), 2.02-2.11 (m, 2 H), 2.34-2.43 (m, 1 H), 2.90 (d, 2 H), 3.38-3.49 (m, 4 H), 3.73-3.79 (m, 1 H), 3.82 (d, 1 H), 3.92-3.95 (m, 2 H), 4.56 (bt, 1 H), 6.33 (s, 1 H), 9.33 (s, 1 H) | 65 | 497 [M − H] |

//

TABLE XXXII-continued

| Structure | ¹H NMR | Yield [%] | m/z [M + H] |
|---|---|---|---|
| 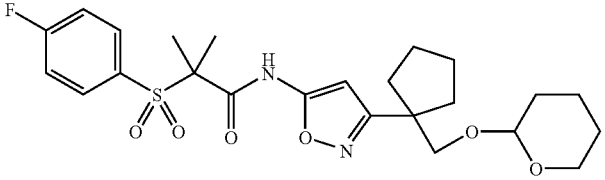 | (400 MHz, CHLOROFORM-d) δ ppm 1.47-1.53 (m, 2 H), 1.57-1.60 (m, 2 H), 1.63-1.95 (m, 14 H), 2.03-2.12 (m, 2 H), 3.42 (d, 1 H), 3.47-3.51 (m, 1 H), 3.74-3.80 (m, 1 H), 3.83 (d, 1 H), 4.58 (bt, 1 H), 6.28 (s, 1 H), 7.22-7.27 (m, 2 H), 7.83-7.87 (m, 2 H), 9.53 (s, 1 H) | 71 | 493 [M − H] |
| 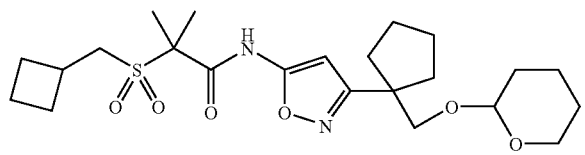 | (400 MHz, CHLOROFORM-d) δ ppm 1.48-2.10 (m, 24 H), 2.20-2.26 (m, 2 H), 2.90-3.00 (m, 1 H), 3.10 (d, 2 H), 3.41 (d, 1 H), 3.44-3.50 (m, 1 H), 3.73-3.79 (m, 1 H), 3.82 (d, 1 H), 4.57 (bt, 1 H), 6.34 (s, 1 H), 9.42 (s, 1 H) | 73 | 467 [M − H] |
| 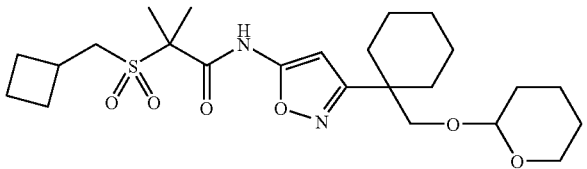 | ᵃ(400 MHz, CHLOROFORM-d) δ ppm 1.43-1.67 (m, 14 H), 1.71 (s, 6 H), 1.86-1.93 (3 H), 1.95-2.02 (m, 1 H), 2.04-2.13 (m, 2 H), 2.21-2.27 (m, 2 H), 2.94-2.99 (m, 1 H), 3.11 (d, 2 H), 3.30 (d, 1 H), 3.43-3.47 (m, 1 H), 3.68-3.76 (m, 2 H), 4.50 (bt, 1 H), 6.33 (s, 1 H), 9.43 (s, 1 H) | 72 | 481 [M − H] |
| 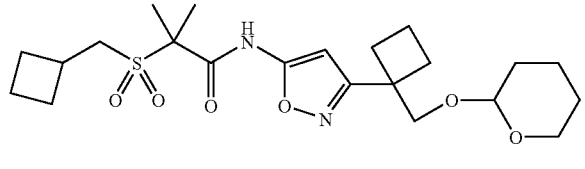 | (400 MHz, CHLOROFORM-d) δ ppm 1.48-1.64 (m, 4 H), 1.65-1.70 (m, 7 H), 1.80-1.94 (m, 4 H), 1.94-2.05 (m, 3 H), 2.91-3.01 (m, 1 H), 3.10 (d, 2 H), 3.48-3.53 (m, 1 H), 3.57 (d, 1 H), 3.79-3.85 (m, 1 H), 4.01 (d, 1 H), 4.63 (bt, 1 H), 6.32 (s, 1 H), 9.44 (s, 1 H) | 47 | 453 [M − H] |
| 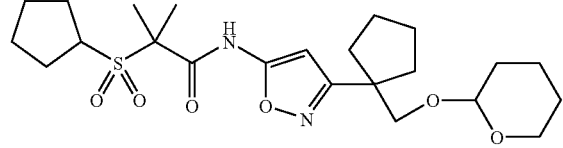 | (400 MHz, CHLOROFORM-d) δ ppm 1.45-1.93 (m, 22 H), 1.96-2.08 (m, 6 H), 3.40 (d, 1 H), 3.44-3.49 (m, 1 H), 3.49-3.58 (m, 1 H), 3.72-3.77 (m, 1 H), 3.82 (d, 1 H), 4.56 (bt, 1 H), 6.32 (s, 1 H), 9.50 (s, 1 H) | 53 | 467 [M − H] |
| 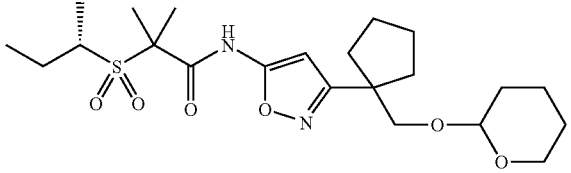 | (400 MHz, CHLOROFORM-d) δ ppm 1.03 (t, 3 H), 1.33 (d, 3 H), 1.48-1.53 (m, 2 H), 1.59-1.66 (m, 4 H), 1.71-1.74 (m, 10 H), 1.78-2.10 (m, 6 H), 3.21-3.24 (m, 1 H), 3.42 (d, 1 H), 3.46-3.51 (m, 1 H), 3.73-3.79 (m, 1 H), 3.84 (d, 1 H), 4.58 (bs, 1 H), 6.33 (s, 1 H), 9.71 (s, 1 H) | 72 | 455 [M − H] |
| 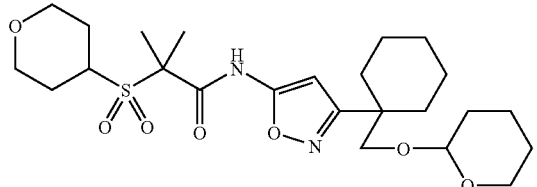 | ᵃ(400 MHz, CHLOROFORM-d) δ ppm 1.41-1.67 (m, 14 H), 1.76 (s, 6 H), 1.86-1.90 (m, 2 H), 1.94-2.14 (m, 4 H), 3.31 (d, 1 H), 3.36-3.52 (m, 4 H), 3.66-3.71 (m, 1 H), 3.75 (d, 1 H), 4.04-4.08 (m, 2 H), 4.51 (bt, 1 H), 6.31 (s, 1 H), 9.56 (s, 1 H) | 55 | 497 [M − H] |
| 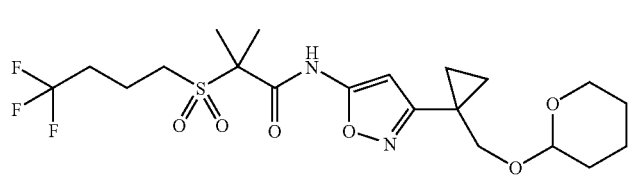 | ᵇLC-MS Retention Time: 1.75 minutes | Quantitative (not purified) | 481 [M − H] |

TABLE XXXII-continued

| Structure | ¹H NMR | Yield [%] | m/z [M + H] |
|---|---|---|---|
| | *(400 MHz, CHLOROFORM-d) δ ppm 1.42-1.63 (m, 14 H), 1.76 (s, 6 H), 2.04-2.24 (m, 4 H), 2.25-2.34 (m, 2 H), 3.11 (t, 2 H), 3.30 (d, 1 H), 3.44-3.47 (m, 1 H), 3.64-3.76 (m, 2 H), 4.50 (bd, 1 H), 6.33 (s, 1 H), 9.21 (s, 1 H) | 55 | 523 [M − H] |
| 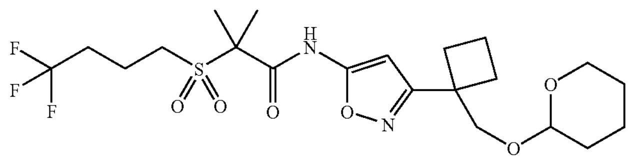 | (400 MHz, CHLOROFORM-d) δ ppm 1.49-1.62 (m, 3 H), 1.65-1.85 (m, 9 H), 1.96-2.09 (m, 2 H), 2.15-2.44 (m, 8 H), 3.10 (t, 2 H), 3.50-3.53 (m, 1 H), 3.56 (d, 1 H), 3.79-3.85 (m, 1 H), 4.01 (d, 1 H), 4.63 (bt, 1 H), 6.32 (s, 1 H), 9.22 (s, 1 H) | 49 | 495 [M − H] |
| 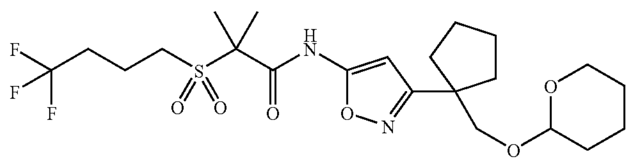 | (400 MHz, CHLOROFORM-d) δ ppm 1.47-1.94 (m, 20 H), 2.01-2.09 (m, 1 H), 2.15-2.22 (m, 2 H), 2.27-2.38 (m, 2 H), 3.10 (t, 2 H), 3.41 (d, 1 H), 3.45-3.50 (m, 1 H), 3.74-3.80 (m, 1 H), 3.83 (d, 1 H), 4.56 (bt, 1 H), 6.35 (s, 1 H), 9.20 (s, 1 H) | 87 | 509 [M − H] |
| 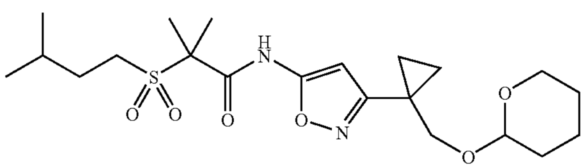 | (400 MHz, CHLOROFORM-d) δ ppm 0.93 (d, 6 H), 1.02-1.05 (m, 2 H), 1.13-1.15 (m, 2 H), 1.58-1.66 (m, 2 H), 1.68-1.76 (m, 13 H), 2.97-3.01 (m, 2 H), 3.48-3.54 (m, 1 H), 3.73-3.89 (m, 3 H), 4.70 (bt, 1 H), 6.32 (s, 1 H), 9.41 (s, 1 H) | 78 | 411 [M − H] |
| | ᵇLC-MS Retention Time: 1.72 minutes | Quantitative (not purified) | 483 [M − H] |
| 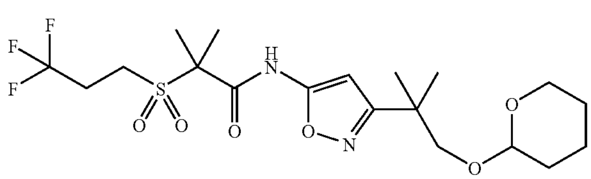 | intermediate not isolated, used without further purification in next step | Quantitative (not purified) | 471 [M + H] |
| 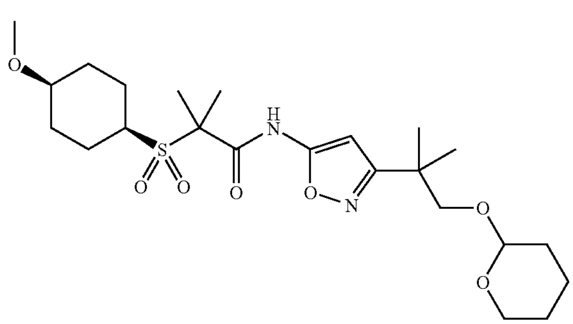 | (500 MHz, CHLOROFORM-d) δ ppm 1.33-1.45 (8 H, m), 1.46-1.64 (4 H, m), 1.65-1.75 (7 H, m), 1.77-1.84 (3 H, m), 1.91-2.03 (2 H, m), 2.08 (2 H, dd, J = 13.43, 2.59 Hz), 3.17-3.25 (1 H, m), 3.28 (3 H, s), 3.38 (1 H, d, J = 9.31 Hz), 3.44 (1 H, t, J = 2.67 Hz), 3.47-3.53 (1 H, m), 3.74-3.82 (2 H, m), 4.59 (1 H, t, J = 3.36 Hz), 6.32 (1 H, s), 9.76 (1 H, s) | 71 | 487 [M + H] |

TABLE XXXII-continued

| Structure | ¹H NMR | Yield [%] | m/z [M + H] |
|---|---|---|---|
| 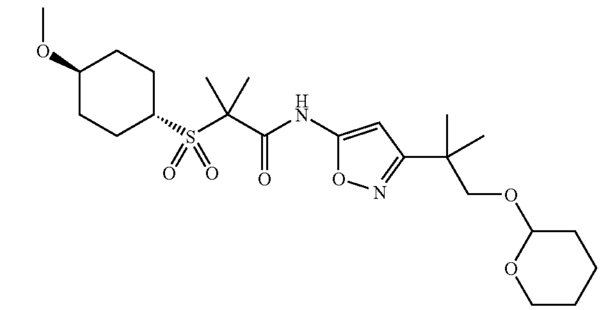 | (500 MHz, CHLOROFORM-d) δ ppm 1.17-1.26 (2 H, m), 1.35 (3 H, s), 1.37 (3 H, s), 1.46-1.87 (14 H, m), 2.10 (2 H, d, J = 12.36 Hz), 2.20 (2 H, dd, J = 13.58, 3.51 Hz), 3.09-3.23 (2 H, m), 3.31-3.40 (4 H, m), 3.46-3.54 (1 H, m), 3.74-3.84 (2 H, m), 4.59 (1 H, t, J = 3.36 Hz), 6.34 (1 H, s), 9.72 (1 H, s) | 80 | 487 [M + H] |

<sup>a</sup>Impurities are present
<sup>b</sup>ESI +/− ion mode, Zorbax Eclipse XDB-C8, 5 μm 4.6 × 150 mm Column; Gradient: 5% B to 95% B (0 min to 1.7 mins), 95% B to 95% B (1.7 mins to 2.0 mins), 95% B to 5% B (2.0 mins to 2.1 mins), 5% B to 5% B (2.1 mins to 2.3 mins).
Flow rate: 2.5 mL/min.
A = (Water + 0.1% Formic Acid)
B = (Acetonitrile + 0.1% Formic Acid). Diode Array Detector

Amide Method B1

Deprotection with MP-TsOH

Synthesis of N-[3-(2-Hydroxy-1,1-dimethyl-ethyl)-isoxazol-5-yl]-2-methyl-2-(tetrahydro-pyran-4-sulfonyl)propionamide (Example 2)

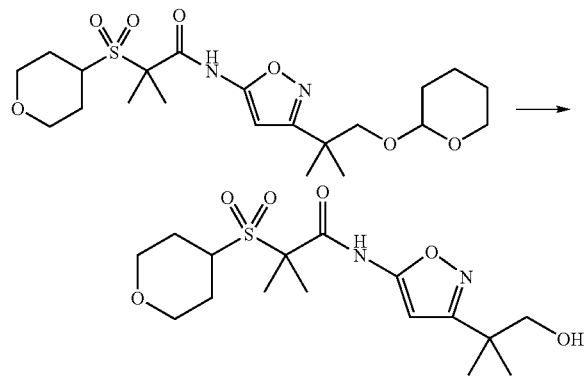

Synthesis of N-[3-(2-Hydroxy-1,1-dimethyl-ethyl)-isoxazol-5-yl]-2-methyl-2-(tetrahydro-pyran-4-sulfonyl)propionamide A solution of 98 g (0.21 mol) of N-{3-[1,1-dimethyl-2-(tetrahydro-pyran-2-yloxy)-ethyl]-isoxazol-5-yl}-2-methyl-2-(tetrahydro-pyran-4-sulfonyl)-propionamide in DCM/ethanol (1/1, 1.2 L) is treated with 129 g (0.42 mol) of MP-TsOH resin (loading 3.3 mmol/g) at room temperature for 18 h. The resin is removed by filtration and washed alternating with DCM (0.5 L) and methanol (0.5 L) twice. The combined filtrates are concentrated under reduced pressure and the resulting tan residue is slurried in heptanes/ethyl acetate (7/3, 4×1 L) to yield 65 g of N-[3-(2-hydroxy-1,1-dimethyl-ethyl)-isoxazol-5-yl]-2-methyl-2-(tetrahydro-pyran-4-sulfonyl)propionamide as a white powder. Yield 82%; ES-MS: m/z 375 [M+H], mp 191-192° C.

Synthesis of N-[3-(2-Hydroxy-1,1-dimethyl-ethyl)-isoxazol-5-yl]-2-methyl-2-(3,3,3-trifluoro-propane-1-sulfonyl)-propionamide (Example 7)

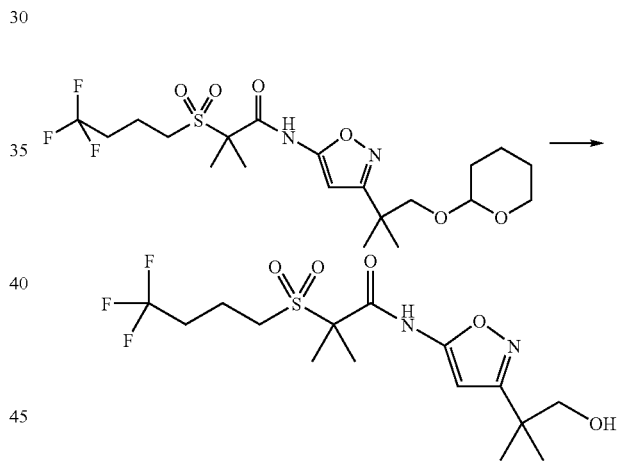

A solution of 163 g (0.34 mol) of N-{3-[1,1-dimethyl-2-(tetrahydro-pyran-2-yloxy)-ethyl]-isoxazol-5-yl}-2-methyl-2-(4,4,4-trifluoro-butane-1-sulfonyl)-propionamide in DCM/ethanol (1/1, 3 L) is treated with 307 g (1.01 mol) of MP-TsOH resin (loading 3.3 mmol/g) at room temperature for 18 h. Additional 100 g of MP-TsOH resin (loading 3.3 mmol/g) is added and the mixtures are stirred at room temperature for further 18 h. The resin is removed by filtration and washed with DCM (1 L) and methanol (3×1 L) twice. The combined filtrates are concentrated under reduced pressure and the resulting tan residue is slurried in diethyl ether (3×0.4 L) to yield 129 g of N-[3-(2-hydroxy-1,1-dimethyl-ethyl)-isoxazol-5-yl]-2-methyl-2-(3,3,3-trifluoro-propane-1-sulfonyl)-propionamide as a white powder. Yield 96%; ES-MS: m/z 401 [M+H], mp 162-163° C.; ¹H NMR (500 MHz, CHLOROFORM-d) δ ppm 1.32 (6H, s), 1.77 (6H, s), 2.13-2.27 (3H, m), 2.27-2.40 (2H, m), 3.11 (2H, t, J=7.50 Hz), 3.69 (2H, d, J=6.79 Hz), 6.34 (1H, s), 9.30 (1H, br. s.)

Compounds in Table XXXVIII, amide method B1, are made according to this procedure with the following modifications to be noted: Example 76 is further purified by column chromatography (silica, eluent: DCM, 0-50% ethyl acetate). Example 107 is further purified by column chromatography (silica, eluent: DCM, 2% MeOH). Examples 117 and 118 are slurried in heptanes. For Example 29 prior to the deprotection, 2-(2,3-difluoro-phenylsulfanyl)-N-{3-[1,1-dimethyl-2-(tetrahydro-pyran-2-yloxy)-ethyl]-isoxazol-5-yl}-2-methyl-propionamide is oxidized according to method F, step 2, to give 2-(2,3-difluoro-benzenesulfonyl)-N-{3-[1,1-dimethyl-2-(tetrahydro-pyran-2-yloxy)-ethyl]-isoxazol-5-yl}-2-methyl-propionamide, Yield: 17%, ES-MS: 509 [M+Na]

Amide Method B2

Deprotection with PPTS

Synthesis of N-[3-(2-Hydroxy-1,1-dimethyl-ethyl)-isoxazol-5-yl]-2-methyl-2-(tetrahydro-pyran-4-sulfonyl)propionamide (Example 2)

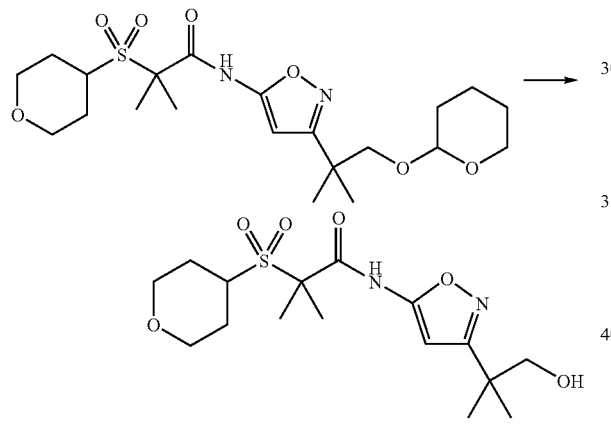

Step 2: Synthesis of N-[3-(2-Hydroxy-1,1-dimethyl-ethyl)-isoxazol-5-yl]-2-methyl-2-(tetrahydro-pyran-4-sulfonyl)propionamide A solution of N-{3-[1,1-Dimethyl-2-(tetrahydro-pyran-2-yloxy)-ethyl]-isoxazol-5-yl}-2-methyl-2-(tetrahydro-pyran-4-sulfonyl)-propionamide (466 mg, 1.02 mmol) and pyridinium p-toluenesulfonate (25.5 mg, 0.102 mmol) in ethanol (5 mL) is stirred at 55° C. for 1.5 h. After this time, the reaction mixture is concentrated and then dispersed in water then filtered to provide the title compound. Yield: 81%; m/z 375 [M+H].

Notes: in some cases, 0.2 equivalent of pyridinium p-toluenesulfonate is used and the reaction temperature is 65° C. and the heating time is between 1 hour and 18 h. In most cases, aqueous workup is used followed by silica gel chromatography.

Compounds in Table XXXVIII, amide method B2, are made according to this procedure.

Amide Method B3

Deprotection with HCl

Synthesis of N-[3-(2-Hydroxy-1,1-dimethyl-ethyl)-isoxazol-5-yl]-2-methyl-2-(tetrahydro-pyran-4-sulfonyl)propionamide (Example 2)

2120 mL 10M HCl in ethanol is added to a mixture of 10.8 kg N-{3-[1,1-Dimethyl-2-(tetrahydro-pyran-2-yloxy)-ethyl]-isoxazol-5-yl}-2-methyl-2-(tetrahydro-pyran-4-sulfonyl)-propionamide in 65 L ethanol at 51° C. The mixture is stirred for 2.5 h at 54° C. and then is cooled to 1° C. The suspension is filtered and the filter cake is washed once with 5 L cold ethanol and once with 7 L ethanol. Drying of the filter cake provides 8001 g product. ES-MS: m/z 375 [M+H];]; $^1$H NMR (400 MHz, DMSO-d6) δ ppm 1.19 (6H, s) 1.59-1.72 (2H, m), 1.68 (6H, s), 1.80-1.86 (2H, m), 3.34-3.43 (4H, m), 3.85-3.94 (3H, m), 4.80 (1H, t, $^3J_{H,H}$=5.5 Hz), 6.30 (1H, s), 11.27 (1H, s).

Amide Method C

Synthesis of N-[5-(2-Hydroxy-1,1-dimethyl-ethyl)-isoxazol-3-yl]-2-methyl-2-[2-(tetrahydro-pyran-4-yl)-ethanesulfonyl]-propionamide (Example 16)

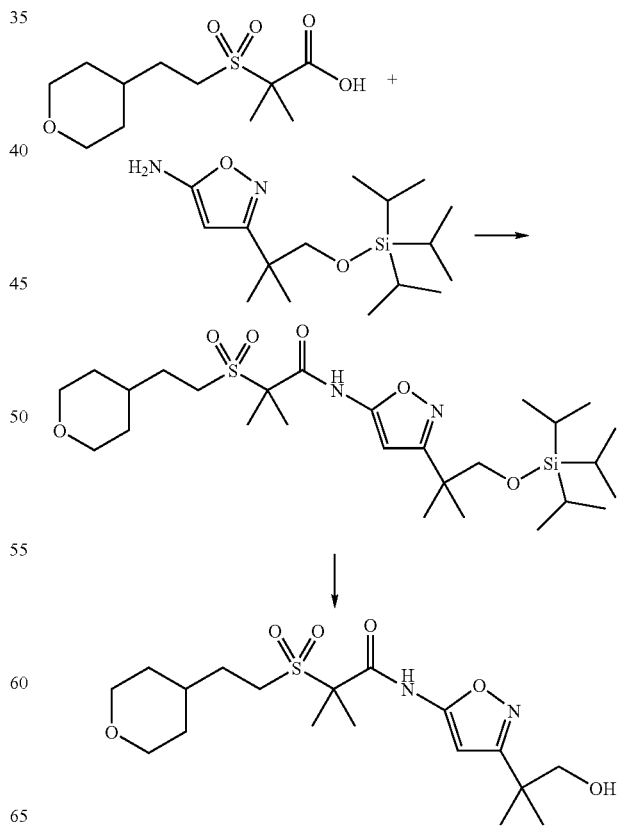

Step 1: Synthesis of N-[5-(1,1-Dimethyl-2-triisopropylsilanyloxy-ethyl)-isoxazol-3-yl]-2-methyl-2-[2-(tetrahydro-pyran-4-yl)-ethanesulfonyl]-propionamide Activation of 200 mg (0.75 mmol) 2-methyl-2-[2-(tetrahydro-pyran-4-yl)-ethanesulfonyl]-propionic acid as its acid chloride is achieved by treatment with oxalyl chloride (0.39 mL, 4.5 mmol) and a catalytic amount of DMF in DCM (5 mL) at room temperature for 5 h. The reaction is concentrated under reduced pressure.

The crude acid chloride is dissolved in DCM (5 mL) and added to a solution of 280 mg (0.90 mmol) of 5-(1,1-dimethyl-2-triisopropylsilanyloxy-ethyl)-isoxazol-3-ylamine and N,N-diisopropylethylamine (0.19 mL) in DCM (2 mL). The reaction is stirred at room temperature for 18 h. The reaction mixture is diluted with DCM, washed with saturated aqueous NaHCO$_3$ solution (10 mL), brine (2 mL) and dried over Na$_2$SO$_4$. Filtration and concentration of the filtrate afforded the crude product. Further purification by column chromatography (silica, eluent: ethyl acetate, 0-20% heptanes) yielded 190 mg of N-[5-(1,1-dimethyl-2-triisopropylsilanyloxy-ethyl)-isoxazol-3-yl]-2-methyl-2-[2-(tetrahydro-pyran-4-yl)-ethanesulfonyl]-propionamide. Yield 45%, ES-MS: m/z 559 [M+H], 581 [M+Na]

According to this method the following amides are made:

Step 2: Synthesis of N-[5-(2-Hydroxy-1,1-dimethyl-ethyl)-isoxazol-3-yl]-2-methyl-2-[2-(tetrahydro-pyran-4-yl)-ethanesulfonyl]-propionamide To a solution of 190 mg (0.34 mmol) of N-[5-(1,1-dimethyl-2-triisopropylsilanyloxy-ethyl)-isoxazol-3-yl]-2-methyl-2-[2-(tetrahydro-pyran-4-yl)-ethanesulfonyl]-propionamide in THF (2 mL) are added 1.7 mL (1M solution in THF, 1.7 mmol) of tetrabutylammonium fluoride. The reaction is stirred at room temperature for 18 h and then diluted with 1M aqueous NH$_4$Cl solution (5 mL). The aqueous layer is extracted with DCM (3×25 mL). The combined organic extracts are dried over Na$_2$SO$_4$ and filtered and the filtrate concentrated under reduced pressure to give 46 mg of N-[5-(2-hydroxy-1,1-dimethyl-ethyl)-isoxazol-3-yl]-2-methyl-2-[2-(tetrahydro-pyran-4-yl)-ethanesulfonyl]-propionamide. Yield: 34%, ES-MS: m/z 403 [M+H]

Compounds in Table XXXVIII, amide method C, are made according to this procedure.

TABLE XXXIII

| Structure | $^1$H-NMR | Yield [%] | m/z [M + H] |
|---|---|---|---|
| 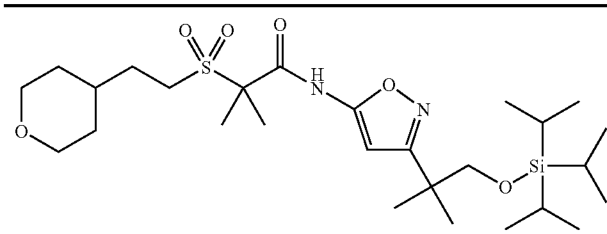 | (500 MHz, CHLOROFORM-d) δ ppm 0.87-1.06 (20 H, m), 1.14-1.31 (8 H, m), 1.45-1.63 (4 H, m), 1.67 (6 H, s), 1.70-1.80 (2 H, m), 2.84-3.05 (2 H, m), 3.28 (2 H, td, J = 11.83, 1.83 Hz), 3.63 (2 H, s), 3.88 (2 H, dd, J = 11.14, 3.97 Hz), 6.27 (1 H, s), 9.29 (1 H, br. s.) | 45 | 559, 581 [M + Na], |
| 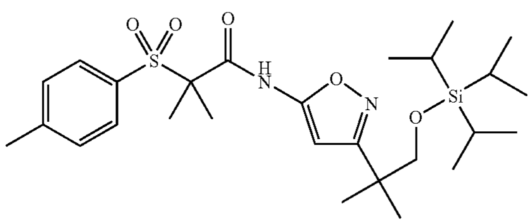 | (250 MHz, CHLOROFORM-d) δ ppm 0.88-1.18 (21 H, m), 1.28-1.40 (6 H, m), 1.55-1.70 (6 H, m), 2.44 (3 H, s), 3.68 (2 H, s), 6.26 (1 H, s), 7.33 (2 H, d, J = 8.07 Hz), 7.68 (2 H, d, J = 8.34 Hz), 9.67 (1 H, br. s.) | 40 | 537 |
| 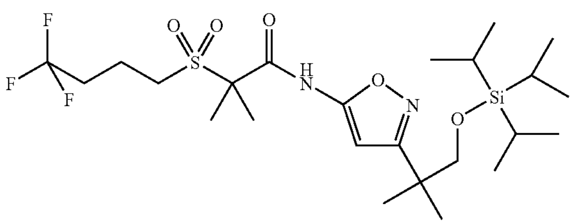 | Intermediate not purified, used as crude in the next step | 75 | 557 |
| 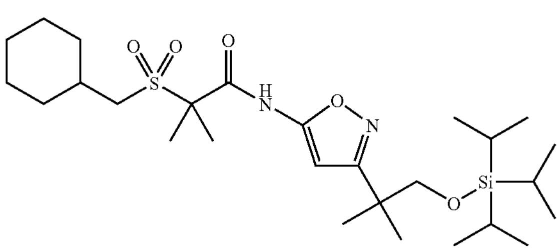 | (500 MHz, CHLOROFORM-d) δ ppm 0.98-1.18 (14 H, m), 1.22-1.38 (8 H, m), 1.44 (12 H, s), 1.67-1.75 (8 H, m), 1.94 (2 H, d, J = 15.29 Hz), 2.84 (2 H, d, J = 6.46 Hz), 3.71 (2 H, s), 6.35 (1 H, s), 9.42 (1 H, s) | 55 | N/A |

Amide Method D

Synthesis of N-[5-(4-Methoxy-phenyl)-4H-[1,2,4]triazol-3-yl]-2-methyl-2-(tetrahydro-pyran-4-yl-methanesulfonyl)-propionamide (Example 4)

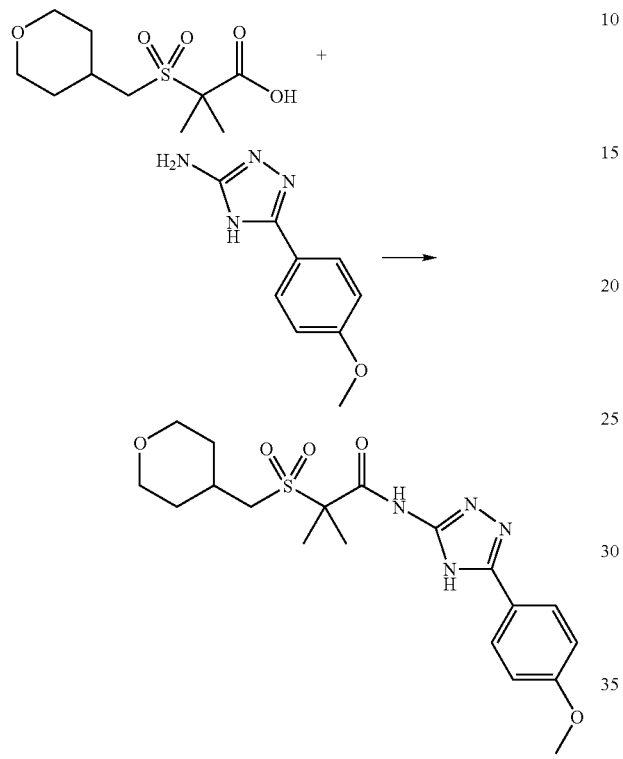

Activation of 0.99 g (3.96 mmol) of 2-methyl-2-(tetrahydro-pyran-4-ylmethanesulfonyl)-propionic acid as the corresponding acid chloride is achieved by treatment with thionyl chloride (0.54 mL, 7.50 mmol) and DMF (cat., 10 mol %) in toluene (20 mL) at 100° C. for 2 h. The reaction is cooled to room temperature and toluene (10 mL) is removed by distillation, whilst adding fresh toluene (10 mL). This process is repeated twice.

This acid chloride solution is added dropwise over 0.5 h to a stirred suspension of 0.5 g (2.6 mmol) of 5-(4-methoxy-phenyl)-4H-[1,2,4]triazol-3-ylamine and 0.91 mL (5.23 mmol) of N,N-diisopropylethylamine in toluene (10 mL) at 50° C. After complete addition the reaction is heated to 100° C. for 17 h. The reaction is cooled to room temperature and the solvent is removed under reduced pressure. The residue is dissolved in DCM (25 mL) and washed with saturated aqueous NaHCO₃ solution (25 mL). The aqueous layer is back-extracted with DCM (2×25 mL). The combined organic layers are dried over Na₂SO₄, filtered and the filtrate is concentrated under reduced pressure. The residue is slurried in DCM/ether (1/1, 10 mL) to yield 0.58 g of N-[5-(4-methoxy-phenyl)-4H-[1,2,4]triazol-3-yl]-2-methyl-2-(tetrahydro-pyran-4-ylmethanesulfonyl)-propionamide. Yield: 52%; ES-MS: m/z 423 [M+H]

Compounds in Table XXXVIII, amide method D, are made according to this procedure.

Amide Method E

Synthesis of 2-Methyl-2-{5-[2-methyl-2-(tetrahydro-pyran-4-sulfonyl)-propionylamino]-isoxazol-3-yl}-propionic Acid (Example 23)

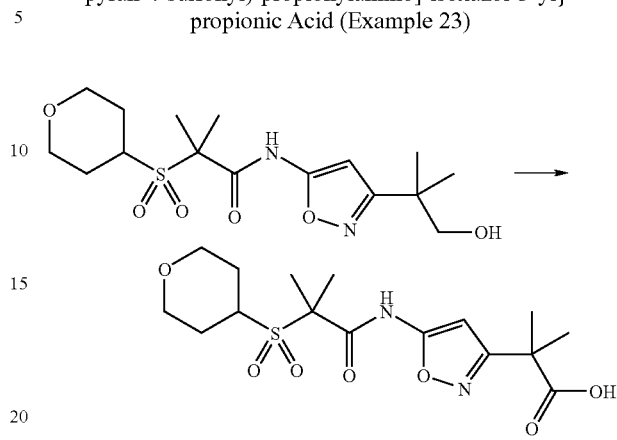

Jones reagent (1.28 mL, 10.24 mmol) is added dropwise to a solution of N-[3-(2-Hydroxy-1,1-dimethyl-ethyl)-isoxazol-5-yl]-2-methyl-2-(tetrahydro-pyran-4-sulfonyl)-propionamide (560 mg, 1.50 mmol) in a mixture of acetone (4 mL) and dichloromethane (4 mL) at 0° C. The reaction mixture is stirred at 0° C. for 3 minutes then room temperature for 2.5 h. After this time, the reaction mixture is diluted with acetone and filtered through celite and the celite is washed with acetone. The filtrate is concentrated under reduced pressure. The residue is dispersed in water and filtered to yield the title compound. Yield: 64%; m/z 389 [M+H].

Compounds in Table XXXVIII, amide method E, are made according to this procedure.

Amide Method F

Synthesis of 2-(2-Fluoro-4-methanesulfonyl-benzenesulfonyl)-N-[3-(2-methoxy-1,1-dimethyl-ethyl)-isoxazol-5-yl]-2-methyl-propionamide (Example 76)

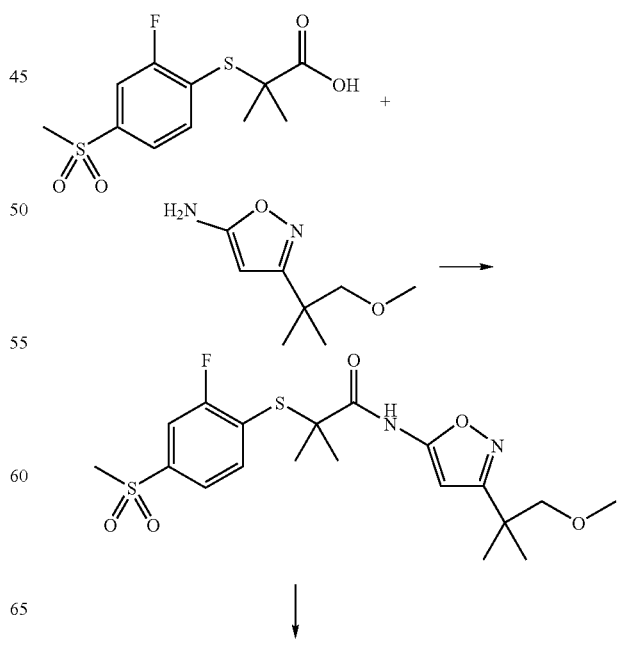

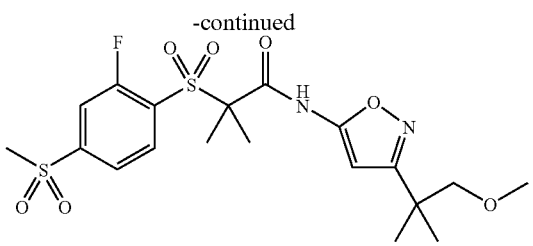

Step 1: Synthesis of 2-(2-Fluoro-4-methanesulfonyl-phenylsulfanyl)-N-[3-(2-methoxy-1,1-dimethyl-ethyl)-isoxazol-5-yl]-2-methyl-propionamide Activation of 336 mg (1.15 mmol) of 2-(2-fluoro-4-methanesulfonyl-phenylsulfanyl)-2-methyl-propionic acid as its acid chloride is achieved by treatment with oxalyl chloride (0.3 mL, 3.45 mmol) and DMF (1 drop) in DCM (15 mL) at room temperature for 3 h. The solvent is removed under reduced pressure and the crude acid chloride is dissolved in toluene (5 mL) and added to a solution of 196 mg (1.15 mmol) of 3-(2-methoxy-1,1-dimethyl-ethyl)-isoxazol-5-ylamine and N,N-diisopropylethylamine (0.40 mL, 2.3 mmol) in toluene. The reaction is heated to 50° C. for 18 h. After cooling to room temperature, the reaction mixture is diluted with ethyl acetate (20 mL) and washed with 1M aqueous HCl solution (2×10 mL), water (2×10 mL), saturated aqueous NaHCO$_3$ solution (2×10 mL), brine (10 mL). The organic layer is dried (Na$_2$SO$_4$), filtered and the filtrate is concentrated under reduced pressure. The residue is purified twice by column chromatography (silica, eluent: heptanes, 20-50% ethyl acetate, followed by heptanes, 10% ethyl acetate) to afford 220 mg of 2-(2-fluoro-4-methanesulfonyl-phenylsulfanyl)-N-[3-(2-methoxy-1,1-dimethyl-ethyl)-isoxazol-5-yl]-2-methyl-propionamide. Yield: 43%, ES-MS: m/z 445 [M+H]

According to this method the following amides are made, with the exception of Example 76 for which the coupling is performed in THF:

TABLE XXXIV

| Structure | $^1$H NMR | Yield [%] | m/z [M + H] |
|---|---|---|---|
| 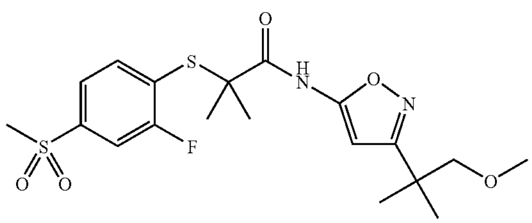 | (250 MHz, CHLOROFORM-d) δ ppm 1.26 (6 H, s), 1.59 (6 H, s), 3.01 (3 H, s), 3.23-3.29 (3 H, m), 3.35 (2 H, s), 6.24 (1 H, s), 7.41-7.72 (3 H, m), 9.34 (1 H, s) | 43 | 445 |
| 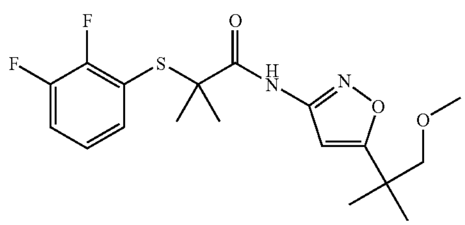 | (500 MHz, CHLOROFORM-d) δ ppm 1.34 (6 H, s), 1.73 (6 H, s), 3.33 (3 H, s), 3.45 (2 H, s), 6.61 (1 H, s), 7.24-7.36 (11 H, m), 7.49-7.58 (1 H, m), 7.59-7.67 (1 H, m), 9.08 (1 H, s) | 62 | 385 |
| 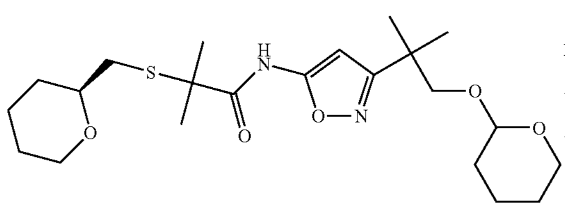 | (500 MHz, CHLOROFORM-d) δ ppm 1.21-1.71 (22 H, m), 1.78-1.90 (2 H, m), 2.58-2.77 (2 H, m), 3.31-3.54 (4 H, m), 3.75-3.82 (2 H, m), 4.14 (1 H, dt, J = 11.29, 2.21 Hz), 4.59 (1 H, t, J = 3.36 Hz), 6.36 (1 H, s), 10.33 (1 H, s) | 52 | 463 [M + Na] |
| 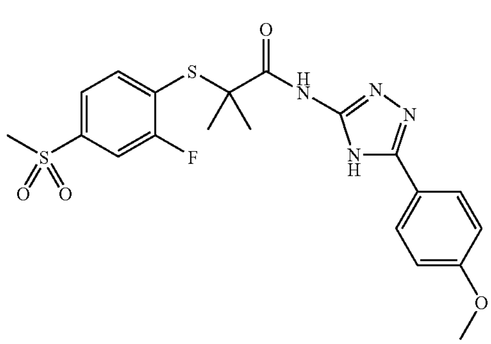 | (250 MHz, CHLOROFORM-d) δ ppm 1.68 (6 H, s), 3.05 (3 H, s), 3.86 (3 H, s), 6.92-7.01 (2 H, m), 7.54-7.72 (3 H, m), 7.92-8.04 (2 H, m) | 96 | 465 |

Step 2: Synthesis of 2-(2-Fluoro-4-methanesulfonyl-benzenesulfonyl)-N-[3-(2-methoxy-1,1-dimethyl-ethyl)-isoxazol-5-yl]-2-methyl-propionamide To a stirred solution of 220 mg (0.50 mmol) of 2-(2-fluoro-4-methanesulfonyl-phenylsulfanyl)-N-[3-(2-methoxy-1,1-dimethyl-ethyl)-isoxazol-5-yl]-2-methyl-propionamide in DCM (10 mL) are added 333 mg (1.49 mmol) of m-chloroperoxybenzoic acid under nitrogen atmosphere. The reaction mixture is stirred at room temperature for 18 h, then diluted with ethyl acetate (20 mL) and washed with water (2×1 mL). The aqueous wash is back-extracted with DCM (15 mL). The organic extracts are washed with saturated aqueous $Na_2SO_3$ solution (2×2 mL), saturated aqueous $NaHCO_3$ solution (2×2 mL) and brine. The combined organic layer is dried over $MgSO_4$, filtered and concentrated under reduced pressure. The residue is purified by column chromatography (silica, eluent: heptanes, 0-50% ethyl acetate) followed by trituration with heptane/DCM to afford 50 mg of 2-(2-fluoro-4-methanesulfonyl-benzenesulfonyl)-N-[3-(2-methoxy-1,1-dimethyl-ethyl)-isoxazol-5-yl]-2-methyl-propionamide. Yield: 21%, ES-MS: m/z 477 [M+H]

Compounds in Table XXXVIII, amide method F, are made according to this procedure with the following modifications to be noted: For Example 145, removal of the tetrahydropyran protecting group also occurs during the oxidation step.

Amide Method G

Synthesis of N-[5-(4-Hydroxy-phenyl)-4H-[1,2,4]triazol-3-yl]-2-methyl-2-(tetrahydro-pyran-4-sulfonyl)-propionamide (Example 15)

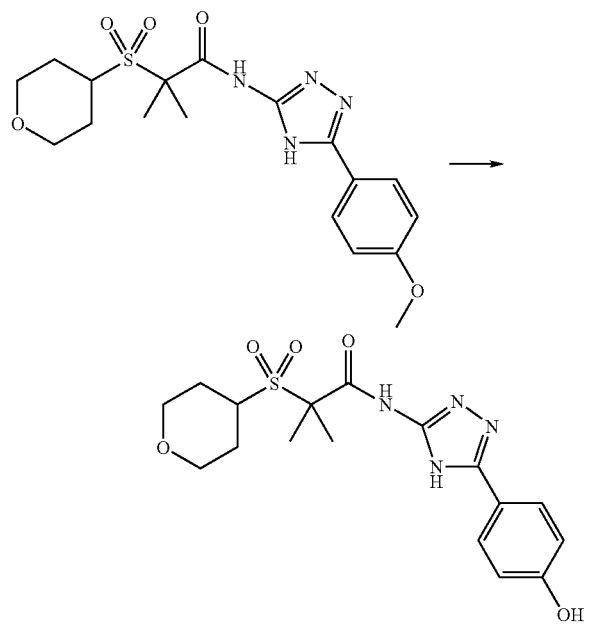

Prepared as described by adaptation of the following reference:
Van Muijlwijk-Koezen et al. *J. Med. Chem.* 2001, 44, (749-762).

To a solution of 118 mg (0.29 mmol) of N-[5-(4-Methoxy-phenyl)-4H-[1,2,4]triazol-3-yl]-2-methyl-2-(tetrahydro-pyran-4-sulfonyl)-propionamide in ethanethiol (5 mL) are added 750 mg (2.9 mmol) of aluminium tribromide. The reaction is stirred at room temperature for 20 h. The reaction is quenched by addition of 12M aqueous HCl solution (2 mL) and diluted with water (10 mL). The aqueous layer is extracted with ethyl acetate (3×20 mL). The combined organic extracts are dried over $Na_2SO_4$, filtered and the filtrate is concentrated under reduced pressure. The residual solid is washed with DCM to afford 45 mg of N-[5-(4-hydroxy-phenyl)-4H-[1,2,4]triazol-3-yl]-2-methyl-2-(tetrahydro-pyran-4-sulfonyl)-propionamide. Yield: 38%, ES-MS: m/z 395 [M+H].

Compounds in Table XXXVIII, amide method G, are made according to this procedure with the following modifications to be noted: For Example 47, 48, 49 and 147 $AlCl_3$ is used instead of $AlBr_3$.

For, Example 113 the compound is purified by column chromatography (silica, eluent: DCM, 0-50% ethyl acetate). Example 74 is purified by recrystallisation from heptanes/ethyl acetate.

For Example 110 the crude product is washed with ethyl acetate. For Example 111, the crude product is isolated by filtration of the aqueous layer and is further purified by mass-triggered preparative LC (neutral method). Example 117 is isolated by filtration of the reaction mixture and purification by column chromatography (silica, eluent: DCM, 1-5% MeOH). Example 120 and 130 are purified by column chromatography (silica, eluent: heptanes, 0-80% ethyl acetate). Example 124, 125, 126 and 128 are purified by mass-triggered preparative LC (neutral method).

Amide Method H

Synthesis of N-[3-(2-Methoxy-1,1-dimethyl-ethyl)-isoxazol-5-yl]-2-methyl-2-(tetrahydro-pyran-4-yl-methanesulfonyl)-propionamide (Example 17)

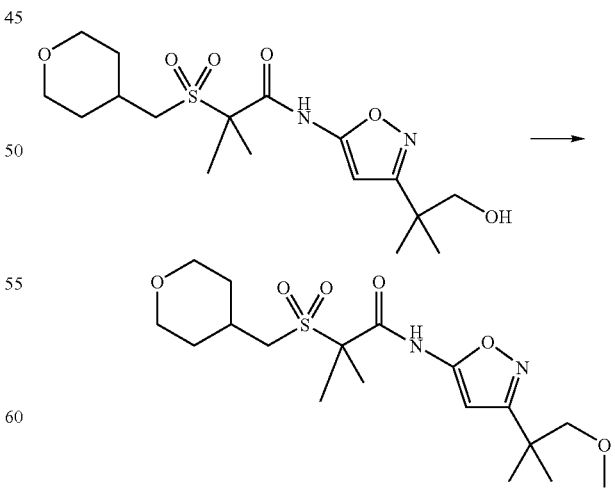

To a solution of 70 mg (0.18 mmol) of N-[3-(2-hydroxy-1,1-dimethyl-ethyl)-isoxazol-5-yl]-2-methyl-2-(tetrahydro-pyran-4-ylmethanesulfonyl)-propionamide in anhydrous THF (2 mL) at 5° C. are added 9 mg (0.36 mmol) of sodium hydride (60% dispersion in mineral oil). The reaction mixture is stirred for 0.5 h and then 32 µL (0.54 mmol) of methyl iodide are added. The reaction is stirred at room temperature for 18 h and is then warmed to 35° C. for 6 h. The reaction is quenched by addition of methanol and concentrated under reduced pressure. The residue is dissolved in DCM and washed with water, saturated aqueous NaHCO₃ solution and brine. The organic layer is dried over Na₂SO₄, filtered and the filtrate is concentrated under reduced pressure. The residue is purified by column chromatography (silica, eluent: DCM, 10% ethyl acetate) followed by preparative HPLC (neutral conditions) to afford 20 mg of N-[3-(2-methoxy-1,1-dimethyl-ethyl)-isoxazol-5-yl]-2-methyl-2-(tetrahydro-pyran-4-ylmethanesulfonyl)-propionamide. Yield: 28%, ES-MS: m/z 403 [M+H]

Compounds in Table XXXVIII, amide method H, are made according to this procedure with the following modifications to be noted: For Example 38 excess of NaH (5 equ.) and methyl iodide (4 equ) are used, the reaction is stirred for 4 d and the crude product is purified by column chromatography (silica, eluent: DCM, 10% Ethyl acetate).

Amide Method I

Synthesis of 2-Cyclopropylmethanesulfonyl-N-[5-(3-methoxy-phenyl)-4H-[1,2,4]triazol-3-yl]-2-methyl-propionamide (Example 109)

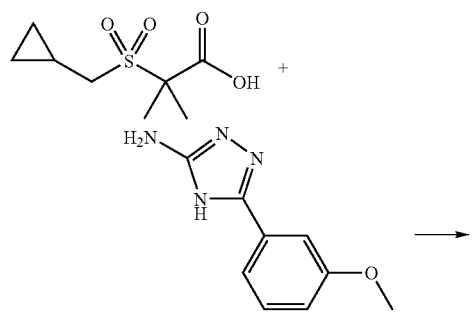

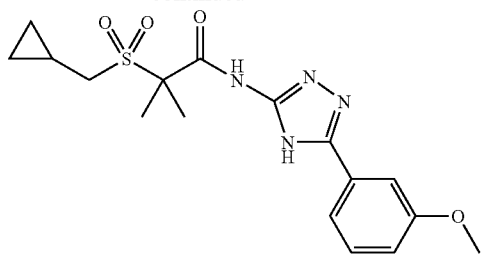

Activation of 0.46 g (2.23 mmol) of 2-cyclopropyl-methanesulfonyl-2-methyl-propionic acid as the corresponding acid chloride is achieved by treatment with thionyl chloride (5 mL, 69 mmol) at 70° C. for 2 h. The reaction is cooled to room temperature and excess thionyl chloride is removed under reduced pressure. The crude acid chloride is dissolved in THF (5 mL) and N,N-diisopropylethylamine (0.54 mL, 5.64 mmol) is added followed by 0.3 g (2.6 mmol) of 5-(3-methoxy-phenyl)-4H-[1,2,4]triazol-3-ylamine. After complete addition the reaction is heated to 70° C. for 36 h. The reaction is cooled to room temperature and the solvent is removed under reduced pressure. The residue is dissolved in DCM (20 mL) and washed with saturated aqueous NaHCO₃ solution (20 mL). The aqueous layer is back-extracted with DCM (2×20 mL). The combined organic layers are dried over Na₂SO₄, filtered and the filtrate is concentrated under reduced pressure. The residue is slurried in DCM/ether (1/1, 10 mL) to yield 0.398 g of 2-cyclopropylmethanesulfonyl-N-[5-(3-methoxy-phenyl)-4H-[1,2,4]triazol-3-yl]-2-methyl-propionamide. Yield: 46%; ES-MS: m/z 379 [M+H]

Compounds in Table XXXVIII, amide method I, are made according to this procedure with the following modifications to be noted: for Example 40, 41, 45, 95 and 99 2-methyltetrahydro-furan is used. For Example 118, 119 and 129, the crude product is slurried in DCM/heptanes (1/9). Example 127 is further purified by recrystallisation from methanol. Example 59 and 39 are purified by normal phase column; eluted with 0-3% MeOH/DCM, and trituated with DCM.

According to this method the following amides are made:

TABLE XXXV

| Structure | LC-MS Retention time[a] | Yield [%] | m/z |
|---|---|---|---|
| 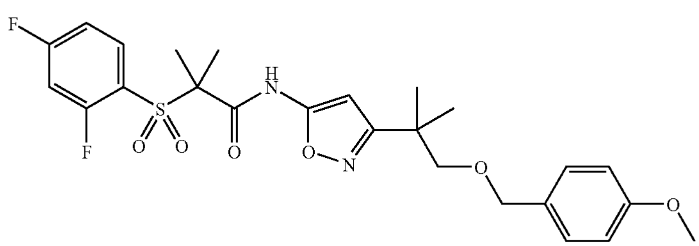 | 1.14 minutes | 8% | 523 [M + H] |

[a] Waters UPLC - ESI+/−ion mode, BEH C18 1.7 µm, 2.1 × 50 mm Column; Gradient: 90% A to 5% A in 1.19 minutes hold at 5% A to 1.70 minutes. Flow rate 0.8 mL/min. A = (95% Water 5% Acetonitrile + 0.05% Formic Acid) B = (Acetonitrile + 0.05% formic Acid). Diode Array Detector

Amide Method I1

PMB Deprotection

Synthesis of Synthesis of 2-(2,4-Difluoro-benzenesulfonyl)-N-[3-(2-hydroxy-1,1-dimethyl-ethyl)-isoxazol-5-yl]-2-methyl-propionamide (Example 44)

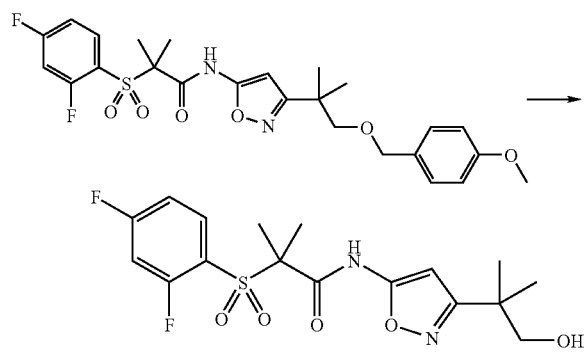

To a solution of 21 mg (0.041 mmol) of 2-(2,4-Difluoro-benzenesulfonyl)-N-{3-[2-(4-methoxy-benzyloxy)-1,1-dimethyl-ethyl]-isoxazol-5-yl}-2-methyl-propionamide in DCE (1 ml) and 4M HCl solution (0.5 mL), a few drops of water are added and the reaction mixture stirred over night for 18 h. The solvents are removed to yield 18 mg of 2-(2,4-difluoro-benzenesulfonyl)-N-[3-(2-hydroxy-1,1-dimethyl-ethyl)-isoxazol-5-yl]-2-methyl-propionamide. Yield 100%, ES-MS: m/z 403 [M+H].

Amide Method J

Synthesis of 2-[(2R)-butane-2-sulfonyl]-N-[5-(4-methoxyphenyl)-4H-1,2,4-triazol-3-yl]-2-methylpropanamide (Example 121)

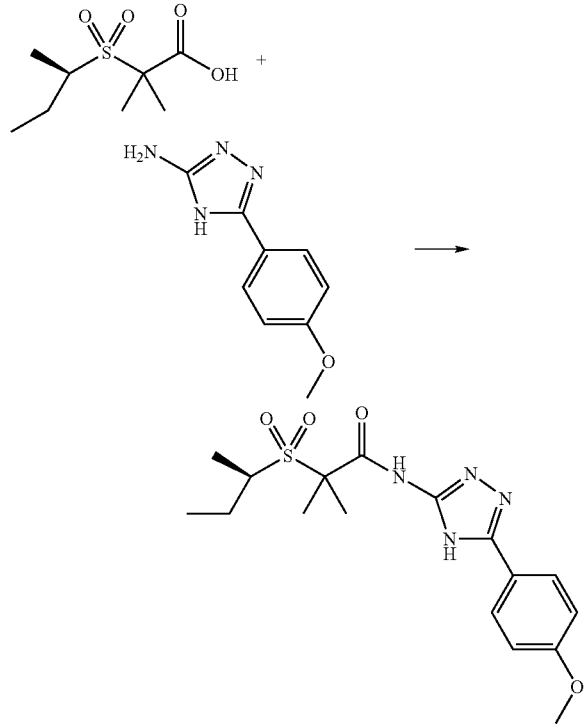

Activation of 0.5 g (2.40 mmol) of 2-[(2R)-butane-2-sulfonyl]-2-methyl-propionic acid as the corresponding acid chloride is achieved by treatment with oxalyl chloride (0.41 mL, 4.80 mmol), DMF (1 drop) in DCM (10 mL) at room temperature for 18 h. The reaction is concentrated under reduced pressure and excess oxalyl chloride is removed by azeotrope distillation with toluene (3×5 mL) under reduced pressure. The crude acid chloride is dissolved in THF (5 mL) and added to a solution of N,N-diisopropylethylamine (0.84 mL, 4.80 mmol) and 0.3 g (1.58 mmol) of 5-(4-methoxyphenyl)-4H-[1,2,4]triazol-3-ylamine in THF (5 mL). After complete addition the reaction is heated to 80° C. for 48 h. The reaction is cooled to room temperature and the solvent is removed under reduced pressure. The residue is dissolved in DCM (20 mL) and washed with saturated aqueous NaHCO₃ solution (20 mL). The aqueous layer is back-extracted with DCM (2×20 mL). The combined organic layers are dried over Na₂SO₄, filtered and the filtrate is concentrated under reduced pressure. The residue is purified by column chromatography (silica, eluent: heptanes, 0-50% ethyl acetate) to yield 0.119 g of 2-[(2R)-butane-2-sulfonyl]-N-[5-(4-methoxyphenyl)-4H-1,2,4-triazol-3-yl]-2-methylpropanamide. Yield: 13%; ES-MS: m/z 381 [M+H]

Compounds in Table XXXVIII, amide method J, are made according to this procedure with the following modifications to be noted: For Example 53 and 54, racemic N-[5-(4-methoxy-phenyl)-4H-[1,2,4]triazol-3-yl]-2-methyl-2-[1-(tetrahydro-furan-3-yl)methanesulfonyl]-propionamide is resolved by chiral preparative LC into its enantiomers. For Example 37 the crude product is slurried in DCM/ether (1/1) and then recrystallised from MeCN/water (1/1).

Amide Method K

Synthesis of N-[3-(2-Methoxy-1,1-dimethyl-ethyl)-isoxazol-5-yl]-2-methyl-2-(4,4,4-trifluoro-butane-1-sulfonyl)-propionamide (Example 77)

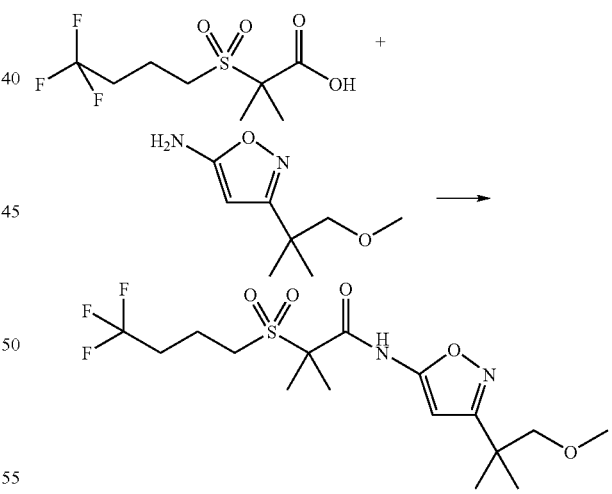

Activation of 0.3 g (1.14 mmol) of 2-methyl-2-(4,4,4-trifluoro-butane-1-sulfonyl)-propionic acid as the corresponding acid chloride is achieved by treatment with thionyl chloride (0.163 mL, 2.26 mmol) and DMF (1 drop) in toluene (4 mL) at 100° C. for 2 h. The reaction is cooled to room temperature and toluene (3 mL) is removed by distillation, whilst adding fresh toluene (3 mL). This process is repeated once.

This solution is added dropwise to a stirred suspension of 0.148 g (0.87 mmol) of 3-(2-methoxy-1,1-dimethyl-ethyl)-isoxazol-5-ylamine, 0.073 g (1.1 mmol) of Zinc-dust and 0.396 mL (2.28 mmol) of N,N-diisopropylethylamine in toluene (2 mL) at 35° C. After complete addition the reaction is heated to 60° C. for 17 h. The reaction is cooled to room temperature and the solvent is removed under reduced pressure. The residue is dissolved in DCM (10 mL) and washed with saturated aqueous NaHCO₃ solution (10 mL). The organic layer is dried (Na₂SO₄), filtered and the filtrate is concentrated under reduced pressure. The residue purified by column chromatography (silica, eluent DCM, 0-40% ethyl acetate), followed by recrystallisation from DCM/heptanes to yield 59 mg of N-[3-(2-methoxy-1,1-dimethyl-ethyl)-isoxazol-5-yl]-2-methyl-2-(4,4,4-trifluoro-butane-1-sulfonyl)-propionamide. Yield: 16%; ES-MS: m/z 415 [M+H].

Compounds in Table XXXVIII, amide method K, are made according to this procedure with the following modifications to be noted: for Example 78, 79 and 80: after column chromatography the solid product is rinsed with heptanes, then diethyl ether. For Example 84: the crude product is purified by column chromatography (silica, eluent DCM, 0-10% ethyl acetate), then recrystallised from diethyl ether/heptanes. For Example 81, 82, 96 and 97: the acid is activated as its acid chloride by treatment with oxalyl chloride (2.3 equ), DMF (1 drop) in DCM at room temperature, during the work-up procedure the reaction mixture is diluted with ethyl acetate (15 mL) and washed with 1M aqueous HCl solution (2×5 mL), saturated aqueous NaHCO₃ solution (2×5 mL), water (7 mL) and brine (7 mL). Example 81 and 82 are purified by mass-triggered preparative LC (neutral method). Example 96 and 97 are purified by column chromatography (silica, eluent: heptanes, 0-10% ethyl acetate). For Example 107 and 94 the acid is activated as its acid chloride by treatment with oxalyl chloride (2.3 equ), DMF (1 drop) in DCM at room temperature and the product is purified by column chromatography (silica, eluent: cyclohexanes, 20% ethyl acetate).

Amide Method L

Synthesis of 2-Methyl-N-[3-(1-methyl-1-methylcarbamoyl-ethyl)-isoxazol-5-yl]-2-(tetrahydro-pyran-4-sulfonyl)-propionamide (Example 46)

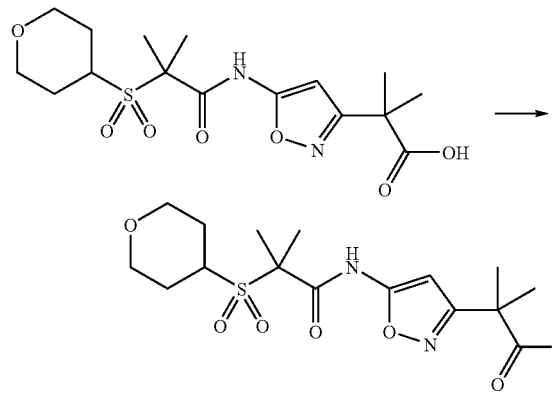

2 Methyl amine (2M solution in THF, 0.125 mL, 0.25 mmol) is added to a solution of 2-Methyl-2-{5-[2-methyl-2-(tetrahydro-pyran-4-sulfonyl)-propionylamino]-isoxazol-3-yl}-propionic acid (50 mg, 0.13 mmol) and O-(7-azabenzotriazol-1-yl)-N,N,N',N'-tetramethyluronium hexafluorophosphate (57 mg, 0.15 mmol) in DMF (1 mL), followed by the addition of N,N-diisopropylethylamine (0.056 mL, 0.32 mmol). The reaction mixture is stirred at room temperature for 65 h. After this time, more O-(7-azabenzotriazol-1-yl)-N,N,N',N'-tetramethyluronium hexafluorophosphate (100 mg, 0.26 mmol) and methylamine (2M solution in THF, 0.125 mL, 0.25 mmol) are added to the reaction mixture. The reaction mixture is stirred for 1 hour at room temperature. After this time, the reaction mixture is diluted with water and extracted with ethyl acetate twice. The combined organic extracts are washed with brine, dried over Na₂SO₄, filtered and concentrated under reduced pressure. Purification by preparative LC-MS affords 12 mg of the title compound. Yield: 23%; m/z 402 [M+H].

Compounds in Table XXXVIII, amide method L, are made according to this procedure.

Amide Method M

Synthesis of 2-Methyl-2-{5-[2-methyl-2-(tetrahydro-pyran-4-sulfonyl)-propionylamino]-isoxazol-3-yl}-propionic acid methyl ester (Example 64)

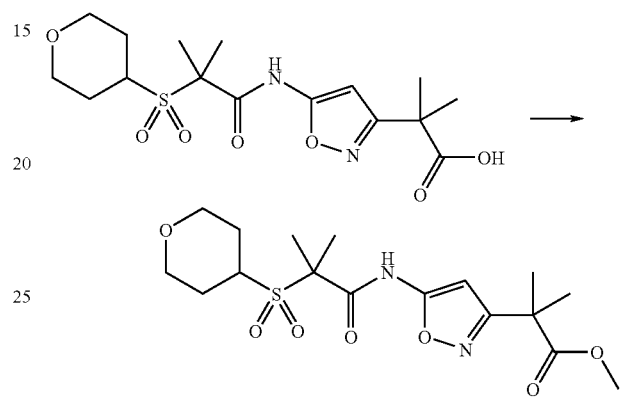

2-Methyl-2-{5-[2-methyl-2-(tetrahydro-pyran-4-sulfonyl)-propionylamino]-isoxazol-3-yl}-propionic acid (208 mg, 0.54 mmol) is suspended in acetonitrile (5 mL). 1,8-Diazabicyclo[5,4,0]undec-7-ene (0.096 mL, 0.64 mmol) is added and followed by the addition of methyl iodide (0.073 mL, 1.18 mmol). The reaction mixture is stirred at room temperature for 3.5 h. After this time, the reaction mixture is quenched with saturated aqueous NH₄Cl solution and extracted with ethyl acetate twice. The combined organics are washed with brine, dried over Na₂SO₄, filtered and concentrated under reduced pressure. The residue is purified by flash column chromatography (silica, eluent: DCM, MeOH) to provide 171 mg of the title compound. Yield: 79%; m/z 403 [M+H].

Compounds in Table XXXVIII, amide method M, are made according to this procedure.

Amide Method N

Synthesis of 2-{5-[2-Methyl-2-(tetrahydro-pyran-4-sulfonyl)-propionylamino]-isoxazol-3-yl}-isobutyramide (Example 131)

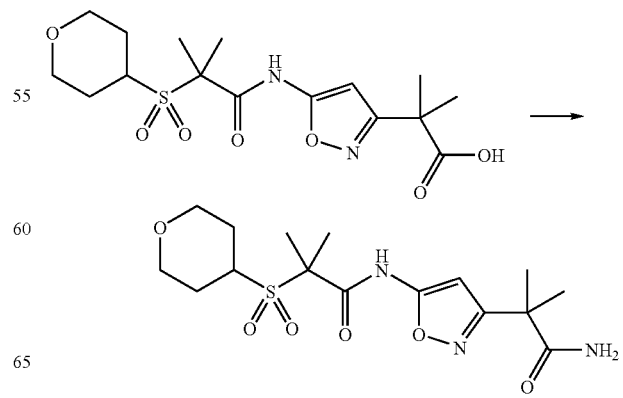

To a solution of 2-methyl-2-{5-[2-methyl-2-(tetrahydro-pyran-4-sulfonyl)-propionylamino]-isoxazol-3-yl}-propionic acid (35 mg, 0.09 mmol), di-tert-butyl dicarbonate (26 mg, 0.12 mmol), and ammonium bicarbonate (14 mg, 0.18 mmol) in the mixture of DMF (0.035 mL) and 1,4-dioxane (0.5 mL) is added pyridine (0.022 mL, 0.27 mmol). The reaction mixture is stirred at room temperature for 1.5 h. After this time, the reaction mixture is diluted with ethyl acetate and washed with 1N aqueous hydrochloric acid solution and brine, dried over $Na_2SO_4$, filtered and concentrated under reduced pressure. Purification of the residue by preparative HPLC provides 3.0 mg of the title compound. Yield: 9%; m/z 388 [M+H].

Compounds in Table XXXVIII, amide method N, are made according to this procedure.

Amide Method O

Synthesis of 2-{5-[2-Methyl-2-(tetrahydro-pyran-4-sulfonyl)-propionylamino]-isoxazol-3-yl}-isobutyramide (Example 132)

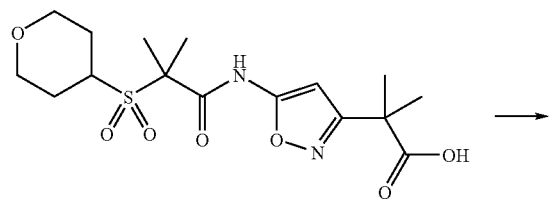

A procedure similar to the one reported for the synthesis of 2-methyl-N-[3-(tetrahydro-furan-2-yl)-isoxazol-5-yl]-2-(tetrahydro-pyran-4-sulfonyl)-propionamide in Amide Method B is followed. Yield: 13%; m/z 416 [M+H].

Compounds in Table XXXVIII, amide method O, are made according to this procedure.

Amide Method P

Synthesis of 2-Cyclobutylmethanesulfonyl-N-[5-(2-methoxy-1,1-dimethyl-ethyl)-isoxazl-3-yl]-2-methyl-propionamide (Example 100)

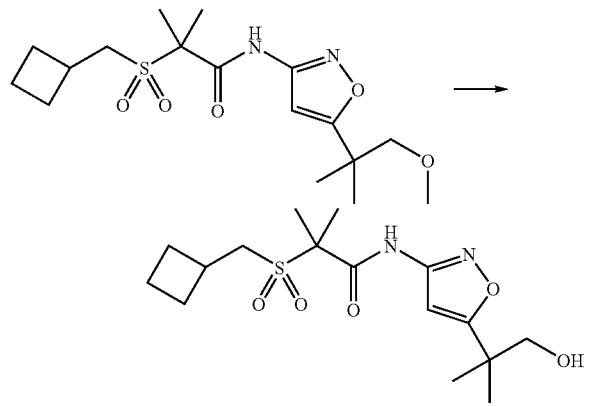

To a stirred solution of 163 mg (0.44 mmol) of 2-cyclobutylmethanesulfonyl-N-[5-(2-methoxy-1,1-dimethyl-ethyl)-isoxazol-3-yl]-2-methyl-propionamide in DCM (3.5 mL) under nitrogen is added dropwise 1M $BBr_3$ in DCM (1.31 mL, 1.31 mmol) at −78° C. The reaction mixture is allowed to warm to 0-10° C. and stirred for 4.5 h. The reaction is quenched with saturated aqueous $NaHCO_3$ solution (4 mL). The layers are separated and the organic layer is concentrated under reduced pressure. The residue is purified by column chromatography (silica, eluent: DCM, 2% MeOH) to afford 133 mg of 2-cyclobutylmethanesulfonyl-N-[5-(2-methoxy-1,1-dimethyl-ethyl)-isoxazl-3-yl]-2-methyl-propionamide. Yield: 85%, ES-MS: 359 [M+H].

Compounds in Table XXXVIII, amide method P, are made according to this procedure with the following modifications to be noted: for Example 83 and 98 the residue is purified by recrystallisation from DCM/heptanes. Example 102 is purified by column chromatography (silica, eluent: heptanes, 50% ethyl acetate).

Amide Method Q

Synthesis of N-[3-(2-Hydroxy-1,1-dimethyl-ethyl)-isoxazol-5-yl]-2-methyl-2-(tetrahydro-pyran-4-sulfonyl)propionamide (Example 113)

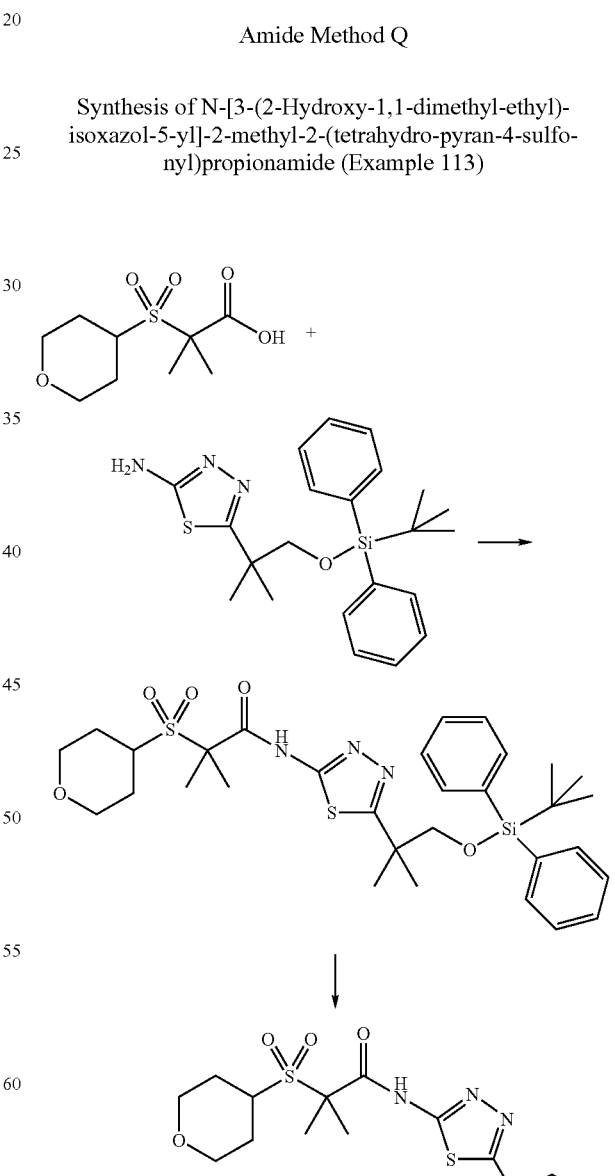

Step 1: Synthesis of N-{5-[2-(tert-Butyl-diphenyl-silanyloxy)-1,1-dimethyl-ethyl]-[1,3,4]thiadiazol-2-yl}-2-methyl-2-(tetrahydro-pyran-4-sulfonyl)-propionamide Activation of 300 mg (1.27 mmol) of 2-methyl-2-(tetrahydro-pyran-4-sulfonyl)-propionic acid as the corresponding acid chloride is achieved by treatment with thionyl chloride (305 mg, 2.54 mmol) and DMF (1 drop) in toluene (3 mL) at 100° C. for 1 h. The reaction is cooled to room temperature and toluene (2 mL) is removed by distillation, whilst adding fresh toluene (2 mL). This process is repeated once.

This acid chloride solution is added dropwise over 0.5 h to a stirred suspension of 418 mg (1.02 mmol) of 5-[2-(tert-butyl-diphenyl-silanyloxy)-1,1-dimethyl-ethyl]-[1,3,4]thiadiazol-2-ylamine and 0.45 mL (2.54 mmol) of N,N-diisopropylethylamine in toluene (2 mL) at 35° C. After complete addition the reaction is heated to 60° C. for 17 h. The reaction is cooled to room temperature and the solvent is removed under reduced pressure. The residue is dissolved in ethyl acetate (20 mL) and washed with saturated aqueous NaHCO$_3$ solution (10 mL) and brine (10 mL). The organic layer is dried (Na$_2$SO$_4$), filtered and concentrated under reduced pressure and the residue purified twice by dry-flash column chromatography (silica, eluent DCM, 0-10% ethyl acetate, then heptanes, 20-50% ethyl acetate) to yield 230 mg of N-{5-[2-(tert-butyl-diphenyl-silanyloxy)-1,1-dimethyl-ethyl]-[1,3,4]thiadiazol-2-yl}-2-methyl-2-(tetrahydro-pyran-4-sulfonyl)-propionamide. Yield: 29%; ES-MS: m/z 630 [M+H].

According to this method the following amides are made with the following modifications to be noted: For N-{4-[2-(tert-butyl-diphenyl-silanyloxy)-1,1-dimethyl-ethyl]-thiazol-2-yl}-2-methyl-2-(tetrahydro-pyran-4-sulfonyl)-propionamide, the acid is activated as its acid chloride by treatment in neat SOCl$_2$ at 70° C. for 4 h.

TABLE XXXVI

| Structure | $^1$H NMR | Yield [%] | m/z [M + H] |
|---|---|---|---|
| 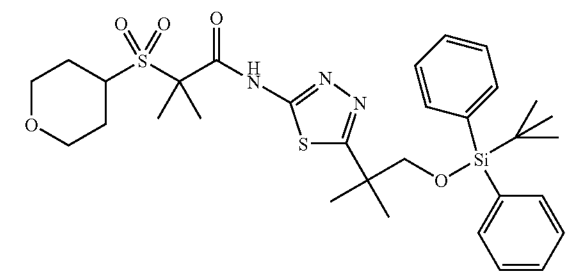 | (250 MHz, CHLOROFORM-d) δ ppm 1.05 (9 H, s), 1.49 (6 H, s), 1.73-2.05 (10 H, m), 3.33 (2 H, td, J = 11.61, 2.51 Hz), 3.41-3.56 (1 H, m), 3.71 (2 H, s), 3.91-4.04 (2 H, m), 7.33-7.50 (6 H, m), 7.54-7.64 (4 H, m) | 29 | 630 |
| 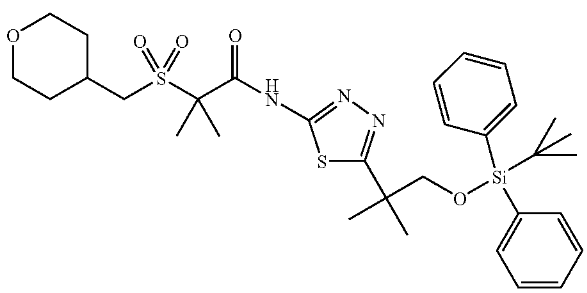 | (500 MHz, CHLOROFORM-d) δ ppm 1.06 (9 H, s), 1.38-1.51 (8 H, m), 1.73-1.87 (8 H, m), 2.31-2.46 (1 H, m), 2.92 (2 H, d, J = 6.56 Hz), 3.41 (2 H, td, J = 11.86, 1.75 Hz), 3.71 (2 H, s), 3.93 (2 H, dd, J = 11.60, 4.27 Hz), 7.34-7.41 (4 H, m), 7.41-7.46 (2 H, m), 7.57-7.63 (4 H, m), 9.97 (1 H, br. s.) | 33 | 644 |
| 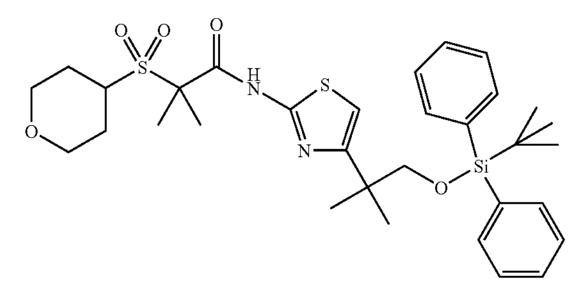 | (250 MHz, CHLOROFORM-d) δ ppm 1.05 (9 H, s), 1.49 (6 H, s), 1.80 (6 H, s), 1.82-2.07 (4 H, m), 3.22-3.40 (2 H, m), 3.40-3.55 (1 H, m), 3.70 (2 H, s), 3.89-4.06 (2 H, m), 7.31-7.49 (6 H, m), 7.51-7.66 (4 H, m) | 54 | 629 |
| 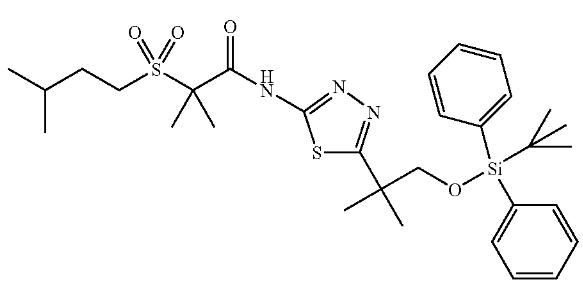 | (500 MHz, CHLOROFORM-d) δ ppm 0.80-0.95 (8 H, m), 1.08 (9 H, s), 1.19-1.39 (4 H, m), 1.55-1.90 (12 H, m), 2.92-3.12 (2 H, m), 3.73 (2 H, s), 7.32-7.52 (6 H, m), 7.62 (4 H, d, J = 6.62 Hz), 10.22 (1 H, br. s.) | 46 | 616 |

| Structure | ¹H NMR | Yield [%] | m/z [M + H] |
|---|---|---|---|
| 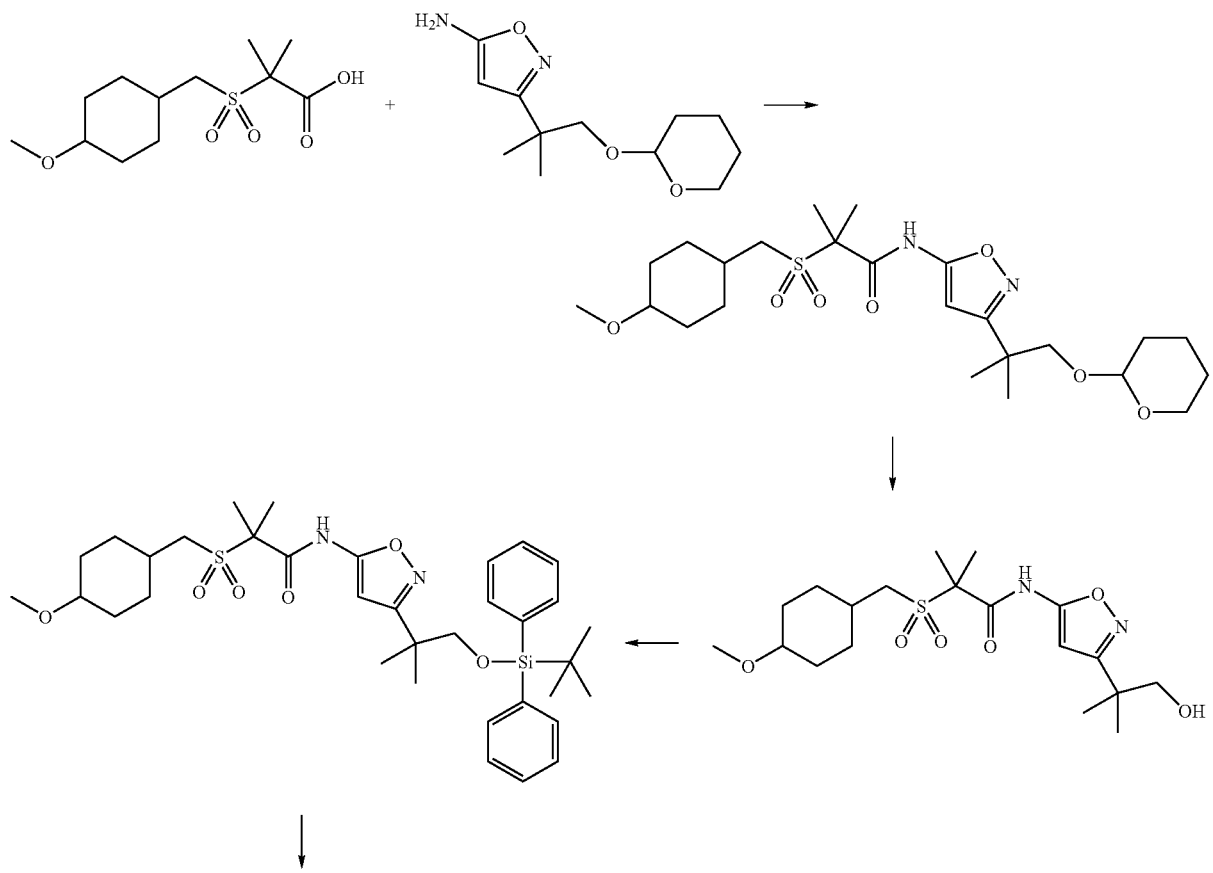 | (500 MHz, CHLOROFORM-d) δ ppm 1.08 (9 H, s), 1.48 (6 H, s), 1.80 (6 H, s), 2.11-2.21 (2 H, m), 2.22-2.37 (2 H, m), 3.15 (2 H, t, J = 7.46 Hz), 3.71 (2 H, s), 7.32-7.47 (6 H, m), 7.55-7.66 (4 H, m), 10.26 (1 H, br. s.) | 62 | 656 |

Step 2: Synthesis of N-[3-(2-Hydroxy-1,1-dimethyl-ethyl)-isoxazol-5-yl]-2-methyl-2-(tetrahydro-pyran-4-sulfonyl)propionamide To a solution of 230 mg (0.37 mmol) of N-{5-[2-(tert-Butyl-diphenyl-silanyloxy)-1,1-dimethyl-ethyl]-[1,3,4]thiadiazol-2-yl}-2-methyl-2-(tetrahydro-pyran-4-sulfonyl)-propionamide in methanol (3 mL) are added HF (65% solution in pyridine, 0.24 mL). The reaction is heated to 50° C. for 18 h. Additional HF (65% solution in pyridine, 0.24 mL) is added and the reaction is heated for 18 h. The reaction mixture is filtered through an isolute AX/SCX-2 column (eluent: MeOH), the filtrate is concentrated under reduced pressure and purified by column chromatography (Isolute SCX-2, eluent: DCM, 40% ethyl acetate to DCM, 5% methanol) to afford 45 mg of N-[3-(2-hydroxy-1,1-dimethyl-ethyl)-isoxazol-5-yl]-2-methyl-2-(tetrahydro-pyran-4-sulfonyl)propionamide. Yield: 32%, ES-MS: 392 [M+H].

Compounds in Table XXXVIII, amide method Q, are made according to this procedure with the following modifications to be noted: for Example 139 and 140 the reaction mixture is filtered through Isolute PE-AX column (eluent DCM, 0-5% MeOH) followed by column chromatography (Isolute SCX-2, eluent: DCM, 0-5% MeOH)

Amide Method R

Synthesis of N-[3-(2-Hydroxy-1,1-dimethyl-ethyl)-isoxazol-5-yl]-2-methyl-2-(4-oxo-cyclohexyl-methanesulfonyl)-propionamide (Example 43)

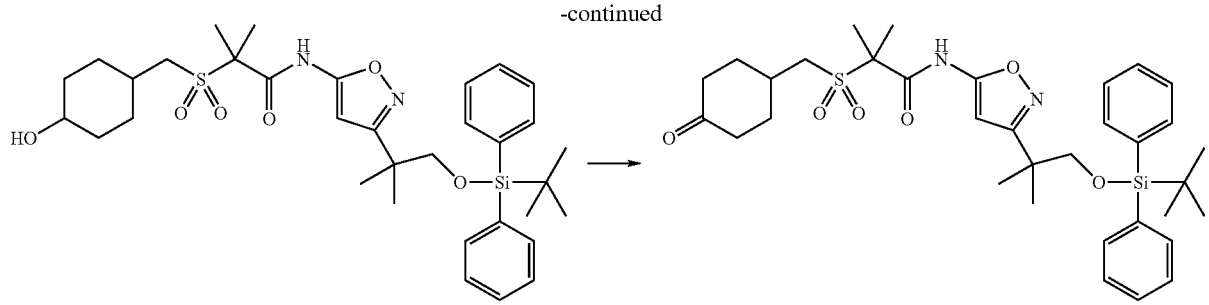

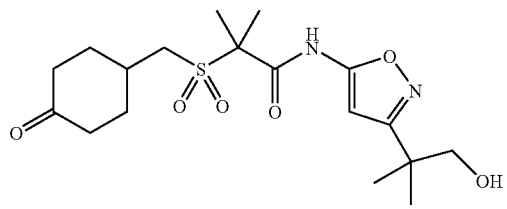

Step 1: Synthesis of N-{3-[1,1-Dimethyl-2-(tetrahydro-pyran-2-yloxy)-ethyl]-isoxazol-5-yl}-2-(4-methoxy-cyclohexylmethanesulfonyl)-2-methyl-propionamide Activation of 0.8 g (2.86 mmol) of 2-(4-methoxy-cyclohexylmethanesulfonyl)-2-methyl-propionic acid (see Acid Method C) as the corresponding acid chloride is achieved by treatment with thionyl chloride (4 mL) in toluene (2 mL) at 60° C. for 2 h. The reaction is cooled to room temperature and excess thionyl chloride is removed by azeotropic distillation with toluene and concentrated to ⅓ of its original volume.

This acid chloride solution is added dropwise to a stirred suspension of 0.68 g (2.86 mmol) of 3-[1,1-dimethyl-2-(tetrahydro-pyran-2-yloxy)-ethyl]-isoxazol-5-ylamine and 1 mL (5.75 mmol) of N,N-diisopropylethylamine in toluene (4 mL) at 35° C. After complete addition the reaction is heated to 70° C. for 17 h. The reaction is cooled to room temperature and the solvent is removed under reduced pressure. The residue is dissolved in DCM and washed with saturated aqueous NaHCO₃ solution, brine, dried (MgSO₄) and filtered. The filtrate is concentrated under reduced pressure to yield 1.31 g of N-{3-[1,1-dimethyl-2-(tetrahydro-pyran-2-yloxy)-ethyl]-isoxazol-5-yl}-2-(4-methoxy-cyclohexylmethanesulfonyl)-2-methyl-propionamide. Yield: 91%; ES-MS: m/z 523 [M+Na].

Step 2: Synthesis of N-[3-(2-Hydroxy-1,1-dimethyl-ethyl)-isoxazol-5-yl]-2-(4-methoxy-cyclohexylmethanesulfonyl)-2-methyl-propionamide A solution of 1.3 g (2.6 mmol) of N-{3-[1,1-dimethyl-2-(tetrahydro-pyran-2-yloxy)-ethyl]-isoxazol-5-yl}-2-(4-methoxy-cyclohexylmethanesulfonyl)-2-methyl-propionamide in DCM/methanol (1/1, 20 mL) is treated with 1.58 g (5.2 mmol) of MP-TsOH resin (loading 3.3 mmol/g) at room temperature for 36 h. The resin is removed by filtration and washed alternating with DCM (10 mL) and methanol (10 mL) twice. The combined filtrates are concentrated under reduced pressure and the resulting residue is purified by column chromatography (Isolute SCX-2, eluent: DCM, 10% ethyl acetate) to yield 0.41 g of N-[3-(2-hydroxy-1,1-dimethyl-ethyl)-isoxazol-5-yl]-2-(4-methoxy-cyclohexylmethanesulfonyl)-2-methyl-propionamide. Yield 38%; ES-MS: m/z 417 [M+H].

Step 3: Synthesis of N-{3-[2-(tert-Butyl-diphenyl-silanyloxy)-1,1-dimethyl-ethyl]-isoxazol-5-yl}-2-(4-methoxy-cyclohexylmethanesulfonyl)-2-methyl-propionamide To a solution of 0.41 g (0.96 mmol) of N-[3-(2-hydroxy-1,1-dimethyl-ethyl)-isoxazol-5-yl]-2-(4-methoxy-cyclohexylmethanesulfonyl)-2-methyl-propionamide in DCM (8 ml) are added imidazoles (0.07 g, 0.96 mmol), followed by tert-Butylchlorodiphenylsilane (0.26 g, 0.96 mmol). The reaction is stirred at room temperature for 20 h. The mixture is diluted with DCM (10 mL) and washed with saturated aqueous $NH_4Cl$ solution, brine, dried ($MgSO_4$) and filtered. The filtrate is concentrated under reduced pressure to give 0.73 g of N-{3-[2-(tert-butyl-diphenyl-silanyloxy)-1,1-dimethyl-ethyl]-isoxazol-5-yl}-2-(4-methoxy-cyclohexyl-methanesulfonyl)-2-methyl-propionamide. Yield: 100%, ES-MS: 655 [M+H].

Step 4: Synthesis of N-{3-[2-(tert-Butyl-diphenyl-silanyloxy)-1,1-dimethyl-ethyl]-isoxazol-5-yl}-2-(4-hydroxy-cyclohexylmethanesulfonyl)-2-methyl-propionamide In a round bottom flask, aluminium tribromide (0.59 g, 2.2 mmol) is added portionwise to ethanethiol (3 mL), followed by a solution of 0.72 g (1.1 mmol) of N-{3-[2-(tert-Butyl-diphenyl-silanyloxy)-1,1-dimethyl-ethyl]-isoxazol-5-yl}-2-(4-methoxy-cyclohexylmethanesulfonyl)-2-methyl-propionamide in ethanethiol (4 mL). The reaction mixture is stirred at room temperature for 1 h. The reaction is quenched by addition of 4M aqueous HCl solution (2 mL), diluted with ice water (10 mL) and extracted with ethyl acetate (2×10 mL). The combined organic extracts are washed with brine, dried ($MgSO_4$), filtered and the solvent is removed under reduced pressure. The residue is dissolved (DCM, 20% ethyl acetate) and filtered through a plug of silica to remove colouration and the filtrate is concentrated under reduced pressure to give 0.21 g of N-{3-[2-(tert-butyl-diphenyl-silanyloxy)-1,1-dimethyl-ethyl]-isoxazol-5-yl}-2-(4-hydroxy-cyclohexylmethane-sulfonyl)-2-methyl-propionamide which is used in the next step without further purification. Yield: 33%, ES-MS: 639 [M−H]

Step 5: Synthesis of N-{3-[2-(tert-Butyl-diphenyl-silanyloxy)-1,1-dimethyl-ethyl]-isoxazol-5-yl}-2-methyl-2-(4-oxo-cyclohexylmethanesulfonyl)-propionamide To a solution of 0.21 g (0.36 mmol) of N-{3-[2-(tert-butyl-diphenyl-silanyloxy)-1,1-dimethyl-ethyl]-isoxazol-5-yl}-2-(4-hydroxy-cyclohexylmethanesulfonyl)-2-methyl-propionamide in DCM (3 mL) is added pyridinium chlorochromate (0.15 g, 0.72 mmol) and the reaction mixture is stirred at room temperature for 18 h. The reaction is diluted with diethyl ether (6 mL) and stirred for 10 min. The mixture is filtered through a plug of silica and the filtrate is concentrated to afford 0.12 g of N-{3-[2-(tert-butyl-diphenyl-silanyloxy)-1,1-dimethyl-ethyl]-isoxazol-5-yl}-2-methyl-2-(4-oxo-cyclohexylmethanesulfonyl)-propionamide, which is used without further purification in the next step. Yield: 54%, ES-MS: 637 [M−H]

Step 6: Synthesis of N-[3-(2-Hydroxy-1,1-dimethyl-ethyl)-isoxazol-5-yl]-2-methyl-2-(4-oxo-cyclohexyl-methanesulfonyl)-propionamide To a solution of 0.12 g (0.19 mmol) of N-{3-[2-(tert-butyl-diphenyl-silanyloxy)-1,1-dimethyl-ethyl]-isoxazol-5-yl}-2-methyl-2-(4-oxo-cyclohexylmethanesulfonyl)-propionamide in THF (2 mL) is added tetrabutylammonium fluoride (0.65 mL, 0.65 mmol, 1M solution in THF) and the reaction is stirred at room temperature for 48 h. The reaction mixture is quenched by addition of saturated aqueous $NH_4Cl$ solution (5 mL) and the mixture is extracted with DCM (8 mL×3). The combined organic extracts are washed with brine (10 mL), dried ($MgSO_4$) and filtered. The filtrate is concentrated under reduced pressure and the residue purified twice by column chromatography (silica, eluent: DCM, 20% ethyl acetate, then DCM, 10% ethyl acetate) to afford 0.03 g of N-[3-(2-hydroxy-1,1-dimethyl-ethyl)-isoxazol-5-yl]-2-methyl-2-(4-oxo-cyclohexylmethanesulfonyl)-propionamide. Yield: 41%, ES-MS: 401 [M+H]

Compounds in Table XXXVIII, amide method R, are made according to this procedure.

Amide Method S

Synthesis of Synthesis of N-[3-(2-Hydroxy-1,1-dimethyl-ethyl)-isoxazol-5-yl]-2-methyl-2-[(R)-2-(tetrahydro-furan-3-yl)-ethanesulfonyl]-propionamide (Example 143)

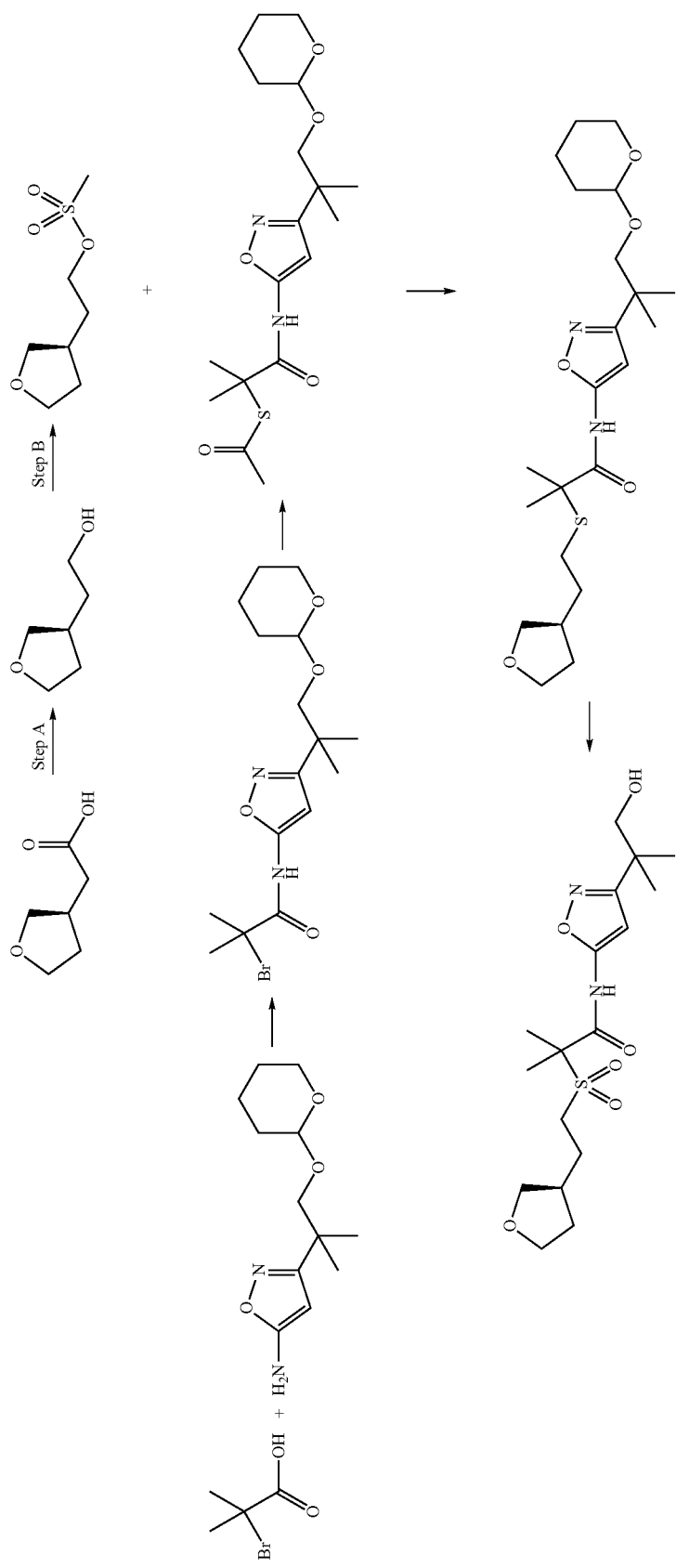

Step A: Synthesis of 2-[(3S)-oxolan-3-yl]ethan-1-ol

To a solution of 1.20 g (9.22 mmol) of 2-[(3R)-oxolan-3-yl]acetic acid (prepared as described in Ghosh, A. K. et al. *J. Med. Chem.* 1993, 36, 2300-2310) in anhydrous THF (10 ml) is added 0.93 ml of borane (14.75 mmol) slowly. The reaction is stirred at room temperature for 4 h, then 3M aqueous NaOH solution (8 mL) is added and the mixture is stirred for 1 h. The pH is then adjusted to 11 with 6M aqueous HCl solution and the aqueous mixture is saturated with potassium carbonate. The basic aqueous solution is extracted with diethyl ether (2×30 mL). The combined organic extracts are dried ($MgSO_4$), filtered and the filtrate is concentrated under reduced pressure to give 0.92 g of 2-[(3S)-oxolan-3-yl]ethan-1-ol. Yield: 86%, $^1$H NMR (500 MHz, CHLOROFORM-d) δ ppm 1.49-1.59 (1H, m), 1.61-1.70 (1H, m), 2.01-2.12 (1H, m), 2.20-2.37 (2H, m), 3.37 (1H, t, J=7.78 Hz), 3.60-3.70 (2H, m), 3.74 (1H, q, J=7.88 Hz), 3.85 (1H, td, J=8.32, 4.58 Hz), 3.91 (1H, t, J=7.78 Hz).

2-[(3R)-oxolan-3-yl]ethan-1-ol is synthesised from 2-[(3S)-oxolan-3-yl]acetic acid (prepared as described in Ghosh, A. K. et al. *J. Med. Chem.* 1993, 36, 2300-2310) according to the above procedure. Yield: 73%; $^1$H NMR (500 MHz, CHLOROFORM-d) δ ppm 1.47-1.73 (3 H, m), 1.98 (1H, br. s.), 2.02-2.12 (1H, m), 2.31 (1H, dt, J=14.80, 7.40 Hz), 3.37 (1H, t, J=7.78 Hz), 3.59-3.79 (3H, m), 3.85 (1H, td, J=8.32, 4.58 Hz), 3.91 (1H, t, J=7.78 Hz).

Step B: Synthesis of 2-[(3R)-oxolan-3-yl]ethyl methanesulfonate

To a solution of 1.00 g (0.861 mmol) of 2-[(3S)-oxolan-3-yl]ethan-1-ol in anhydrous THF (1.5 mL) are added triethyl amine (0.13 mL, 0.947 mmol) and methanesulfonyl chloride (0.07 mL, 0.947 mmol) slowly at 0° C. The reaction is stirred at room temperature for 2 h. The mixture is diluted with ethyl acetate (20 mL) and washed with saturated aqueous $NaHCO_3$ solution (2×5 mL) and 1M aqueous HCl solution (2×5 mL). The organic layer is dried ($MgSO_4$), filtered and the filtrate is concentrated under reduced pressure to afford 167 mg of 2-[(3R)-oxolan-3-yl]ethyl methanesulfonate. Yield: 100%, $^1$H NMR (250 MHz, CHLOROFORM-d) δ ppm 1.40-1.60 (1H, m), 1.70-1.87 (1H, m), 1.95-2.12 (1H, m), 2.16-2.37 (1H, m), 2.96 (3H, s), 3.32 (1H, dd, J=8.22, 7.16 Hz), 3.62-3.91 (3H, m), 4.13-4.24 (2H, m).

2-[(3S)-oxolan-3-yl]ethyl methanesulfonate is synthesised from 2-[(3R)-oxolan-3-yl]ethan-1-ol according to the above procedure. Yield: 100%; $^1$H NMR (250 MHz, CHLOROFORM-d) δ ppm 1.48-1.62 (1H, m), 1.78-1.93 (1H, m), 2.01-2.20 (1H, m), 2.24-2.43 (1H, m), 3.02 (3H, s), 3.40 (1H, t, J=7.69 Hz), 3.73-3.99 (3H, m), 4.26 (2H, t, J=6.47 Hz)

Step 1: Synthesis of 2-Bromo-N-{3-[1,1-dimethyl-2-(tetrahydro-pyran-2-yloxy)-ethyl]-isoxazol-5-yl}-2-methyl-propionamide Oxalyl chloride (156.0 mL, 1.80 mol) is slowly added at 0° C. to a solution of 2-bromo-2-methyl-propionic acid (50.0 g, 299.4 mmol) in DMF (1 mL) and DCM (0.5 L). The reaction mixture is stirred at room temperature for 3 h, the solvent is removed under reduced pressure to afford 50.0 g of 2-bromo-2-methyl-propionyl chloride as a liquid, that is used without further purification in the next step.

The above material is slowly added at 0° C. to a solution of 3-[1,1-Dimethyl-2-(tetrahydro-pyran-2-yloxy)-ethyl]-isoxazol-5-ylamine (64.8 g, 270.0 mmol) and N,N-diisopropyl-ethylamine (69.7 g, 540.4 mmol) in DCM (0.7 L). After stirring the reaction mixture at room temperature for 12 h, water and DCM are added and the two phases are separated. The organic layer is washed with brine, dried over anhydrous $Na_2SO_4$, filtered and concentrated under reduced pressure. The residue is purified by column chromatography on silica to afford 27 g of 2-bromo-N-{3-[1,1-dimethyl-2-(tetrahydro-pyran-2-yloxy)-ethyl]-isoxazol-5-yl}-2-methyl-propionamide as a liquid. Yield: 26%; m/z 411/413 [M+Na], $^1$H NMR (400 MHz, CHLOROFORM-d) δ ppm 1.3 (3H, s), 1.4 (3H, s), 1.5-1.8 (6H, m), 2.1 (6H, s), 3.4 (1H, m), 3.5 (1H, m), 3.8 (2H, m), 4.6 (1H, m), 6.4 (1H, s), 9.0 (1H, s).

Step 2: Synthesis of Thioacetic acid S-(1-{3-[1,1-dimethyl-2-(tetrahydro-pyran-2-yloxy)-ethyl]isoxazol-5-ylcarbamoyl}-1-methyl-ethyl)ester Potassium thioacetate (6.6 g, 58.0 mmol) is added at 0° C. to a solution of 2-bromo-N-{3-[1,1-dimethyl-2-(tetrahydro-pyran-2-yloxy)-ethyl]-isoxazol-5-yl}-2-methyl-propionamide (15.0 g, 38.6 mmol) in DMF (150 mL). After stirring the reaction mixture at room temperature for 12 h, ice water and diethyl ether are added. The two phases are separated, the organic layer is washed with brine, dried over anhydrous $Na_2SO_4$, filtered and concentrated under reduced pressure to afford the crude product that is purified by silica gel chromatography to afford 8.7 g of thioacetic acid S-(1-{3-[1,1-dimethyl-2-(tetrahydro-pyran-2-yloxy)-ethyl]-isoxazol-5-ylcarbamoyl}-1-methyl-ethyl) ester as a pale yellow solid. Yield: 58%; m/z 383 [M−H]; $^1$H NMR (250 MHz, CHLOROFORM-d) δ ppm 1.35 (6H, d, J=8.07 Hz), 1.45-1.88 (12H, m), 2.37 (3H, s), 3.30-3.58 (2H, m), 3.69-3.87 (2H, m), 4.58 (1H, t), 6.35 (1H, s), 9.44 (1H, br. s.).

Step 3: Synthesis of 2-Methyl-N-{3-[2-methyl-1-(oxan-2-yloxy)propan-2-yl]-1,2-oxazol-5-yl}-2-({2-[(3R)-oxolan-3-yl]ethyl}sulfanyl)propanamide To a solution of 379 mg (1.95 mmol) of 2-[(3R)-oxolan-3-yl]ethyl methanesulfonate and 421 mg (7.8 mmol) of NaOMe in ethanol (5 ml) are added 750 mg (1.95 mmol) of 2-bromo-N-{3-[1,1-dimethyl-2-(tetrahydro-pyran-2-yloxy)-ethyl]-isoxazol-5-yl}-2-methyl-propionamide and the reaction mixture is heated in the microwave at 130° C. for 0.5 h. The solvent is removed under reduced pressure. The residue is diluted with (20 mL), washed with saturated aqueous $NaHCO_3$ solution (2×5 mL) and 1M aqueous HCl solution (2×5 mL). The organic layer is dried ($MgSO_4$), filtered and the filtrate is concentrated under reduced pressure. The residue is purified by column chromatography (silica, eluent: heptanes/) to give 238 mg of 2-methyl-N-{3-[2-methyl-1-(oxan-2-yloxy)propan-2-yl]-1,2-oxazol-5-yl}-2-({2-[(3R)-oxolan-3-yl]ethyl}sulfanyl)propanamide. Yield: 28%, m/z 463 [M+Na]

TABLE XXXVII

| Structure | ¹H NMR | Yield [%] | m/z [M + H] |
|---|---|---|---|
| (structure) | (250 MHz, CHLOROFORM-d) δ ppm 1.35 (3 H, s), 1.36 (3 H, s), 1.41-1.90 (15 H, m), 1.93-2.35 (2 H, m), 2.43-2.62 (2 H, m), 3.23-3.58 (3 H, m), 3.65-3.95 (5 H, m), 4.58 (1 H, t), 6.34 (1 H, s), 9.48 (1 H, br. s.) | 28 | 463 [M + Na] |
| (structure) | (250 MHz, CHLOROFORM-d) δ ppm 1.35 (3 H, s), 1.36 (3 H, s), 1.40-1.90 (15 H, m), 1.93-2.10 (1 H, m), 2.13-2.35 (1 H, m), 2.42-2.62 (2 H, m), 3.26-3.41 (2 H, m), 3.41-3.56 (1 H, m), 3.66-3.93 (5 H, m), 4.58 (1 H, t), 6.33 (1 H, s), 9.51 (1 H, s) | 25 | 463 [M + Na] |

Step 4: Synthesis of N-[3-(1-hydroxy-2-methylpropan-2-yl)-1,2-oxazol-5-yl]-2-methyl-2-({2-[(3R)-oxolan-3-yl]ethane}sulfonyl)propanamide To a solution of 187 mg (0.42 mmol) of 2-methyl-N-{3-[2-methyl-1-(oxan-2-yloxy)propan-2-yl]-1,2-oxazol-5-yl}-2-({2-[(3R)-oxolan-3-yl]ethyl}sulfanyl)propanamide in 1,4-dioxane (5 mL) and water (1.3 mL) is added 522 mg (0.85 mmol) potassium monopersulfate triple salt (OXONE®) and the reaction stirred at room temperature for 3 h. The crude reaction mixture is diluted with ethyl acetate (20 mL) and washed with saturated aqueous NaHCO₃-solution (2×2 mL). the organic layer is dried (MgSO₄), filtered and concentrated under reduced pressure. The residue is dissolved in DCM/MeOH (1/1) and passed through an Isolute SCX-2 column. The filtrate is concentrated under reduced pressure. The residue is purified by column chromatography (silica, eluent: heptanes, ethyl acetate) followed by recrystallization from DCM/heptanes to give 83 mg of N-[3-(1-hydroxy-2-methylpropan-2-yl)-1,2-oxazol-5-yl]-2-methyl-2-({2-[(3R)-oxolan-3-yl]ethane}sulfonyl)propanamide. Yield 51%, m/z 389 [M+H].

Compounds in Table XXXVIII, amide method S, are made according to this procedure.

Amide Method U

Synthesis of N-[5-(1-hydroxy-2-methylpropan-2-yl)-1,3,4-thiadiazol-2-yl]-2-methyl-2-{[(2R)-oxan-2-ylmethane]sulfonyl}propanamide (Example 148)

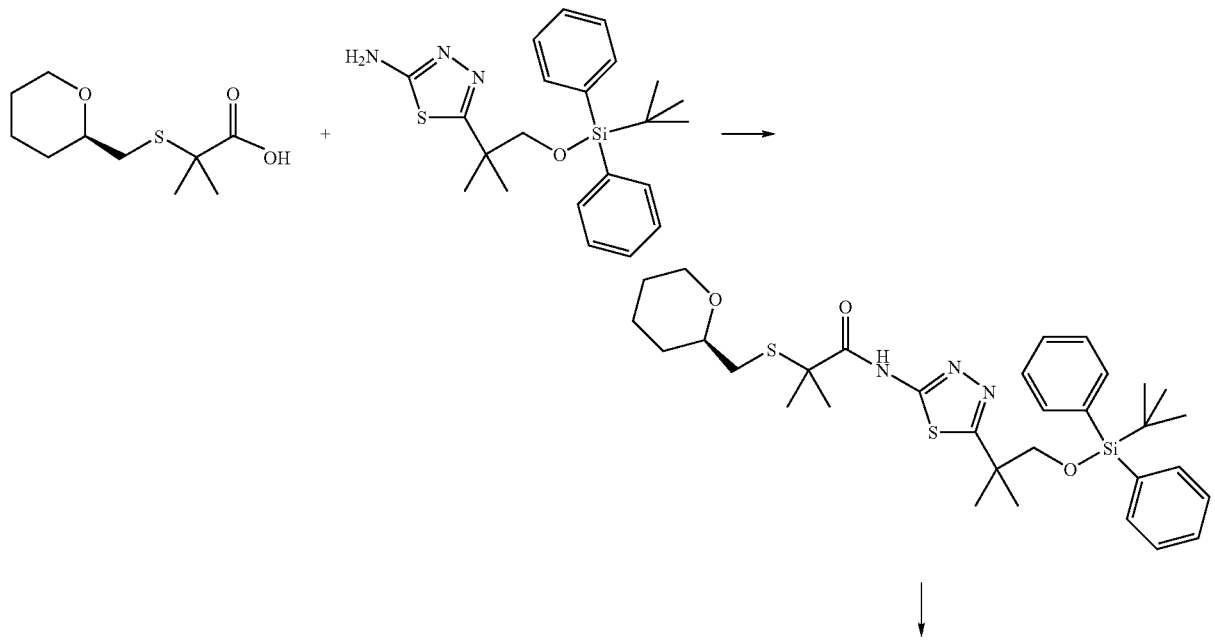

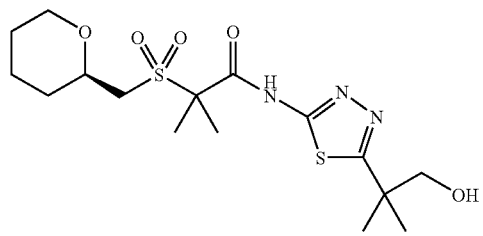 ← 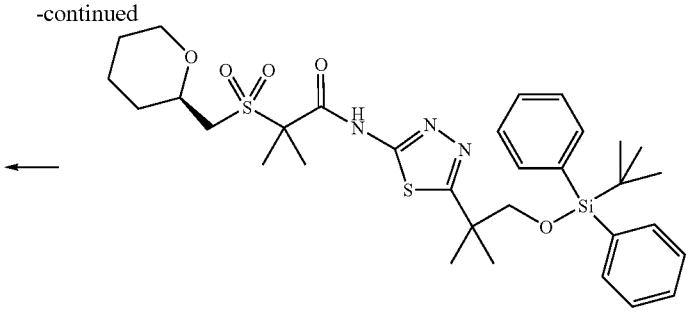

Step 1: Synthesis of N-(5-{1-[(tert-butyldiphenylsilyl)oxy]-2-methylpropan-2-yl}-1,3,4-thiadiazol-2-yl)-2-methyl-2-{[(2R)-oxan-2-ylmethyl]sulfanyl}propanamide Activation of 300 mg (1.27 mmol) of 2-methyl-2-{[(2R)-oxan-2-ylmethyl]sulfanyl}propanoic acid as the corresponding acid chloride is achieved by treatment with oxalyl chloride (305 mg, 2.54 mmol) and DMF (1 drop) in DCM (10 mL) at room temperature for 18 h. The solvent is removed by distillation, and then azeotroped with toluene (3×5 mL).

This acid chloride is dissolved in toluene (5 mL) and added dropwise to a stirred suspension of 565 mg (1.37 mmol) of 5-[2-(tert-butyl-diphenyl-silanyloxy)-1,1-dimethyl-ethyl]-[1,3,4]thiadiazol-2-ylamine and 0.48 mL (2.75 mmol) of N,N-diisopropylethylamine in toluene (10 mL) at room temperature. After complete addition the reaction is heated to 60° C. for 18 h. The reaction is cooled to room temperature and the solvent is removed under reduced pressure. The residue is purified by column chromatography (silica, eluent: heptanes, 0-20% ethyl acetate) to yield 658 mg of N-(5-{1-[(tert-butyl-diphenylsilyl)oxy]-2-methylpropan-2-yl}-1,3,4-thiadiazol-2-yl)-2-methyl-2-{[(2R)-oxan-2-ylmethyl]sulfanyl}propanamide. Yield: 73%; m/z 612 [M+H], $^1$H NMR (500 MHz, CHLOROFORM-d) δ ppm 1.01-1.09 (9H, m), 1.21-1.70 (17H, m), 1.75-1.84 (1H, m), 2.57-2.72 (2H, m), 3.33 (1H, td, J=11.71, 2.06 Hz), 3.38-3.47 (1H, m), 3.70-3.75 (2H, m), 4.10-4.17 (1H, m), 7.34-7.47 (6H, m), 7.56-7.64 (4H, m), 10.94 (1H, br. s.)

Step 2: Synthesis of N-(5-{1-[(tert-butyldiphenylsilyl)oxy]-2-methylpropan-2-yl}-1,3,4-thiadiazol-2-yl)-2-methyl-2-{[(2R)-oxan-2-ylmethane]sulfonyl}propanamide To a solution of 658 mg (1.00 mmol) of N-(5-{1-[(tert-butyldiphenylsilyl)oxy]-2-methylpropan-2-yl}-1,3,4-thiadiazol-2-yl)-2-methyl-2-{[(2R)-oxan-2-ylmethyl]sulfanyl}propanamide in DCM is added 673 mg (77% wt, 3.0 mmol) of 3-chloroperoxybenzoic acid at room temperature. After complete addition, the mixture is stirred at room temperature for 18 h. The mixture is diluted with DCM and washed with 10% aqueous sodium sulfite solution (5 mL) and saturated aqueous NaHCO$_3$ solution (5 mL). The organic layer is dried (MgSO$_4$), filtered and concentrated under reduced pressure. The residue is purified by column chromatography (silica, eluent: heptanes, 0-30% ethyl acetate) to give 315 mg of N-(5-{1-[(tert-butyldiphenylsilyl)oxy]-2-methylpropan-2-yl}-1,3,4-thiadiazol-2-yl)-2-methyl-2-{[(2R)-oxan-2-ylmethane]sulfonyl}propanamide. Yield: 37%, m/z 644 [M+H], 1H-NMR (500 MHz, CHLOROFORM-d) δ ppm 1.02-1.11 (9H, m), 1.19-1.56 (12H, m), 1.55-1.69 (1H, m), 1.69-1.87 (6H, m), 2.91-3.10 (2H, m), 3.46 (1H, dd, J=14.72, 9.23 Hz), 3.60-3.77 (3H, m), 3.88 (1H, dd, J=10.99, 9.31 Hz), 7.30-7.49 (5H, m), 7.53-7.68 (4H, m)

Step 3: Synthesis of N-[5-(1-hydroxy-2-methylpropan-2-yl)-1,3,4-thiadiazol-2-yl]-2-methyl-2-{[(2R)-oxan-2-ylmethane]sulfonyl}propanamide To a solution of 315 mg (0.49 mmol) of N-(5-{1-[(tert-butyldiphenylsilyl)oxy]-2-methylpropan-2-yl}-1,3,4-thiadiazol-2-yl)-2-methyl-2-{[(2R)-oxan-2-ylmethane]sulfonyl}propanamide in methanol (10 mL) is added HF (65% solution in pyridine, 0.4 mL). The reaction is heated to 70° C. for 18 h. Additional HF (65% solution in pyridine, 0.4 mL) is added and the reaction is heated for 48 h. The reaction mixture is filtered through Isolute PE-AX column (eluent: methanol) and the filtrate is concentrated under reduced pressure. The residue is purified by column chromatography (Isolute SCX-2, eluent: heptanes, 0-50% ethyl acetate), followed by recrystallization from ethyl acetate/heptanes to afford 59 mg of N-[5-(1-hydroxy-2-methylpropan-2-yl)-1,3,4-thiadiazol-2-yl]-2-methyl-2-{[(2R)-oxan-2-ylmethane]sulfonyl}propanamide. Yield: 30%, m/z 406 [M+H].

Compounds in Table XXXVIII, amide method U, are made according to this procedure.

TABLE XXXVIII

Examples

| # | Structure | $^1$H NMR | m/z [M+H] | Acid Method | Amine Method | Amide Method |
|---|---|---|---|---|---|---|
| 1 | 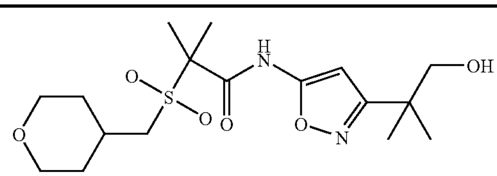 | (250 MHz, CHLOROFORM-d) δ ppm 1.31 (6 H, s), 1.39-1.58 (2 H, m), 1.74 (6 H, s), 1.80-1.92 (2 H, m), 2.31-2.52 (1 H, m), 2.92 (2 H, d, J = 6.62 Hz), 3.37-3.51 (2 H, m), 3.69 (2 H, s), 3.96 (2 H, d, J = 6.28 Hz), 6.34 (1 H, s), 9.44 (1 H, s) | 389 | B | A or B | A or B |

TABLE XXXVIII-continued

Examples

| # | Structure | ¹H NMR | m/z [M + H] | Acid Method | Amine Method | Amide Method |
|---|---|---|---|---|---|---|
| 2 | 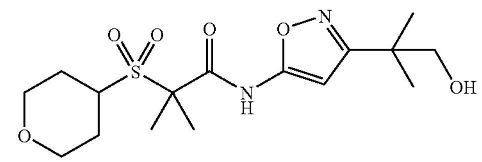 | (500 MHz, CHLOROFORM-d) δ ppm 1.31 (6 H, s), 1.76 (6 H, s), 1.83-1.91 (2 H, m), 1.99 (2 H, qd, J = 12.41, 4.43 Hz), 2.26 (1 H, t, J = 6.71 Hz), 3.34-3.52 (3 H, m), 3.69 (2 H, d, J = 6.26 Hz), 4.08 (2 H, dd, J = 11.75, 4.12 Hz), 6.30 (1 H, s), 9.67 (1 H, s) | 375 | F | A or B | A or B1, 2 or 3 |
| 3 | 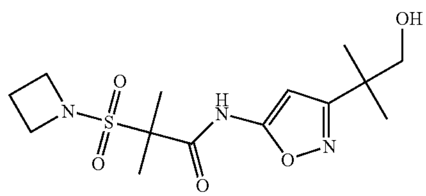 | (400 MHz, DMSO-d6) δ ppm 1.19 (6 H, s), 1.59 (6 H, s), 2.21 (2 H, q, J = 15 Hz), 3.41 (2 H, d, J = 11 Hz), 3.92 (4 H, t, J = 15 Hz), 4.78 (1 H, t, J = 11 Hz), 6.28 (1 H, s), 11.1 (1 H, s) | 346 | G | A | A |
| 4 | 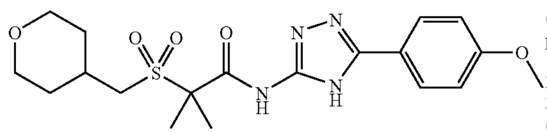 | (250 MHz, CHLOROFORM-d) δ ppm 1.32-1.61 (2 H, m), 1.69-1.92 (8 H, m), 2.26-2.57 (1 H, m), 2.99 (2 H, d, J = 6.55 Hz), 3.27-3.51 (2 H, m), 3.85 (3 H, s), 3.92 (2 H, dd, J = 11.25, 3.64 Hz), 6.94 (2 H, d, J = 8.79 Hz), 7.95 (2 H, d, J = 8.76 Hz) | 423 | B | F | D |
| 5 | 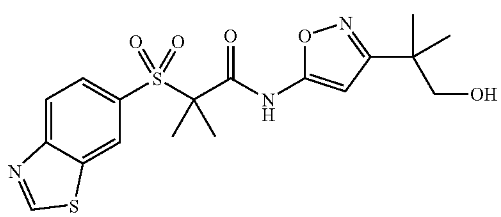 | (500 MHz, CHLOROFORM-d) δ ppm 1.31 (6 H, s), 1.71 (6 H, s), 2.34 (1 H, t, J = 6.19 Hz), 3.70 (2 H, d, J = 5.41 Hz), 6.27 (1 H, s), 7.95 (1 H, dd, J = 8.67, 1.88 Hz), 8.31 (1 H, d, J = 8.67 Hz), 8.52 (1 H, d, J = 1.79 Hz), 9.29 (1 H, s), 9.69 (1 H, s) | 424 | D | A | A |
| 6 | 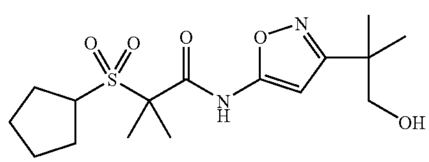 | (250 MHz, CHLOROFORM-d) δ ppm 1.31 (6 H, s), 1.60-1.70 (2 H, m), 1.74 (6 H, s), 1.77-1.86 (2 H, m), 1.98-2.10 (4 H, m), 2.28 (1 H, t, J = 6.87 Hz), 3.55 (1 H, quin, J = 8.34 Hz), 3.69 (2 H, d, J = 6.85 Hz), 6.32 (1 H, s), 9.62 (1 H, br. s.) | 359 | A | A | A |
| 7 | 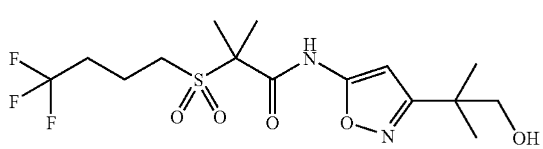 | (500 MHz, CHLOROFORM-d) δ ppm 1.32 (6 H, s), 1.77 (6 H, s), 2.13-2.27 (3 H, m), 2.27-2.40 (2 H, m), 3.11 (2 H, t, J = 7.50 Hz), 3.69 (2 H, d, J = 6.79 Hz), 6.34 (1 H, s), 9.30 (1 H, br. s.) | 401 | C | A or B or C | A or B1 or C |
| 8 | 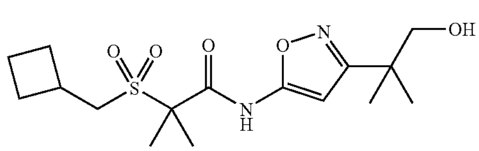 | (500 MHz, CHLOROFORM-d) δ ppm 1.31 (6 H, s), 1.72 (6 H, s), 1.83-1.95 (3 H, m), 1.96-2.08 (1 H, m), 2.18-2.36 (3 H, m), 2.89-3.03 (1 H, m), 3.11 (2 H, d, J = 7.34 Hz), 3.69 (2 H, d, J = 5.87 Hz), 6.34 (1 H, s), 9.54 (1 H, s) | 359 | C | A | A |
| 9 | 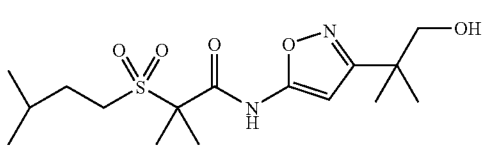 | (500 MHz, CHLOROFORM-d) δ ppm 0.94 (6 H, d, J = 6.46 Hz), 1.31 (6 H, s), 1.64-1.84 (9 H, m), 2.01-2.61 (1 H, m), 2.83-3.13 (2 H, m), 3.45-3.90 (2 H, m), 6.34 (1 H, s), 9.51 (1 H, br. s.) | 361 | C | A | A |

TABLE XXXVIII-continued

Examples

| # | Structure | ¹H NMR | m/z [M + H] | Acid Method | Amine Method | Amide Method |
|---|---|---|---|---|---|---|
| 10 | 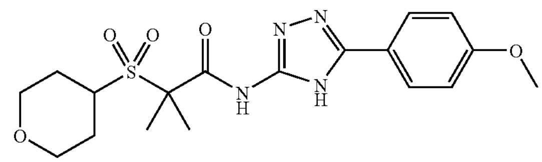 | (500 MHz, MeOD) δ ppm 1.78 (6 H, s), 1.83-1.93 (2 H, m), 1.93-2.01 (2 H, m), 3.46 (2 H, td, J = 11.78, 2.11 Hz), 3.84 (3 H, s), 3.87-3.93 (1 H, m), 3.95-4.03 (2 H, m), 7.02 (2 H, d, J = 8.62 Hz), 7.92 (2 H, d, J = 8.62 Hz) | 409 | F | F | A |
| 11 | 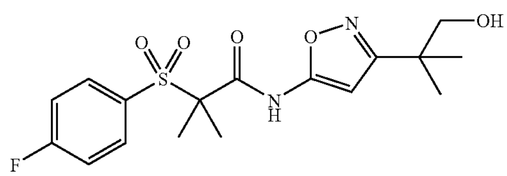 | (500 MHz, CHLOROFORM-d) δ ppm 1.31 (6 H, s), 1.67 (6 H, s), 2.28 (1 H, t, J = 6.83 Hz), 3.70 (2 H, d, J = 6.79 Hz), 6.27 (1 H, s), 7.17-7.39 (2 H, m), 7.78-7.95 (2 H, m), 9.63 (1 H, br. s.) | 385 | A | A | A |
| 12 | 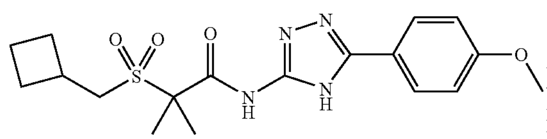 | (500 MHz, DMSO-d6) δ ppm 1.67 (6 H, s), 1.74-1.97 (4 H, m), 2.07-2.17 (2 H, m), 2.81 (1 H, dt, J = 15.82, 7.77 Hz), 3.38 (2 H, d), 3.81 (3 H, s), 7.04 (2 H, d, J = 8.62 Hz), 7.90 (2 H, d) | 393 | C | F | D |
| 13 | 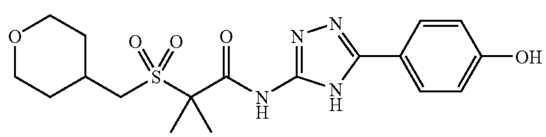 | (500 MHz, MeOD) δ ppm 1.37-1.59 (2 H, m), 1.77 (6 H, s), 1.87 (2 H, dd, J = 13.24, 1.89 Hz), 2.22-2.55 (1 H, m), 3.25 (2 H, d, J = 6.62 Hz), 3.44 (2 H, td, J = 11.90, 2.05 Hz), 3.91 (2 H, dd, J = 11.66, 2.52 Hz), 6.87 (2 H, d, J = 8.51 Hz), 7.83 (2 H, d, J = 8.51 Hz) | 400 | not applicable | not applicable | G |
| 14 | 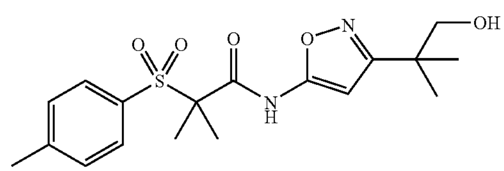 | (500 MHz, CHLOROFORM-d) δ ppm 1.31 (6 H, s), 1.65 (6 H, s), 2.29 (1 H, t, J = 6.90 Hz), 2.47 (3 H, s), 3.70 (2 H, d, J = 6.88 Hz), 6.27 (1 H, s), 7.37 (2 H, d, J = 8.12 Hz), 7.71 (2 H, d, J = 8.34 Hz), 9.76 (1 H, s) | 381 | A | C | C |
| 15 | 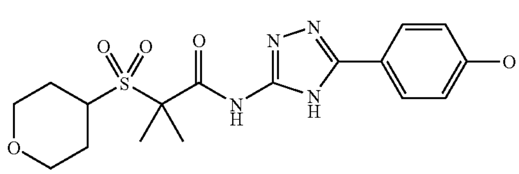 | (500 MHz, MeOD) δ ppm 1.78 (6 H, s), 1.83-1.94 (2 H, m), 1.94-2.00 (2 H, m), 3.47 (2 H, td, J = 11.75, 2.14 Hz), 3.89 (1 H, tt, J = 11.75, 4.12 Hz), 3.96-4.04 (2 H, m), 6.87 (2 H, d), 7.83 (2 H, d, J = 8.85 Hz) | 395 | not applicable | not applicable | G |
| 16 | 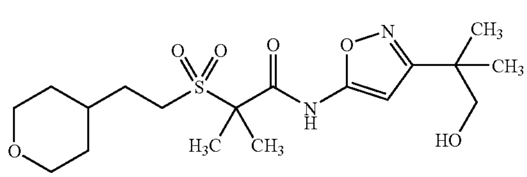 | (500 MHz, MeOD) δ ppm 1.22-1.28 (2 H, m), 1.29 (6 H, s), 1.61-1.71 (3 H, m), 1.71-1.78 (8 H, m), 3.24-3.29 (2 H, m), 3.39 (2 H, td, J = 11.90, 1.83 Hz), 3.58 (2 H, s), 3.92 (2 H, dd, J = 11.29, 3.97 Hz), 6.41 (1 H, s) | 403 | E | C | C |
| 17 | 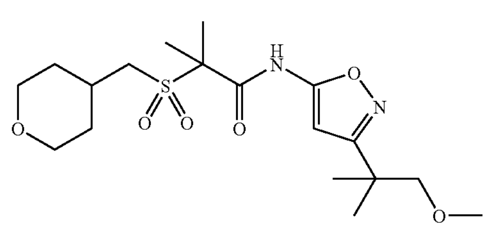 | (500 MHz, CHLOROFORM-d) δ ppm 1.34 (6 H, s), 1.39-1.55 (2 H, m), 1.74 (6 H, s), 1.86 (2 H, dd, J = 13.08, 1.73 Hz), 2.29-2.54 (1 H, m), 2.75-2.99 (2 H, m), 3.36 (3 H, s), 3.39-3.50 (4 H, m), 3.96 (2 H, dd, J = 11.03, 3.78 Hz), 6.34 (1 H, s), 9.37 (1 H, s) | 403 | not applicable | not applicable | H |

TABLE XXXVIII-continued

Examples

| # | Structure | ¹H NMR | m/z [M + H] | Acid Method | Amine Method | Amide Method |
|---|---|---|---|---|---|---|
| 18 | 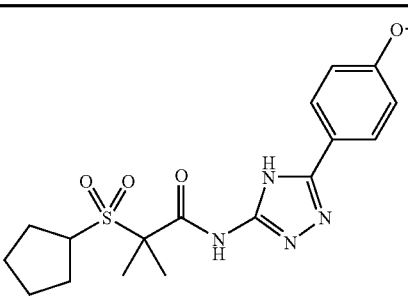 | (500 MHz, MeOD) δ ppm 1.56-1.68 (2 H, m), 1.68-1.82 (8 H, m), 2.03 (4 H, q, J = 7.02 Hz), 3.84 (3 H, s), 3.93 (1 H, quin, J = 8.24 Hz), 7.01 (2 H, d, J = 8.85 Hz), 7.92 (2 H, d, J = 8.85 Hz) | 393 | A | F | D |
| 19 | 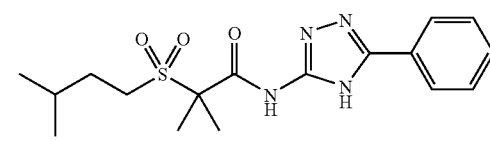 | (500 MHz, MeOD) δ ppm 0.87-1.00 (6 H, m), 1.66-1.76 (3 H, m), 1.76 (6 H, s), 3.22-3.30 (2 H, m), 3.85 (3 H, s), 7.02 (2 H, d, J = 7.63 Hz), 7.92 (2 H, d, J = 8.24 Hz) | 395 | C | F | D |
| 20 | 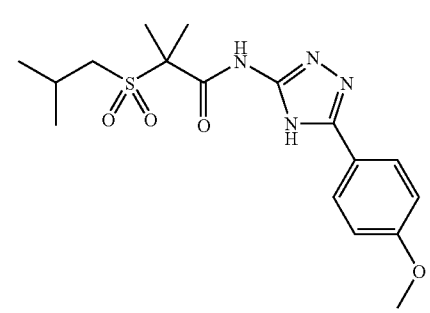 | (500 MHz, MeOD) δ ppm 1.15 (6 H, d, J = 6.62 Hz), 1.77 (6 H, s), 2.20-2.54 (1 H, m), 3.19 (2 H, d, J = 6.62 Hz), 3.87 (3 H, s), 7.04 (2 H, d, J = 8.51 Hz), 7.95 (2 H, d, J = 8.51 Hz) | 381 | C | F | D |
| 21 | 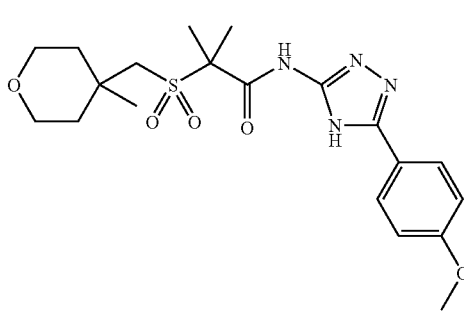 | (500 MHz, MeOD) δ ppm 1.38 (3 H, s), 1.54-1.65 (2 H, m), 1.76 (6 H, s), 1.80-1.94 (2 H, m), 3.37 (2 H, s), 3.59-3.75 (4 H, m), 3.85 (3 H, br.s.), 7.03 (2 H, d), 7.93 (2 H, d, J = 12.93 Hz) | 437 | F | F | D |
| 22 | 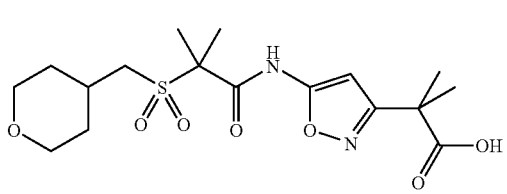 | (400 MHz, MeOD) δ ppm 1.40-1.55 (2 H, m), 1.6 (6 H, s), 1.7 (6 H, s), 1.80-1.90 (2 H, m), 2.22-2.37 (1 H, m), 3.2 (2 H, d), 3.38-3.48 (2 H, m), 3.86-3.95 (2 H, m), 6.4 (1 H, s) | 401 | not applicable | not applicable | E |
| 23 | 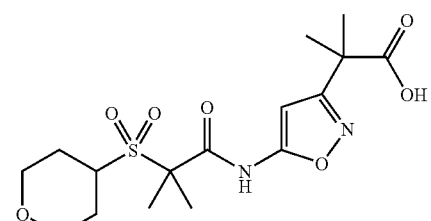 | (400 MHz, MeOD) δ ppm 1.55 (6 H, s), 1.7 (6 H, s), 1.76-1.94 (4 H, m), 3.40-3.50 (2 H, m), 3.78-3.88 (1 H, m), 3.93-4.00 (2 H, m), 6.4 (1 H, s) | 389 | not applicable | not applicable | E |

TABLE XXXVIII-continued

Examples

| # | Structure | ¹H NMR | m/z [M + H] | Acid Method | Amine Method | Amide Method |
|---|---|---|---|---|---|---|
| 24 | 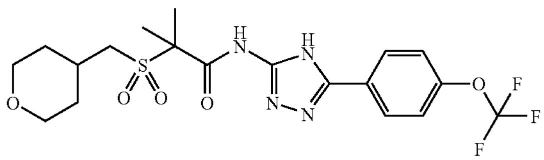 | (500 MHz, MeOD) δ ppm 1.41-1.56 (2 H, m), 1.77 (6 H, s), 1.86 (2 H, dd, J = 13.12, 1.83 Hz), 2.27-2.41 (1 H, m), 3.25 (2 H, d, J = 6.71 Hz), 3.43 (2 H, td, J = 11.90, 1.83 Hz), 3.84-3.97 (2 H, m), 7.36 (2 H, d, J = 8.24 Hz), 8.08-8.16 (2 H, m) | 477 | B | F | D |
| 25 | 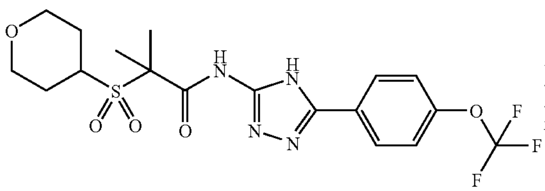 | (500 MHz, MeOD) δ ppm 1.78 (6 H, s), 1.82-1.92 (2 H, m), 1.91-2.01 (2 H, m), 3.46 (2 H, td, J = 11.83, 2.29 Hz), 3.89 (1 H, tt, J = 11.75, 4.12 Hz), 3.94-4.04 (2 H, m), 7.36 (2 H, d, J = 8.24 Hz), 8.12 (2 H, d, J = 8.85 Hz) | 463 | F | F | D |
| 26 | 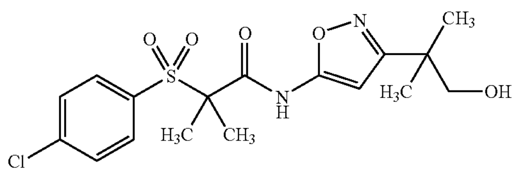 | (400 MHz, DMSO-d6) δ ppm 1.19 (6 H, s), 1.59 (6 H, s), 3.34 (2 H, d, J = 14 Hz), 4.83 (1 H, t, J = 14 Hz), 6.21 (1 H, s), 7.71-7.77 (4 H, m), 11.36 (1 H, s) | 401 | A | A | A |
| 27 | 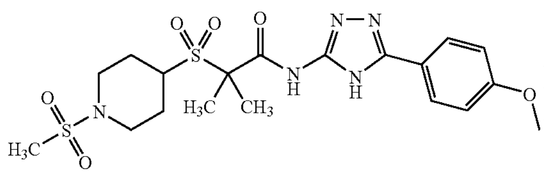 | (500 MHz, DMSO-d6) δ ppm 1.64-1.75 (8 H, m), 2.12 (2 H, d, J = 12.28 Hz), 2.80-2.91 (5 H, m), 3.63 (2 H, d, J = 12.21 Hz), 3.81 (3 H, s), 3.87 (1 H, br. s.), 7.04 (2 H, br. s.), 7.90 (2 H, d, J = 8.54 Hz) | 486 | I | F | D |
| 28 | 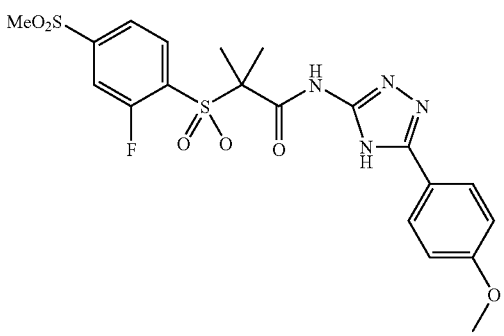 | (250 MHz, MeOD) δ ppm 1.79 (6 H, s), 3.22 (3 H, s), 3.86 (3 H, s), 7.02 (2 H, d, J = 8.68 Hz), 7.94 (4 H, m), 8.15 (1 H, m) | 497 | H | F | F |
| 29 | 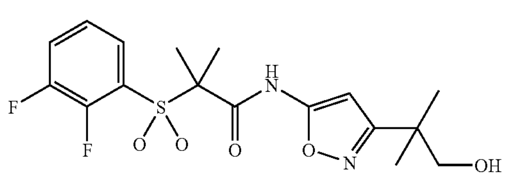 | (500 MHz, CHLOROFORM-d) δ ppm 1.32 (6 H, s), 1.73 (6 H, s), 2.28 (1 H, t, J = 6.87 Hz), 3.70 (2 H, d, J = 6.87 Hz), 6.29 (1 H, s), 7.29-7.36 (1 H, m), 7.52-7.60 (1 H, m), 7.60-7.66 (1 H, m), 9.43 (1 H, br. s.) | 403 | H | B | B1 |
| 30 | 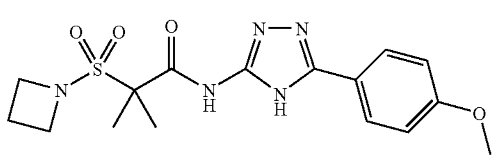 | (400 MHz, DMSO-d6) δ ppm 1.63 (6 H, s), 2.21 (2 H, q, J = 20 Hz), 3.80 (3 H, s), 3.95 (4 H, t, J = 19 Hz), 7.01-7.11 (2 H, m), 7.88-7.92 (2 H, m), 11.30 (1 H, s), 13.55 (1 H, s) | 380 | G | F | A |

TABLE XXXVIII-continued

Examples

| # | Structure | ¹H NMR | m/z [M + H] | Acid Method | Amine Method | Amide Method |
|---|---|---|---|---|---|---|
| 31 | 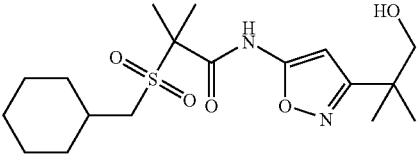 | (500 MHz, CHLOROFORM-d) δ ppm 1.07-1.20 (3 H, m), 1.29-1.35 (7 H, m), 1.65 (1 H, d, J = 4.73 Hz), 1.68-1.77 (8 H, m), 1.95 (2 H, d, J = 16.48 Hz), 2.16 (1 H, br. s.), 2.24 (1 H, t, J = 6.87 Hz), 2.86 (2 H, d, J = 6.41 Hz), 3.69 (2 H, d, J = 6.79 Hz), 6.33 (1 H, s), 9.51 (1 H, br. s.) | 387 | C | C | C |
| 32 | 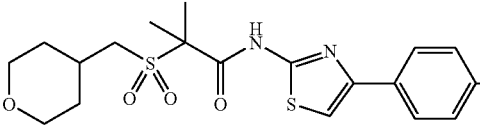 | (400 MHz, DMSO-d6) δ ppm 1.32-1.42 (2 H, m), 1.71 (6 H, s), 1.75 (2 H, broad s), 2.15 (1 H, broad s), 3.22-3.25 (2 H, m), 3.27-3.30 (2 H, m), 3.77-3.80 (5 H, m), 7.00 (2 H, d, J = 22), 7.54 (1 H, s), 7.86 (2 H, d, J = 22), 12.10 (1 H, s) | 439 | B | commercial | A |
| 33 | 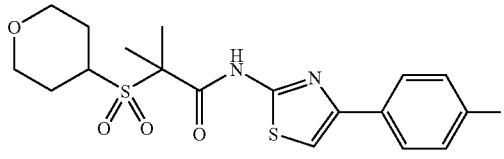 | (400MHz, DMSO-d6) δ ppm 1.58-1.68 (2 H, m), 1.74 (6 H, s), 1.78-1.81 (2 H, m), 3.38-3.41 (2 H, m), 3.79 (3 H, s), 3.86-3.90 (2 H, m), 3.95-3.97 (1 H, m), 7.00 (2 H, d, J = 22), 7.54 (1 H, s), 7.86 (2 H, d, J = 22), 12.08 (1 H, s) | 425 | F | commercial | A |
| 34 | 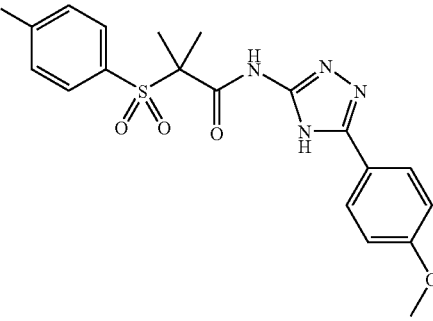 | (500 MHz, CHLOROFORM-d) δ ppm 1.71 (7 H, s), 3.88 (3 H, s), 6.99 (2 H, d, J = 8.85 Hz), 7.20-7.34 (2 H, m), 7.87 (2 H, dd, J = 8.85, 4.73 Hz), 8.01 (2 H, d, J = 8.70 Hz), 9.85 (1 H, br. s.) | 419 | A | F | D |
| 36 | 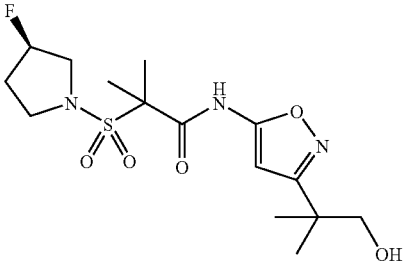 | (500 MHz, CHLOROFORM-d) δ ppm 1.31 (6 H, s), 1.74 (6 H, s), 1.96-2.15 (1 H, m), 2.22-2.36 (2 H, m), 3.56 (1 H, td, J = 10.26, 6.33 Hz), 3.61-3.78 (5 H, m), 5.18-5.36 (1 H, m), 6.33 (1 H, s), 9.56 (1 H, br. s.) | 378 | G | B | B1 |
| 37 | 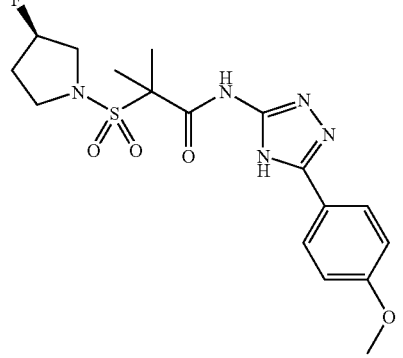 | (500 MHz, MeOD) δ ppm 1.76 (6 H, s), 2.01-2.29 (2 H, m), 3.55-3.81 (4 H, m), 3.85 (3 H, s), 5.17-5.34 (1 H, m), 7.02 (2 H, d, J = 8.77 Hz), 7.93 (2 H, d, J = 8.85 Hz) | 412 | G | F | J |

TABLE XXXVIII-continued

Examples

| # | Structure | ¹H NMR | m/z [M + H] | Acid Method | Amine Method | Amide Method |
|---|---|---|---|---|---|---|
| 38 | 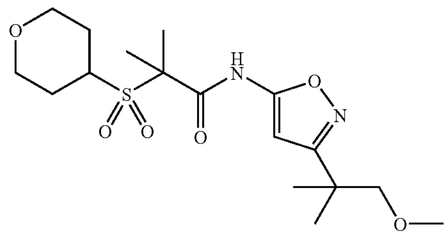 | (500 MHz, CHLOROFORM-d) δ ppm 1.25 (6 H, s), 1.67 (6 H, s), 1.75-1.84 (2 H, m), 1.84-2.00 (2 H, m), 3.16-3.51 (8 H, m), 3.84-4.14 (2 H, m), 6.23 (1 H, s), 9.52 (1 H, s) | 389 | not applicable | not applicable | H |
| 39 | 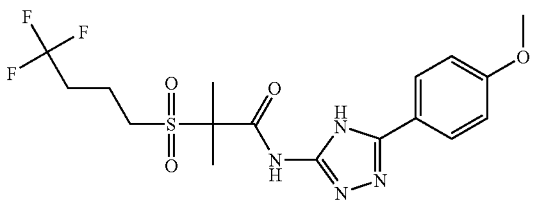 | ¹H NMR (500 MHz, MeOD) δ ppm 1.78 (6 H, s), 2.11 (2 H, quin, J = 7.74 Hz), 2.33-2.51 (2 H, m), 3.43 (2 H, t, J = 7.40 Hz), 3.86 (3 H, s), 7.02 (2 H, d, J = 8.39 Hz), 7.93 (2 H, d, J = 8.24 Hz) | 435 | C | F | I |
| 40 | 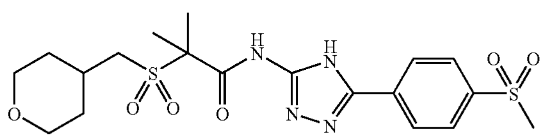 | (500 MHz, DMSO-d6) δ ppm 1.39 (2 H, qd, J = 12.24, 4.26 Hz), 1.59-1.85 (8 H, m), 2.12-2.32 (1 H, m), 3.12-3.35 (7 H, m), 3.81 (2 H, dd, J = 11.35, 2.21 Hz), 8.04 (2 H, d, J = 8.51 Hz), 8.22 (2 H, d, J = 8.20 Hz), 11.59 (1 H, br. s.), 13.97 (1 H, br. s.) | 471 | B | F | I |
| 41 | 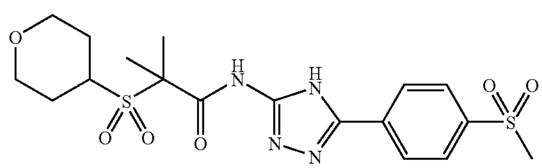 | (500 MHz, CHLOROFORM-d) δ ppm 1.82 (6 H, s), 1.86-1.95 (2 H, m), 1.95-2.11 (2 H, m), 3.12 (3 H, s), 3.41 (2 H, t, J = 11.51 Hz), 3.47-3.62 (1 H, m), 4.09 (2 H, dd, J = 11.51, 3.63 Hz), 8.04 (2 H, d, J = 8.20 Hz), 8.29 (2 H, d, J = 8.20 Hz), 10.04 (1 H, br. s.), 11.85 (1 H, br. s.) | 457 | F | F | I |
| 42 | 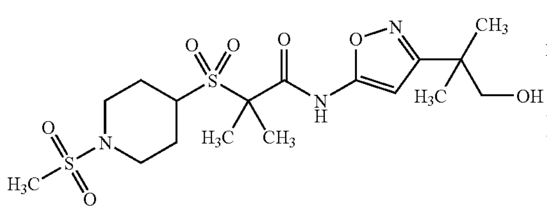 | (500 MHz, CHLOROFORM-d) δ ppm 1.32 (6 H, s), 1.76 (6 H, s), 1.97-2.07 (2 H, m), 2.08-2.15 (2 H, m), 2.16-2.33 (1 H, m), 2.74-2.90 (5 H, m), 3.24-3.42 (1 H, m), 3.70 (2 H, s), 3.82-3.97 (2 H, m), 6.31 (1 H, s), 9.53 (1 H, s) | 452 | I | B | B1 |
| 43 | 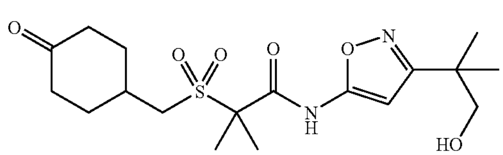 | (500 MHz, CHLOROFORM-d) δ ppm 1.32 (6 H, s), 1.58-1.68 (2 H, m), 1.76 (6 H, s), 2.23 (1 H, t, J = 6.78 Hz), 2.33 (2 H, dd, J = 10.56, 4.10 Hz), 2.39-2.47 (4 H, m), 2.63 (1 H, dt, J = 6.70, 3.11 Hz), 3.00 (2 H, d, J = 6.62 Hz), 3.69 (2 H, d, J = 6.62 Hz), | 401 | C | B | R |
| 44 | 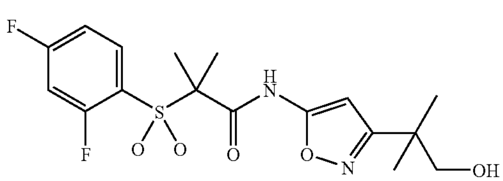 | (400 MHz, DMSO-d6) δ ppm 1.19 (6 H, s), 1.64 (6 H, s), 3.41 (2 H, d, J = 14 Hz), 4.84 (1 H, t, J = 14 Hz), 6.23 (1 H, s), 7.38 (1 H, t, J = 22 Hz), 7.62 (1 H, t, J = 22 Hz), 7.83 (1 H, q, J = 21 Hz), 11.38 (1 H, s) | 403 | A | E | I1 |

TABLE XXXVIII-continued

Examples

| # | Structure | ¹H NMR | m/z [M + H] | Acid Method | Amine Method | Amide Method |
|---|---|---|---|---|---|---|
| 45 | 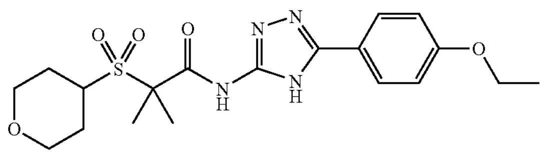 | (500 MHz, CHLOROFORM-d) δ ppm 1.45 (3 H, t, J = 7.02 Hz), 1.80 (6 H, s), 1.84-1.92 (2 H, m), 1.95-2.07 (2 H, m), 3.38 (2 H, td, J = 11.90, 1.83 Hz), 3.44-3.63 (1 H, m), 3.94-4.24 (4 H, m), 6.96 (2 H, d, J = 8.85 Hz), 7.97 (2 H, d, J = 8.85 Hz), 10.05 (1 H, br. s.), 11.64 (1 H, br. s.) | 423 | F | F | I |
| 46 | 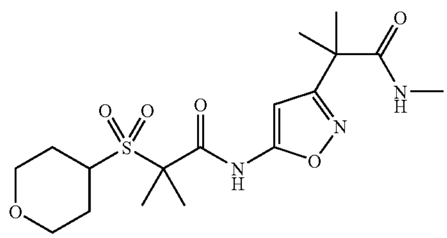 | (400 MHz, MeOD) δ ppm 1.55 (6 H, s), 1.75 (6 H, s), 1.78-1.98 (4 H, m), 2.7 (3 H, s), 3.5 (2 H, t), 3.80-3.90 (1 H, m), 3.95-4.05 (2 H, m), 6.4 (1 H, s) | 402 | not applicable | not applicable | L |
| 47 | 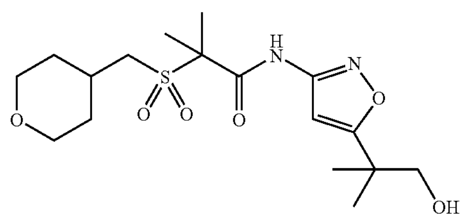 | (400 MHz, DMSO-d6) δ ppm 1.2 (6 H, s), 1.30-1.42 (2 H, m), 1.65 (6 H, s), 1.68-1.77 (2 H, m), 2.10-2.25 (1 H, m), 3.2 (2 H, d), 3.25-3.35 (2 H, m), 3.45 (2 H, d), 3.75-3.85 (2 H, m), 4.95 (1 H, t), 6.6 (1 H, s), 10.65 (1 H, s) | 389 | not applicable | not applicable | G |
| 48 | 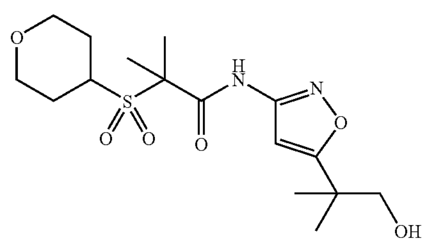 | (400 MHz, DMSO-d6) δ ppm 1.2 (6 H, s), 1.65 (6 H, s), 1.58-1.75 (2 H, m), 1.78-1.88 (2 H, m), 3.30-3.43 (2 H, m), 3.45 (2 H, s), 3.83-4.00 (2 H, m), 6.6 (1 H, s), 10.6 (1 H, s) | 375 | not applicable | not applicable | G |
| 49 | 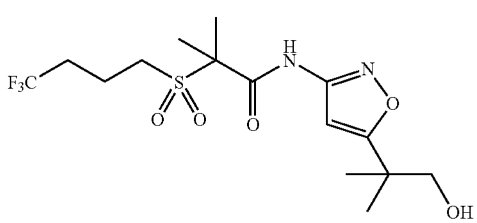 | (400 MHz, DMSO-d6) δ ppm 1.2 (6 H, s), 1.65 (6 H, s), 1.86-1.95 (2 H, m), 2.40-2.60 (2 H, m), 3.34-3.41 (2 H, m), 3.45 (2 H, d), 4.95 (1 H, t), 6.6 (1 H, s), 10.7 (1 H, s) | 401 | not applicable | not applicable | G |
| 50 | 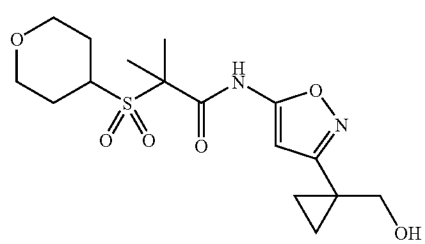 | (400 MHz, CHLOROFORM-d) δ ppm 1.75 (s, 6 H), 1.83-1.87 (m, 2 H), 1.75 (s, 6 H), 3.39 (td, 2 H), 3.43-3.48 (m, 1 H), 3.81 (s, 2 H), 4.07 (dd, 2 H), 6.04 (s, 1 H), 9.64 (s, 1 H) | 373 | F | B | B2 |
| 51 | 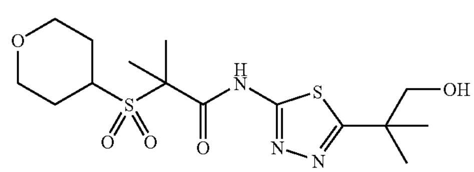 | (500 MHz, CHLOROFORM-d) δ ppm 1.46 (6 H, s), 1.78-1.90 (8 H, m), 1.92-2.03 (2 H, m), 3.39 (2 H, td, J = 11.75, 1.37 Hz), 3.53 (1 H, tt, J = 11.88, 3.99 Hz), 3.78 (2 H, s), 4.05 (2 H, dd, J = 11.60, 3.36 Hz) | 392 | F | G | Q |

TABLE XXXVIII-continued

Examples

| # | Structure | ¹H NMR | m/z [M + H] | Acid Method | Amine Method | Amide Method |
|---|---|---|---|---|---|---|
| 52 | 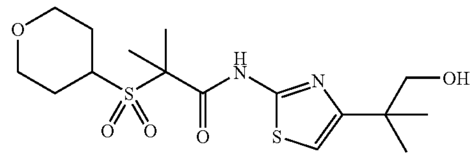 | (500 MHz, CHLOROFORM-d) δ ppm 1.31 (6 H, s), 1.59 (2 H, s), 1.79 (6 H, s), 1.84-1.92 (2 H, m), 1.98 (2 H, qd, J = 12.36, 4.58 Hz), 3.11 (1 H, br.s.), 3.39 (2 H, td, J = 11.86, 1.91 Hz), 3.46-3.54 (1 H, m), 4.05 (2 H, dd, J = 11.52, 3.74 Hz), 6.69 (1 H, s), 10.00 (1 H, br. s.) | 391 | F | H | Q |
| 53 | Chiral | (500 MHz, CHLOROFORM-d) δ ppm 1.70-1.88 (7 H, m), 2.22-2.37 (1 H, m), 2.86-2.98 (1 H, m), 3.15 (2 H, d, J = 6.87 Hz), 3.55-3.64 (1 H, m), 3.77 (1 H, q, J = 7.99 Hz), 3.83-3.94 (4 H, m), 4.01 (1 H, t, J = 7.93 Hz), 6.98 (2 H, d, J = 8.39 Hz), 7.97 (2 H, d, J = 8.55 Hz), 9.72 (1 H, br. s.) | 409 | F | F | J |
| 54 | Chiral | (500 MHz, CHLOROFORM-d) δ ppm 1.70-1.89 (7 H, m), 2.23-2.35 (1 H, m), 2.92 (1 H, d, J = 7.17 Hz), 3.15 (2 H, d, J = 7.02 Hz), 3.55-3.64 (1 H, m), 3.77 (1 H, q, J = 7.63 Hz), 3.84-3.94 (4 H, m), 4.01 (1 H, t, J = 8.01 Hz), 6.97 (2 H, d, J = 8.54 Hz), 7.97 (2 H, d, J = 8.54 Hz), 9.74 (1 H, br. s.) | 409 | F | F | J |
| 55 | 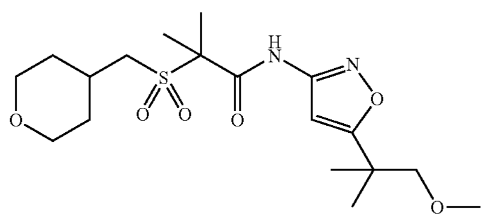 | (400 MHz, DMSO-d6) δ ppm 1.25 (6 H, s), 1.32-1.44 (2 H, m), 1.65 (6 H, s), 1.70-1.77 (2 H, m), 2.11-2.25 (1 H, m), 3.15 (2 H, s), 3.17-3.22 (2 H, m), 3.23 (3 H, s), 3.25-3.35 (2 H, m), 3.75-3.85 (2 H, m), 6.60 (1 H, s), 10.7 (1 H, s) | 403 | B | D | B |
| 56 | 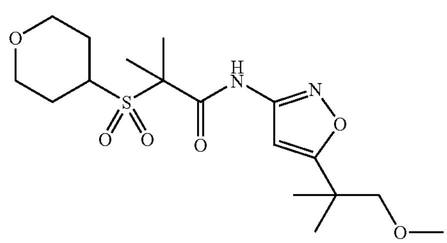 | (400 MHz, DMSO-d6) δ ppm 1.25 (6 H, s), 1.60-1.75 (2 H, m), 1.65 (6 H, s), 1.80-1.90 (2 H, m), 3.23 (3 H, s), 3.33-3.43 (2 H, m), 3.40 (2 H, s), 3.85-3.93 (2 H, m), 3.85-4.00 (1 H, m), 6.55 (1 H, s), 10.6 (1 H, s) | 389 | F | D | B |
| 57 | 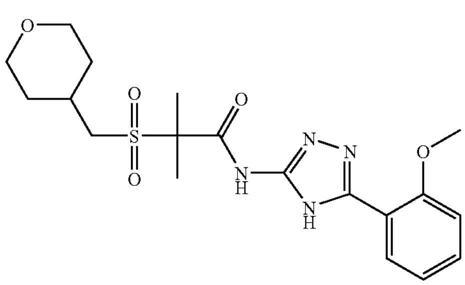 | (400 MHz, DMSO-d6) δ ppm 1.34-1.42 (2 H, m), 1.66 (6 H, s), 1.76 (2 H, d, J = 26), 2.24 (1 H, broad s), 3.23 (2 H, broad d, J = 13), 3.34 (2 H, broad d, J = 24), 3.80 (2 H, broad d, J = 19), 3.97 (3 H, s), 7.09 (1 H, t, J = 15), 7.21 (1 H, d, J = 17), 7.48 (1 H, t, J = 15), 8.01 (1 H, d, J = 15), 10.03 (1 H, s), 13.53 (1 H, s) | 423 | B | commercial | I |

TABLE XXXVIII-continued

Examples

| # | Structure | ¹H NMR | m/z [M + H] | Acid Method | Amine Method | Amide Method |
|---|---|---|---|---|---|---|
| 58 | 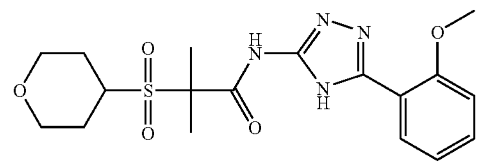 | (400 MHz, DMSO-d6) ppm 1.68 (6 H, s), 1.68-1.74 (2 H, m), 1.92-1.95 (2 H, m), 3.38-3.40 (2 H, m), 3.90-3.97 (6 H, m), 7.10 (1 H, t, J = 18), 7.22 (1 H, d, J = 22), 7.49 (1 H, t, J = 20), 8.01 (1 H, d, J = 17), 10.08 (1 H, s), 13.59 (1 H, s) | 409 | F | commercial | I |
| 59 | 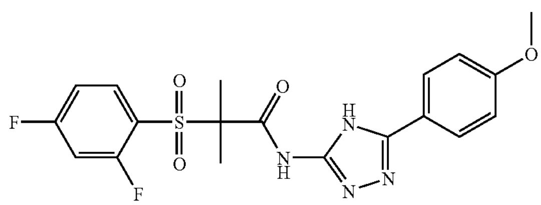 | Mixture of tautomers (400 MHz, DMSO-d6) δ ppm major - 1.69 (6 H, s), 3.80 (3 H, s), 7.02 (2 H, d, J = 22 Hz), 7.37 (1 H, t, J = 22 Hz), 7.60 (1 H, t, J = 22 Hz), 7.86 (1 H, q, J = 22 Hz), 7.90 (2 H, d, J = 22 Hz), 11.55 (1 H, s), 13.49 (1 H, s); minor - 1.65 (6 H, s), 3.82 (3 H, s), 7.10 (2 H, d, J = 22 Hz), 7.37 (1 H, t, J = 22 Hz), 7.60 (1 H, t, J = 22 Hz), 7.86 (1 H, q, J = 22 Hz), 7.90 (2 H, d, J = 22 Hz), 10.09 (1 H, s), 14.08 (1 H, s) | 437 | A | F | I |
| 60 | 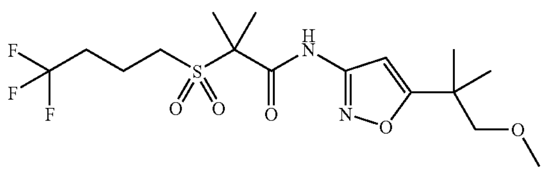 | (400 MHz, DMSO-d6) δ ppm 1.25 (6 H, s), 1.65 (6 H, s), 1.85-1.95 (2 H, m), 2.35-2.60 (2 H, m), 3.22 (3 H, s), 3.33-3.40 (2 H, m), 3.4 (2 H, s), 6.6 (1 H, s), 10.7 (1 H, s) | 415 | C | D | B |
| 61 | 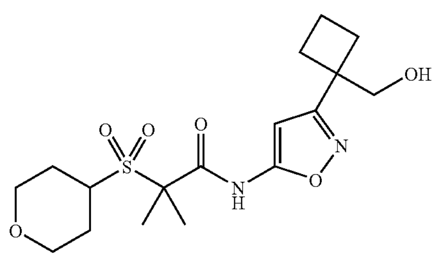 | (400 MHz, CHLOROFORM-d) δ ppm 1.77 (s, 6 H), 1.81-1.88 (m, 2 H), 1.96 (td, 2 H), 2.02-2.13 (m, 2 H), 2.14-2.23 (m, 2 H), 2.32-2.40 (m, 2 H), 3.38 (td, 2 H), 3.43-3.49 (m, 1 H), 3.93 (s, 2 H), 4.07 (dd, 2 H), 6.37 (s, 1 H), 9.60 (s, 1 H) | 387 | F | B | B2 |
| 62 | 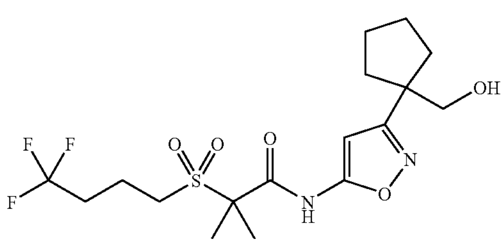 | (400 MHz, CHLOROFORM-d) δ ppm 1.75-1.79 (m, 9 H), 1.84-1.97 (m, 5 H), 2.17-2.26 (m, 2 H), 2.28-2.40 (m, 2 H), 3.11 (t, 2 H), 3.70 (s, 2 H), 6.32 (s, 1 H), 9.29 (s, 1 H) | 427 | C | B | B2 |
| 63 | 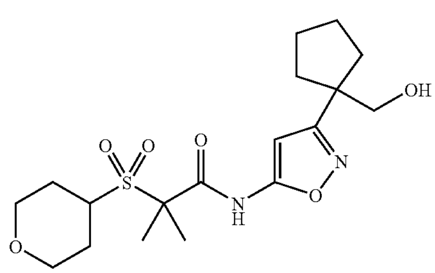 | (400 MHz, CHLOROFORM-d) δ ppm 1.71-1.78 (m, 10 H), 1.85-2.03 (m, 8 H), 3.39 (td, 2 H), 3.45 (tt, 1 H), 3.68 (s, 2 H), 4.07 (dd, 2 H), 6.27 (s, 1 H), 9.67 (s, 1 H) | 401 | F | B | B2 |

TABLE XXXVIII-continued

| # | Structure | ¹H NMR | m/z [M + H] | Acid Method | Amine Method | Amide Method |
|---|---|---|---|---|---|---|
| 64 | 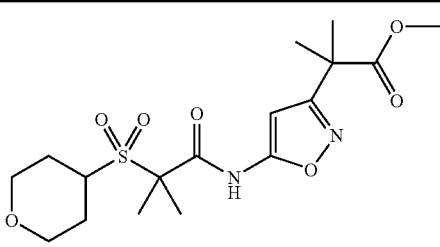 | (400 MHz, CHLOROFORM-d) δ ppm 1.6 (6 H, s), 1.75 (6 H, s), 1.80-1.90 (2 H, m), 1.90-2.03 (2 H, m), 3.33-3.43 (2 H, m), 3.42-3.48 (1 H, m), 3.7 (3 H, s), 4.00-4.10 (2 H, m), 6.3 (1 H, s), 9.6 (1 H, s) | 403 | not applicable | not applicable | M |
| 65 | 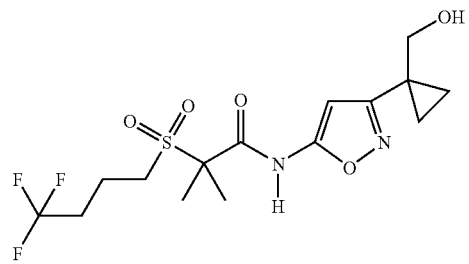 | (400 MHz, CHLOROFORM-d) δ ppm 1.02 (s, 4 H), 1.74 (s, 6 H), 2.13-2.21 (m, 2 H), 2.25-2.36 (m, 2 H), 3.07 (t, 2 H), 3.78 (d, 2 H), 6.06 (s, 1 H), 9.24 (s, 1 H) | 399 | C | B | B2 |
| 66 | 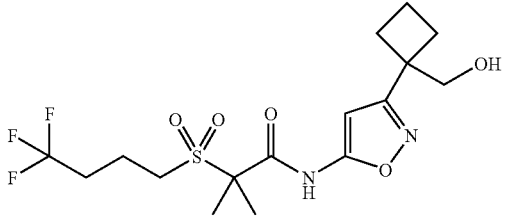 | (400 MHz, CHLOROFORM-d) δ ppm 1.71 (s, 6 H), 1.98-2.12 (m, 2 H), 2.14-2.22 (m, 4 H), 2.27-2.39 (m, 4 H), 2.45 (bs, 2 H), 3.11 (t, 2 H), 3.92 (bs, 2 H), 6.40 (s, 1 H), 9.33 (s, 1 H) | 413 | C | B | B2 |
| 67 | 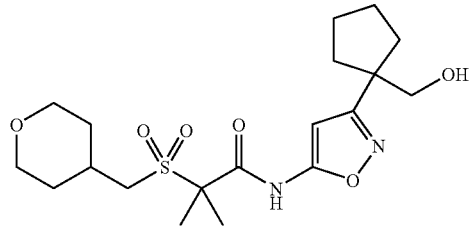 | (400 MHz, CHLOROFORM-d) δ ppm 1.48 (qd, 2 H), 1.73-1.76 (m, 9 H), 1.83-1.95 (m, 7 H), 2.38-2.44 (m, 1 H), 2.90 (d, 2 H), 3.43 (td, 2 H), 3.69 (s, 2 H), 3.93-3.97 (m, 2 H), 6.31 (s, 1 H), 9.39 (s, 1 H) | 415 | B | B | B2 |
| 68 | 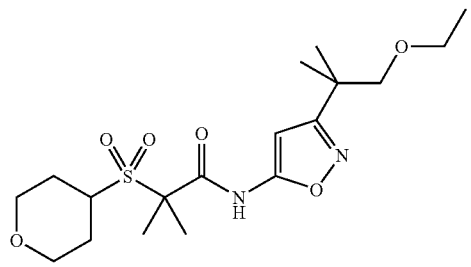 | (400 MHz, DMSO-d6) δ ppm 1.05 (3 H, t), 1.20 (6 H, s), 1.55-1.72 (2 H, m), 1.65 (6 H, s), 1.75-1.85 (2 H, m), 3.30 (2 H, s), 3.40 (2 H, q), 3.30-3.40 (2 H, m), 3.80-3.95 (3 H, m), 6.3 (1 H, s), 11.3 (1 H, s) | 403 | F | E | B |
| 69 | 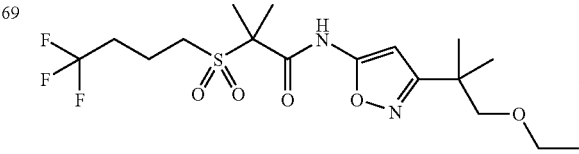 | (400 MHz, DMSO-d6) δ ppm 1.05 (3 H, t), 1.20 (6 H, s), 1.65 (6 H, s), 1.85-1.95 (2 H, m), 2.40-2.55 (2 H, m), 3.6 (2 H, s), 3.6 (2 H, q), 3.30-3.40 (2 H, m), 6.3 (1 H, s), 11.4 (1 H, s) | 429 | C | E | B |

TABLE XXXVIII-continued

Examples

| # | Structure | ¹H NMR | m/z [M + H] | Acid Method | Amine Method | Amide Method |
|---|---|---|---|---|---|---|
| 70 | 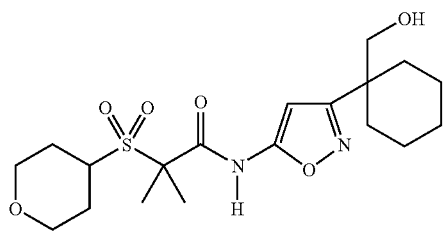 | (400 MHz, CHLOROFORM-d) δ ppm 1.40-1.68 (m, 8 H), 1.77 (s, 6 H), 1.86-2.05 (m, 6 H), 3.40 (td, 2 H), 3.44-3.50 (m, 1 H), 3.66 (s, 2 H), 4.07-4.09 (m, 2 H), 6.31 (s, 1 H), 9.69 (s, 1 H) | 415 | F | B | B2 |
| 71 | 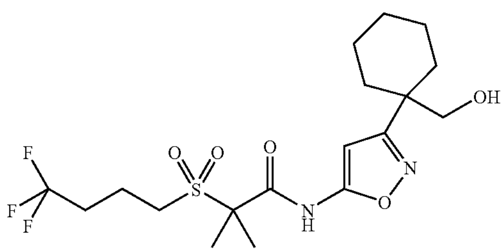 | (400 MHz, CHLOROFORM-d) δ ppm 1.40-1.68 (m, 8 H), 1.75 (s, 6 H), 1.99-2.03 (m, 2 H), 2.16-2.23 (m, 2 H), 2.27-2.39 (m, 2 H), 3.11 (t, 2 H), 3.63 (s, 2 H), 6.34 (s, 1 H), 9.31 (s, 1 H) | 441 | C | B | B2 |
| 72 | 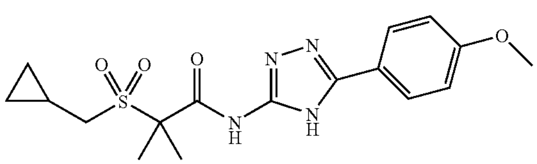 | (500 MHz, Acetone-d6) δ ppm 0.38-0.46 (2 H, m), 0.58-0.68 (2 H, m), 1.08-1.20 (1 H, m), 1.79 (6 H, s), 3.28 (2 H, d, J = 7.02 Hz), 3.84 (3 H, s), 7.00 (2 H, d, J = 8.85 Hz), 7.97 (2 H, d) | 379 | C | F | D |
| 73 | 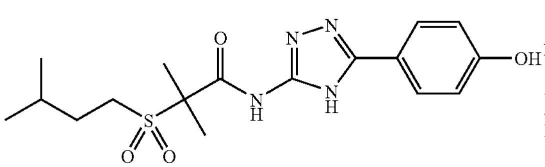 | (500 MHz, CHLOROFORM-d) δ ppm 0.93 (6 H, d, J = 6.48 Hz), 1.68-1.74 (1 H, m), 1.78 (8 H, m), 2.97-3.10 (2 H, m), 6.90 (2 H, d, J = 8.70 Hz), 7.93 (2 H, d, J = 8.62 Hz) | 381 | not applicable | not applicable | G |
| 74 | 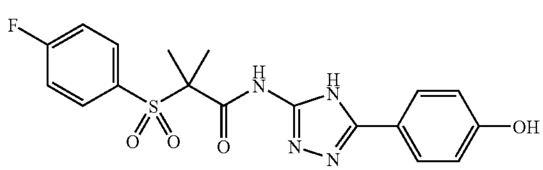 | 1H NMR (500 MHz, MeOD) δ ppm 1.70 (6 H, s), 6.87 (2 H, d, J = 8.54 Hz), 7.36 (2 H, t, J = 8.70 Hz), 7.83 (2 H, d, J = 8.54 Hz), 7.96 (2 H, dd, J = 8.54, 5.04 Hz) | 405 | not applicable | not applicable | G |
| 75 | 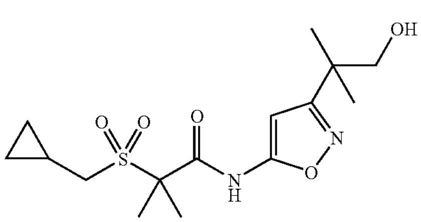 | (500 MHz, CHLOROFORM-d) δ ppm 0.38-0.46 (2 H, m), 0.63-0.74 (2 H, m), 1.05-1.16 (1 H, m), 1.31 (6 H, s), 1.74 (6 H, s), 2.28 (1 H, t, J = 6.87 Hz), 3.02 (2 H, d, J = 7.02 Hz), 3.69 (2 H, d, J = 6.71 Hz), 6.32 (1 H, s), 9.67 (1 H, br. s.) | 345 | C | B | B1 |
| 76 | 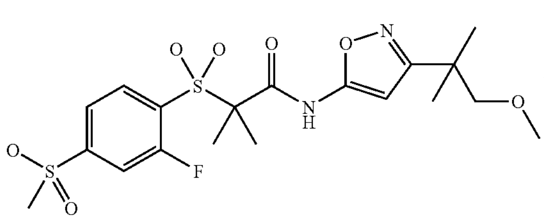 | (250 MHz, Acetone-d6) δ ppm 1.29 (6 H, s), 1.81 (6 H, s), 3.23-3.36 (6 H, m), 3.41 (2 H, s), 6.29 (1 H, s), 7.87-8.23 (3 H, m), 10.47 (1 H, br. s.) | 477 | H | E | F |

TABLE XXXVIII-continued

Examples

| # | Structure | ¹H NMR | m/z [M + H] | Acid Method | Amine Method | Amide Method |
|---|---|---|---|---|---|---|
| 77 | 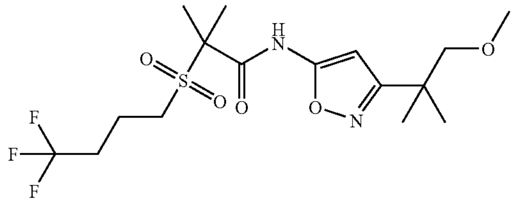 | (250 MHz, CHLOROFORM-d) δ ppm 1.33 (6 H, s), 1.76 (6 H, s), 2.11-2.43 (4 H, m), 3.05-3.17 (2 H, m), 3.35 (3 H, s), 3.42 (2 H, s), 6.34 (1 H, s), 9.27 (1 H, s) | 415 | C | E | K |
| 78 | 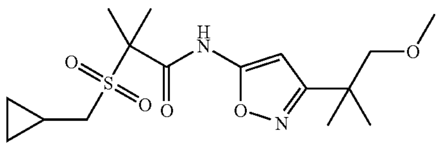 | (500 MHz, CHLOROFORM-d) δ ppm 0.40-0.47 (2 H, m), 0.68-0.75 (2 H, m), 1.08-1.18 (1 H, m), 1.34 (6 H, s), 1.75 (6 H, s), 3.03 (2 H, d, J = 7.32 Hz), 3.36 (3 H, s), 3.43 (2 H, s), 6.33 (1 H, s), 9.63 (1 H, s) | 359 | C | E | K |
| 79 | 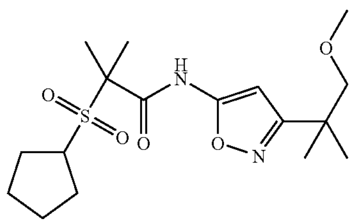 | (500 MHz, CHLOROFORM-d) δ ppm 1.33 (6 H, s), 1.61-1.68 (2 H, m), 1.73 (6 H, s), 1.76-1.86 (2 H, m), 1.95-2.12 (4 H, m), 3.35 (3 H, s), 3.43 (2 H, s), 3.54 (1 H, quin, J = 8.39 Hz), 6.32 (1 H, s), 9.56 (1 H, s) | 373 | A | E | K |
| 80 | 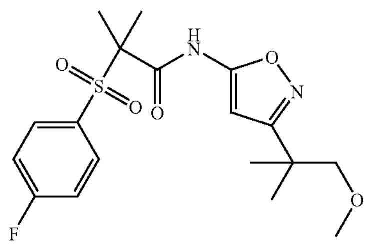 | (500 MHz, CHLOROFORM-d) δ ppm 1.33 (6 H, s), 1.67 (6 H, s), 3.35 (3 H, s), 3.42 (2 H, s), 6.27 (1 H, s), 7.21-7.31 (2 H, m), 7.80-7.93 (2 H, m), 9.58 (1 H, s) | 399 | A | E | K |
| 81 | 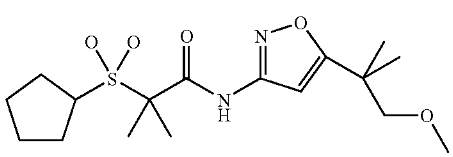 | (250 MHz, CHLOROFORM-d) δ ppm 1.33 (6 H, s), 1.55-1.68 (2 H, m), 1.71 (6 H, s), 1.74-1.87 (2 H, m), 1.88-2.15 (4 H, m), 3.32 (3 H, s), 3.44 (2 H, s), 3.47-3.64 (1 H, m), 6.65 (1 H, s), 9.25 (1 H, s) | 373 | A | D | K |
| 82 | 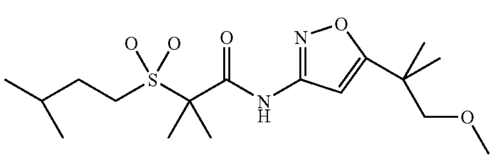 | (250 MHz, CHLOROFORM-d) δ ppm 0.93 (6 H, d), 1.33 (6 H, s), 1.61-1.87 (9 H, m), 2.98-3.14 (2 H, m), 3.32 (3 H, s), 3.44 (2 H, s), 6.69 (1 H, s), 9.35 (1 H, s) | 375 | C | D | K |
| 83 | 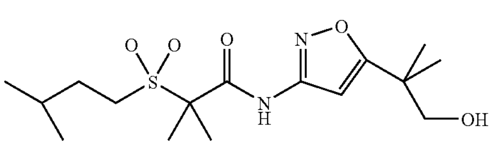 | (250 MHz, CHLOROFORM-d) δ ppm 0.92 (6 H, d), 1.34 (6 H, s), 1.60-1.87 (10 H, m), 2.92-3.12 (2 H, m), 3.68 (2 H, s), 6.72 (1 H, s), 9.27 (1 H, s) | 361 | not applicable | not applicable | P |
| 84 | 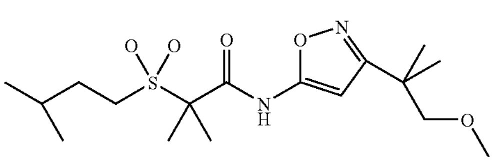 | (500 MHz, CHLOROFORM-d) δ ppm 0.94 (6 H, d), 1.33 (6 H, s), 1.64-1.81 (9 H, m), 2.85-3.06 (2 H, m), 3.35 (3 H, s), 3.42 (2 H, s), 6.34 (1 H, s), 9.44 (1 H, s) | 375 | C | E | K |

TABLE XXXVIII-continued
Examples
| # | Structure | ¹H NMR | m/z [M + H] | Acid Method | Amine Method | Amide Method |
|---|---|---|---|---|---|---|
| 85 | 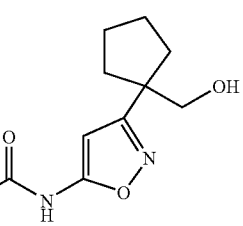 | (400 MHz, CHLOROFORM-d) δ ppm 1.70-1.76 (m, 11 H), 1.83-1.93 (m, 9 H), 2.21-2.72 (m, 2 H), 2.91-2.99 (m, 1 H), 3.09 (d, 2 H), 3.69 (s, 2 H), 6.30 (s, 1 H), 9.50 (s, 1 H) | 385 | C | B | B2 |
| 86 | 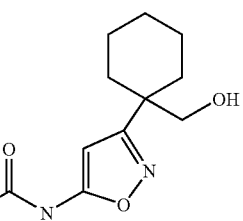 | (400 MHz, CHLOROFORM-d) δ ppm 1.43-1.65 (m, 7 H), 1.71 (s, 6 H), 1.84-2.04 (m, 7 H), 2.23-2.29 (m, 2 H), 2.93-3.00 (m, 1 H), 3.12 (d, 2 H), 3.64 (d, 2 H), 6.34 (s, 1 H), 9.52 (s, 1 H) | 399 | C | B | B2 |
| 87 | 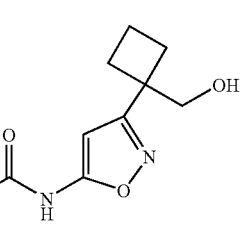 | (400 MHz, CHLOROFORM-d) δ ppm 1.71 (s, 6 H), 1.86-1.95 (m, 3 H), 1.96-2.28 (m, 8 H), 2.33-2.40 (m, 2 H), 2.91-2.99 (m, 1 H), 3.09 (d, 2 H), 3.93 (s, 2 H), 6.40 (s, 1 H), 9.52 (s, 1 H) | 371 | C | B | B2 |
| 88 | 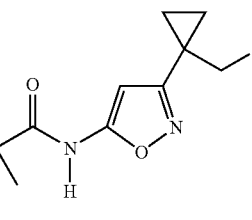 | (400 MHz, CHLOROFORM-d) δ ppm 0.93 (d, 6 H), 1.04-1.05 (m, 4 H), 1.60-1.70 (m, 9 H), 2.96-3.00 (m, 2 H), 3.80 (s, 2 H), 6.07 (s, 1 H), 9.46 (s, 1 H) | 359 | C | B | B2 |
| 89 | Chiral 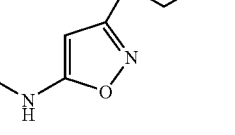 | (400 MHz, CHLOROFORM-d) δ ppm 1.02 (t, 3 H), 1.32 (d, 3 H), 1.55-1.65 (m, 3 H), 1.71-1.77 (m, 8 H), 1.82-1.92 (m, 4 H), 1.94-2.04 (m, 1 H), 2.34 (bs, 1 H), 3.16-3.25 (m, 1 H), 3.68 (bs, 2 H), 6.26 (s, 1 H), 9.79 (s, 1 H) | 373 | F | B | B2 |

TABLE XXXVIII-continued

Examples

| # | Structure | ¹H NMR | m/z [M + H] | Acid Method | Amine Method | Amide Method |
|---|---|---|---|---|---|---|
| 90 | 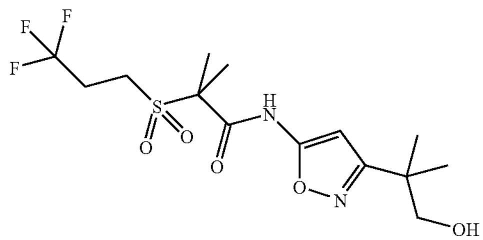 | (400 MHz, CHLOROFORM-d) δ ppm 1.24 (6 H, s), 1.72 (6 H, s), 2.42 (2 H, bs), 2.54-2.7 (2 H, m), 3.17-3.23 (2 H, m), 3.62 (2 H, s), 6.29 (1 H, s), 9.18 (1 H, s) | 387 | E | B | B2 |
| 91 | 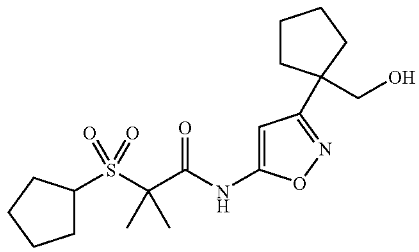 | (400 MHz, CHLOROFORM-d) δ ppm 1.60-1.67 (m, 2 H), 1.72-1.93 (m, 17 H), 1.97-2.07 (m, 4 H), 2.34 (bs, 1 H), 3.53 (m, 1 H), 3.68 (s, 2 H), 6.28 (s, 1 H), 9.59 (s, 1 H) | 385 | A | B | B2 |
| 92 | Chiral | (400 MHz, CHLOROFORM-d) δ ppm 1.72-1.75 (m, 10 H), 1.80-1.90 (m, 4 H), 2.22-2.30 (m, 1 H), 2.83-3.00 (m, 3 H), 3.08 (d, 2 H), 3.55 (dd, 1 H), 3.67-3.77 (m, 3 H), 3.87 (td, 1 H), 3.97 (dd, 1 H), 6.29 (s, 1 H), 9.42 (s, 1 H). | 401 | F | B | B2 |
| 93 | 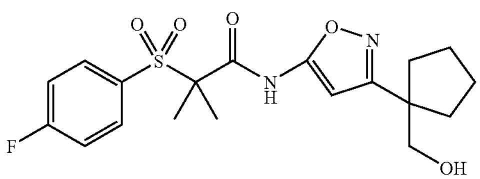 | (400 MHz, CHLOROFORM-d) δ ppm 1.64 (s, 6 H), 1.70-1.74 (m, 4 H), 1.85-1.90 (m, 4 H), 3.68 (s, 2 H), 6.22 (s, 1 H), 7.22-7.26 (m, 2 H), 7.81-7.85 (m, 2 H) 9.59 (s, 1 H) | 411 | A | B | B2 |
| 94 | 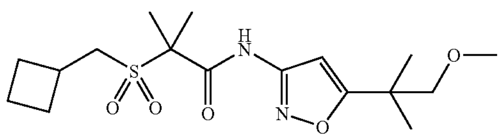 | (500 MHz, CHLOROFORM-d) δ ppm 1.35 (6 H, s), 1.71 (6 H, s), 1.84-1.95 (3 H, m), 1.95-2.07 (1 H, m), 2.20-2.31 (2 H, m), 2.98 (1 H, spt, J = 7.78 Hz), 3.13 (2 H, d, J = 7.32 Hz), 3.34 (3 H, s), 3.46 (2 H, s), 6.69 (1 H, s), 9.15 (1 H, s) | 373 | C | D | K |
| 95 | 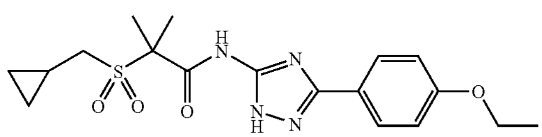 | (500 MHz, CHLOROFORM-d) δ ppm 0.26-0.53 (2 H, m), 0.57-0.82 (2 H, m), 1.04-1.27 (1 H, m), 1.45 (3 H, t, J = 7.02 Hz), 1.72 (6 H, s), 3.06 (2 H, d, J = 7.02 Hz), 4.09 (2 H, q, J = 7.02 Hz), 6.76-7.06 (2 H, m), 7.79-8.22 (2 H, m), 9.89 (1 H, br. s.), 11.55 (1 H, br. s.) | 393 | C | F | I |
| 96 | 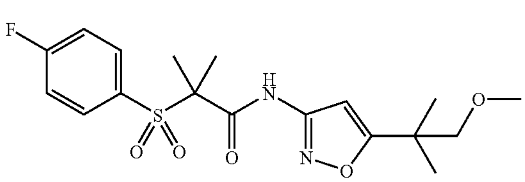 | (250 MHz, CHLOROFORM-d) δ ppm 1.32 (6 H, s), 1.66 (6 H, s), 3.31 (3 H, s), 3.43 (2 H, s), 6.59 (1 H, s), 7.12-7.28 (2 H, m), 7.77-7.94 (2 H, m), 9.44 (1 H, s) | 399 | A | D | K |

TABLE XXXVIII-continued

Examples

| # | Structure | ¹H NMR | m/z [M + H] | Acid Method | Amine Method | Amide Method |
|---|---|---|---|---|---|---|
| 97 | 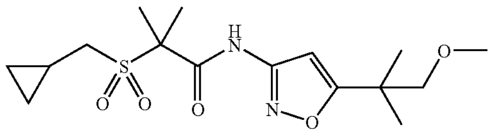 | (250 MHz, CHLOROFORM-d) δ ppm 0.25-0.49 (2 H, m), 0.59-0.76 (2 H, m), 1.00-1.21 (1 H, m), 1.30 (6 H, s), 1.71 (6 H, s), 3.02 (2 H, d, J = 7.31 Hz), 3.29 (3 H, s), 3.41 (2 H, s), 6.65 (1 H, s), 9.39 (1 H, s) | 359 | C | D | K |
| 98 | 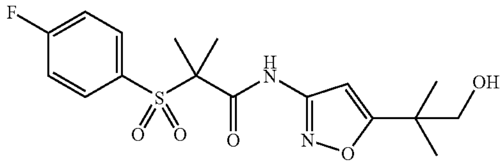 | (250 MHz, CHLOROFORM-d) δ ppm 1.34 (6 H, s), 1.66 (6 H, s), 3.69 (2 H, s), 6.63 (1 H, s), 7.17-7.29 (2 H, m), 7.79-7.94 (2 H, m), 9.34 (1 H, s) | 385 | not applicable | not applicable | P |
| 99 | 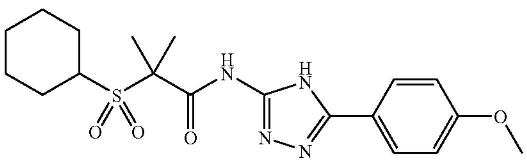 | (250 MHz, CHLOROFORM-d) δ ppm 1.12-1.39 (3 H, m), 1.47-1.73 (3 H, m), 1.77 (6 H, s), 1.82-1.96 (2 H, m), 1.97-2.13 (2 H, m), 3.10-3.38 (1 H, m), 3.87 (3 H, s), 6.82-7.10 (2 H, m), 7.86-8.12 (2 H, m), 10.10 (1 H, br. s.) | 407 | A | F | I |
| 100 | 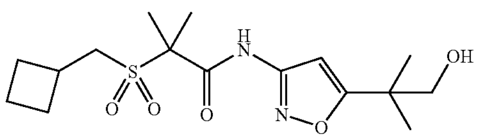 | (500 MHz, CHLOROFORM-d) δ ppm 1.36 (6 H, s), 1.71 (6 H, s), 1.83-1.95 (3 H, m), 1.94-2.07 (1 H, m), 2.20-2.31 (2 H, m), 2.91-3.04 (1 H, m), 3.13 (2 H, d, J = 7.48 Hz), 3.70 (2 H, s), 6.73 (1 H, s), 9.19 (1 H, s) | 359 | not applicable | not applicable | P |
| 101 | 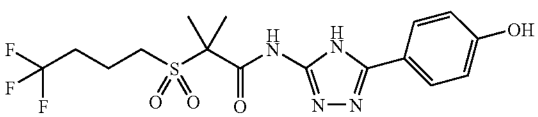 | (500 MHz, MeOD) δ ppm 1.72 (6 H, s), 1.88-2.26 (2 H, m), 2.26-2.58 (2 H, m), 3.38-3.48 (2 H, m), 6.87 (2 H, d, J = 8.54 Hz), 7.82 (2 H, d, J = 8.54 Hz) | 421 | not applicable | not applicable | P |
| 102 | 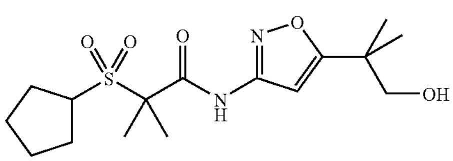 | (250 MHz, CHLOROFORM-d) δ ppm 1.33 (6 H, s), 1.50-1.68 (2 H, m), 1.71 (6 H, s), 1.74-1.84 (2 H, m), 1.88-2.11 (4 H, m), 3.58 (1 H, quin), 3.67 (2 H, d, J = 5.48 Hz), 6.69 (1 H, s), 9.38 (1 H, s) | 359 | not applicable | not applicable | P |
| 103 | 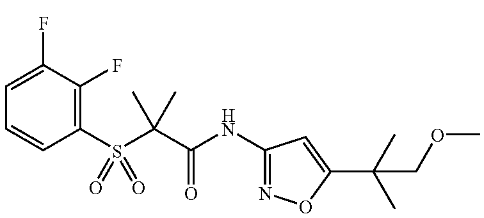 | (500 MHz, CHLOROFORM-d) δ ppm 1.34 (6 H, s), 1.73 (6 H, s), 3.33 (3 H, s), 3.45 (2 H, s), 6.61 (1 H, s), 7.24-7.36 (11 H, m), 7.49-7.58 (1 H, m), 7.59-7.67 (1 H, m), 9.08 (1 H, s) | 417 | H | D | F |
| 104 | 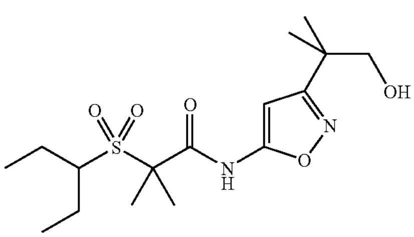 | (500 MHz, CHLOROFORM-d) δ ppm 1.04 (6 H, t, J = 7.48 Hz), 1.31 (6 H, s), 1.73 (6 H, s), 1.77-1.94 (4 H, m), 2.23-2.33 (1 H, m), 3.05-3.14 (1 H, m), 3.69 (2 H, d, J = 6.26 Hz), 6.31 (1 H, s), 9.76 (1 H, br. s.) | 361 | C | B | B1 |

TABLE XXXVIII-continued

| # | Structure | ¹H NMR | m/z [M + H] | Acid Method | Amine Method | Amide Method |
|---|---|---|---|---|---|---|
| 105 | 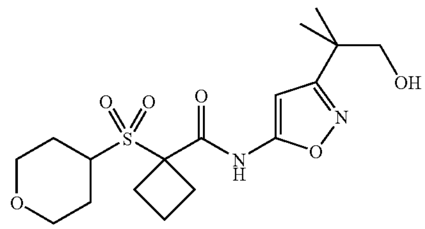 | (500 MHz, CHLOROFORM-d) δ ppm 1.32 (6 H, s), 1.82-1.90 (2 H, m), 1.90-2.03 (2 H, m), 2.10-2.23 (2 H, m), 2.25 (1 H, t, J = 6.87 Hz), 2.69-2.80 (2 H, m), 2.96-3.09 (2 H, m), 3.17 (1 H, tt, J = 11.83, 4.04 Hz), 3.37 (2 H, td, J = 11.86, 2.06 Hz), 3.71 (2 H, d, J = 6.87 Hz), 4.06 (2 H, dd, J = 11.37, 4.04 Hz), 6.38 (1 H, s), 9.25 (1 H, s) | 387 | F | B | B1 |
| 106 | 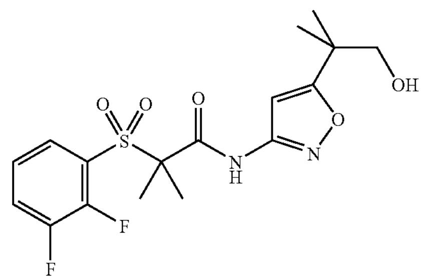 | (500 MHz, CHLOROFORM-d) δ ppm 1.37 (6 H, s), 1.73 (6 H, s), 3.70 (2 H, d, J = 6.41 Hz), 6.66 (1 H, s), 7.28-7.35 (1 H, m), 7.49-7.59 (1 H, m), 7.63 (1 H, dd, J = 7.71, 5.87 Hz), 9.12 (1 H, s) | 403 | not applicable | not applicable | P |
| 107 | 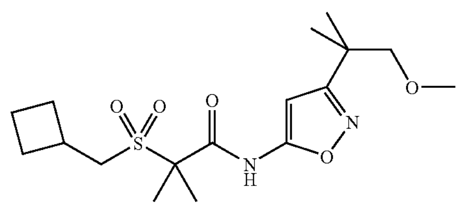 | (500 MHz, CHLOROFORM-d) δ ppm 1.34 (6 H, s), 1.72 (6 H, s), 1.82-2.09 (4 H, m), 2.20-2.32 (2 H, m), 2.89-3.05 (1 H, m), 3.11 (2 H, d, J = 7.32 Hz), 3.36 (3 H, s), 3.43 (2 H, s), 6.34 (1 H, s), 9.47 (1 H, s) | 373 | C | E | K |
| 108 | 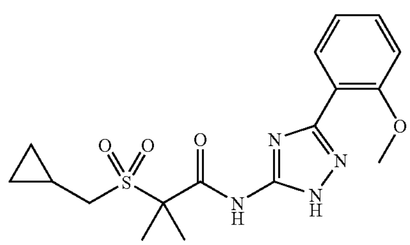 | (500 MHz, CHLOROFORM-d) δ ppm 0.36-0.50 (2 H, m), 0.63-0.76 (2 H, m), 1.20-1.28 (1 H, m), 1.78 (6 H, s), 3.13 (2 H, d, J = 7.02 Hz), 3.99 (3 H, s), 7.00 (1 H, d, J = 8.54 Hz), 7.07 (1 H, t, J = 7.48 Hz), 7.41 (1 H, ddd, J = 8.47, 7.25, 1.68 Hz), 8.16-8.32 (1 H, m), 10.18 (1 H, br. s.), 12.11 (1 H, br. s.) | 379 | C | commercial | I |
| 109 | 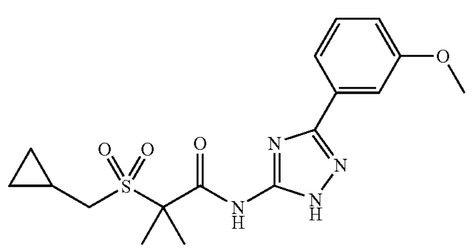 | (500 MHz, Acetone-d6) δ ppm 0.35-0.51 (2 H, m), 0.55-0.72 (2 H, m), 1.05-1.21 (1 H, m), 1.81 (6 H, s), 3.28 (2 H, d, J = 7.32 Hz), 3.85 (3 H, s), 6.97 (1 H, dd, J = 8.24, 2.75 Hz), 7.35 (1 H, t, J = 7.93 Hz), 7.59 (1 H, d, J = 2.44 Hz), 7.63 (1 H, d, J = 7.63 Hz), 10.36 (1 H, br. s.) | 379 | C | F | I |
| 110 | 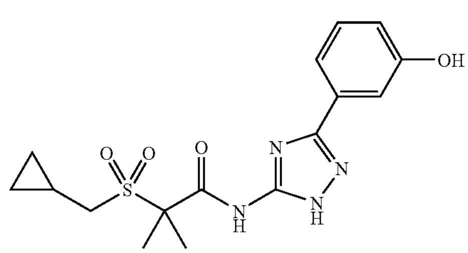 | (500 MHz, MeOD) δ ppm 0.32-0.46 (2 H, m), 0.53-0.67 (2 H, m), 1.02-1.15 (1 H, m), 1.65 (6 H, s), 3.23 (2 H, d, J = 7.32 Hz), 6.80 (1 H, dd, J = 7.78, 1.98 Hz), 7.20 (1 H, t, J = 7.93 Hz), 7.32-7.43 (2 H, m) | 365 | not applicable | not applicable | G |

TABLE XXXVIII-continued

Examples

| # | Structure | ¹H NMR | m/z [M + H] | Acid Method | Amine Method | Amide Method |
|---|---|---|---|---|---|---|
| 111 | 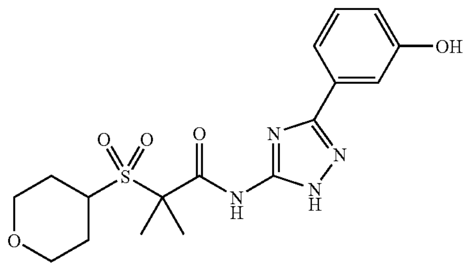 | (500 MHz, MeOD) δ ppm 1.80 (6 H, s), 1.82-1.94 (2 H, m), 1.93-2.00 (2 H, m), 3.47 (2 H, td, J = 11.83, 1.98 Hz), 3.85-3.94 (1 H, m), 3.96-4.03 (2 H, m), 6.99 (1 H, dd, J = 8.24, 2.44 Hz), 7.33-7.39 (1 H, m), 7.39-7.46 (2 H, m) | 395 | not applicable | not applicable | G |
| 112 | 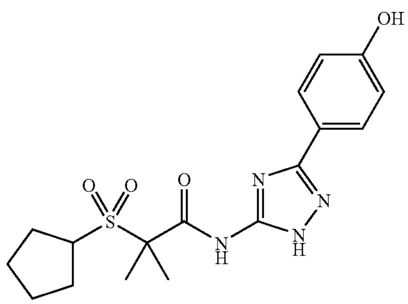 | (500 MHz, MeOD) δ ppm 1.57-1.69 (2 H, m), 1.70-1.82 (8 H, m), 2.00-2.12 (4 H, m), 3.93 (1 H, quin, J = 8.24 Hz), 6.73-7.00 (2 H, m), 7.82 (2 H, d, J = 8.67 Hz) | 379 | not applicable | not applicable | G |
| 113 | 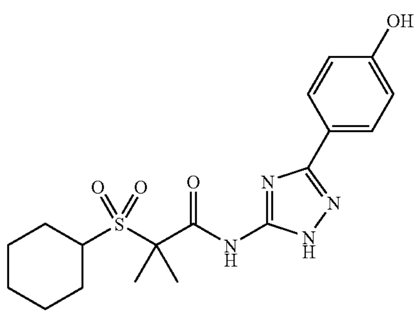 | (500 MHz, CHLOROFORM-d) δ ppm 1.11-1.37 (3 H, m), 1.51-1.64 (2 H, m), 1.65-1.72 (1 H, m), 1.76 (6 H, s), 1.88 (2 H, d, J = 13.08 Hz), 1.98-2.13 (2 H, m), 3.07-3.45 (1 H, m), 6.90 (2 H, d, J = 8.35 Hz), 7.94 (2 H, d, J = 8.51 Hz), 10.25 (1 H, br. s.) | 393 | not applicable | not applicable | G |
| 114 | 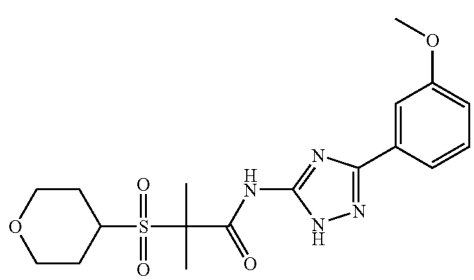 | (500 MHz, CHLOROFORM-d) δ ppm 1.80 (6 H, s), 1.89 (2 H, dd, J = 12.51, 1.83 Hz), 1.94-2.09 (2 H, m), 3.40 (2 H, td, J = 11.90, 1.83 Hz), 3.45-3.57 (1 H, m), 3.89 (3 H, s), 4.07 (2 H, dd, J = 11.60, 3.66 Hz), 6.99 (1 H, dd, J = 8.24, 2.44 Hz), 7.37 (1 H, t, J = 7.93 Hz), 7.61 (1 H, d, J = 1.53 Hz), 7.66 (1 H, d, J = 7.63 Hz), 9.97 (1 H, br. s.) | 409 | F | F | I |
| 115 | 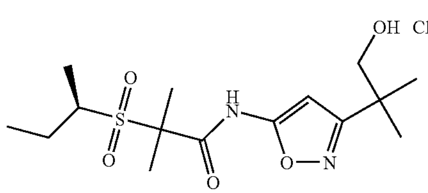 | (500 MHz, CHLOROFORM-d) δ ppm 1.04 (3 H, t, J = 7.48 Hz), 1.26-1.37 (9 H, m), 1.46-1.70 (1 H, m), 1.73 (3 H, s), 1.74 (3 H, s), 1.95-2.08 (1 H, m), 2.29 (1 H, br. s.), 3.17-3.28 (1 H, m), 3.69 (2 H, s), 6.30 (1 H, s), 9.82 (1 H, s) | 347 | F | B | B1 |

TABLE XXXVIII-continued

Examples

| # | Structure | ¹H NMR | m/z [M + H] | Acid Method | Amine Method | Amide Method |
|---|---|---|---|---|---|---|
| 116 | 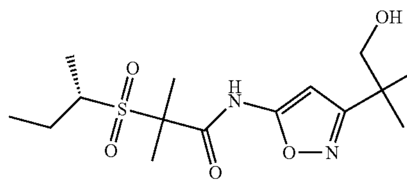 | (500 MHz, CHLOROFORM-d) δ ppm 1.04 (3 H, t, J = 7.48 Hz), 1.27-1.39 (9 H, m), 1.50-1.70 (1 H, m), 1.73 (3 H, s), 1.74 (3 H, s), 1.95-2.07 (1 H, m), 2.29 (1 H, br. s.), 3.16-3.30 (1 H, m), 3.69 (2 H, s), 6.30 (1 H, s), 9.82 (1 H, s) | 347 | F | B | B1 |
| 117 | 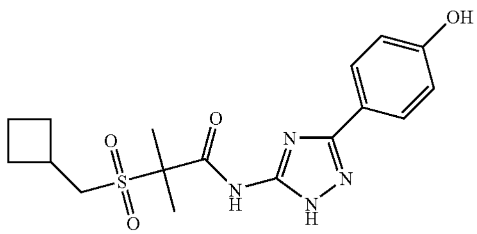 | (500 MHz, MeOD) δ ppm 1.73 (6 H, s), 1.82-2.06 (4 H, m), 2.10-2.31 (2 H, m), 2.83-3.03 (1 H, m), 3.39 (2 H, d, J = 7.32 Hz), 6.86 (2 H, d, J = 6.41 Hz), 7.82 (2 H, d, J = 7.63 Hz) | 379 | not applicable | not applicable | G |
| 118 | 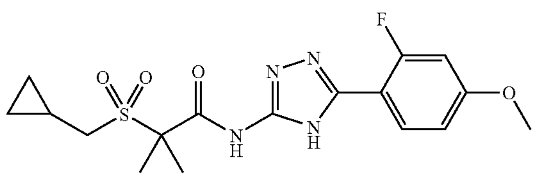 | (500 MHz, CHLOROFORM-d) δ ppm 0.37-0.47 (2 H, m), 0.63-0.75 (2 H, m), 1.07-1.22 (1 H, m), 1.79 (6 H, s), 3.08 (2 H, d, J = 7.25 Hz), 3.86 (3 H, s), 6.74 (1 H, dd, J = 13.08, 2.36 Hz), 6.81 (1 H, dd, J = 8.67, 2.36 Hz), 7.99 (1 H, t, J = 8.67 Hz), 10.02 (1 H, br. s.), 11.03 (1 H, s) | 397 | C | F | I |
| 119 | 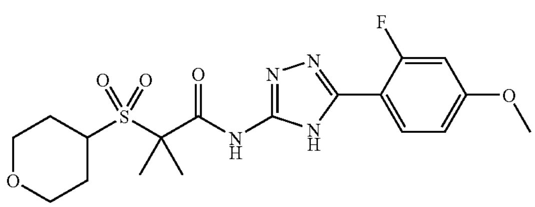 | (500 MHz, CHLOROFORM-d) δ ppm 1.72 (6 H, s), 1.80-1.88 (2 H, m), 1.89-2.02 (2 H, m), 3.32 (2 H, td, J = 11.78, 1.81 Hz), 3.41-3.55 (1 H, m), 3.80 (3 H, s), 3.98 (2 H, dd, J = 11.66, 3.47 Hz), 6.66 (1 H, dd, J = 13.16, 2.29 Hz), 6.75 (1 H, dd, J = 8.83, 2.21 Hz), 7.93 (1 H, t, J = 8.67 Hz), 9.81 (1 H, br. s.) | 427 | F | F | I |
| 120 | 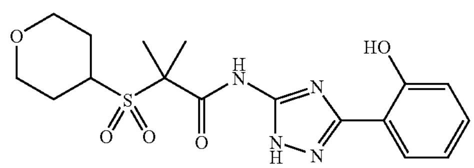 | (500 MHz, CHLOROFORM-d) δ ppm 1.81 (6 H, s), 1.84-1.95 (2 H, m), 1.95-2.12 (2 H, m), 3.40 (2 H, td, J = 11.90, 1.98 Hz), 3.46-3.61 (1 H, m), 4.08 (2 H, d, J = 7.78 Hz), 6.90-7.02 (1 H, m), 7.05 (1 H, d, J = 7.63 Hz), 7.30-7.40 (1 H, m), 8.01 (1 H, dd, J = 7.78, 1.37 Hz), 10.02 (2 H, br. s.) | 395 | not applicable | not applicable | G |
| 121 | 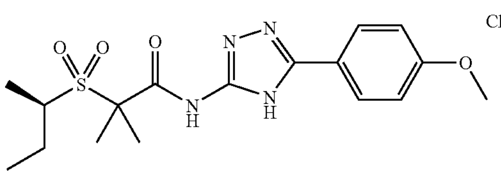 | Chiral (500 MHz, CHLOROFORM-d) δ ppm 1.04 (3 H, t, J = 7.48 Hz), 1.35 (3 H, d, J = 6.87 Hz), 1.51-1.69 (1 H, m), 1.77 (3 H, s), 1.78 (3 H, s), 1.97-2.08 (1 H, m), 3.21-3.31 (1 H, m), 3.87 (3 H, s), 6.98 (2 H, d, J = 8.85 Hz), 8.00 (2 H, d, J = 8.70 Hz), 10.03 (1 H, br. s.), 11.58 (1 H, br. s.) | 381 | F | F | J |
| 122 | 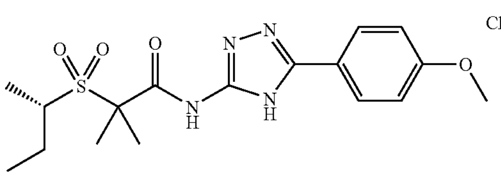 | Chiral (500 MHz, CHLOROFORM-d) δ ppm 1.04 (3 H, t, J = 7.40 Hz), 1.35 (3 H, d, J = 6.87 Hz), 1.60-1.70 (1 H, m), 1.77 (3 H, s), 1.78 (3 H, s), 2.02 (1 H, ddd, J = 13.81, 7.40, 3.66 Hz), 3.21-3.30 (1 H, m), 3.87 (3 H, s), 6.98 (2 H, d, J = 8.85 Hz), 8.00 (2 H, d, J = 8.85 Hz), 10.02 (1 H, br. s.), 11.54 (1 H, br. s.) | 381 | F | F | J |

TABLE XXXVIII-continued

Examples

| # | Structure | ¹H NMR | m/z [M + H] | Acid Method | Amine Method | Amide Method |
|---|---|---|---|---|---|---|
| 123 | 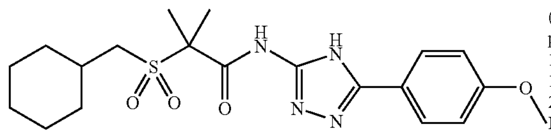 | (500 MHz, CHLOROFORM-d) δ ppm 1.01-1.21 (3 H, m), 1.24-1.39 (2 H, m), 1.60-1.83 (9 H, m), 1.96 (2 H, d, J = 13.87 Hz), 2.09-2.26 (1 H, m), 2.90 (2 H, d, J = 6.31 Hz), 3.87 (3 H, s), 6.80-7.06 (2 H, m), 7.99 (2 H, d, J = 8.83 Hz), 9.72 (1 H, br. s.), 11.56 (1 H, br. s.) | 421 | C | F | I |
| 124 | 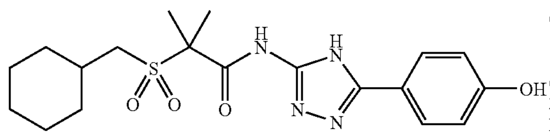 | (500 MHz, MeOD) δ ppm 1.10-1.28 (3 H, m), 1.29-1.41 (2 H, m), 1.62-1.70 (1 H, m), 1.70-1.81 (8 H, m), 1.88-2.03 (2 H, m), 2.03-2.20 (1 H, m), 3.17 (2 H, d, J = 6.31 Hz), 6.89 (2 H, d, J = 8.20 Hz), 7.84 (2 H, d, J = 8.20 Hz) | 407 | not applicable | not applicable | G |
| 125 | 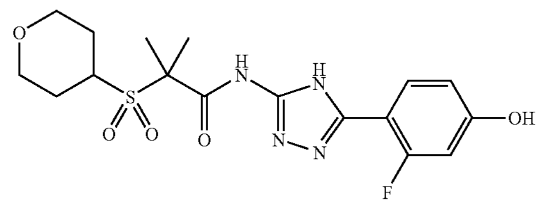 | (500 MHz, MeOD) δ ppm 1.69 (6 H, s), 1.73-1.84 (2 H, m), 1.84-1.91 (2 H, m), 3.37 (2 H, td, J = 11.74, 2.05 Hz), 3.80 (1 H, tt, J = 11.76, 4.24 Hz), 3.90 (2 H, dd, J = 11.11, 3.39 Hz), 6.62 (1 H, dd, J = 12.93, 2.21 Hz), 6.69 (1 H, dd, J = 8.67, 2.21 Hz), 7.73 (1 H, t, J = 8.67 Hz) | 413 | not applicable | not applicable | G |
| 126 | 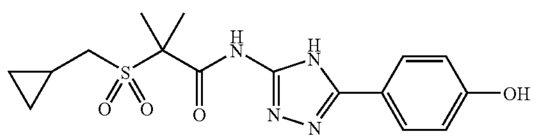 | (500 MHz, MeOD) δ ppm 0.40-0.51 (2 H, m), 0.63-0.74 (2 H, m), 1.11-1.24 (1 H, m), 1.78 (6 H, s), 3.28 (2 H, d, J = 7.25 Hz), 6.88 (2 H, d, J = 8.20 Hz), 7.84 (2 H, d, J = 8.51 Hz) | 365 | not applicable | not applicable | G |
| 127 | 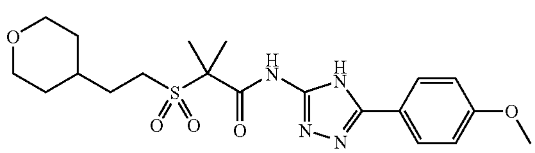 | (500 MHz, CHLOROFORM-d) δ ppm 1.20-1.39 (2 H, m), 1.50-1.72 (3 H, m), 1.79 (6 H, s), 1.82-1.90 (2 H, m), 2.93-3.23 (2 H, m), 3.34 (2 H, td, J = 11.79, 1.60 Hz), 3.87 (3 H, s), 3.94 (2 H, dd, J = 11.29, 3.97 Hz), 6.97 (2 H, d, J = 8.85 Hz), 7.97 (2 H, d, J = 8.70 Hz), 9.84 (1 H, br. s.), 11.59 (1 H, br. s.) | 437 | E | F | I |
| 128 | 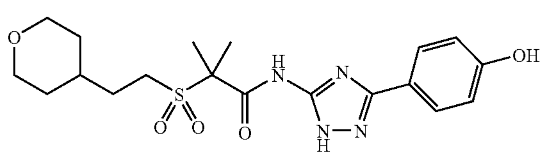 | (500 MHz, MeOD) δ ppm 1.20-1.36 (2 H, m), 1.61-1.69 (2 H, m), 1.70 (1 H, br. s.), 1.77 (6 H, s), 1.78-1.84 (2 H, m), 3.32-3.35 (2 H, m), 3.38 (2 H, td, J = 11.83, 1.68 Hz), 3.91 (2 H, dd, J = 11.22, 4.20 Hz), 6.87 (2 H, d, J = 8.70 Hz), 7.82 (2 H, d, J = 8.70 Hz) | 423 | not applicable | not applicable | G |
| 129 | 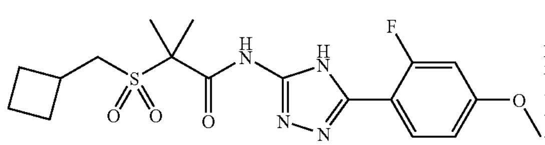 | (500 MHz, CHLOROFORM-d) δ ppm 1.76 (6 H, s), 1.82-1.95 (3 H, m), 1.95-2.05 (1 H, m), 2.16-2.33 (2 H, m), 2.98 (1 H, dt, J = 15.53, 7.68 Hz), 3.18 (2 H, d, J = 7.41 Hz), 3.87 (3 H, s), 6.74 (1 H, dd, J = 13.08, 2.36 Hz), 6.81 (1 H, dd, J = 8.75, 2.29 Hz), 7.99 (1 H, t, J = 8.67 Hz), 9.64 (1 H, br. s.), 11.48 (1 H, br. s.) | 411 | C | F | I |
| 130 | 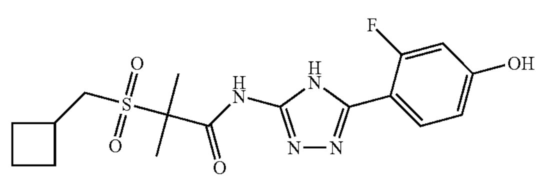 | (500 MHz, MeOD) δ ppm 1.76 (6 H, s), 1.83-2.10 (4 H, m), 2.16-2.33 (2 H, m), 2.87-3.09 (1 H, m), 3.41 (2 H, d, J = 7.41 Hz), 4.61 (1 H, s), 6.67 (1 H, d, J = 13.40 Hz), 6.75 (1 H, d, J = 8.67 Hz), 7.85 (1 H, t, J = 8.43 Hz) | 397 | not applicable | not applicable | G |

TABLE XXXVIII-continued

Examples

| # | Structure | ¹H NMR | m/z [M + H] | Acid Method | Amine Method | Amide Method |
|---|-----------|--------|-------------|-------------|--------------|--------------|
| 131 | 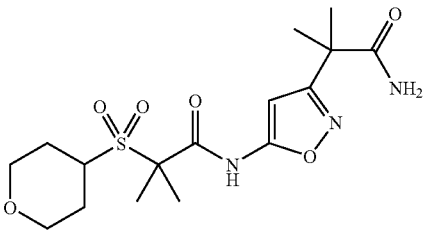 | (400 MHz, MeOD) δ ppm 1.55 (6 H, s), 1.7 (6 H, s), 1.75-1.95 (4 H, m), 3.38-3.48 (2 H, m), 3.77-3.87 (1 H, m), 3.90-4.00 (2 H, m), 6.4 (1 H, s) | 388 | not applicable | not applicable | N |
| 132 | 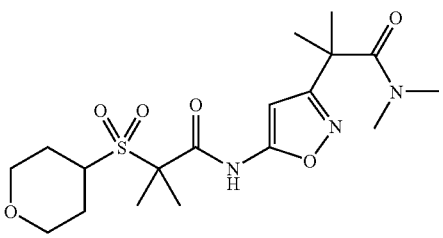 | (400 MHz, MeOD) δ ppm 1.55 (6 H, s), 1.7 (6 H, s), 1.78-1.94 (4 H, m), 2.75 (3 H, s), 2.9 (3 H, s), 3.40-3.50 (2 H, m), 3.80-3.90 (1 H, m), 3.92-4.02 (2 H, m), 6.25 (1 H, s) | 416 | not applicable | not applicable | O |
| 133 | 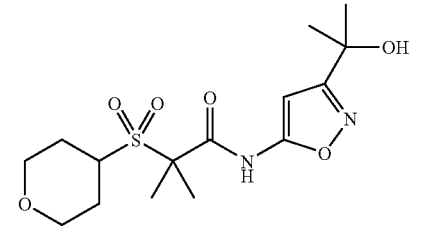 | (400 MHz, DMSO-d6) δ ppm 1.4 (6 H, s), 1.55-1.70 (2 H, m), 1.66 (6 H, s), 1.75-1.85 (2 H, m), 3.30-3.40 (2 H, m), 3.80-3.90 (3 H, m), 5.4 (1 H, s), 6.35 (1 H, s), 11.3 (1 H, s) | 361 | F | B | B2 |
| 134 | 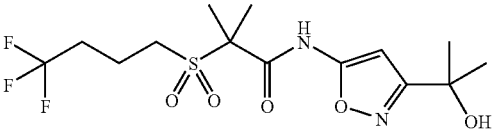 | (400 MHz, CHLOROFORM-d) δ ppm 1.6 (6 H, s), 1.75 (6 H, s), 2.1-2.23 (2 H, m), 2.25 (1 H, s), 2.25-2.40 (2 H, m), 3.1 (2 H, t), 6.4 (1 H, s), 9.3 (1 H, s) | 387 | C | B | B2 |
| 135 | 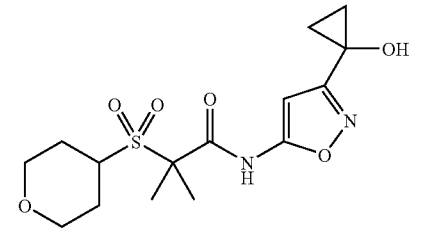 | (400 MHz, DMSO-d6) δ ppm 0.95-1.02 (2 H, m), 1.02-1.08 (2 H, m), 1.55-1.70 (2 H, m), 1.66 (6 H, s), 1.75-1.84 (2 H, m), 3.3-3.4 (2 H, m), 3.8-3.9 (3 H, m), 6.3 (1 H, s), 6.4 (1 H, s), 11.4 (1 H, s). | 359 | F | B | B2 |
| 136 | 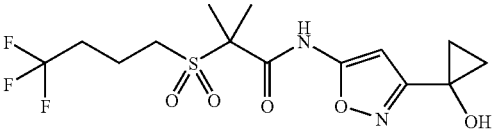 | (400 MHz, DMSO-d6) δ ppm 0.96-1.02 (2 H, m), 1.05-1.12 (2 H, m), 1.65 (6 H, s), 1.87-1.97 (2 H, m), 2.4-2.55 (2 H, m), 3.3-3.4 (2 H, m), 6.3 (1 H, s), 6.35 (1 H, s), 11.4 (1 H, s). | 385 | C | B | B2 |
| 137 | 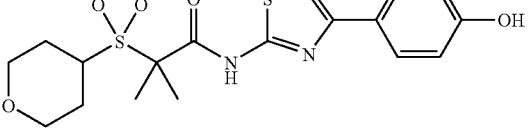 | (500 MHz, CHLOROFORM-d) δ ppm 1.80 (6 H, s), 1.84-1.91 (2 H, m), 1.91-2.05 (2 H, m), 3.38 (2 H, td, J = 11.90, 2.14 Hz), 3.45-3.57 (1 H, m), 4.04 (2 H, dd, J = 11.44, 3.81 Hz), 5.25 (1 H, br. s.), 6.89 (2 H, d, J = 8.54 Hz), 7.05 (1 H, s), 7.67-7.80 (2 H, m), 10.15 (1 H, br. s.) | 411 | not applicable | not applicable | G |

TABLE XXXVIII-continued

Examples

| # | Structure | ¹H NMR | m/z [M + H] | Acid Method | Amine Method | Amide Method |
|---|-----------|--------|-------------|-------------|--------------|--------------|
| 138 | 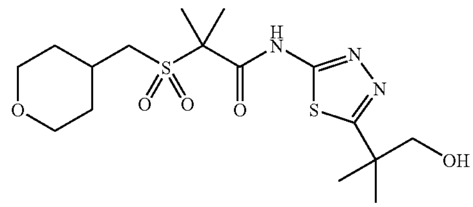 | (500 MHz, CHLOROFORM-d) δ ppm 1.42-1.55 (8 H, m), 1.80 (6 H, s), 1.83-1.89 (2 H, m), 2.33-2.47 (1 H, m), 2.96 (2 H, d, J = 6.56 Hz), 3.43 (2 H, td, J = 11.71, 1.30 Hz), 3.80 (2 H, s), 3.95 (2 H, dd, J = 11.06, 3.89 Hz) | 406 | B | G | Q |
| 139 | 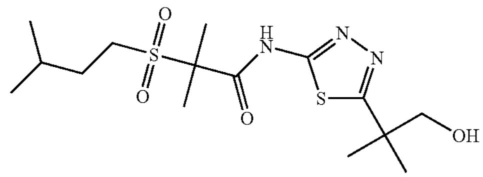 | (500 MHz, CHLOROFORM-d) δ ppm 0.94 (6 H, d, J = 6.41 Hz), 1.47 (6 H, s), 1.63-1.73 (1 H, m), 1.73-1.80 (2 H, m), 1.81 (6 H, s), 2.99-3.09 (2 H, m), 3.81 (2 H, s) | 378 | C | G | Q |
| 140 | 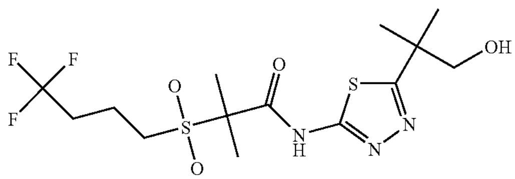 | (500 MHz, CHLOROFORM-d) δ ppm 1.47 (6 H, s), 1.85 (6 H, s), 2.16-2.24 (2 H, m), 2.27-2.42 (2 H, m), 3.19 (2 H, t, J = 7.63 Hz), 3.80 (2 H, s) | 418 | C | G | Q |
| 141 | 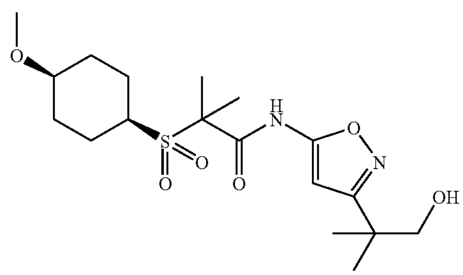 | (400 MHz, CHLOROFORM-d) δ ppm 1.32 (6 H, s), 1.36-1.46 (2 H, m), 1.74 (6 H, s), 1.77-1.85 (2 H, m), 1.91-2.05 (2 H, m), 2.01-2.2 (2 H, m), 3.19-3.27 (1 H, m), 3.31 (3 H, s), 3.44-3.48 (1 H, m), 3.71 (2 H, s), 6.31 (1 H, s), 9.87 (1 H, s) | 403 | E | B | B2 |
| 142 | 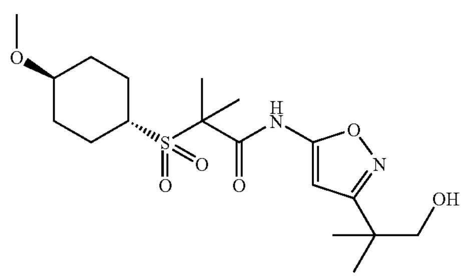 | (400 MHz, CHLOROFORM-d) δ ppm 1.19-1.31 (2 H, m), 1.32 (6 H, s), 1.64-1.71 (2 H, m), 1.74 (6 H, s), 2.08-2.15 (2 H, m), 2.19-2.24 (2 H, m), 2.47-2.54 (1 H, bs), 3.1-3.23 (2 H, m), 3.34 (3 H, s), 3.7 (2 H, s), 6.32 (1 H, s), 9.82 (1 H, s) | 403 | E | B | B2 |
| 143 | 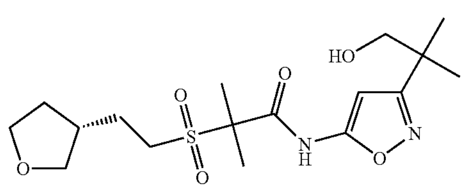 | (250 MHz, CHLOROFORM-d) δ ppm 1.32 (6 H, s), 1.44-1.65 (1 H, m), 1.77 (6 H, s), 1.85-2.19 (4 H, m), 2.26-2.43 (1 H, m), 2.94-3.13 (2 H, m), 3.31-3.47 (1 H, m), 3.62-3.98 (5 H, m), 6.35 (1 H, s), 9.42 (1 H, s) | 389 | not applicable | B | S |
| 144 | 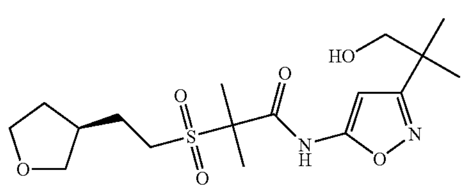 | (250 MHz, CHLOROFORM-d) δ ppm 1.31 (6 H, s), 1.44-1.63 (1 H, m), 1.75 (6 H, s), 1.89-2.19 (4 H, m), 2.19-2.43 (1 H, m), 2.93-3.10 (2 H, m), 3.39 (1 H, dd, J = 8.53, 6.40 Hz), 3.53-3.97 (5 H, m), 6.35 (1 H, s), 9.43 (1 H, s) | 389 | not applicable | B | S |

TABLE XXXVIII-continued

Examples

| # | Structure | ¹H NMR | m/z [M + H] | Acid Method | Amine Method | Amide Method |
|---|---|---|---|---|---|---|
| 145 | 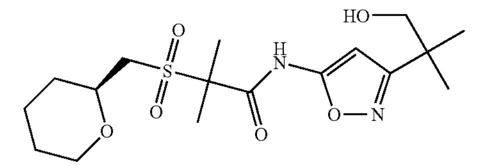 | (500 MHz, CHLOROFORM-d) δ ppm 1.23-1.81 (18 H, m), 1.86 (1 H, d, J = 4.10 Hz), 2.99 (1 H, dd, J = 14.98, 2.36 Hz), 3.07 (1 H, td, J = 11.39, 2.76 Hz), 3.45 (1 H, dd, J = 14.82, 9.30 Hz), 3.64-3.76 (3 H, m), 3.82-3.91 (1 H, m), 6.32 (1 H, s), 9.92 (1 H, s) | 389 | J | B | F |
| 146 | 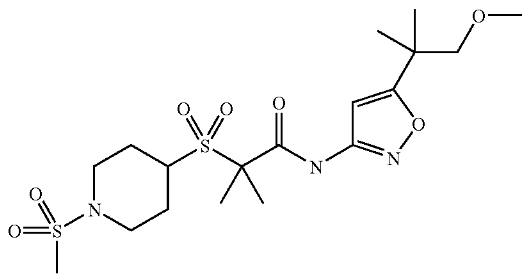 | (400 MHz, CHLOROFORM-d) δ ppm 1.35 (6 H, s), 1.75 (6 H, s), 1.97-2.19 (4 H, m), 2.81 (3 H, s), 2.82-2.88 (2 H, m), 3.34 (3 H, s), 3.32-3.40 (1 H, m), 3.46 (2 H, s), 3.80-3.90 (2 H, m), 6.61 (1 H, s), 9.19 (1 H, s). | 466 | I | D | B |
| 147 | 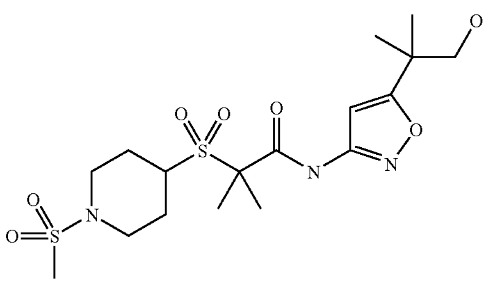 | (400 MHz, CHLOROFORM-d) δ ppm 1.36 (6 H, s), 1.75 (6 H, s), 1.98-2.19 (4 H, m), 2.80 (3 H, s), 2.81-2.88 (2 H, m), 3.30-3.41 (1 H, m), 3.71 (2 H, s), 3.80-3.89 (2 H, m), 6.68 (1 H, s), 9.21 (1 H, s). | 452 | not applicable | not applicable | G |
| 148 | 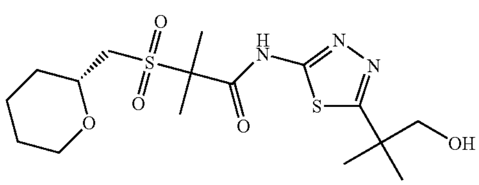 | (500 MHz, CHLOROFORM-d) δ ppm 1.29-1.56 (9 H, m), 1.62 (1 H, d, J = 2.21 Hz), 1.73-1.94 (8 H, m), 2.97-3.07 (2 H, m), 3.47 (1 H, dd, J = 14.82, 9.46 Hz), 3.62-3.70 (1 H, m), 3.80 (2 H, dd, J = 12.14, 11.35 Hz), 3.85-3.92 (1 H, m), 10.66 (1 H, br. s.) | 406 | J | G | U |
| 149 | 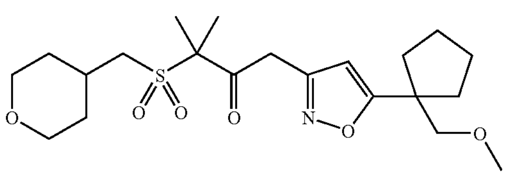 | (400 MHz, CHLOROFORM-d) δ ppm 1.47 (qd, 2 H), 1.71-1.74 (m, 10 H), 1.80-1.87 (m, 4 H), 1.96-2.03 (m, 2 H), 2.35-2.43 (m, 1 H), 2.93 (d, 2 H), 3.32 (s, 3 H), 3.42 (td, 2 H), 3.50 (s, 2 H), 3.94 (dd, 2 H), 6.69 (s, 1 H), 9.05 (s, 1 H). | 429 | B | D | B |

Assessment of Biological Properties

The biological properties of the compounds of the formula I are assessed using the assays described below.

A. Human CB1 and CB2 Receptor Binding:

Experimental Method:

CB2 membranes are purchased and made from HEK293 EBNA cells stably transfected with human CB2 receptor cDNA (Perkin Elmer Life and Analytical Sciences). CB1 membranes are isolated from HEK cells stably co-transfected with human CB1 receptor and Gα16 cDNA's. The membrane preparation is bound to scintillation beads (Ysi-Poly-L-lysine SPA beads, GE Healthcare) for 4 h at room temperature in assay buffer containing 50 mM Tris, pH 7.5, 2.5 mM EDTA, 5 mM $MgCl_2$, 0.8% fatty acid free Bovine Serum Albumin. Unbound membrane is removed by washing in assay buffer. Membrane-bead mixture is added to 96-well assay plates in the amounts of 15 ug membrane per well (CB2) or 2.5 ug per well (CB1) and 1 mg SPA bead per well. Compounds are added to the membrane-bead mixture in dose-response concentrations ranging from $1 \times 10^{-5}$M to $1 \times 10^{-10}$M with 0.25% DMSO, final. The competition reaction is initiated with the addition of ³H-CP55940 (Perkin Elmer Life and Analytical Sciences) at a final concentration of 1.5 nM (CB2) or 2.5 nM (CB1). The reaction is incubated at room temperature for 18 h and read on TopCount NXT plate reader. Total and non-specific binding is determined in the absence and presence of 1.25 uM Win 55212 (Sigma). IC50 values for each compound are calculated as the concentration of compound that inhibits the specific binding of the radioactively labeled ligand to the receptor by 50% using the XLFit 4.1 four parameter logistic model. IC50 values are converted to inhibition constant (Ki) values using Cheng-Prusoff equation.

B. CB2R Mediated Modulation of cAMP Synthesis:

Compounds of the invention are evaluated for their CB2 agonist or inverse agonistic activity in accordance with the following experimental method. Compounds which are shown to bind to CB2 by the binding assay described above but which are not shown to exhibit CB2R-mediated modulation of cAMP synthesis by this assay are presumed to be CB2 antagonists.

Experimental Method:

CHO cells expressing human CB2R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

C. CB1R Mediated Modulation of cAMP Synthesis:

Compounds of the invention are evaluated for their CB1 agonist or inverse agonistic activity in accordance with the following experimental method. Compounds which are shown to bind to CB1 by the binding assay described above but which are not shown to exhibit CB1R-mediated modulation of cAMP synthesis by this assay are presumed to be CB1 antagonists.

Experimental Method:

CHO cells expressing human CB1R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

Compounds Having Agonist Activity

Through the use of the above described assays compounds are found to exhibit agonistic activity and thus to be particularly well suited for the treatment of pain as well as for the treatment of inflammation. Preferred compounds of the invention will have an activity range of CB2 (<500 nM) and CB1 (>20000).

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area eg tinnitus; allergic rhinitis or hay fever; otitis externa; caused by contact eczema, infection, etc.; and otitis media;
(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;
(xiii) Blood diseases: acquired hemolytic anemia; aplastic anemia, and idiopathic thrombocytopenia;
(xiv) Tumor diseases: acute lymphatic leukemia; Hodgkin's disease, malignant lymphoma; lymphogranulomatoses; lymphosarcoma; solid malignant tumors; extensive metastases;
(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);
(xvi) Organ and tissue transplantations and graft-versus-host diseases;
(xvii) Severe states of shock, e.g., septic shock, anaphylactic shock, and systemic inflammatory response syndrome (SIRS);
(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;
(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;
(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.
(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;
(xxii) Cancer pain induced by or associated with tumors such as lymphatic leukemia; Hodgkin's disease, malignant lymphoma; lymphogranulomatoses; lymphosarcoma; solid malignant tumors; extensive metastases;
(xxiii) Headache such as cluster headache, migraine with and without aura, tension type headache, headache with different origins, headache disorders including prophylactic and acute use;
(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for Example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:
1. A compound of the formula (I)

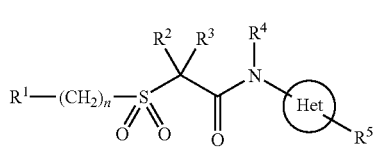

wherein:
Het is a 5-membered heteroaryl ring;
$R^1$ is $C_{1-10}$ alkyl, $C_{1-10}$ alkoxy, $C_{3-10}$ cycloalkyl, 3-10 membered saturated heterocyclic ring, 5-10 membered mono or bicyclic heteroaryl ring or phenyl each optionally independently substituted with 1-3 substituents chosen from $C_{1-4}$ alkyl, $C_{1-4}$ alkoxy, $C_{3-10}$ cycloalkyl, $C_{1-4}$ alkylsulfonyl, acyl, oxo, cyano, phenyl, hydroxyl and halogen;
$R^2$ and $R^3$ are $C_1$-$C_4$ alkyl or hydrogen with the proviso that both $R^2$ and $R^3$ cannot be hydrogen; or $R^2$ and $R^3$ together with the carbon atom to which they are attached form a 3- to 6-membered cycloalkyl or heterocyclic ring;
$R^4$ is hydrogen or methyl;
$R^5$ is chosen from

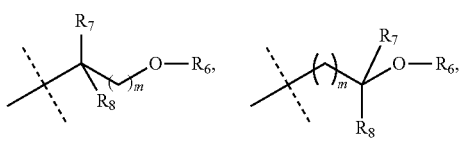

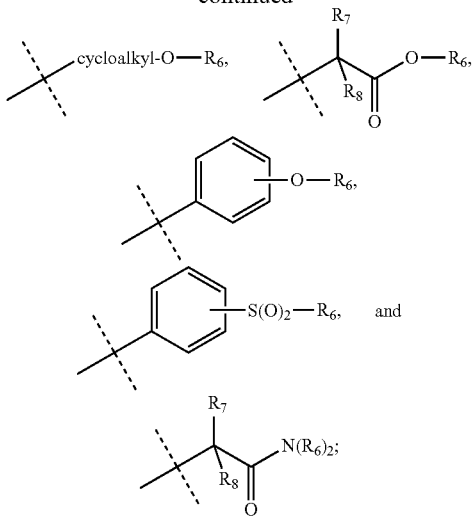

m is 0, 1, 2 or 3
$R^6$ is hydrogen or $C_{1-4}$ alkyl;
wherein $R^7$ and $R^8$ are each independently hydrogen or $C_{1-4}$ alkyl with the proviso that both $R^7$ and $R^8$ cannot be hydrogen; and wherein $R^7$ and $R^8$ optionally can cyclize to form a $C_{3-7}$ cycloalkyl ring;
n is 0, 1 or 2;
wherein any carbon atom on the formula (I) or any R substituent listed above is optionally partially or fully halogenated where possible;
or a pharmaceutically acceptable salt thereof.
2. The compound according to claim 1, and wherein Het is

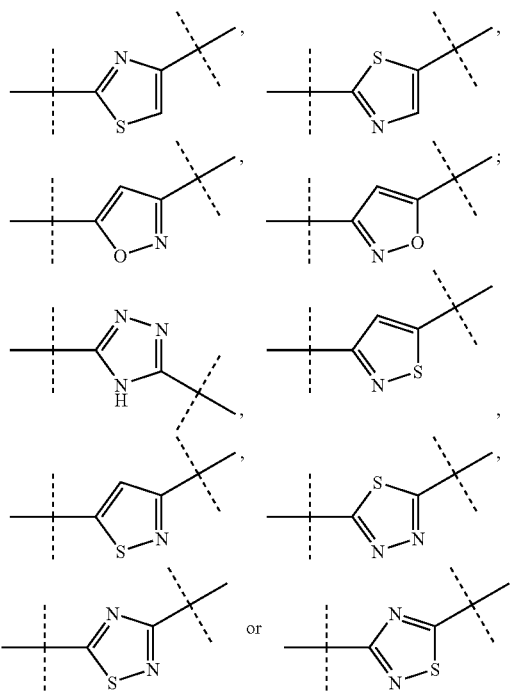

$R^1$ is $C_{1-4}$ alkyl, phenyl, cyclopropyl, cyclobutyl, cyclopentyl, cyclohexyl, cycloheptyl, cyclooctyl, tetrahydrofuranyl, tetrahydropyranyl, azetidinyl, piperidinyl; benzoxazolyl, benzothiazolyl, benzimidazolyl, dioxanyl, oxazolyl, isoxazolyl, thiazolyl, pyrazolyl, pyrrolyl, imidazolyl, thienyl, thiomorpholinyl, 1,1-Dioxo-1λ⁶-thiomorpholinyl, morpholinyl, pyridinyl, pyrimidinyl, pyridazinyl, pyrazinyl, triazinyl, pyrrolidinyl, piperazinyl, purinyl, quinolinyl, Dihydro-2H-quinolinyl, isoquinolinyl, quinazolinyl, indazolyl, indolyl, benzofuranyl, benzopyranyl or benzodioxolyl each optionally substituted by a substituent chosen from halogen, $C_{1-4}$ alkyl, $C_{1-4}$ alkylsulfonyl and oxo;

$R^2$ and $R^3$ are independently methyl, ethyl, n-propyl, isopropyl or hydrogen with the proviso that both $R^2$ and $R^3$ cannot be hydrogen; or $R^2$ and $R^3$ together with the carbon to which they are attached form a cyclopropyl, cyclobutyl or cyclopentyl ring;

$R^4$ is hydrogen;

$R^5$ is chosen from

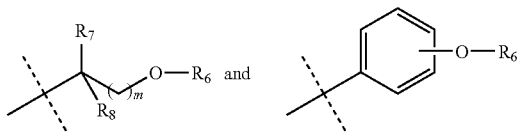

$R^6$ is hydrogen or $C_{1-3}$ alkyl;

wherein $R^7$ and $R^8$ are each $C_{1-3}$ alkyl or $C_{3-6}$ cycloalkyl or a pharmaceutically acceptable salt thereof.

3. The compound according to claim 2, and wherein $R^1$ is $C_{1-4}$ alkyl, cyclopropyl, cyclobutyl, cyclopentyl, cyclohexyl, cycloheptyl, cyclooctyl, tetrahydrofuranyl, tetrahydropyranyl, azetidinyl, piperidinyl, dioxanyl, thiomorpholinyl, 1,1-Dioxo-1λ⁶-thiomorpholinyl, morpholinyl, pyrrolidinyl or piperazinyl, each optionally substituted by a substituent chosen from halogen, $C_{1-4}$ alkyl, $C_{1-4}$ alkylsulfonyl and oxo or a pharmaceutically acceptable salt thereof.

4. The compound according to claim 1, and wherein $R^1$ is $C_{1-4}$ alkyl, cyclopropyl, cyclobutyl, cyclopentyl, cyclohexyl, cycloheptyl, cyclooctyl, tetrahydrofuranyl, tetrahydropyranyl, azetidinyl, piperidinyl, dioxanyl, thiomorpholinyl, 1,1-Dioxo-1λ⁶-thiomorpholinyl, morpholinyl, pyrrolidinyl or piperazinyl, optionally substituted by a substituent chosen from halogen, $C_{1-4}$ alkyl, $C_{1-4}$ alkoxy, $C_{1-4}$ alkylsulfonyl and oxo or a pharmaceutically acceptable salt thereof.

5. The compound according to claim 2, and wherein

Het is

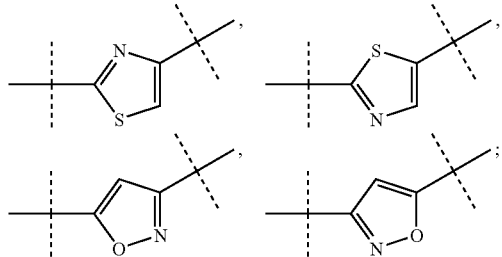

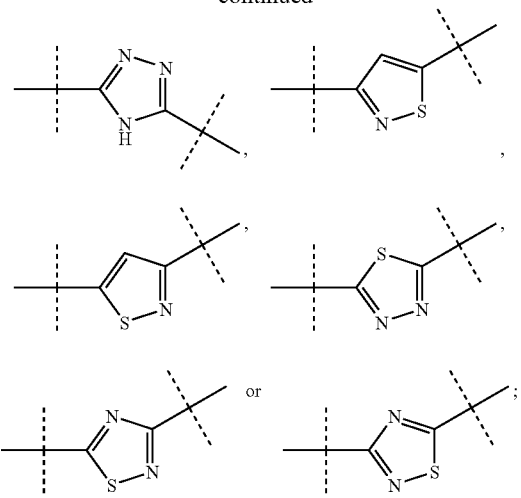

$R^1$ is phenyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, purinyl, quinolinyl, Dihydro-2H-quinolinyl, isoquinolinyl, quinazolinyl, indazolyl, indolyl, benzofuranyl, benzopyranyl or benzodioxolyl each optionally substituted by a substituent chosen from halogen, $C_{1-4}$ alkyl, $C_{1-4}$ alkylsulfonyl and oxo;

$R^2$ and $R^3$ are independently methyl, ethyl, n-propyl, isopropyl or hydrogen with the proviso that both $R^2$ and $R^3$ cannot be hydrogen; or $R^2$ and $R^3$ together with the carbon to which they are attached form a cyclopropyl, cyclobutyl or cyclopentyl ring or a pharmaceutically acceptable salt thereof.

6. The compound according to claim 5, and wherein

Het is

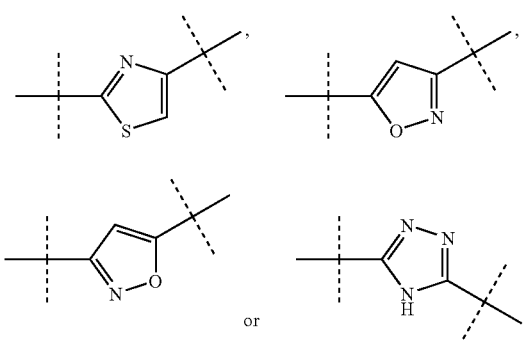

$R^1$ is phenyl or benzimidazoyl each optionally substituted by a substituent chosen from halogen, $C_{1-4}$ alkyl, $C_{1-4}$ alkylsulfonyl and oxo;

$R^2$ and $R^3$ are methyl; or $R^2$ and $R^3$ together with the carbon to which they are attached form a cyclopropyl or cyclobutyl ring;

$R^6$ is hydrogen or $C_{1-2}$ alkyl;

$R^7$ and $R^8$ are each $C_{1-2}$ alkyl or a pharmaceutically acceptable salt thereof.

7. The compound according to claim 3, and wherein Het is

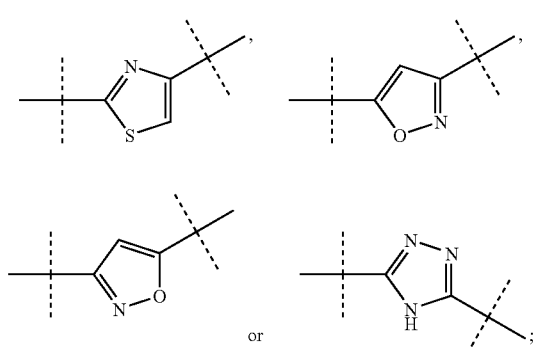

R$^1$ is C$_{1-2}$ alkyl, cyclopropyl, cyclobutyl, cyclopentyl, cyclohexyl, tetrahydropyranyl, tetrahydrofuranyl, azetidinyl, pyrrolidinyl or piperidinyl each optionally substituted by a substituent chosen from by halogen, C$_{1-4}$ alkyl, C$_{1-4}$ alkylsulfonyl and oxo;

R$^2$ and R$^3$ are methyl, or R$^2$ and R$^3$ together with the carbon to which they are attached form a cyclopropyl or cyclobutyl ring;

R$^6$ is hydrogen or C$_{1-2}$ alkyl;

R$^7$ and R$^8$ are each C$_{1-2}$ alkyl or a pharmaceutically acceptable salt thereof.

8. The compound according claim 6 and wherein Het is

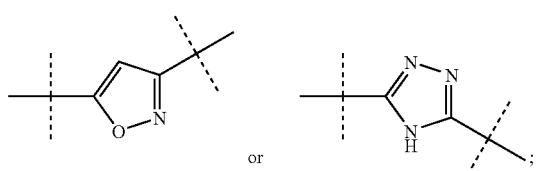

R$^1$ is phenyl optionally substituted by a substituent chosen from by halogen, C$_{1-4}$ alkyl and C$_{1-4}$ alkylsulfonyl or a pharmaceutically acceptable salt thereof.

9. The compound according to claim 7, and wherein Het is

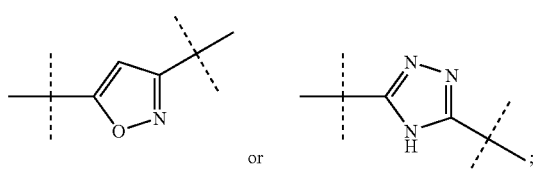

R$^1$ is cyclopropyl, cyclobutyl, tetrahydropyranyl, tetrahydrofuranyl or azetidinyl each optionally substituted by a substituent chosen from by halogen, C$_{1-4}$ alkyl, C$_{1-4}$ alkylsulfonyl and oxo or a pharmaceutically acceptable salt thereof.

10. The compound according to claim 3, and wherein Het is

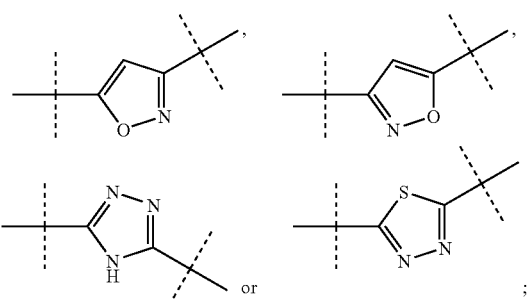

R$^2$ and R$^3$ are methyl or a pharmaceutically acceptable salt thereof.

11. The compound according to claim 10, and wherein Het is

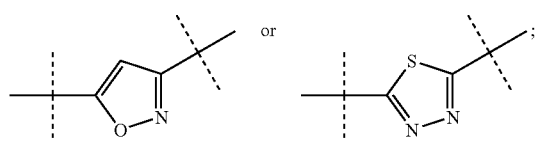

and R$^5$ is

or a pharmaceutically acceptable salt thereof.

12. The compound according to claim 11, and wherein Het is

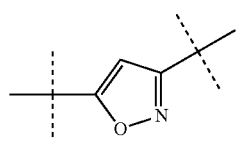

or a pharmaceutically acceptable salt thereof.

13. The compound according to claim 11, and wherein R$^5$ is

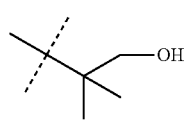

or a pharmaceutically acceptable salt thereof.

14. The compound according to claim 11, and wherein R$^1$ is C$_{1-4}$ alkyl, cyclopropyl, cyclobutyl, cyclopentyl, cyclohexyl, tetrahydropyranyl, tetrahydrofuranyl, azetidinyl, piperidinyl or pyrrolidinyl each optionally substituted by a substituent chosen from by halogen, C$_{1-4}$ alkyl, $C_{1-4}$ alkoxy, $C_{1-4}$ alkylsulfonyl and oxo or a pharmaceutically acceptable salt thereof.

15. The compound according to claim 11, and wherein $R^1$ is $CF_3$—$CH_2$—$CH_2$—$CH_2$— or tetrahydropyranyl or a pharmaceutically acceptable salt thereof.

16. A compound of the formula (I)

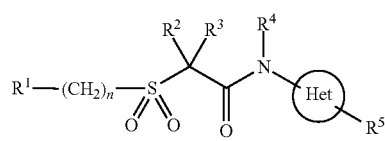
(III)

wherein

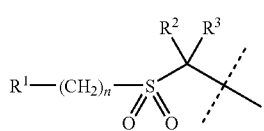

of the formula (I) is chosen from column A1-A26 in Table I, and

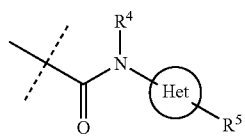

of the formula (I) is chosen from column B1-B20 in Table I,

TABLE I

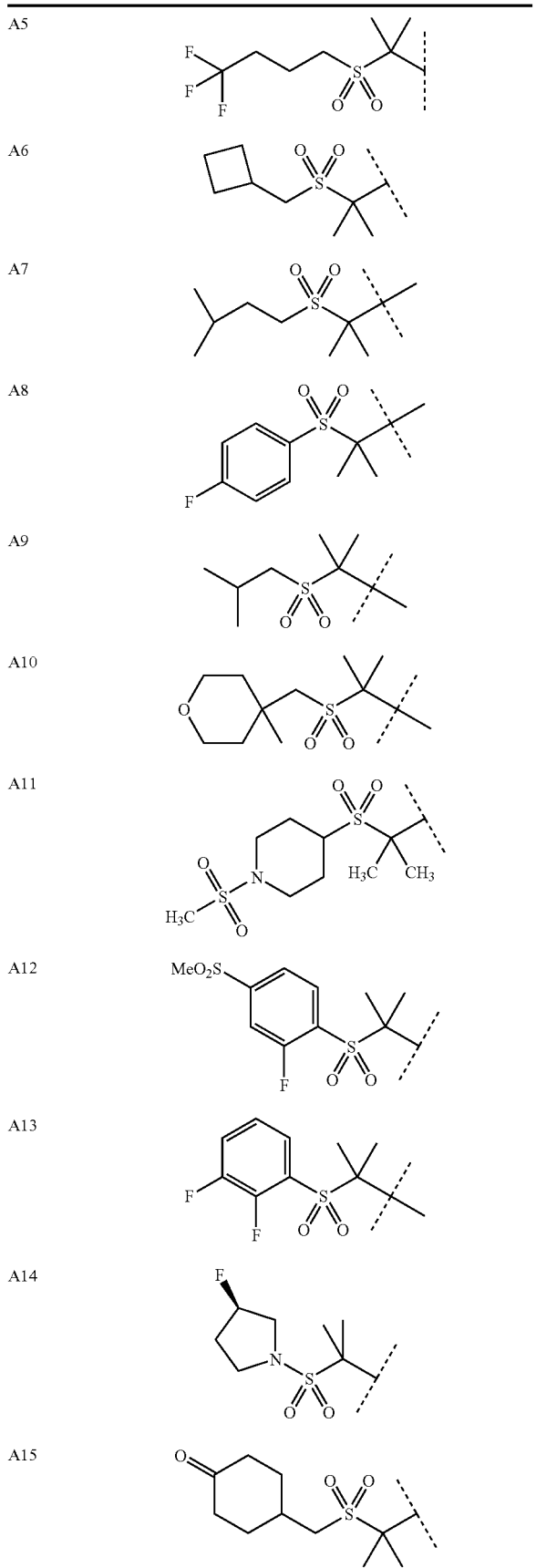

TABLE I-continued
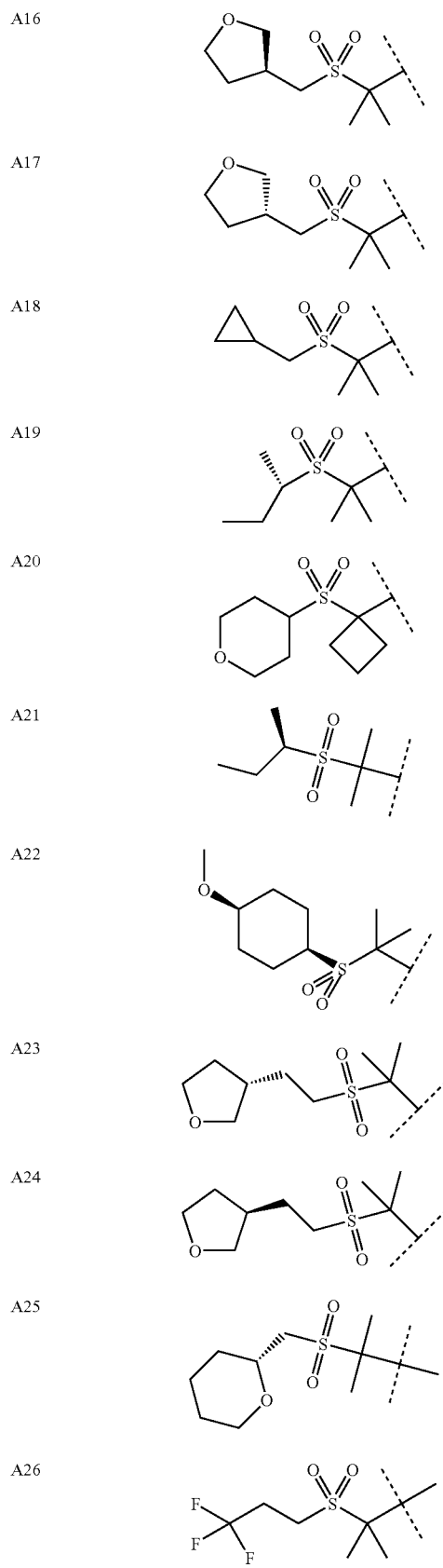
TABLE I-continued
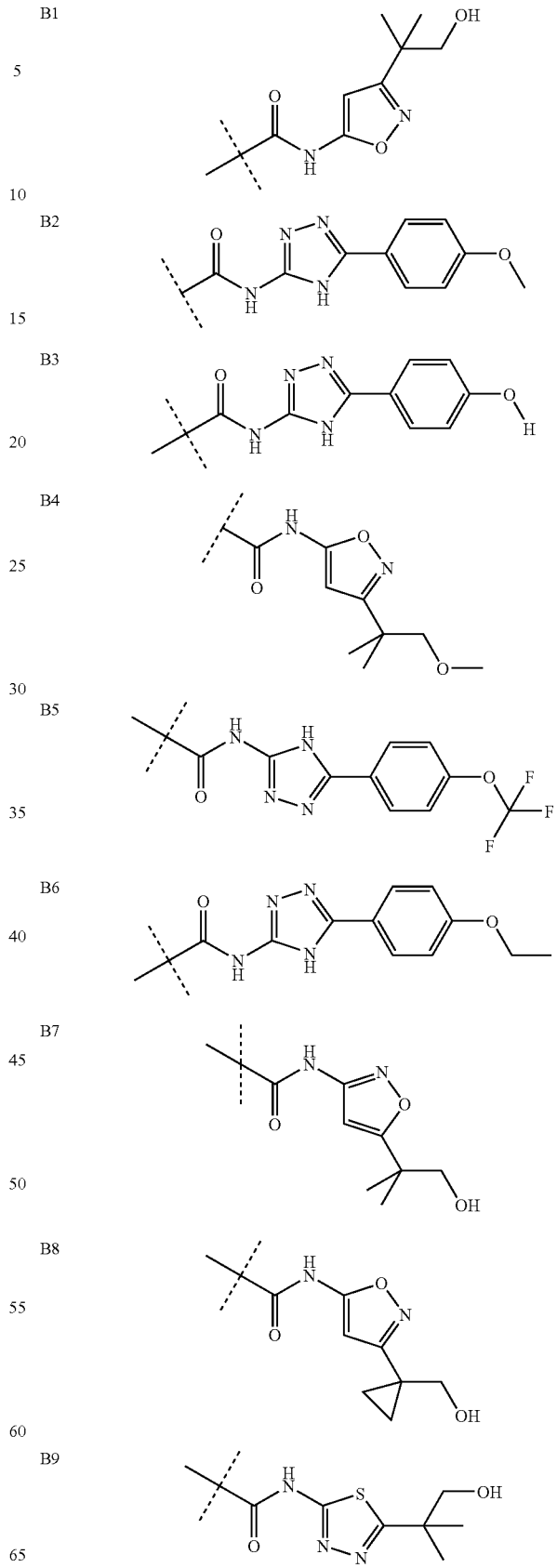

TABLE I-continued

B10 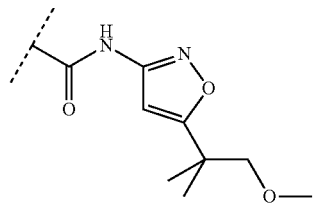

B11 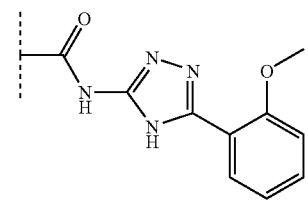

B12 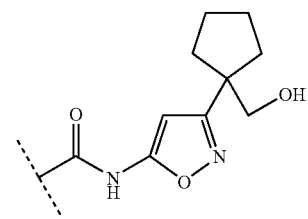

B13 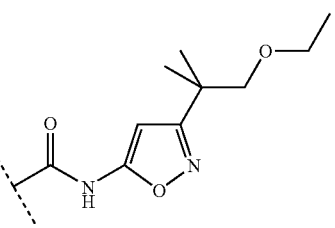

B14 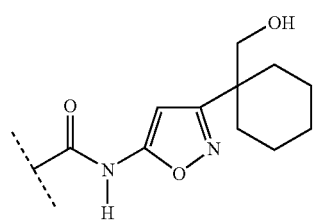

B15 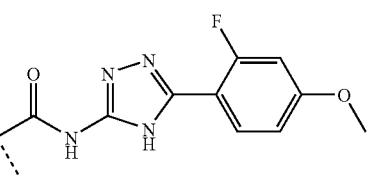

B16 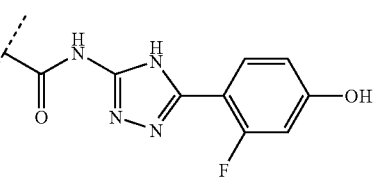

TABLE I-continued

B17 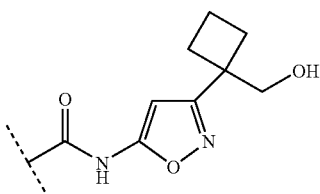

B18 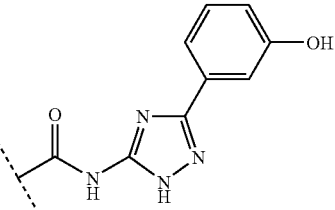

B19 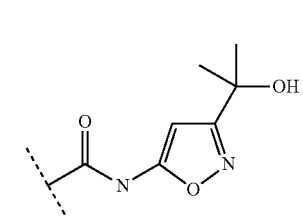

B20 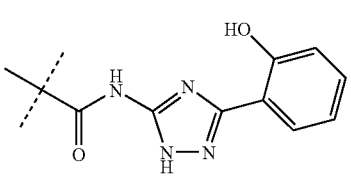

or a pharmaceutically acceptable salt thereof.

17. A pharmaceutical composition comprising a therapeutically effective amount of a compound according to claim 1 and one or more pharmaceutically acceptable carriers and/or adjuvants.

18. A compound wherein the compound is

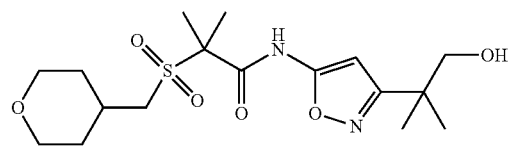

or a pharmaceutically acceptable salt thereof.

19. A compound wherein the compound is

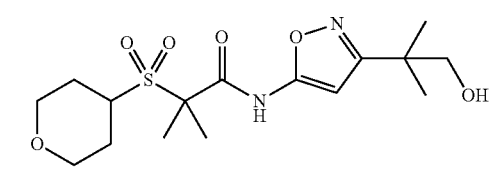

or a pharmaceutically acceptable salt thereof.

20. A compound wherein the compound is

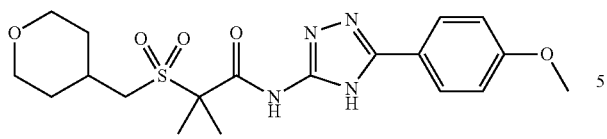

or a pharmaceutically acceptable salt thereof.

21. A compound wherein the compound is

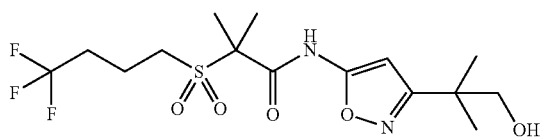

or a pharmaceutically acceptable salt thereof.

22. A compound wherein the compound is

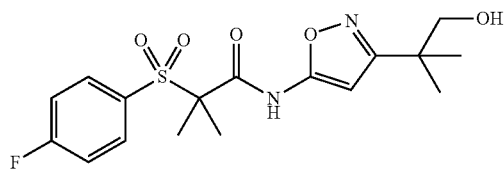

or a pharmaceutically acceptable salt thereof.

23. A compound wherein the compound is

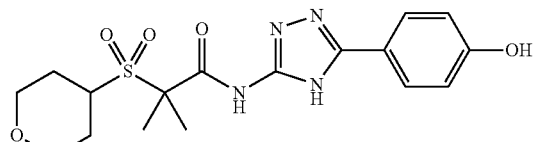

or a pharmaceutically acceptable salt thereof.

24. A compound wherein the compound is

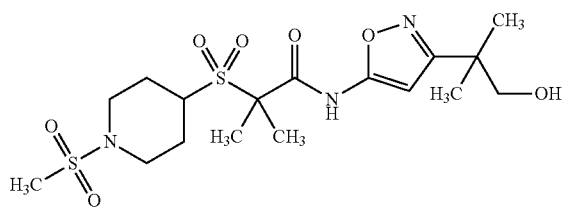

or a pharmaceutically acceptable salt thereof.

25. A compound wherein the compound is

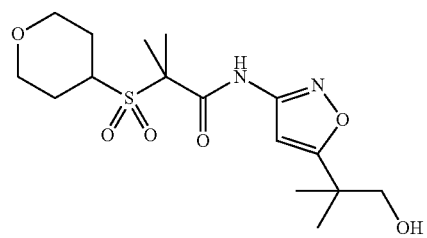

or a pharmaceutically acceptable salt thereof.

26. A compound wherein the compound is

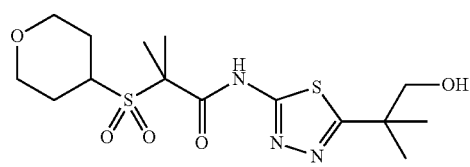

or a pharmaceutically acceptable salt thereof.

27. A compound wherein the compound is

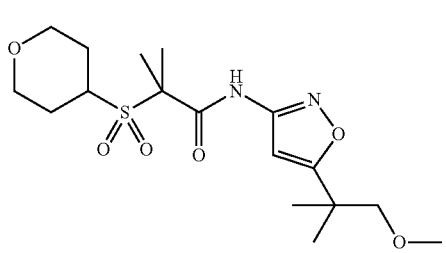

or a pharmaceutically acceptable salt thereof.

28. A compound wherein the compound is

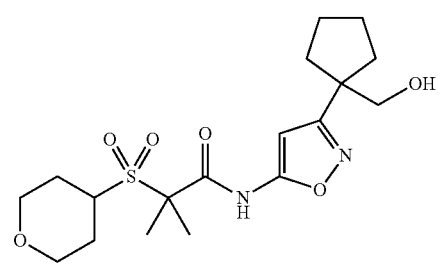

or a pharmaceutically acceptable salt thereof.

29. A compound wherein the compound is

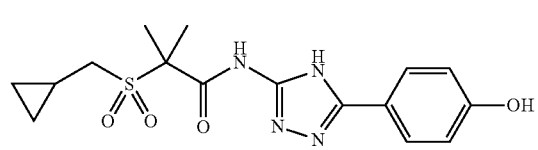

or a pharmaceutically acceptable salt thereof.

30. A compound wherein the compound is

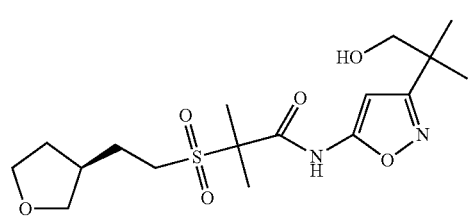

or a pharmaceutically acceptable salt thereof.

31. A compound wherein the compound is
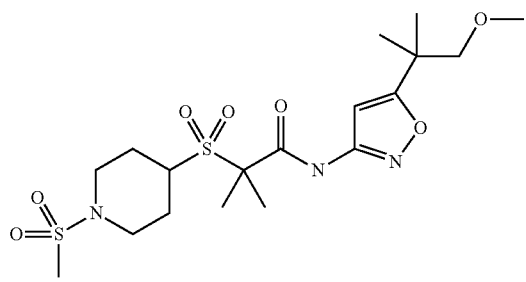
or a pharmaceutically acceptable salt thereof.
32. A compound wherein the compound is
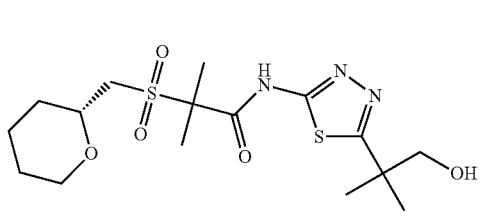
or a pharmaceutically acceptable salt thereof.
* * * * *